(12) United States Patent
Xu

(10) Patent No.: US 12,370,208 B2
(45) Date of Patent: *Jul. 29, 2025

(54) ADENOSINE DERIVATIVE AND PHARMACEUTICAL COMPOSITION COMPRISING THE SAME

(71) Applicant: Brii Biosciences, Inc., Durham, NC (US)

(72) Inventor: Lianhong Xu, Durham, NC (US)

(73) Assignee: Brii Biosciences, Inc., Durham, NC (US)

( * ) Notice: Subject to any disclaimer, the term of this patent is extended or adjusted under 35 U.S.C. 154(b) by 456 days.

This patent is subject to a terminal disclaimer.

(21) Appl. No.: 17/630,403

(22) PCT Filed: Jul. 27, 2020

(86) PCT No.: PCT/US2020/043713
§ 371 (c)(1),
(2) Date: Jan. 26, 2022

(87) PCT Pub. No.: WO2021/021717
PCT Pub. Date: Feb. 4, 2021

(65) Prior Publication Data
US 2022/0288098 A1 Sep. 15, 2022

Related U.S. Application Data

(60) Provisional application No. 62/879,414, filed on Jul. 27, 2019.

(51) Int. Cl.
| | | |
|---|---|---|
| *A61K 31/7076* | (2006.01) | |
| *A61K 9/00* | (2006.01) | |
| *A61K 9/107* | (2006.01) | |
| *A61K 9/14* | (2006.01) | |
| *A61P 31/18* | (2006.01) | |
| *A61K 47/10* | (2017.01) | |
| *A61K 47/38* | (2006.01) | |

(52) U.S. Cl.
CPC ........ *A61K 31/7076* (2013.01); *A61K 9/0019* (2013.01); *A61K 9/107* (2013.01); *A61K 9/14* (2013.01); *A61P 31/18* (2018.01); *A61K 47/10* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,880,154 | A | 3/1999 | Boukrinskaia et al. |
| 7,339,053 | B2 | 3/2008 | Kohgo et al. |
| 7,625,877 | B2 | 12/2009 | Kohgo et al. |
| 8,039,614 | B2 | 10/2011 | Kohgo et al. |
| 10,537,589 | B2 | 1/2020 | Hazuda et al. |
| 11,793,827 | B2 | 10/2023 | Xu |
| 11,890,297 | B2 | 2/2024 | Xu et al. |
| 2005/0215512 | A1 | 9/2005 | Kohgo et al. |
| 2016/0199396 | A1 | 7/2016 | Shahar et al. |
| 2018/0002366 | A1 | 1/2018 | Girijavallabhan et al. |
| 2018/0099989 | A1 | 4/2018 | Ivachtchenko et al. |
| 2019/0185508 | A1 | 6/2019 | Alexandre et al. |
| 2019/0321380 | A1 | 10/2019 | De Lera Ruiz et al. |
| 2020/0079814 | A1 | 3/2020 | Ivachtchenko et al. |
| 2020/0101098 | A1 | 4/2020 | Hazuda et al. |
| 2022/0233567 | A1 | 7/2022 | Xu |
| 2022/0249532 | A1 | 8/2022 | Xu et al. |
| 2023/0226093 | A1 | 7/2023 | Xu |
| 2024/0180949 | A1 | 6/2024 | Xu et al. |
| 2024/0245716 | A1 | 7/2024 | Xu |

FOREIGN PATENT DOCUMENTS

| | | |
|---|---|---|
| CN | 109053803 A | 12/2018 |
| RU | 2728829 C1 | 7/2020 |
| WO | WO-2005025583 A2 | 3/2005 |
| WO | WO-2007022073 A2 | 2/2007 |
| WO | WO-2008011406 A2 | 1/2008 |
| WO | WO-2011058582 A1 | 5/2011 |
| WO | WO-2015187596 A2 | 12/2015 |
| WO | WO-2017053216 A2 | 3/2017 |
| WO | WO-2017139519 A1 | 8/2017 |
| WO | WO-2018022221 A1 | 2/2018 |
| WO | WO-2020031131 A1 | 2/2020 |
| WO | WO-2020044257 A1 | 3/2020 |
| WO | WO-2020178767 A1 | 9/2020 |
| WO | WO-2021021717 A1 | 2/2021 |
| WO | WO-2021038509 A1 | 3/2021 |
| WO | WO-2021050961 A1 | 3/2021 |
| WO | WO-2021260641 A1 | 12/2021 |
| WO | WO-2022159872 A1 | 7/2022 |

(Continued)

OTHER PUBLICATIONS

Tichy et al. Bioorganic & Medicinal Chemistry vol. 19 No 11, pp. 3527-3539. (Year: 2011).*
International Search Report and Written Opinion for Application No. PCT/US2022/013660, mailed Jun. 14, 2022, 10 pages.
Patel et al., "Synthesis of Islatravir Enabled by a Catalytic, Enantioselective Alkynylation of a Ketone," Organic Letters, vol. 22, No. 12, Jun. 9, 2020, pp. 4659-4664, https://doi.org/10.1021/acs.orglett.0c01431.
Ghosh et al., "Organic Carbamates in Drug Design and Medical Chemistry," Journal of Medicinal Chemistry, American Chemical Society, Jan. 7, 2015, vol. 58, Issue 7, pp. 2895-2940.
Hayakawa et al., "Potential of 4'-C-substituted nucleosides for the treatment of HIV-1," Antiviral Chemistry & Chemotherapy, 15: 169-187, Aug. 2004.

(Continued)

*Primary Examiner* — Katherine Peebles
(74) *Attorney, Agent, or Firm* — Cooley LLP

(57) ABSTRACT

Disclosed here is an adenosine derivative prodrug that can have reverse transcriptase inhibitor activity in vivo. This disclosure is also directed to a pharmaceutical composition comprising the adenosine derivative that can be used for the treatment of HIV infection or RNA virus infection.

10 Claims, 7 Drawing Sheets

(56) References Cited

FOREIGN PATENT DOCUMENTS

WO    WO-2023196832 A2    10/2023

OTHER PUBLICATIONS

International Preliminary Report on Patentability for International Application No. PCT/US2020/043713, mailed Feb. 10, 2022, 8 Pages.
International Search Report and Written Opinion for Application No. PCT/US2020/043713, mailed Dec. 15, 2020, 10 pages.
Invitation to Pay Additional Fees for Application No. PCT/US2022/013660, mailed Apr. 6, 2022, 2 pages.
Iyidogan et al., "Current Perspectives on HIV-1 Antiretroviral Drug Resistance," Viruses, Oct. 2014, 6, pp. 4095-4139.
Michailidis et al., "4'-Ethynyl-2-fluoro--2'-deoxyadenosine (EFdA) Inhibits HIV-1 Reverse Transcriptase with Multiple Mechanisms," The Journal of Biological Chemistry, Aug. 2014, vol. 289, No. 35, pp. 24533-24548.
Ohrui et al., "Syntheses of 4'-C-Ethynyl-β-D-arabino-and 4'-C-Ethynyl-2'-deoxy-β-D-ribo-pentofuranosylpyrimidines and -purines and Evaluation of Their Anti-HIV Activity," Journal of Medicinal Chemistry, Nov. 2000, 43, pp. 4516-4525.
Pauwels, Rudi, "Aspects of successful drug discovery and development", Antiviral Research 71(2-3), Sep. 2006, pp. 77-89.
Singh et al., "Long-Acting Anti-HIV Drugs Targeting HIV-1 Reverse Transcriptase and Integrase," Pharmaceuticals, 12, 62, Jun. 2019, 14 pages.
Solyev et al., "Synthesis and Anti-HIV Properties of New Carbamate Prodrugs of AZT," Chemical Biology & Drug Design, Dec. 2012, vol. 80, pp. 947-952.
Stella et al, eds, "Prodrugs: Challenges and Rewards," Part 2, Chapter "Prodrugs of Carboxylic Acids", Springer, 2007, 29 pages.
Subbaiah et al., "Coupling of an Acyl Migration Prodrug Strategy with Bio-activation To Improve Oral Delivery of the HIV-1 Protease Inhibitor Atazanavir," Journal of Medicinal Chemistry, Apr. 2018, vol. 61, pp. 4176-4188.
Third Party Observation for European Application No. 20848596.1, mailed Mar. 4, 2022, 10 pages.
Tichy et al., "New prodrugs of Adefovir and Cidofovir," Bioorganic & Medicinal Chemistry, vol. 19, Issue 11, Elsevier Science, Apr. 22, 2011, pp. 3527-3539.
International Preliminary Report on Patentability for Application No. PCT/US2022/013660, mailed Jul. 20, 2023, 7 pages.
Non-Final Office Action for U.S. Appl. No. 18/176,204 dated May 9, 2023, 19 pages.
Office Action and Search report for Chinese Application No. CN20208066036 dated Jul. 6, 2023, 13 pages.
Non-Final Office Action for U.S. Appl. No. 18/176,204 dated May 22, 2024, 23 pages.
Non-Final Office Action for U.S. Appl. No. 18/467,985 dated Apr. 25, 2024, 11 pages.
PubChem [Internet]. Bethesda (MD): National Library of Medicine (US), National Center for Biotechnology Information; 2004-. PubChem Compound Summary for CID 6483431, 4'-Ethynyl-2-Fluoro-2'-Deoxyadenosine; [cited Jul. 31, 2024], 34 pages. Available from: https://pubchem.ncbi.nlm.nih.gov/compound/4_-Ethynyl-2-Fluoro-2_-Deoxyadenosine.
Office Action and Search report for Russian Application No. RU2022104985 dated Dec. 29, 2023, 29 pages.
Office Action and Search Report for Singapore Application No. SG11202200159S dated Apr. 2, 2024, 7 pages.
Office Action for Chinese Application No. CN20208066036 dated May 21, 2024, 14 pages.
Office Action for Eurasian Application No. 202392087 mailed Jul. 29, 2024, 12 pages.
Office Action for Indian Application No. IN202217003901 mailed May 13, 2024, 7 pages.
Office Action for Taiwan Patent Application No. TW20200125342 dated Mar. 7, 2024, 9 pages.
Rautio et al., "Prodrugs: design and clinical applications". Nature reviews Drug discovery. Mar. 2008; 7(3): 255-70.
Wanka et al., "The lipophilic bullet hits the targets: medicinal chemistry of adamantane derivatives". Chemical reviews. May 8, 2013; 113(5): 3516-604.
Belikov, V.G, "Pharmaceutical Chemistry. Chapter 2.6 Relationship between the chemical structure, properties of substances and their effect on the body", MEDpress-inform (2007); pp. 27-29; 14 pages with English translation.
Dyson, G., et al., "Chemistry of Synthetic Drugs", Moscow, MIR, 1964, pp. 12-19; 25 pages with English machine translation.
Kümmerer, K., "Pharmaceuticals in the Environment", Annual Review of Environment and Resources (2010); 35: 57-75.
Mashkovskiy, M.D., "Drugs", Moscow: "Medicine" (1993) Part 1, pp. 8; 3 pages with English Summary.
Simplicio et al., "Prodrugs for amines". Molecules. Mar. 3, 2008; 13(3): 519-47.
Extended European Search Report for European Application No. EP20848596.1 dated Sep. 15, 2023, 9 pages.
Final Office Action for U.S. Appl. No. 18/176,204 dated Aug. 30, 2023, 21 pages.
Kageyama, M., et al., "Enantioselective Total Synthesis of the Potent Anti-HIV Nucleoside EFdA", Organic Letters, vol. 13, No. 19, Oct. 7, 2011, pp. 5264-5266, DOI: 10.1021/01202116k.
Non-Final Office Action for U.S. Appl. No. 17/583,805 dated Mar. 16, 2023, 11 pages.
International Preliminary Report on Patentability for PCT/US2023/065355 mailed Oct. 8, 2024, 7 pages.
International Search Report and Written Opinion for International Application No. PCT/US2023/065355, mailed on Aug. 28, 2023, 14 pages.
Matthews et al., "Safety and Pharmacokinetics of Once-Daily Multiple-Dose Administration of Islatravir in Adults Without HIV". J Acquir. Immune Defic Syndr. Nov. 1, 2021;88(3): 314-321.
Merck "News Release—Merck Announces Clinical Holds on Studies Evaluation Islatravir for the Treatment and Prevention of HIV-1 Infection". Dec. 13, 2021, 8 pages. Retrieved from Internet Jan. 15, 2025. https://www.merck.com/news/merck-announces-clinical-holds-on-studies-evaluating-islatravir-for-the-treatment-and-prevention-of-hiv-1-infection/.
Notice of Allowance for Chinese Application No. 202080066036.3 mailed Dec. 20, 2024, with English translation, 8 pages.
Third Party Observation submitted in International Patent Application No. PCT/US2023/065355 Aug. 6, 2024, 7 pages.
Notice of Reasons for Refusal for Japanese Application No. 2022-505447 mailed Sep. 5, 2024, with English translation, 10 pages.
Office Action and Search Report for Chinese Patent Application No. CN202080066036.3 dated Jan. 26, 2024, with English Translation, 16 pages.
Office Action for Mexican Application No. MX/a/2022/000563 mailed Oct. 24, 2024, with English translation, 8 pages.
Office Action for Israel Application No. 289925 mailed Nov. 4, 2024, 4 pages.
Tatani et al., "Identification of 8-aminoadenosine derivatives as a new class of human concentrative nucleoside transporter 2 inhibitors". ACS Medicinal Chemistry Letters. Mar. 12, 2015; 6(3): 244-8.
Office Action and Search Report for Chinese Application No. 202280009277.3 mailed Apr. 14, 2025, with English translation, 20 pages.

\* cited by examiner

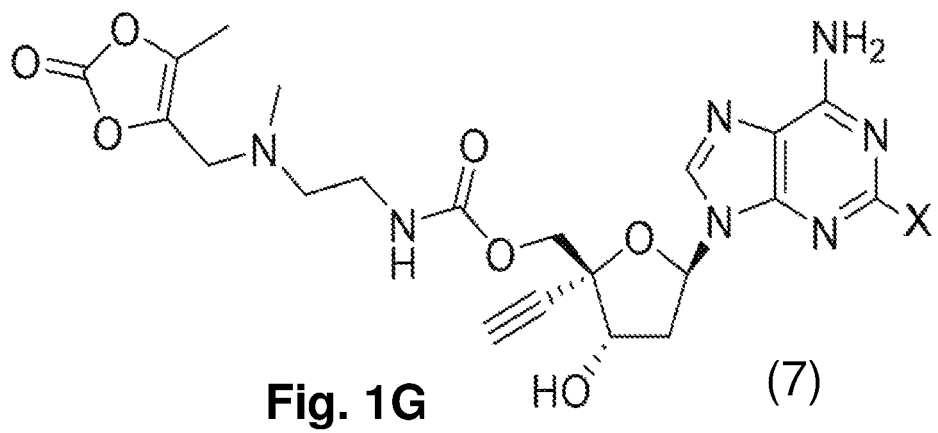
Fig. 1G (7)
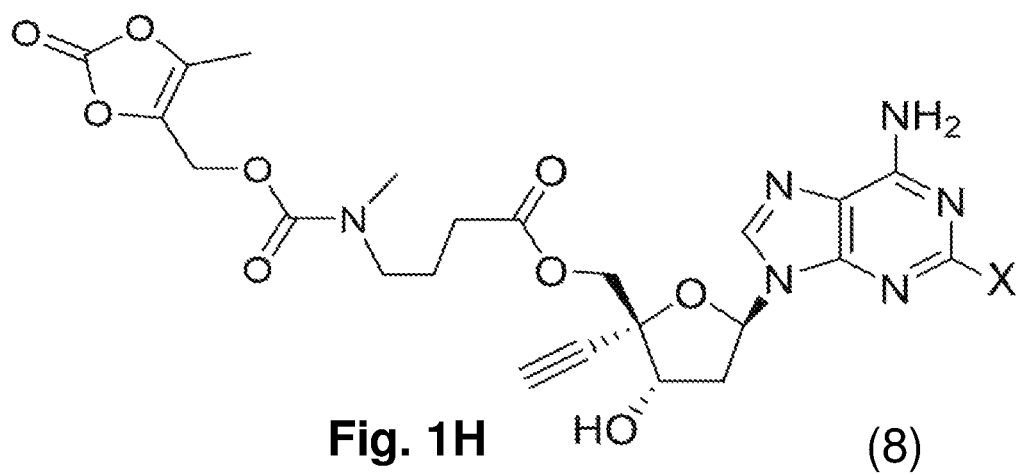
Fig. 1H (8)
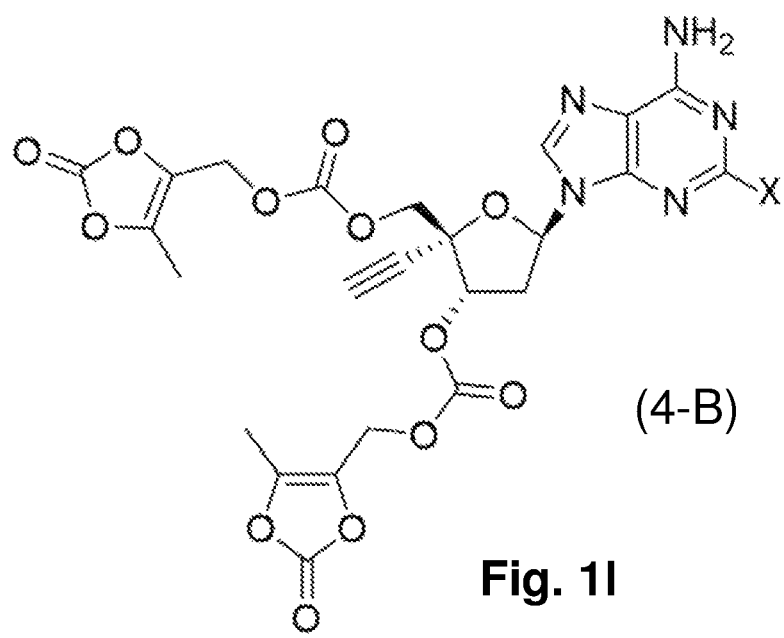
(4-B)
Fig. 1I

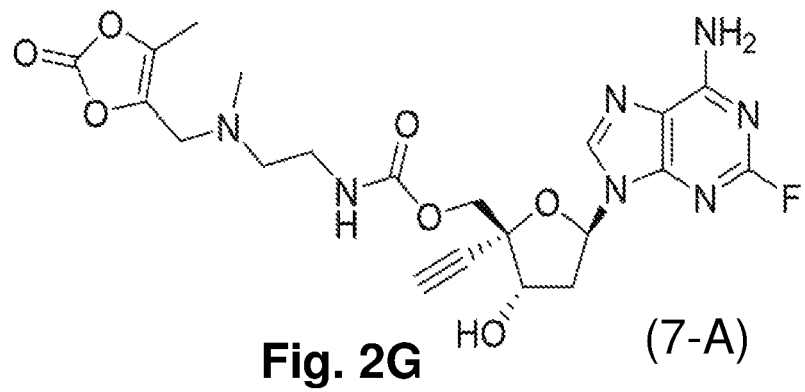
Fig. 2G (7-A)
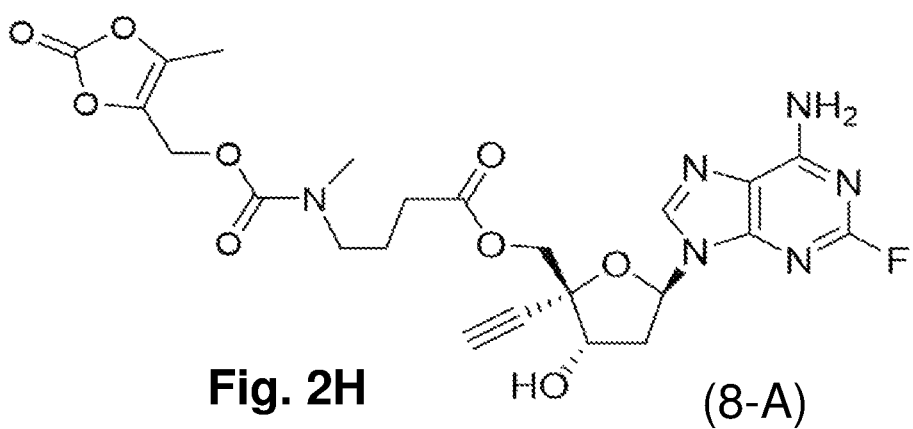
Fig. 2H (8-A)
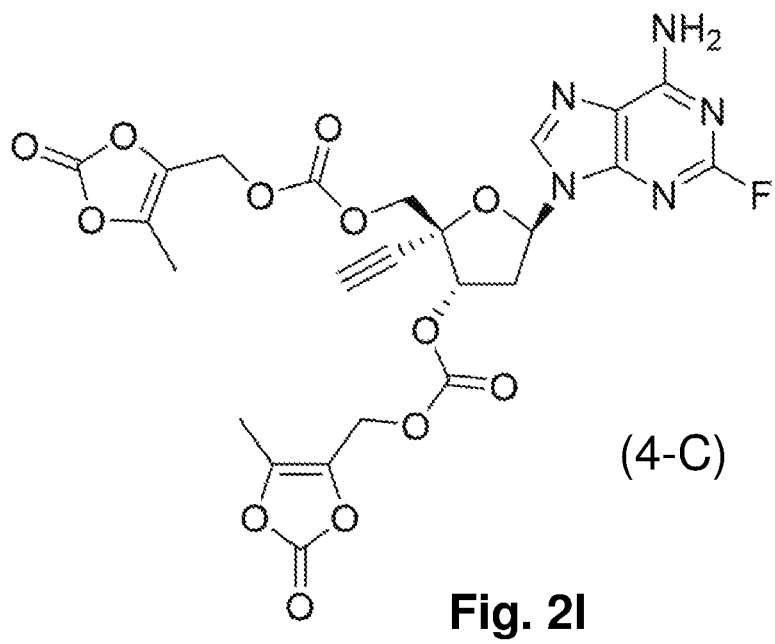
(4-C)
Fig. 2I

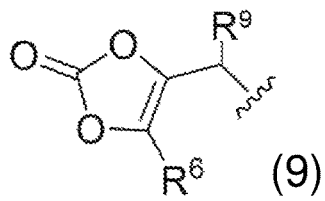
Fig. 3A (9)
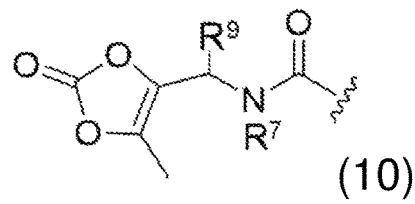
Fig. 3B (10)
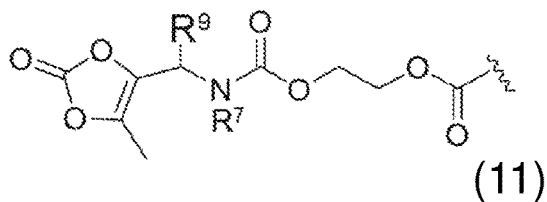
Fig. 3C (11)
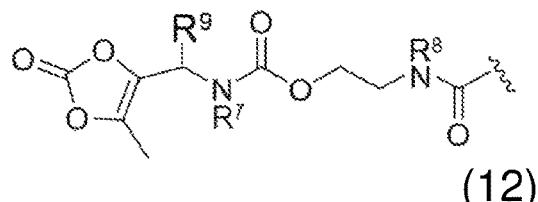
Fig. 3D (12)
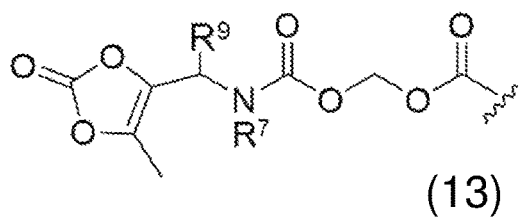
Fig. 3E (13)
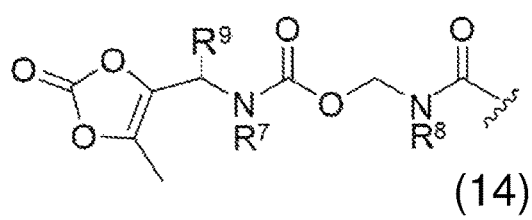
Fig. 3F (14)
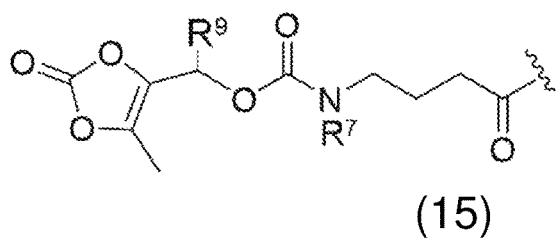
Fig. 3G (15)
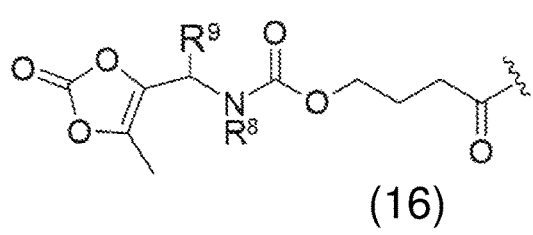
Fig. 3H (16)
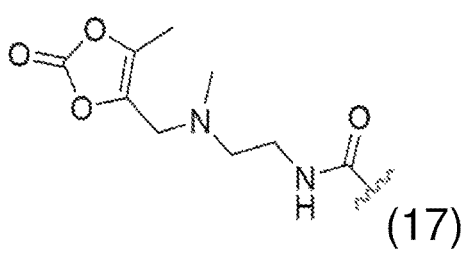
Fig. 3I (17)
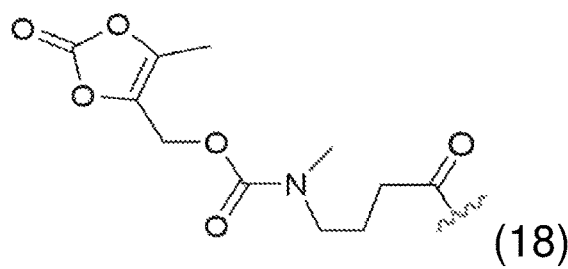
Fig. 3J (18)

(19)

(20)

(21)

(22)

(23)

(24)

(T-1)

(T-1A)

ADENOSINE DERIVATIVE AND PHARMACEUTICAL COMPOSITION COMPRISING THE SAME

CROSS REFERENCE TO RELATED APPLICATIONS

This application is a U.S. National Phase of International Application No. PCT/US2020/043713, filed on Jul. 27, 2020, which claims priority under 35 U.S.C. § 119(e) to U.S. Provisional Application Ser. No. 62/879,414, filed Jul. 27, 2019, each of which is herein incorporated by reference in its entirely.

FIELD

This disclosure is directed to adenosine derivative prodrugs that can inhibit reverse transcriptase. This disclosure is also directed to pharmaceutical compositions comprising an adenosine derivative prodrug that can be used for the treatment of acquired immunodeficiency syndrome (AIDS), HIV-1, HIV-2, multidrug resistant HIV or a combination thereof.

BACKGROUND

Retroviruses such as human immunodeficiency virus (HIV) has been linked to the immunosuppressive disease known as acquired immunodeficiency syndrome (AIDS). Multiple strains of retrovirus, such as HIV type-1 (HIV-1) and type-2 (HIV-2) are known to be related to the diseases. The HIV retrovirus infected individuals can be initially asymptomatic, but then develop AIDS related complex (ARC) followed by AIDS. Replication of HIV by a host cell requires integration of the viral genome into the DNA of host cells. A key step in the process involves transcription of the viral RNA genome into DNA via an enzyme known as reverse transcriptase (RT).

A reverse transcriptase typically can have multiple enzymatic functions that can act (1) as an RNA-dependent DNA polymerase transcribing a single-stranded DNA copy of the viral RNA (first DNA), (2) as a ribonuclease destroying the original viral RNA and frees the DNA just produced from the original RNA, and (3) as a DNA-dependent DNA polymerase producing a second, complementary DNA strand using the first DNA strand as a template. The two DNA strands then form double-stranded DNA, which is integrated into the genome of the host cells by an integrase enzyme.

A number of compounds can inhibit reverse transcriptase (RT) activity. These compounds can be useful for the treatment of HIV infection in humans by inhibiting HIV replication in infected cells or individuals. Examples of the compounds approved for use in treating HIV infection and AIDS include nucleoside RT inhibitors (NRTI) such as 3'-azido-3'-deoxythymidine (AZT, also known as Zidovudine (ZDV), azidothymidine (AZT)), 2',3'-dideoxyinosine (ddI), 2',3'-dideoxycytidine (ddC), d4T, 3TC, abacavir, emtricitabine, and tenofovir disoproxil fumarate, as well as non-nucleoside RT inhibitors (NNRTI) such as nevirapine, delavirdine, efavirenz, rilpivirine and doravirine (DHHS guidelines: https://aidsinfo.nih.gov/understanding-hiv-aids, Iyidogan & Anderson, Viruses, 6, 4095-4139, 2014, doi: 10.3390/v6104095; Hayakawa et al., Antiviral Chem & Chemotherapy, 15:169-187, 2004; Ohrul et al., J. Med. Chem. 43, 4516-4525, 2000; Pauwels, Antiviral Research, 71, 77-89, 2006).

An adenosine derivative EFdA (4'-ethynyl-2-fluoro-2'-deoxyadenosine, also known as MK-8591, islatravir) is a long-acting (LA) NRTI that has been demonstrated to have anti-HIV activity via inhibiting reverse transcriptase by preventing translocation (U.S. Pat. Nos. 7,339,053, 7,625,877, 8,039,614. Singh et al., Pharmaceuticals, 12, 62, 2019, DOI: 10.3390/ph12020062, each of which is incorporated by reference herein in its entirety). This compound has broad inhibitory activity and potency for different subtypes and mutations including HIV-1, HIV-2, and multidrug resistant (MDR) and wildtype (WT) strains, and reverse transcriptase inhibitor (RTI) resistant viruses. Some modified EFdAs and prodrugs have been described in U.S. Patent Publication No.: 2018/0002366, incorporated by reference herein in its entirety.

A common issue that arises from the treatment of HIV infection with anti-retroviral inhibitory compounds is resistance of the viruses to the inhibitors. Such resistance is typically the result of mutations that occur in the reverse transcriptase segment of the pol gene. The continued use of antiviral compounds, such as the inhibitory compounds, to prevent HIV infection will inevitably result in the emergence of new resistant strains of HIV. Therefore, there is a continuing need for new RT inhibitors that are effective against HIV strains including mutant HIV and multidrug-resistant HIV strains.

SUMMARY

The present disclosure is related to adenosine derivatives and compositions thereof that can be used to treat retroviral diseases such as HIV and AIDS.

In some embodiments, the present disclosure provides an adenosine derivative or stereoisomer, pharmaceutically acceptable salt, tautomer, or solvate thereof having a formula (1):

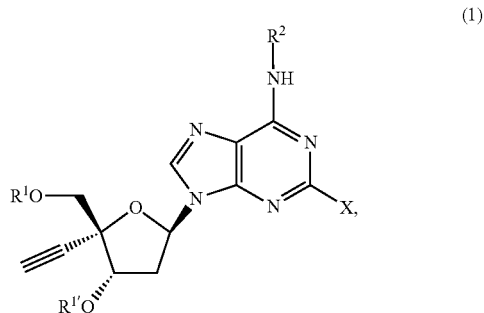

(1)

wherein,
$R^1$, $R^{1'}$, and $R^2$ each is independently —H, —C(O)N($R^3$)($R^{3'}$), —C(O)O$R^4$, —$R^5$, -$L^1$-$R^5$, or —Z-$L^4$-$R^5$, wherein at least one of $R^1$ and $R^2$ is not —H;

$R^3$, $R^{3'}$ and $R^4$ each is independently —H, C1-C10 alkyl, C2-C10 alkenyl, C3-C10 cycloalkyl, 3- to 10-membered heterocycloalkyl, aryl, or heteroaryl;

$R^5$ is:

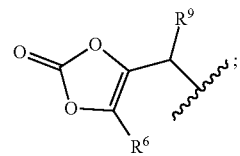

R⁶ is —H, C1-C10 alkyl, C2-C10 alkenyl, C3-C10 cycloalkyl, 3- to 10-membered heterocycloalkyl, aryl, or heteroaryl;

-L¹-R⁵ is —(C1-C10 alkylene)-N(R⁷)—R⁵, —(C1-C10 alkylene)-O—R⁵, —(C1-C10 alkylene)-S—R⁵, —(C2-C10 alkenylene)-N(R⁷)—R⁵, —(C2-C10 alkenylene)-O—R⁵, —(C2-C10 alkenylene)-S—R⁵, —C(O)O—R⁵, —C(O)O-L²-N(R⁷)—R⁵, —C(O)O-L²-O—R⁵, —C(O)O-L²-S—R⁵, —C(O)O-L²-C(O)O—R⁵, —C(O)O-L²-C(O)N(R⁷)—R⁵, —C(O)O-L²-C(O)N(R⁷)-L³-N(R⁷)—R⁵, —C(O)O-L²-C(O)N(R⁷)-L³-O—R⁵, —C(O)O-L²-C(O)N(R⁷)-L³-S—R⁵, —C(O)N(R⁷)—R⁵, —C(O)N(R⁷)-L²-N(R⁷)—R⁵, —C(O)N(R⁷)-L²-O—R⁵, —C(O)N(R⁷)-L²-S—R⁵, —C(O)N(R⁷)-L²-C(O)O—R⁵, —C(O)N(R⁷)-L²-C(O)N(R⁸)—R⁵—, —C(O)N(R⁷)-L²-C(O)N(R⁸)-L³-N(R⁷)—R⁵, —C(O)O-L²-N(R⁷)C(O)O—R⁵, —C(O)N(R⁸)-L²-N(R⁷)C(O)O—R⁵, —C(O)O-L²-N(R⁷)C(O)N(R⁸)—R⁵, —C(O)N(R⁷)-L²-N(R⁷)C(O)N(R⁸)—R⁵, —C(O)N(R⁷)-L²-C(O)N(R⁸)-L³-O—R⁵ or —C(O)N(R⁷)-L²-C(O)N(R⁸)-L³-S—R⁵;

—Z— is a divalent —C(O)—, —C(O)O—, or —C(O)N(R⁷)—;

-L⁴-R⁵ is —(C1-C10 alkylene)-N(R⁷)—R⁵, —(C1-C10 alkylene)-O—R⁵, —(C1-C10 alkyl)-S—R⁵, —(C2-C10 alkenylene)-N(R⁷)—R⁵, —(C2-C10 alkenylene)-O—R⁵ or —(C2-C10 alkenylene)-S—R⁵;

R⁷, R⁸ and R⁹ each is independently —H, C1-C10 alkyl, or C2-C10 alkenyl;

L² and L³ each is —(C1-C10 alkylene)-, or —(C2-C10 alkenylene)-; and

X is a halogen atom.

In some embodiments, the adenosine derivative is selected from the group consisting of:

formula (2-A)

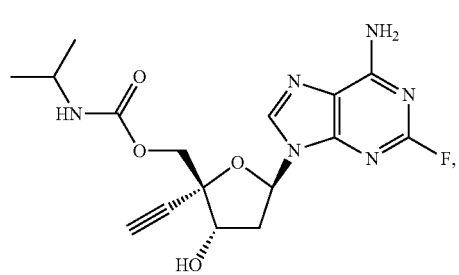

formula (3-A)

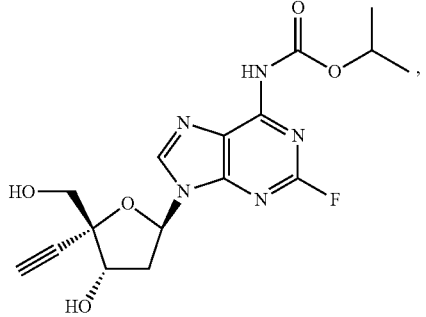

formula (4-A)

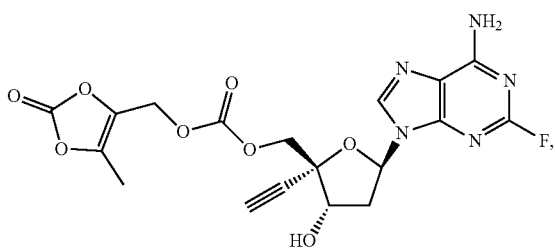

formula (5-A)

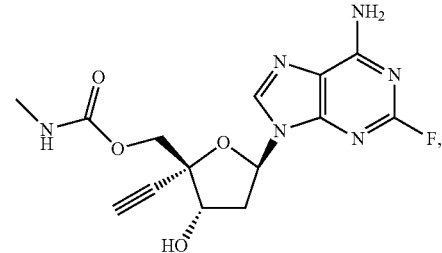

formula (6-A)

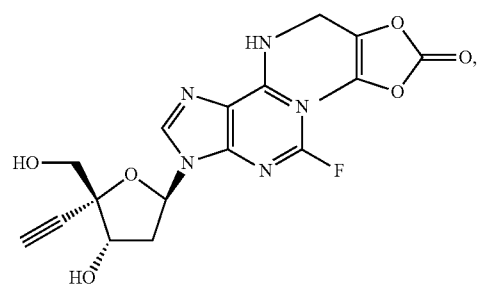

formula (7-A)

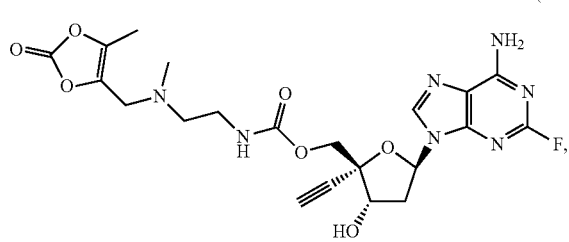

formula (8-A)

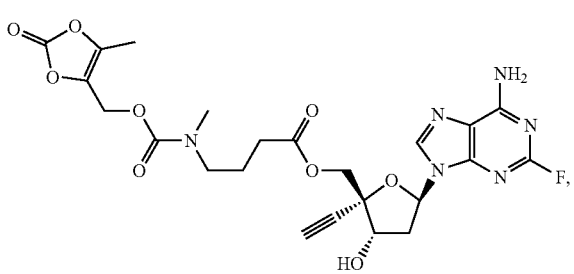

formula (4-C)
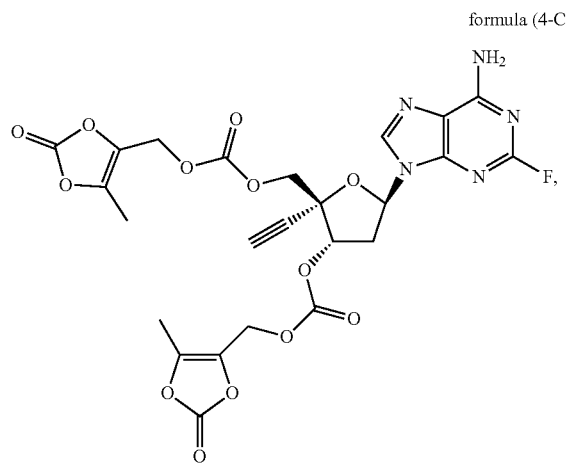
or a stereoisomer, pharmaceutically acceptable salt, tautomer, or solvate thereof.
In some embodiments of formula (1), the adenosine derivative comprises an $R^1$, $R^{1'}$, $R^2$ or a structure selected from formulas 9-24:
(9)
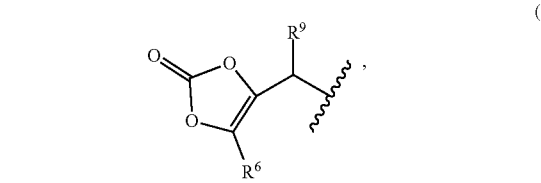
(10)
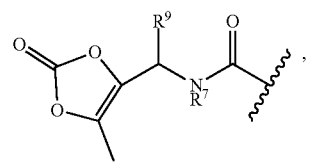
(11)
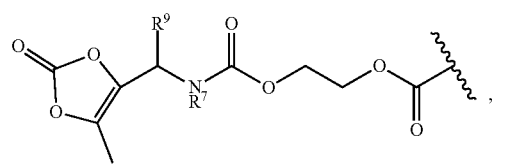
(12)
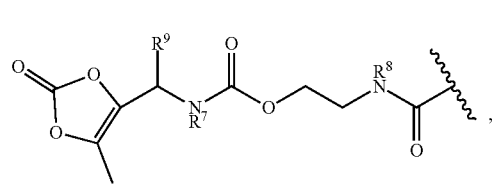
(13)
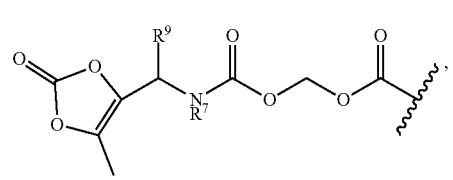
(14)
(15)
(16)
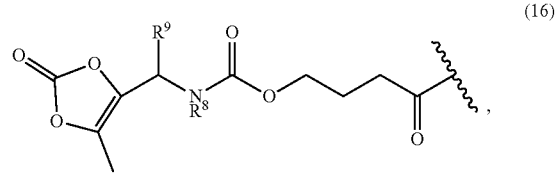
(17)
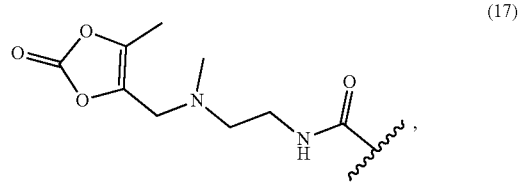
(18)
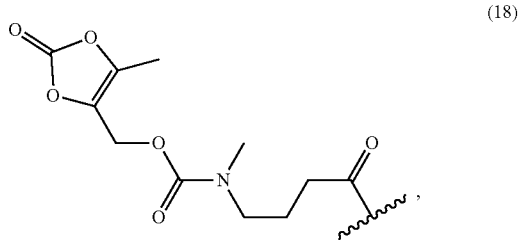
(19)
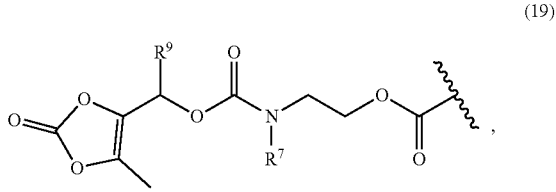
(20)
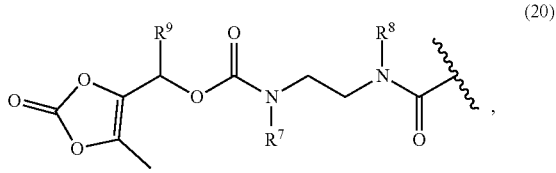
(21)
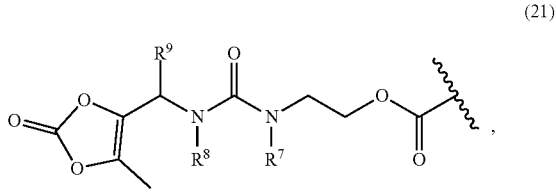

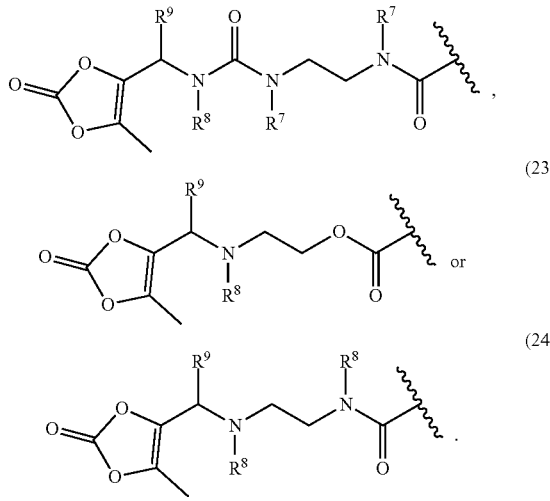

The present disclosure is further directed to a pharmaceutical composition comprising one or more adenosine derivatives, pharmaceutically acceptable salts, stereoisomers, or a combination thereof disclosed herein, and one or more pharmaceutically acceptable carriers.

The present disclosure is also directed to a method for the treatment of a disease (e.g., Acquired Immune Deficiency Syndrome (AIDS) or human immunodeficiency virus (HIV)), the method comprising administering to a subject in need thereof an effective dosage of a pharmaceutical composition comprising one or more of the adenosine derivatives disclosed herein.

The present disclosure is also directed to a method for the prevention of infection, the method comprising administering to a subject in need thereof an effective dosage of a pharmaceutical composition comprising one or more of the adenosine derivatives disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

FIG. 1A-FIG. 1I show exemplary chemical structures of adenosine derivatives having a halogen atom with formulas (1)-(8) and 4-B.

FIG. 2A-FIG. 2I show exemplary chemical structures of adenosine derivatives having a fluorine atom with formulas (1-A)-(8-A) and 4-C.

FIG. 3A-FIG. 3J show exemplary chemical structures of the —$R^5$, -$L^1$-$R^5$ or —Z-$L^4$-$R^5$ groups of the adenosine derivatives with formulas (9)-(18).

DETAILED DESCRIPTION

Figure 1A:
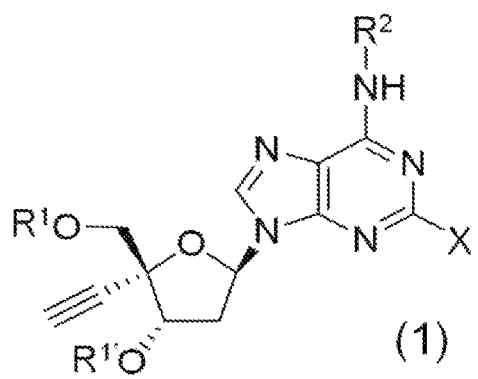
Figure 1B:
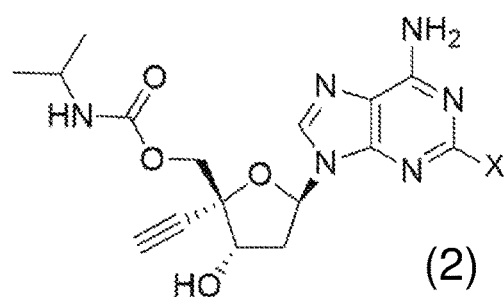
Figure 1C:
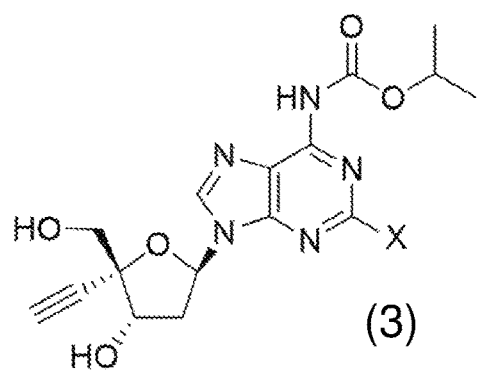
Figure 1D:
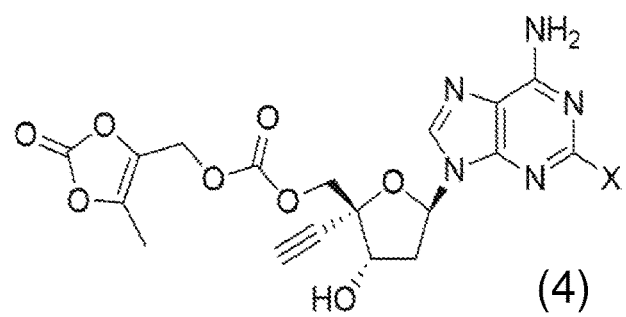
Figure 1E:
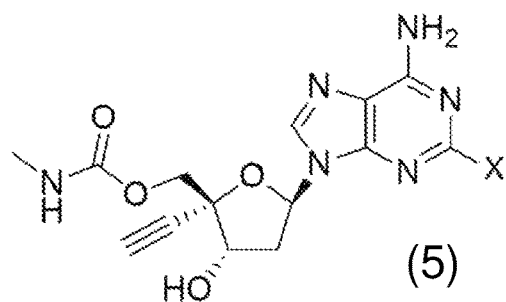
Figure 1F:
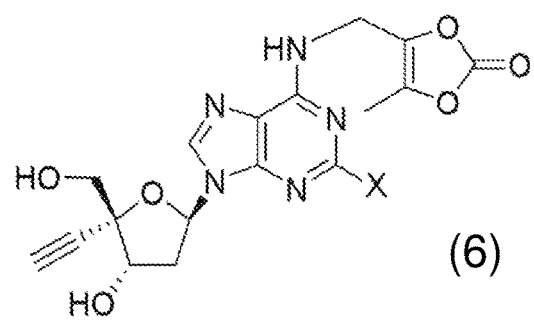
Figure 2A:
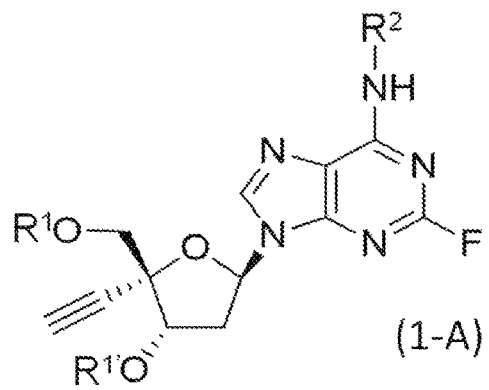
Figure 2B:
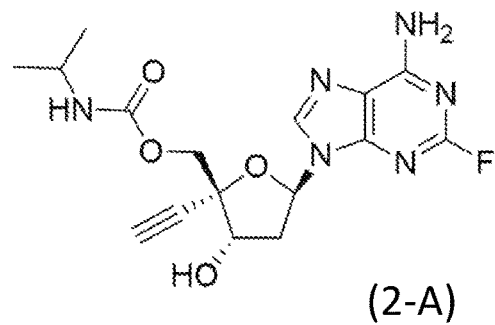
Figure 2C:
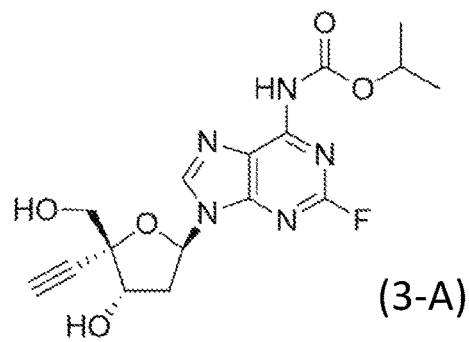
Figure 2D:
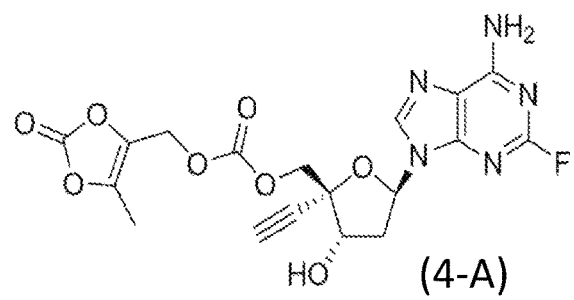
Figure 2E:
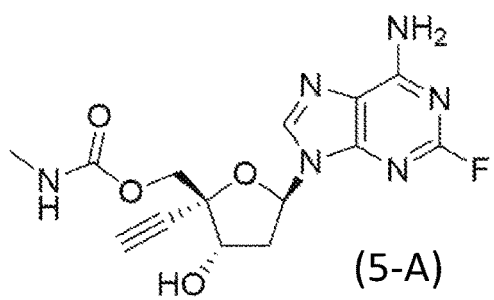
Figure 2F:
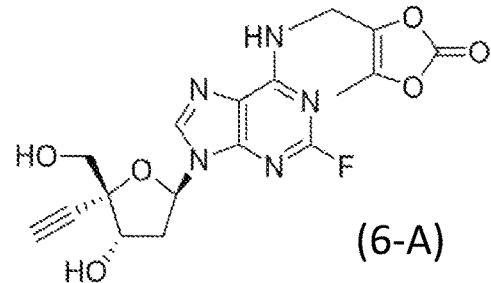
Figure 4A:
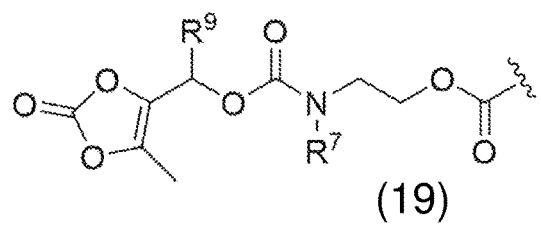
FIG. 4A-FIG. 4F show exemplary chemical structures of the -$L^1$-$R^5$ or —Z-$L^4$-$R^5$ groups of the adenosine derivatives with formulas (19)-(24).
Figure 4B:
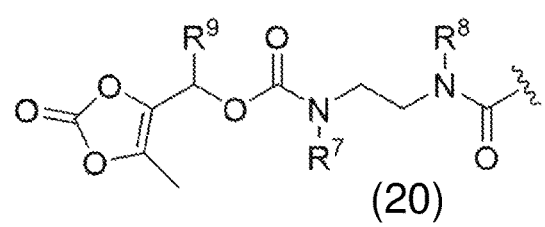
Figure 4C:
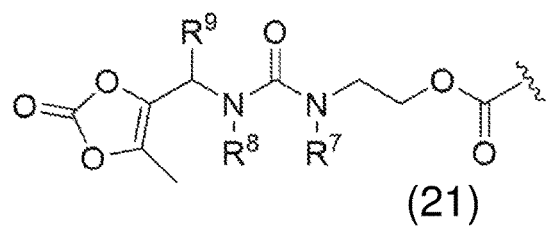
Figure 4D:
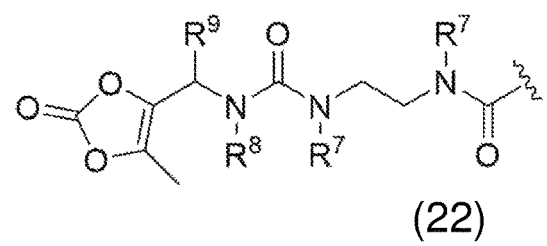
Figure 4E:
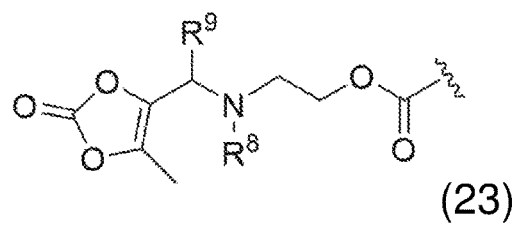
Figure 4F:
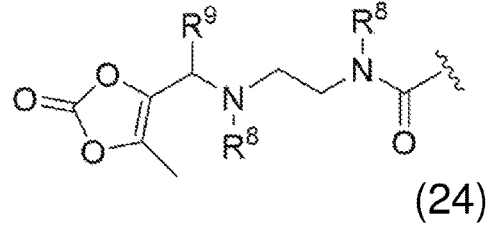

Following are more detailed descriptions of various concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

As used herein, the term "alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes CH and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

As used herein, the term "alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

As used herein, the term "alkenyl" or "alkenyl group" refers to a linear or branched chain aliphatic hydrocarbon radical containing at least one carbon-carbon double bond and having a number of carbon atoms in the specified range. For example, "C2-C10 alkenyl" (or "$C_2$-$C_{10}$ alkenyl") refers to any of alkenyl having 2 to 10 carbon atoms that is linear or branched, or isomers. In another example C2-C6 alkenyl can have 1-butenyl, 2-butenyl, 3-butenyl, isobutenyl, 1-propenyl, 2-propenyl, and ethenyl (or vinyl). The points of attachment of the alkylene chain to the rest of the molecule and to the radical group can be through one carbon or any two carbons within the chain. Unless stated otherwise specifically in the specification, an alkylene chain can be optionally substituted.

As used herein, the term "alkenylene" or "alkenylene chain" refers to an unsaturated, straight or branched divalent hydrocarbon chain radical having one or more olefins and from two to twelve carbon atoms. Non-limiting examples of $C_2$-$C_{12}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

As used herein, the term "cycloalkyl" refers to a stable non-aromatic monocyclic or polycyclic fully saturated hydrocarbon consisting solely of carbon and hydrogen atoms, which can include fused or bridged ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. In some embodiments, "cycloalkyl" refers to any monocyclic ring of an alkane having a number of carbon atoms in the specified range. For example, "C3-C10 cycloalkyl" (or "$C_3$-$C_{10}$ cycloalkyl") refers to monocyclic ring of an alkane having 3 to 10 carbon atoms, such as cyclopropyl, cyclobutyl, cyclopentyl, cyclohexyl, and cycloheptyl. Unless otherwise stated specifically in the specification, a cycloalkyl group can be optionally substituted.

As used herein, the term heterocycloalkyl," "heterocyclic ring" or "heterocycle" refers to a saturated, or partially saturated 3- to 20-membered ring which consists of two to nineteen carbon atoms and from one to six heteroatoms selected from the group consisting of nitrogen, oxygen and sulfur, and which is attached to the rest of the molecule by a single bond. Unless stated otherwise specifically in the specification, the heterocycloalkyl can be a monocyclic, bicyclic, tricyclic or tetracyclic ring system, which can include fused or bridged ring systems; and the nitrogen, carbon or sulfur atoms in the heterocycloalkyl can be optionally oxidized, e.g., to form an N-oxide, sulfoxide, or sulfone and/or the nitrogen atom can be optionally quaternized, e.g., to form a quaternary ammonium cation. Examples of such heterocycloalkyls include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, 1-oxo-thiomorpholinyl, and 1,1-dioxo-thiomorpholinyl. In some embodiments, "3- to 10-membered heterocycloalkyl" refers to a cycloalkyl comprising one or more heteroatoms, selected from the group consisting of N, O, and S. In some embodiments, heterocycloalkyl," "heterocyclic ring" or "heterocycle" refers to a 3-10 member ring structure having carbon atoms and one or more heteroatoms selected from N, O, S or a combination thereof as members of the ring structure. Unless stated otherwise specifically in the specification, a heterocycloalkyl group can be optionally substituted and include saturated and/or unsaturated rings.

As used herein, the term "halogen" (or "halo") refers to fluorine, chlorine, bromine and iodine (alternatively referred to as fluoro (—F), chloro (—Cl), bromo (—Br), and iodo (—I)).

As used herein, the term "aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, "aryl" refers to phenyl or one or more fused cyclic hydrocarbon ring systems in which at least one ring is aromatic. Unless stated otherwise specifically in the specification, the "aryl" can be optionally substituted.

As used herein, the term "heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized, e.g., to form an N-oxide, sulfoxide, or sulfone and/or the nitrogen atom can be optionally quaternized, e.g., to form a quaternary ammonium cation. Non-limiting examples of heteroaryls can include pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydro uinolinyl, tetrahydroisoquinolinyl, isoindolyl, benzodioxolyl, benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl. Unless stated otherwise specifically in the specification, a heteroaryl group can be optionally substituted.

It is understood that, unless expressly stated to the contrary in a particular context, any of the various cyclic rings and ring systems described herein may be attached to the rest of the compound at any ring atom (i.e., any carbon atom or any heteroatom) provided that the attachment is chemically allowed.

As used herein, the term "substituted" means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the term "isomer" refers to a structural isomer, such as a group or an atom positioned at different locations of a molecule; stereoisomer, such as a chiral isomers, enantiomers, diastereomers and cis/trans isomers; a tautomer, such as amino isomer, imino isomer, or a combination thereof. In non-limiting examples, an adenosine derivative of the present disclosure can have an amino isomer, an imino isomer or a combination thereof. In another non-limiting example, in instances where an —OH substituent is permitted on a heteroaromatic ring and keto-enol tautomerism is possible, it is understood that the substituent might in fact be present, in whole or in part, in the oxo (=O) form. A mixture of isomers can also be suitable. A mixture of isomers can comprise the respective isomers in all ratios. A salt of an isomer can also be suitable. An adenosine derivative of the present disclosure can comprise isomers thereof, one or more salts thereof, one or more solvates including hydrates thereof, solvated salts thereof or a mixture thereof. Absolute stereochemistry or isomer configuration may be determined by X-ray crystallography, by Vibrational Circular Dichroism (VCD) spectroscopy analysis or a combination thereof.

The adenosine derivatives can be identified by names based on the nomenclature recommended by International Union of Pure and Applied Chemistry (IUPAC) or based on nucleosides (Nucleoside-based nomenclature). The adenosine derivatives can also be identified by chemical structure drawings. Unless expressly stated to the contrary in a particular context, the names and the structures may be used interchangeably.

Any of the atoms in a compound disclosed herein may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds disclosed herein.

The compounds can be administered in the form of pharmaceutically acceptable salts or solvates. The term "pharmaceutically acceptable salt" refers to a salt or a solvate which is not biologically or otherwise undesirable (e.g., is neither toxic nor otherwise deleterious to the recipient or subject thereof). A mixture of a compound disclosed herein and one or more salts or solvates thereof is also contemplated herein. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

Furthermore, compounds disclosed herein can exist in amorphous form and/or one or more crystalline forms, or a combination thereof.

The term "RNA virus infection" refers to a disease caused by an RNA virus, such as the common cold, influenza, SARS, COVID-19, hepatitis C, hepatitis E, West Nile fever, Ebola virus disease, rabies, polio, and measles.

The term "HIV infection" refers to a disease caused by the human immunodeficiency virus (HIV), such as HIV-1 and HIV-2. In some cases, the HIV infection can be caused by wild-type HIV-1, NRTI-resistant HIV-1, HIV-2, HIV having M184V mutations, HIV having K65R, or multidrug resistant HIV. The term "AIDS" refers to acquired immunodeficiency syndrome, which is caused by HIV infection and an advanced form of the disease.

The term "prodrug" refers to a compound that may be converted under physiological conditions or by solvolysis to a biologically active compound described herein. Thus, the term "prodrug" refers to a precursor of a biologically active compound that is pharmaceutically acceptable. A prodrug may be a biologically inactive or substantially inactive compound which can be metabolized in the body, i.e., in vivo, to produce a drug having a desired activity. The term "substantially inactive" means that a prodrug can have about 1% to about 10% of the activity of the corresponding drug or after being metabolized in vivo, percentage based on weight of the prodrug. In some embodiments, the term "substantially inactive" means that a prodrug has less than about 5% of the activity of the corresponding drug or after being metabolized in vivo, percentage based on weight of the prodrug. The doses for a prodrug and its biologically active compound are considered to be does-equivalent when they are the same molar amount.

The term "anti-HIV agent", "anti-viral agent" or a grammatical variant refers to a compound, a mixture of one or more compounds, a formulation, a chemical agent or a biological agent such as antibody, protein, peptides, nucleotide, other biological compound, or a combination thereof, that can be directly or indirectly effective in the inhibition of HIV, the treatment or prophylaxis of HIV infection, and/or the treatment, prophylaxis or delay in the onset or progression of AIDS and/or diseases or conditions arising therefrom or associated therewith, an RNA virus infection, or a combination thereof. The anti-HIV agents can comprise HIV antiviral agents, immunomodulators, anti-infectives, vaccines or a combination thereof useful for treating HIV infection or AIDS. Examples of antiviral agents for Treating HIV infection or AIDS include, but are not limited to, under respective trademarks or registered trademarks with respective owners, abacavir (ABC, Ziagen®), abacavir+lamivudine (Epzicom®), abacavir+lamivudine+zidovudine (Trizivir®), amprenavir (Agenerase®), atazanavir (Reyataz®), AZT (zidovudine, azidothymidine or Retrovir®), capravirine, darunavir (Prezista®), ddC (zalcitabine, dideoxycytidine or Hivid®), ddI (didanosine, dideoxyinosine or Videx®), ddI (enteric coated, Videx EC®), delavirdine (DLV or Rescriptor®), dolutegravir (Tivicay®), doravirine (MK-1439), efavirenz (EFV, Sustiva®, Stocrin®), efavirenz+emtricitabine+tenofovir DF (Atripla®), EFdA (4'-ethynyl-2-fluoro-2'-deoxyadenosine), elvitegravir, cabotegravir, dolutegravir, bictegravir, emtricitabine (FTC, Emtriva®), emtricitabine+tenofovir DF (Truvada®), emvirine (Coactinon®), enfuvirtide (Fuzeon®), enteric coated didanosine (Videx EC®), etravirine (TMC-125), fosamprenavir calcium (Lexiva®), indinavir (Crixivan®, lamivudine (3TC, Epivir®), lamivudine+zidovudine (Combivir®), lopinavir, lopinavir+ritonavir (Kaletra®), maraviroc (Selzentry®), nelfinavir (Viracept®), nevirapine (NVP, Viramune®), PPL-100 (also known as PL-462) (Ambrilia), raltegravir (MK-0518 or Isentress™), rilpivirine (Edurant®), ritonavir (Norvir®), saquinavir (Invirase®, or Fortovase®), stavudine (d4T, didehydrodeoxythymidine or Zerit®), tenofovir DF (DF=disoproxil fumarate, TDF, Viread®), Tenofovir (hexadecyloxypropyl (CMX-157), Tenofovir alafenamide fumarate (GS-7340), tipranavir (Aptivus®) and vicriviroc. Some of the anti-HIV agents shown above can be used in a salt form; for example, abacavir sulfate, delavirdine mesylate, indinavir sulfate, atazanavir sulfate, nelfinavir mesylate, saquinavir mesylate or other salts. An anti-HIV agent can have one or more activities such as entry inhibitor (EI), fusion inhibitor (FI); integrase inhibitor (InI); protease inhibitor (PI); nucleoside reverse transcriptase inhibitor (nRTI or NRTI) or non-nucleoside reverse transcriptase inhibitor (nnRTI or NNRTI). An anti-HIV agent can comprise two or more agents disclosed herein. The adenosine derivative of the present disclosure can be an anti-HIV agent along or in combination with other anti-HIV agent or agents.

Unless expressly stated to the contrary, all ranges cited herein are inclusive. For example, a heteroaryl ring described as comprising in a range of from "1 to 4 heteroatoms" means the ring can comprise 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. In other examples, C1-C10 alkyl means an alkyl comprises 1, 2, 3, 4, 5, 6, 7, 8, 9 and 10 carbon atoms including all sub-ranges. Thus, a C1-C10 alkyl can be a methyl, ethyl, C4 alkyl, C5 alkyl, C6 alkyl, C7 alkyl, C8 alkyl, C9 alkyl and C10 alkyl, linear or branched. A divalent C1-C10 alkyl can be a —$CH_2$—, —$C_2H_4$—, —$C_3H_6$—, —$C_5H_{10}$—, —$C_6H_{12}$—, —$C_7H_{17}$—, —$C_8H_{18}$—, —$C_9H_{18}$— or —$C_{10}H_{20}$—, linear or a branched. Similarly, C2-C10 alkenyl means an alkenyl comprises 2, 3, 4, 5, 6, 7, 8, 9 and 10 carbon atoms, linear or branched, including all sub-ranges. A linear or a branched alkenyl can be suitable. A C3-C10 cycloalkyl means a cycloalkyl comprises 3, 4, 5, 6, 7, 8, 9 and 10 carbon atoms, linear or branched.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present disclosure.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The pharmaceutical composition can be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, e.g., intranasally, orally, vaginally, rectally, sublingually or topically. The pharmaceutical composition can be in the form of sterile aqueous solutions or dispersions. The pharmaceutical composition can also be formulated in a microemulsion, liposome, or other ordered structure suitable to high drug concentration.

In some embodiments, the present disclosure provides an adenosine derivative or a pharmaceutically acceptable salt, tautomer, or solvate thereof, having a formula (1):

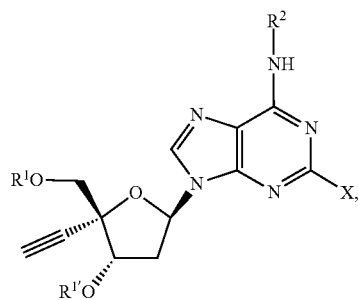

wherein,
$R^1$, R1', and $R^2$ each is independently —H, —C(O)N($R^3$)($R^{3'}$), —C(O)O$R^4$, —$R^5$, -$L^1$-$R^5$, or —Z-$L^4$-$R^5$, wherein at least one of $R^1$ and $R^2$ is not —H;
$R^3$, $R^{3'}$ and $R^4$ each is independently —H, C1-C10 alkyl, C2-C10 alkenyl, C3-C10 cycloalkyl, 3- to 10-membered heterocycloalkyl, aryl, or heteroaryl;

$R^5$ is:

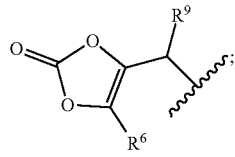

$R^6$ is —H, C1-C10 alkyl, C2-C10 alkenyl, C3-C10 cycloalkyl, 3- to 10-membered heterocycloalkyl, aryl, or heteroaryl;

-$L^1$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$—S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$—, —C(O)N($R^7$)-$L^2$-C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)N($R^8$)-$L^3$-O—$R^5$ or —C(O)N($R^7$)-$L^2$-C(O)N($R^8$)— $L^3$-S—$R^5$;

—Z— is a divalent —C(O)—, —C(O)O—, or —C(O)N($R^7$)—;

-$L^4$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$ or —(C2-C10 alkenylene)-S—$R^5$;

$R^7$, $R^8$ and $R^9$ each is independently —H, C1-C10 alkyl, or C2-C10 alkenyl;

$L^2$ and $L^3$ each is intendedly divalent —(C1-C10 alkylene)-, or —(C2-C10 alkenylene)-; and X is a halogen atom.

An adenosine derivative of the present disclosure can be free from a monophosphate group, diphosphate group, tri-phosphate group or a combination thereof. In some embodiments, the $R^1$, $R^{1'}$ or $R^2$ group of an adenosine derivative of the present disclosure is free from a monophosphate group, diphosphate group, tri-phosphate group or a combination thereof. Non-limiting examples of adenosine derivatives having a halogen atom are shown in formulas (1)-(8) and (4-B) (FIG. 1A-FIG. 1I).

In some embodiments, the C1-C10 alkyl and C2-C10 alkenyl of formula (1) is linear or branched. In some embodiments, the compounds of formula (1) comprise a combination of C1-C10 alkyl, C2-C10 alkenyl, C3-C10 cycloalkyl, 3- to 10-membered heterocycloalkyl, aryl and heteroaryl groups.

In some embodiments of formula (1), $R^1$ is H and $R^2$ is —C(O)N($R^3$)($R^{3'}$). In some embodiments, $R^1$ is —C(O)N($R^3$)($R^{3'}$) and $R^2$ is H. In some embodiments, $R^3$ is C1-C5 alkyl or C3-C6 cycloalkyl and $R^{3'}$ is H. In some embodiments, $R^3$ is methyl, ethyl, or isopropyl and $R^{3'}$ is H.

In some embodiments of formula (1), $R^1$ is H and $R^2$ is —$R^5$ or -$L^1$-$R^5$. In some embodiments, $R^1$ is -$L^1$-$R^5$ and $R^2$ is H. In some embodiments, -$L^1$-$R^5$ is —C(O)N($R^7$)-$L^2$-N($R^7$)—$R^5$, —C(O)O-$L^2$-O$R^5$, —C(O)N($R^7$)-$L^2$-N($R^7$)—C(O)O—$R^5$, —C(O)O-$L^2$-N($R^7$)—C(O)O—$R^{5'}$—C(O)N($R^7$)-$L^2$-N($R^8$)—C(O)N($R^8$)—$R^5$, or —C(O)O-$L^2$-N($R^8$)—C(O)N($R^8$)—$R^5$. In some embodiments, $R^5$ is

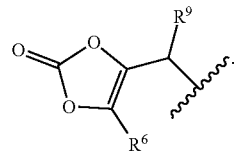

In some embodiments, $R^6$ is C1-C5 alkyl. In some embodiments, $R^6$ is methyl, ethyl, or isopropyl. In some embodiments, $R^6$ is methyl. In some embodiments, $R^7$ is each independently H or Me. In some embodiments, $R^9$ is H, F, or Me. In some embodiments, $R^9$ is H. In some embodiments, $L^2$ is C2-C5 alkylene. In some embodiments, $L^2$ is ethylene or propylene. In some embodiments, $L^2$ is ethylene.

In some embodiments of formula (1), $R^1$ is —C(O)O—$R^5$ or —$R^5$ and $R^2$ is H. In some embodiments, $R^1$ is H and $R^2$ is —C(O)O—$R^5$ or —$R^5$. In some embodiments, $R^5$ is

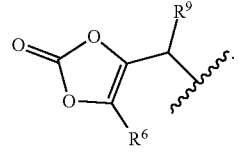

In some embodiments, $R^6$ is C1-C5 alkyl. In some embodiments, $R^6$ is methyl, ethyl, or isopropyl. In some embodiments, $R^6$ is methyl. In some embodiments, $R^9$ is H, F, or Me. In some embodiments, $R^9$ is H.

In some embodiments of formula (1), $R^1$ is -$L^1$-$R^5$. In some embodiments, $R^{1'}$ is —H or -$L^1$-$R^5$. In some embodiments, $R^{1'}$ is —H. In some embodiments, $R^{1'}$ is -$L^1$-$R^5$. In some embodiments, $R^1$ is -$L^1$-$R^5$ and $R^{1'}$ is H. In some embodiments, $R^1$ is -$L^1$-$R^5$ and $R^{1'}$ is -$L^1$-$R^5$. In some embodiments, $R^1$ is -$L^1$-$R^5$, is H, and $R^2$ is H. In some embodiments, $R^1$ is -$L^1$-$R^5$, $R^{1'}$ is -$L^1$-$R^5$, and $R^2$ is H. In some embodiments, -$L^1$-$R^5$ is selected from the group consisting of —(C1-C10 alkylene)-N($R^7$)—$R^5$, —(C1-C10 alkylene)-O—$R^5$, —C(O)O-$L^2$-N($R^7$)—$R^5$, —C(O)O-$L^2$-O—$R^5$, —C(O)O-$L^2$-C(O)O—$R^5$, —C(O)O-$L^2$-C(O)N($R^7$)—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)O-$L^2$-N($R^7$)C(O)O—$R^5$, —C(O)N($R^8$)-$L^2$-N($R^7$)C(O)O—$R^5$, —C(O)O-$L^2$—N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)O—$R^5$, and —C(O)N($R^7$)-$L^2$-C(O)N($R^8$)—$R^5$—. In some embodiments, -$L^1$-$R^5$ is selected from the group consisting of —C(O)O—$R^5$, —C(O)O-$L^2$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-N($R^7$)—$R^5$, and —C(O)N($R^7$)-$L^2$-C(O)N($R^8$)—$R^5$—. In some embodiments, -$L^1$-$R^5$ is —C(O)O—$R^5$. In some embodiments, $R^2$ is H.

The divalent linker $L^1$ can also comprise one or more repeats of a same group or a combination of different groups. In some embodiments, the $L^1$ comprises —C(O)O— and C1-C10 alkyl. In some embodiments, the $L^1$ comprises two or more repeats of —C(O)O—. In some embodiments, the $L^1$ comprises two or more repeats of —C(O)O(CH$_2$)$_n$—. In some embodiments, the $L^1$ comprises two or more repeats of —C(O)N($R^7$)—. In some embodiments, the $L^1$ comprises two or more repeats of —C(O)N($R^7$)($CH_2$)$_n$—. In some embodiments, the $L^1$ comprises a combination of —C(O)O—, C1-C10 alkyl, and —C(O)N($R^7$)—. In some embodiments, the $L^1$ comprises a combination of —C(O)O—, —($CH_2$)$_n$— and —C(O)N($R^7$)—. In some embodiments, the $L^1$ comprises a combination of —C(O)N($R^7$)— and C1-C10 alkyl. In some embodiments, the $L^1$ comprises two or more repeats of —C(O)O($CH_2$)$_n$—C(O)N($R^7$)—. In some embodiments, n is an integer from 0 to 10. In some embodiments, n is an integer from 1 to 3. As understood in the art, the above combination are non-limiting examples, and other chemically possible combinations of $L^1$ are also contemplated by the present disclosure.

An adenosine derivative of this disclosure can comprise one or more isomers thereof. An isomer can comprise a chiral isomer, also known as stereoisomer, that comprises one or more chiral centers, a tautomer that can interconvert via the relocation of a proton or other atom, such as amino isomer, imino isomer, or a combination thereof. In examples, an adenosine derivative can have an amino isomer, an imino isomer or a combination thereof. In further examples, an adenosine derivative can comprise enantiomers, diastereomers and cis/trans isomers, tautomers or a combination thereof. An isomer that can have reverse transcriptase inhibitor (RTI) activity in vivo can be particularly preferred.

In some embodiments of formula (1), the X is a halogen atom selected from the group consisting of fluorine, chlorine, bromine and iodine (alternatively referred to as fluoro (F), chloro (Cl), bromo (Br), and iodo (I)). In some embodiments, X is F. In some embodiments, X is Cl. In some embodiments, X is Br.

In some embodiments, the present disclosure is directed to an adenosine derivative or pharmaceutically acceptable salt, tautomer, or solvate thereof having a formula (1a):

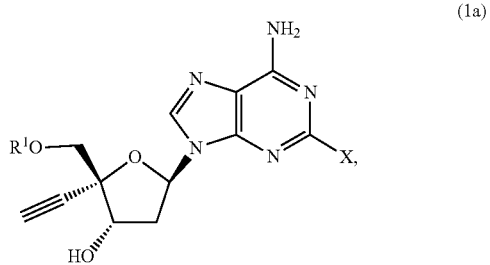

(1a)

wherein $R^1$ and X are as defined above for formula (1).

In some embodiments, the present disclosure is directed to an adenosine derivative or pharmaceutically acceptable salt, tautomer, or solvate thereof having a formula (1b):

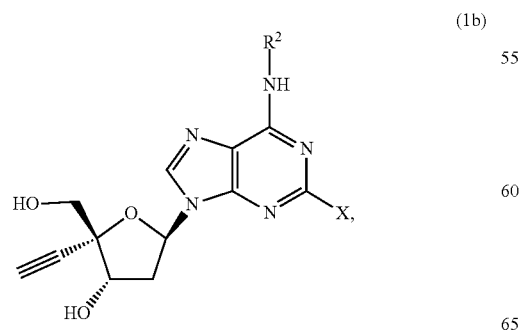

(1b)

wherein $R^2$ and X are as defined above for formula (1).

In some embodiments, the adenosine derivative of the present disclosure is selected from the group consisting of:

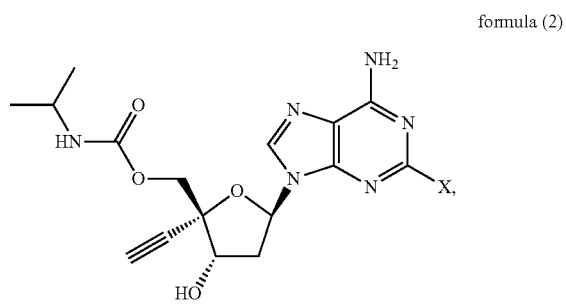

formula (2)

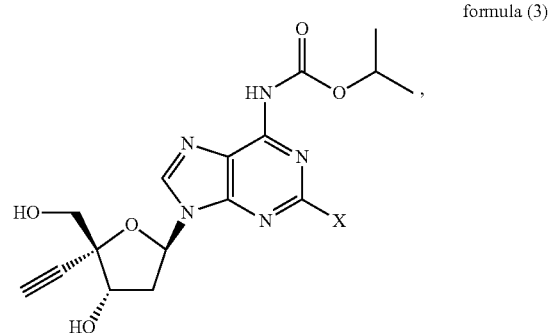

formula (3)

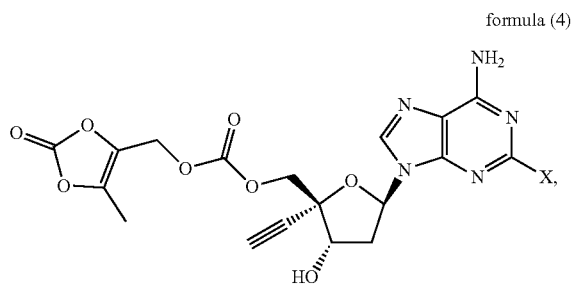

formula (4)

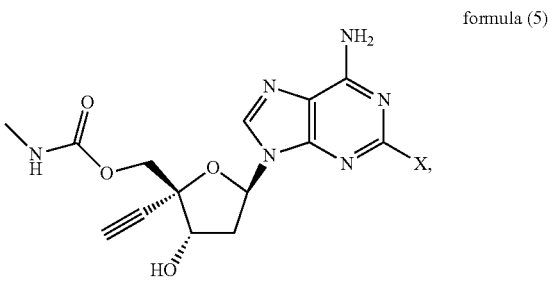

formula (5)

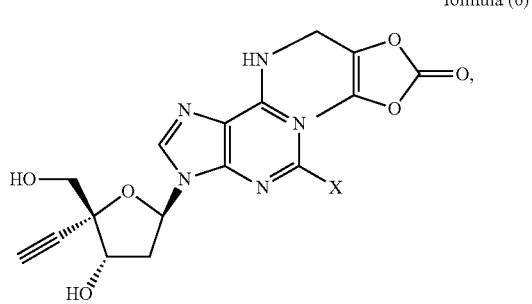

formula (6)

-continued
formula (7)
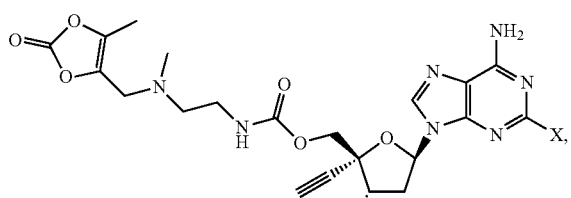
formula (8)
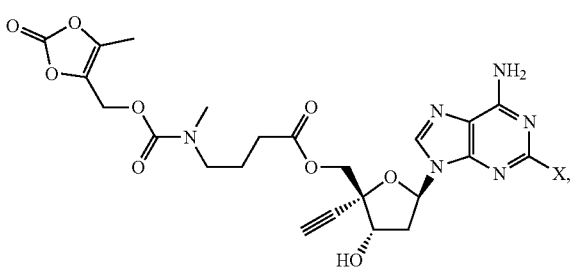
formula (4-B)
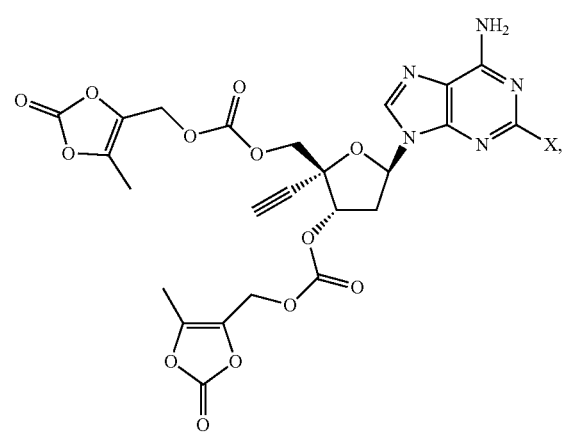
or a pharmaceutically acceptable salt, tautomer, or solvate thereof.
In some embodiments, X is Cl, F or Br. In some embodiments, X is F.
In further embodiments, an adenosine derivative of the present disclosure is selected from the group consisting of:
formula (2-A)
-continued
formula (3-A)
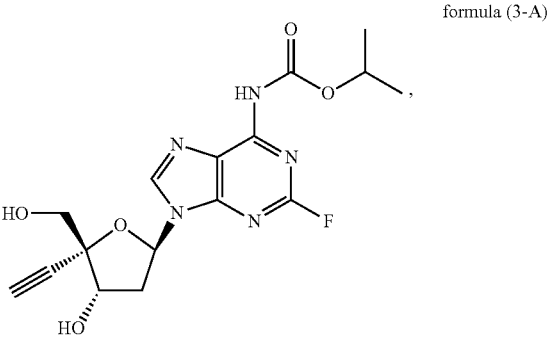
formula (4-A)
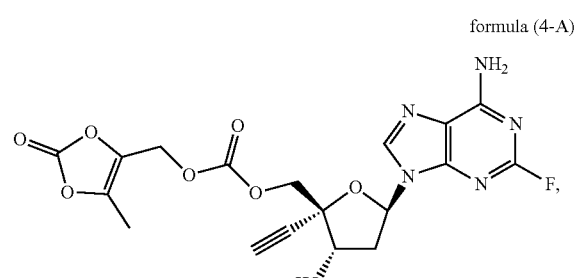
formula (5-A)
formula (6-A)
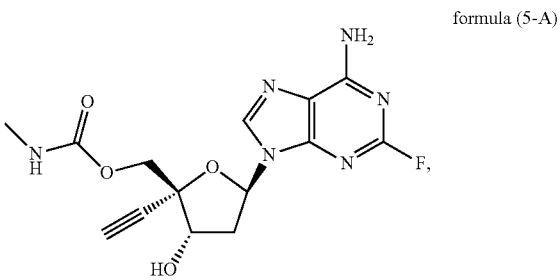
formula (7-A)

-continued

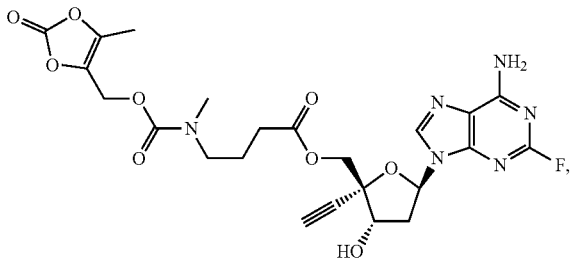

formula (8-A)

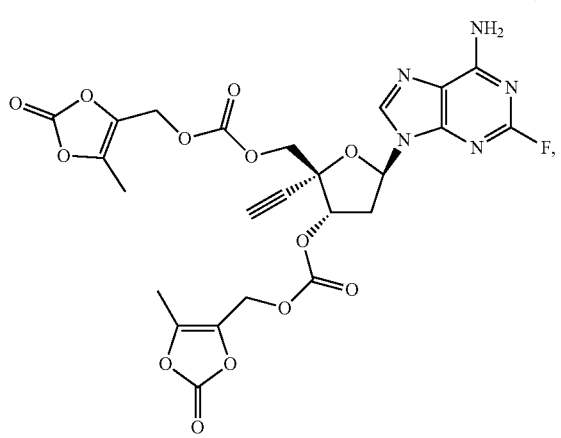

formula (4-C)

or a stereoisomer, pharmaceutically acceptable salt, tautomer, or solvate thereof (FIG. 2A-FIG. 2I).

In some embodiments, the adenosine compound of the present disclosure is an isomer of formula (1)-(8), formula (1a), formula (1b), or formula (1-A)-(8-A). In some embodiments, the isomer is a stereoisomer, e.g., an enantiomer or a diastereomer. In some embodiments, the isomer is an inhibitor of reverse transcriptase having in vivo activity.

As disclosed herein, an adenosine derivative of the present disclosure comprises ((2R,3S,5R)-5-(6-amino-2-fluoro-9H-purin-9-yl)-2-ethynyl-3-hydroxytetrahydrofuran-2-yl)methyl isopropylcarbamate, isopropyl (9-((2R,4S,5R)-5-ethynyl-4-hydroxy-5-(hydroxymethyl)tetrahydrofuran-2-yl)-2-fluoro-9H-purin-6-yl)carbamate, ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate, ((2R,3S,5R)-5-(6-amino-2-fluoro-9H-purin-9-yl)-2-ethynyl-3-hydroxytetrahydrofuran-2-yl)methyl methylcarbamate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate, [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino]butanoate, or a pharmaceutically acceptable salt thereof.

In some embodiments, the adenosine derivative of the present disclosure comprises $R^1$, $R^{1'}$, or $R^2$, each independently comprising one or more 5- to 10-membered heterocyclic rings. The $R^1$, $R^{1'}$, or $R^2$ each can independently comprise a 5-member heterocyclic ring in one embodiments, a 6-member heterocyclic ring in another embodiment, or a 6-10-member heterocyclic ring in yet another embodiments. A heterocyclic ring of the present disclosure can have one or more substituents. In some embodiments, a 5-membered heterocyclic ring, comprises carbon atoms and a range of from 1 to 4 heteroatoms selected from the group consisting of N, O, S. In some embodiments, a 5-membered heterocyclic ring comprises from 1 to 3 O atoms. In further embodiments, $R^1$, $R^{1'}$, or $R^2$ each independently comprises a 5-membered heterocyclic ring of formulas 9-24. In even further embodiments, an adenosine derivative of the present disclosure comprises $R^1$, $R^{1'}$, or $R^2$ that each independently comprise an aforementioned —$R^5$, -$L^1$-$R^5$, —Z-$L^4$-$R^5$ group. In some embodiments, the —$R^5$, -$L^1$-$R^5$, —Z-$L^4$-$R^5$ is selected from formulas 9-24 (FIG. 3A-FIG. 3J and FIG. 4A-FIG. 4F):

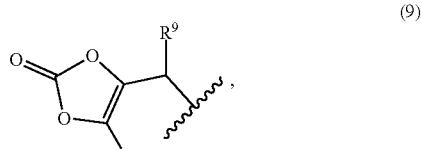
(9)

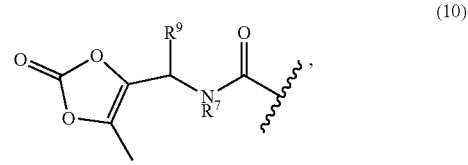
(10)

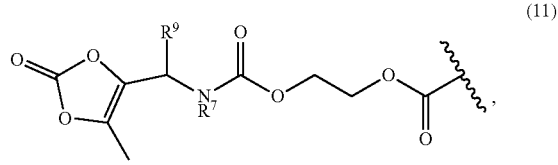
(11)

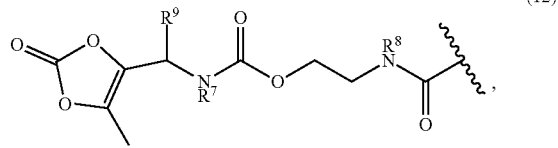
(12)

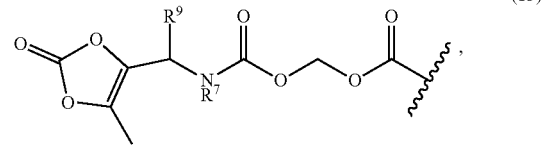
(13)

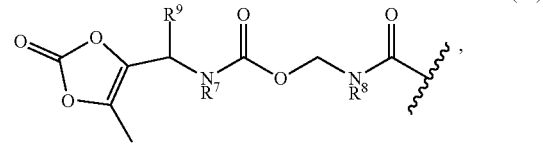
(14)

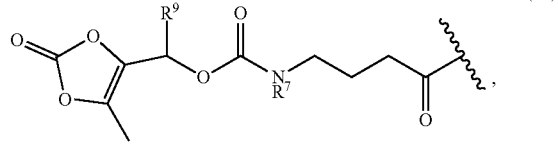
(15)

-continued

(16)
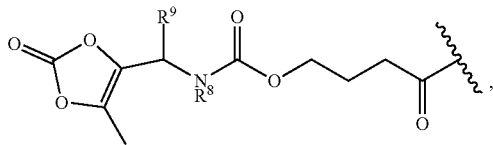

(17)
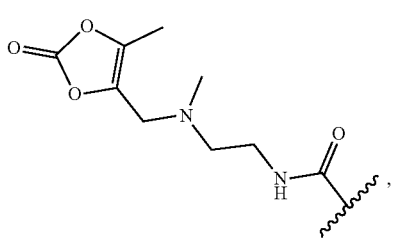

(18)
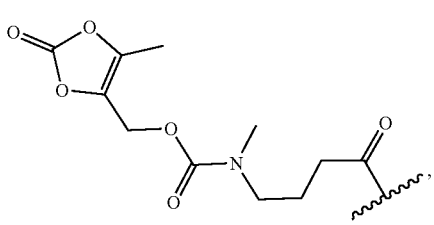

(19)
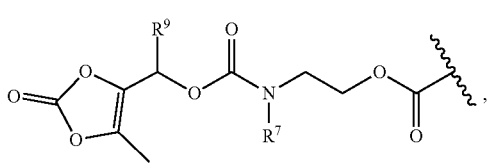

(20)
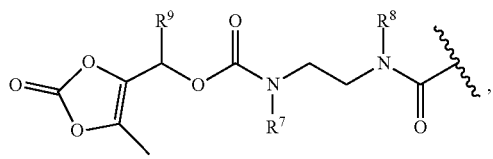

(21)
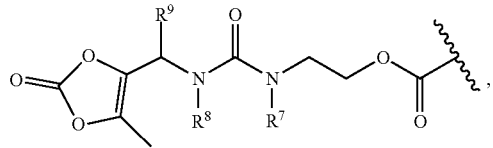

(22)
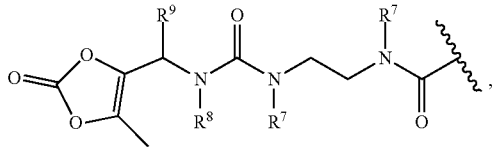

(23)
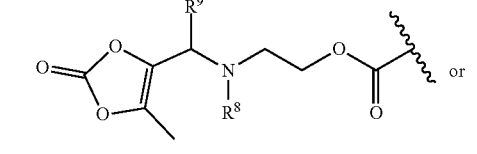
or

(24)
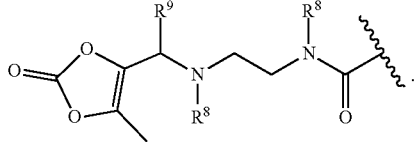

In some embodiments, the $-R^5$, $-L^1\text{-}R^5$, $-Z\text{-}L^4\text{-}R^5$ is selected from group consisting of:

(9)
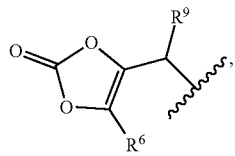

(17)
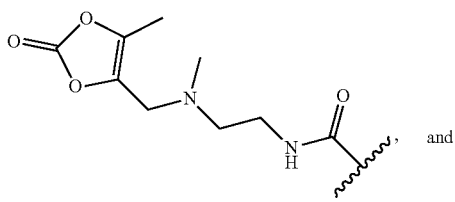
, and

(18)
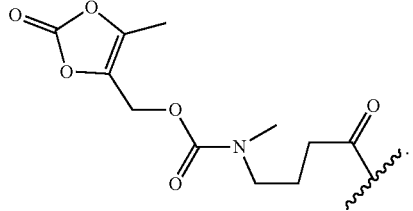

In some embodiments, an adenosine derivative of the present disclosure comprises $R^1$ and $R^{1'}$ that each is —H, —C(O)N($R^3$)($R^{3'}$) or —C(O)O$R^4$ and $R^2$ that is —C(O)N($R^3$)($R^{3'}$), —C(O)O$R^4$ or one of formulas 9-24.

In another embodiment, an adenosine derivative of the present disclosure comprises $R^1$ and $R^{1'}$ that each is —C(O)N($R^3$)($R^{3'}$) or —C(O)O$R^4$ and $R^2$ that is —H, —C(O)N($R^3$)($R^{3'}$), —C(O)O$R^4$ or one of formulas 9-24.

In yet another embodiment, an adenosine derivative of the present disclosure comprises $R^2$ that is —H, —C(O)N($R^3$)($R^{3'}$) or —C(O)O$R^4$ and $R^1$ that is —C(O)N($R^3$)($R^{3'}$) or —C(O)O$R^4$ or one of formulas 9-24.

In yet another embodiment, an adenosine derivative of the present disclosure comprises $R^2$ that is —C(O)N($R^3$)($R^{3'}$) or —C(O)O$R^4$ and $R^1$ that is —H, —C(O)N($R^3$)($R^{3'}$), —C(O)O$R^4$ or one of formulas 9-24.

In yet another embodiment, an adenosine derivative of the present disclosure comprises $R^1$ and $R^{1'}$ that each that is —H, —C(O)N($R^3$)($R^{3'}$), —C(O)O$R^4$, —$R^5$, -$L^1$-$R^5$, —Z-$L^4$-$R^5$ or one of one of formulas 9-24 and $R^2$ that is —C(O)N($R^3$)($R^{3'}$), —C(O)O$R^4$, —$R^5$, -$L^1$-$R^5$, —Z-$L^4$-$R^5$ or one of formulas 9-24.

In yet another embodiment, an adenosine derivative of the present disclosure comprise $R^1$ that is —C(O)N($R^3$)($R^{3'}$), —C(O)O$R^4$, —$R^5$, -$L^1$-$R^5$, —Z-$L^4$-$R^5$ or one of one of formulas 9-24 and $R^2$ that is —H, —C(O)N($R^3$)($R^{3'}$), —C(O)O$R^4$, —$R^5$, -$L^1$-$R^5$, —Z-$L^4$-$R^5$ or one of formulas 9-24.

In yet further embodiments, each of $R^1$, $R^{1'}$ and $R^2$ is independently selected from one of formulas 9-24.

An adenosine derivative of the present disclosure can undergo conversion to a target drug and can comprise reverse transcriptase inhibitor activity in vivo, reverse transcriptase chain terminator activity in vivo, DNA translocation inhibitor activity in vivo, or a combination thereof.

An adenosine derivative of the present disclosure can be a prodrug that has no or limited activity in its original form shown herein and can be metabolized in vivo to exhibit the desired activity of a target drug including a reverse transcriptase inhibitor activity, a reverse transcriptase chain terminator activity, DNA translocation inhibitor activity, or a combination thereof.

Not wishing to be bound by a particular mechanism or theory, Applicants discovered that adenosine derivatives of the present disclosure can be metabolized in vivo to produce a compound or a mixture of compounds similar to or the same as a target drug 4'-ethynyl-2-fluoro-2'-deoxyadenosine (EFdA) that has reverse transcriptase inhibitor and other antiviral activities.

As disclosed herein an adenosine derivative of the present disclosure can comprise isomers (e.g., enantiomers, diastereomers, and/or tautomers) thereof, one or more pharmaceutically acceptable salts thereof, one or more solvates including hydrates thereof, solvated salts thereof or a mixture thereof.

The present disclosure is further directed to a pharmaceutical composition comprising an adenosine derivative disclosed herein and a pharmaceutically acceptable carrier. In some embodiments, the pharmaceutical composition comprises an adenosine derivative having a formula (1):

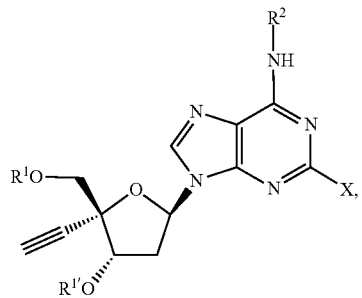

wherein, $R^1$, $R^{1'}$, and $R^2$ each is independently —H, —C(O)N($R^3$)($R^{3'}$), —C(O)O$R^4$, —$R^5$, -$L^1$-, $R^5$, or —Z-$L^4$-$R^5$, wherein at least one of $R^1$ and $R^2$ is not —H;

$R^3$, $R^{3'}$ and $R^4$ each is independently —H, C1-C10 alkyl, C2-C10 alkenyl, C3-C10 cycloalkyl, 3- to 10-membered heterocycloalkyl, aryl, or heteroaryl;

$R^5$ is:

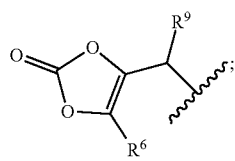

$R^6$ is —H, C1-C10 alkyl, C2-C10 alkenyl, C3-C10 cycloalkyl, 3- to 10-membered heterocycloalkyl, aryl, or heteroaryl;

-$L^1$-$R^5$ is —(C1-C10 alkylene)-N($R^7$)—$R^5$, —(C1-C10 alkylene)-O—$R^5$, —(C1-C10 alkyl)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$—, —C(O)N($R^7$)-$L^2$-C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)N($R^8$)-$L^3$-O—$R^5$ or —C(O)N($R^7$)-$L^2$-C(O)N($R^8$)-$L^3$-S—$R^5$;

—Z— is a divalent —C(O)—, —C(O)O—, or —C(O)N($R^7$)—;

-$L^4$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$ or —(C2-C10 alkenylene)-S—$R^5$;

$R^7$, $R^8$ and $R^9$ each is independently —H, C1-C10 alkyl, or C2-C10 alkenyl;

$L^2$ and $L^3$ each is intendedly divalent —(C1-C10 alkylene)-, or —(C2-C10 alkenylene)-; and X is a halogen atom.

As disclosed above, a pharmaceutical composition of the present disclosure comprising an adenosine derivative can be free from monophosphate group, diphosphate group, tri-phosphate group or a combination thereof. In some embodiments, an $R^1$ and/or $R^2$ group of an adenosine derivative of disclosed herein is free from monophosphate group, diphosphate group, tri-phosphate group or a combination thereof.

In some embodiments, the C1-C10 alkyl and C2-C10 alkenyl is linear or branched. In some embodiments, the adenosine derivative of the pharmaceutical compositions comprises a combination of C1-C10 alkyl, C2-C10 alkenyl, C3-C10 cycloalkyl, 3- to 10-membered heterocycloalkyl, aryl and heteroaryl.

In some embodiments of the pharmaceutical composition, the adenosine derivative includes a divalent linker $L^1$ that comprises one or more repeats of a same group or a combination of different groups as disclosed herein. Non-limiting examples of the linker $L^1$ and other chemically possible combinations include those described above, e.g., in formula (1).

In some embodiments, an adenosine derivative of the pharmaceutical composition is an isomer of formula (1)-(8), formula (1a), formula (1b), formula (1-A)-(8-A), formula (4-B), or formula (4-C). Isomers described above, such as tautomers, enantiomers, diastereomers, cis/trans isomers or a combination thereof can be suitable. In some embodiments, the isomer is an inhibitor of reverse transcriptase that has in vivo activity.

In some embodiments, the X is a halogen atom selected from the group consisting of fluorine, chlorine, bromine and iodine (alternatively referred to as fluoro (F), chloro (Cl), bromo (Br), and iodo (I)). In one embodiment, X is F. In another embodiment, X is Cl. In yet another embodiment, X is Br. Non-limiting examples of adenosine derivatives of the present disclosure are shown in FIG. 1A-FIG. 1I.

In some embodiments, the pharmaceutical composition of the present disclosure comprises an adenosine derivative having a formula selected from the group consisting of:

formula (2)

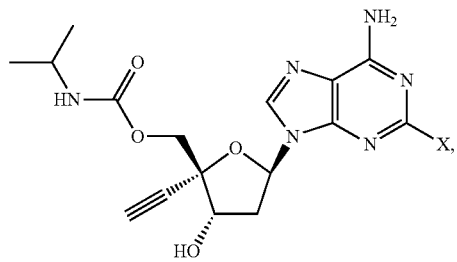

formula (3)

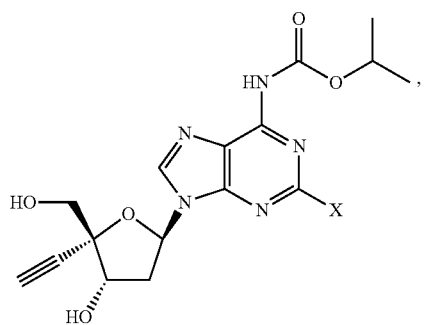

formula (4)

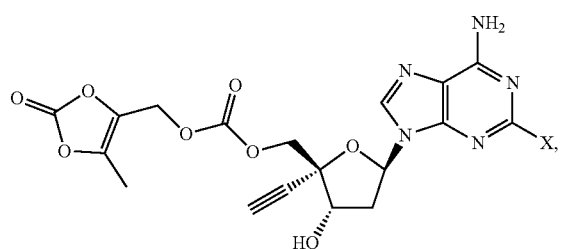

formula (5)

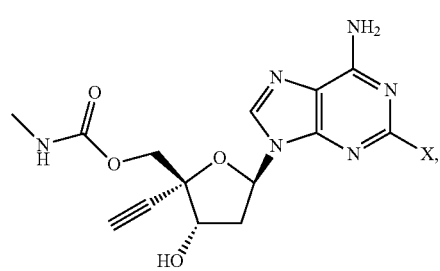

formula (6)

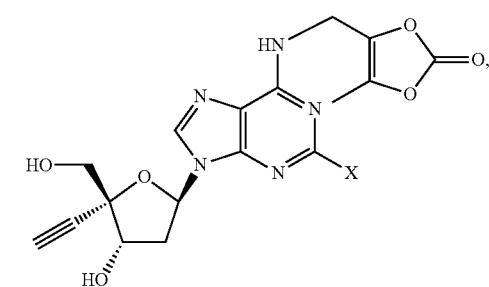

formula (7)

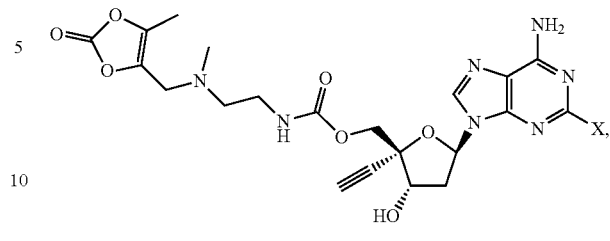

and formula (8)

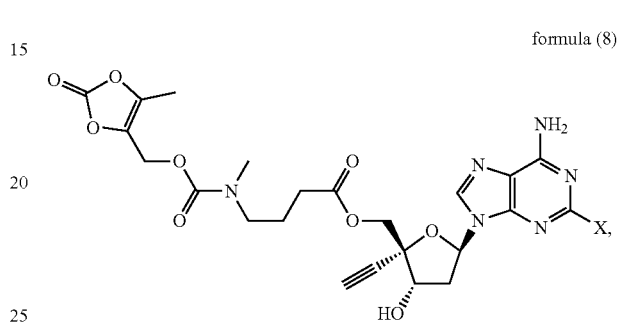

formula (4-B)

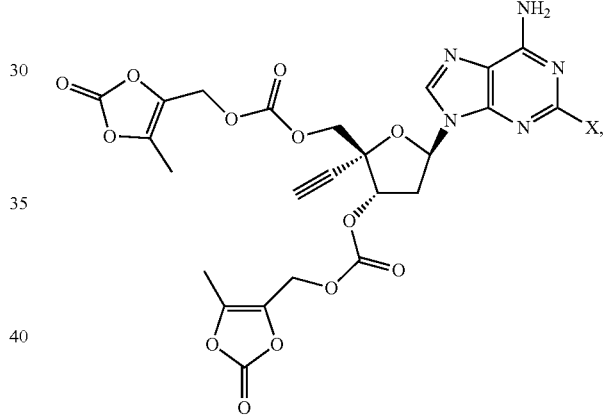

or a pharmaceutically acceptable salt, tautomer, solvate, or a combination thereof.

In some embodiments, X is Cl, F or Br. In some embodiments, X is F.

In some embodiments, the pharmaceutical composition of the present disclosure comprises an adenosine derivative having a formula selected from the group consisting of:

formula (2-A)

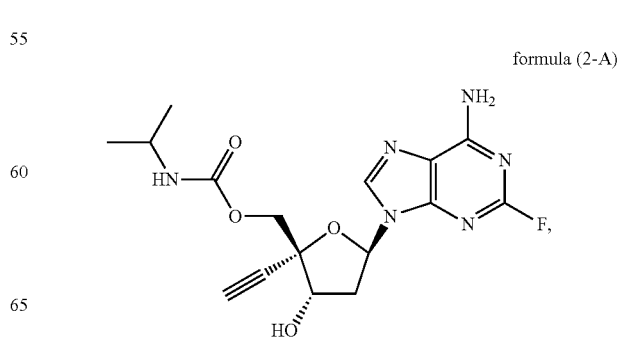

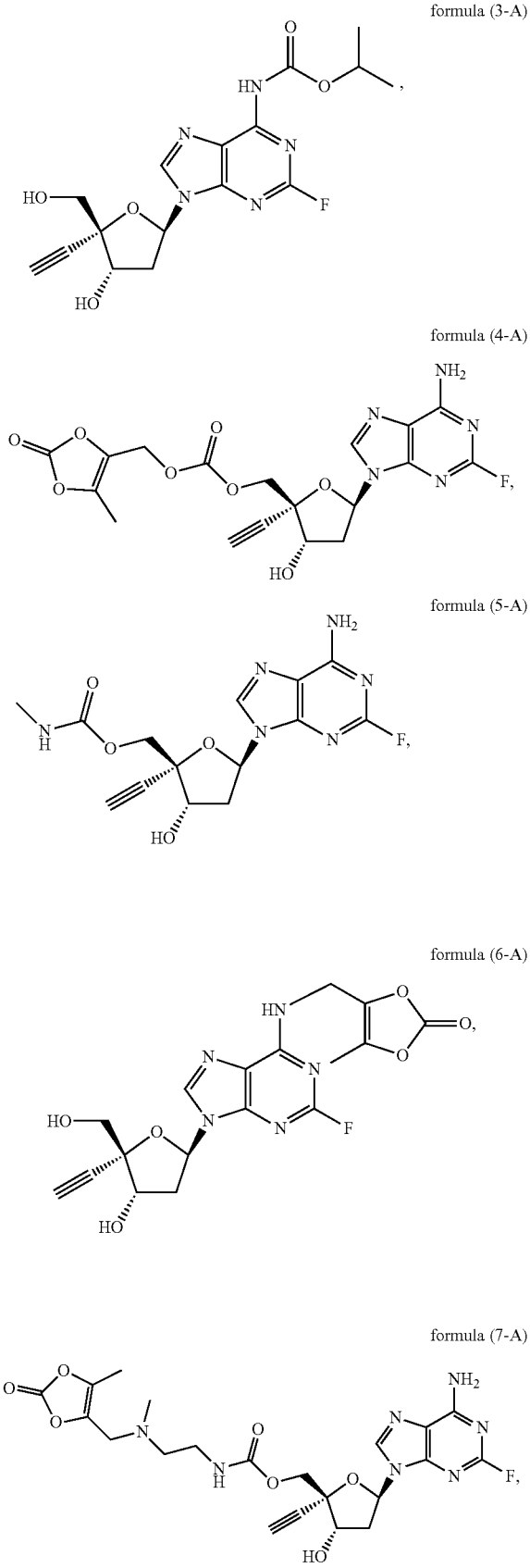
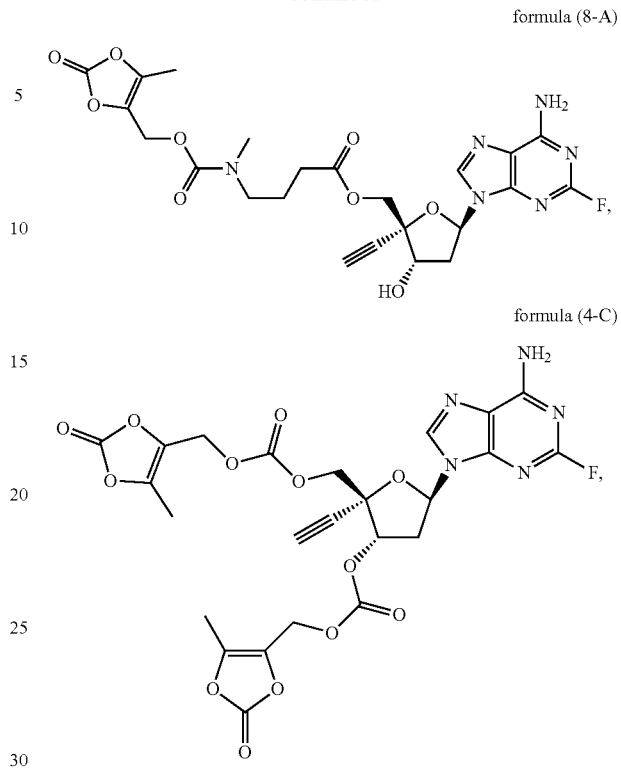

an stereoisomer thereof, a pharmaceutically acceptable salt thereof, or a combination thereof (FIG. 2A-FIG. 2I).

In some embodiments, the adenosine compound of the present disclosure is an isomer of formula (1)-(8), formula (1a), formula (1b), formula (1-A)-(8-A), formula (4-B), or formula (4-C). In some embodiments, the isomer is a stereoisomer, e.g., an enantiomer or a diastereomer. In some embodiments, the isomer is an inhibitor of reverse transcriptase having in vivo activity.

As disclosed herein, the pharmaceutical composition of the present disclosure comprises an adenosine derivative selected from the group consisting of: ((2R,3 S,5R)-5-(6-amino-2-fluoro-9H-purin-9-yl)-2-ethynyl-3-hydroxytetrahydrofuran-2-yl)methyl isopropylcarbamate, isopropyl (9-((2R,4S,5R)-5-ethynyl-4-hydroxy-5-(hydroxymethyl) tetrahydrofuran-2-yl)-2-fluoro-9H-purin-6-yl)carbamate, ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate, ((2R,3S,5R)-5-(6-amino-2-fluoro-9H-purin-9-yl)-2-ethynyl-3-hydroxytetrahydrofuran-2-yl)methyl methylcarbamate, 4-(((9-((2R,4S,5R)-5-ethynyl-4-hydroxy-5-(hydroxymethyl)tetrahydrofuran-2-yl)-2-fluoro-9H-purin-6-yl)amino) methyl)-5-methyl-1,3-dioxol-2-one, ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate, [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino] butanoate, and any pharmaceutically acceptable salts thereof.

In some embodiments, the pharmaceutical composition of the present disclosure includes an adenosine derivative comprising an $R^5$, $-L^1-R^5$ or $-Z-L^4-R^5$ selected from formulas 9-24:

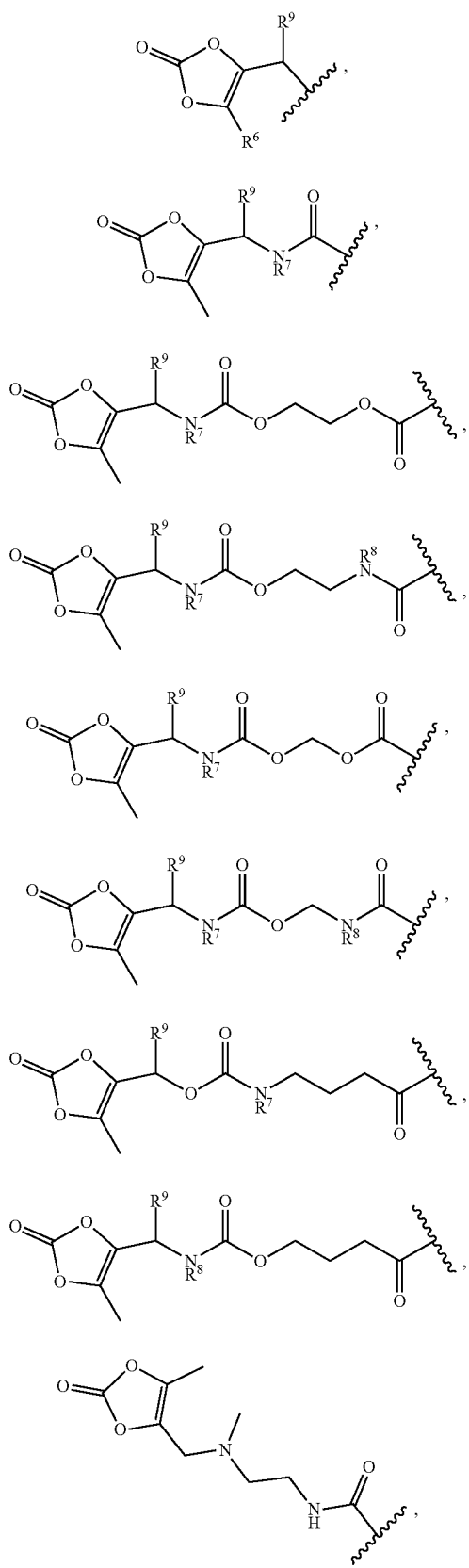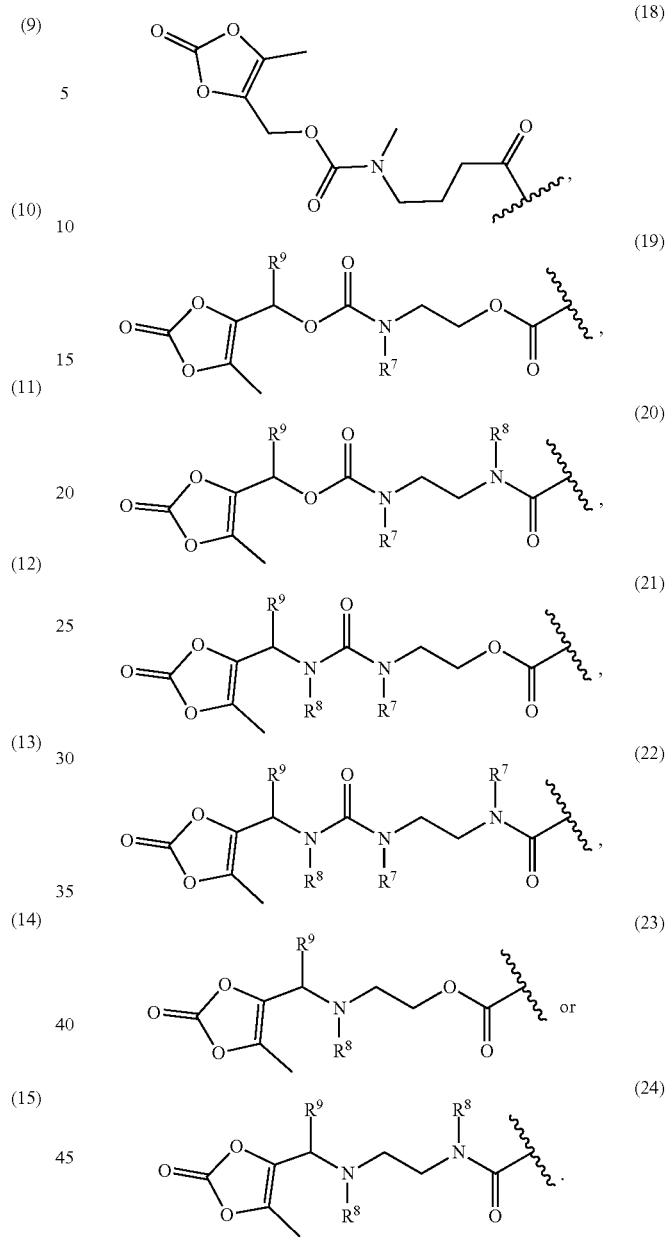

In some embodiments, a pharmaceutical composition of the present disclosure comprises an adenosine derivative that comprises $R^1$ and R" that each is —H, —C(O)N($R^3$)($R^{3'}$) or —C(O)O$R^4$ and $R^2$ that is —C(O)N($R^3$)($R^{3'}$), —C(O)O$R^4$ or one of formulas 9-24.

In another embodiment, a pharmaceutical composition of the present disclosure comprises an adenosine derivative that comprises $R^1$ that is —C(O)N($R^3$)($R^{3'}$) or —C(O)O$R^4$ and $R^2$ that is —H, —C(O)N($R^3$)($R^{3'}$), —C(O)O$R^4$ or one of formulas 9-24.

In yet another embodiment, a pharmaceutical composition of the present disclosure comprises an adenosine derivative that comprises $R^2$ that is —H, —C(O)N($R^3$)($R^{3'}$) or —C(O)O$R^4$ and $R^1$ that is —C(O)N($R^3$)($R^{3'}$) or —C(O)O$R^4$ or one of formulas 9-24.

In yet another embodiment, a pharmaceutical composition of the present disclosure comprises an adenosine derivative that comprises $R^2$ that is —C(O)N($R^3$)($R^{3'}$) or —C(O)O$R^4$ and $R^1$ and $R^{1'}$ that is each —H, —C(O)N($R^3$)($R^{3'}$), —C(O)O$R^4$ or one of formulas 9-24.

In yet another embodiment, a pharmaceutical composition of the present disclosure comprises an adenosine derivative that comprises $R^1$ and $R^{1'}$ that is each —H, —C(O)N($R^3$)($R^{3'}$), —C(O)O$R^4$, —$R^5$, -$L^1$-$R^5$, —Z-$L^4$-$R^5$ or one of one of formulas 9-24 and $R^2$ that is selected from —C(O)N($R^3$)($R^{3'}$), —C(O)O$R^4$, —$R^5$, -$L^1$-$R^5$, —Z-$L^4$-$R^5$ or one of formulas 9-24.

In yet another embodiment, a pharmaceutical composition of the present disclosure comprises an adenosine derivative that comprises $R^1$ that is —C(O)N($R^3$)($R^{3'}$), —C(O)O$R^4$, —$R^5$, -$L^1$-$R^5$, —Z-$L^4$-$R^5$ or one of one of formulas 9-24 and $R^2$ that is selected from —H, —C(O)N($R^3$)($R^{3'}$), —C(O)O$R^4$, —$R^5$, -$L^1$-$R^5$, —Z-$L^4$-$R^5$ or one of formulas 9-24.

In yet further embodiments, a pharmaceutical composition of the present disclosure comprises an adenosine derivative that comprises $R^1$, $R^{1'}$, and $R^2$ each is independently selected from one of formulas 9-24.

In some embodiments, $R^3$, $R^{3'}$ and $R^4$ each is independently —H, C1-C10 alkyl, C2-C10 alkenyl, or C3-C10 cycloalkyl. In some embodiments, $R^3$, $R^{3'}$ and $R^4$ each is independently —H, C1-C5 alkyl, C2-C5 alkenyl, or C3-C6 cycloalkyl. In some embodiments, $R^3$, $R^{3'}$ and $R^4$ each is independently —H or C1-C5 alkyl. In some embodiments, the C1-C5 alkyl is methyl, ethyl, or isopropyl. In some embodiments, $R^3$, $R^{3'}$ and $R^4$ each is independently —H, methyl, or isopropyl.

In some embodiments, $R^6$ is —H, C1-C10 alkyl, C2-C10 alkenyl, or C3-C10 cycloalkyl. In some embodiments, $R^6$ is —H, C1-C5 alkyl, C2-C5 alkenyl, or C3-C6 cycloalkyl. In some embodiments, $R^6$ is —H, C1-C3 alkyl, or C2-C4 alkenyl. In some embodiments, $R^6$ is selected from the group consisting of —H, methyl, ethyl, isopropyl, or cyclopropyl. In some embodiments, $R^6$ is methyl.

In some embodiments, $R^7$ and $R^8$ each is independently —H, C1-C10 alkyl, or C3-C6 cycloalkyl. In some embodiments, $R^7$ and $R^8$ each is independently —H, C1-C5 alkyl, or C3-C6 cycloalkyl. In some embodiments, $R^7$ and $R^8$ each is independently —H, methyl, ethyl, isopropyl, or cyclopropyl.

In some embodiments, $R^9$ is —H, F, C1-C10 alkyl, or C2-C10 alkenyl. In some embodiments $R^9$ is —H, F, C1-C3 alkyl, or C2-C4 alkenyl. In some embodiments, $R^9$ is —H, F, or C1-C3 alkyl. In some embodiments, $R^9$ is —H.

As described, the pharmaceutical composition of the present disclosure comprises a pharmaceutically acceptable carrier.

Non-limiting examples of a pharmaceutically acceptable carrier include a pharmaceutical excipients surfactant, emulsifier, filler, carrier, isotonicifier, dispersing agent, viscosity modifier, resuspending agent, buffer or a combination thereof. Pharmaceutical excipients typically do not have properties of a medicinal or drug active ingredient, also known as active pharmaceutical ingredient (API) and are typically used to streamline the manufacture process or packaging of the active ingredients, or to deliver an API to a patient or other subject. Pharmaceutical acceptable carrier, excipients or inactive ingredients from the Inactive Ingredients Database available from US FDA (https://www.fda.gov/drugs/drug-approvals-and-databases/inactive-ingredients-database-download) can be suitable. Some of Generally Recognized As Safe (GRAS) food substances available form US FDA's GRAS Substances (SCOGS) Database (https://www.fda.gov/food/generally-recognized-safe-gras/gras-substances-scogs-database) can also be suitable.

In some embodiments of the present disclosure, the pharmaceutical acceptable carrier comprises acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxypropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, or combinations thereof.

In further embodiments, the pharmaceutical acceptable carrier comprises dextrose, glycerin, histidine, hydrochloric acid, hydroxypropyl cellulose, hydroxypropyl-β-cyclodextrin (HPBCD), hypromellose (hydroxypropyl methylcellulose (HPMC)), polyoxyethylene (20) sorbitan monolaurate (Tween 20, Polysorbate 20), polyethylene glycols (PEG 400, PEG 3350, PEG 4000, PEG 6000), polyoxyethylene-polyoxypropylene copolymer (Poloxamer 188, Poloxamer 407), polyoxyethylene (20) sorbitan monooleate (Tween 80, Polysorbate 80), saline, sodium chloride, sodium citrate, sodium citrate dihydrate, sodium lauryl sulfate, sodium phosphate monobasic, sodium phosphate dibasic, or a combination thereof.

The pharmaceutical composition of the present disclosure can further comprise an effective dosage of one or more anti-HIV agents (also referred to as anti-HIV agent) selected from abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc or a combination thereof.

In some embodiments, the pharmaceutical composition of the present disclosure comprises an adenosine derivative, e.g., formula (1)-(8), formula (1a), formula (1b), or formula (1-A)-(8-A), and the one or more anti-HIV agents in a single formulation that can be administered to a subject together. The pharmaceutical composition of the present disclosure can comprise the adenosine derivative and the one or more anti-HIV agents in separate formulations that can be administered to a subject simultaneously or sequentially. The pharmaceutical composition of the present disclosure can also be mixed together with one or more anti-HIV agents in separate formulations that can be administered to a subject simultaneously.

The present disclosure is further directed to a method for the treatment of a disease. The method can comprise administering a subject in need thereof an effective dosage of a pharmaceutical composition comprising an adenosine derivative having a formula (1):

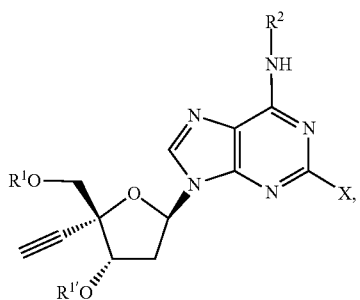

wherein,

R$^1$, R$^{1'}$, and R$^2$ each is independently —H, —C(O)N(R$^3$)(R$^{3'}$), —C(O)OR$^4$, —R$^5$, -L$^1$-, R$^5$, or —Z-L$^4$-R$^5$, wherein at least one of R$^1$ and R$^2$ is not —H;

R$^3$, R$^{3'}$ and R$^4$ each is independently —H, C1-C10 alkyl, C2-C10 alkenyl, C3-C10 cycloalkyl, 3- to 10-membered heterocycloalkyl, aryl, or heteroaryl;

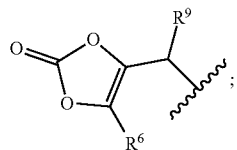

R$^5$ is:

R$^6$ is —H, C1-C10 alkyl, C2-C10 alkenyl, C3-C10 cycloalkyl, 3- to 10-membered heterocycloalkyl, aryl, or heteroaryl;

-L$^1$-R$^5$ is —(C1-C10 alkylene)-N(R$^7$)—R$^5$, —(C1-C10 alkylene)-O—R$^5$, —(C1-C10 alkylene)-S—R$^5$, —(C2-C10 alkenylene)-N(R$^7$)—R$^5$, —(C2-C10 alkenylene)-O—R$^5$, —(C2-C10 alkenylene)-S—R$^5$, —C(O)O—R$^5$, —C(O)O-L$^2$-N(R$^7$)—R$^5$, —C(O)O-L$^2$-O—R$^5$, —C(O)O-L$^2$-S—R$^5$, —C(O)O-L$^2$-C(O)O—R$^5$, —C(O)O-L$^2$-C(O)N(R$^7$)—R$^5$, —C(O)O-L$^2$-C(O)N(R$^7$)-L$^3$-N(R$^7$)—R$^5$, —C(O)O-L$^2$-C(O)N(R$^7$)-L$^3$-O—R$^5$, —C(O)O-L$^2$-C(O)N(R$^7$)-L$^3$-S—R$^5$, —C(O)N(R$^7$)—R$^5$, —C(O)N(R$^7$)-L$^2$-N(R$^7$)—R$^5$, —C(O)N(R$^7$)-L$^2$-O—R$^5$, —C(O)N(R$^7$)-L$^2$-S—R$^5$, —C(O)N(R$^7$)-L$^2$-C(O)O—R$^5$, —C(O)N(R$^7$)-L$^2$-C(O)N(R$^8$)—R$^5$—, —C(O)N(R$^7$)-L$^2$-C(O)N(R$^8$)-L$^3$-N(R$^7$)—R$^5$, —C(O)O-L$^2$-N(R$^7$)C(O)O—R$^5$, —C(O)N(R$^8$)-L$^2$-N(R$^7$)C(O)O—R$^5$, —C(O)O-L$^2$-N(R$^7$)C(O)N(R$^8$)—R$^5$, —C(O)N(R$^7$)-L$^2$-N(R$^7$)C(O)N(R$^8$)—R$^5$, —C(O)N(R$^7$)-L$^2$-C(O)N(R$^8$)-L$^3$-O—R$^5$ or —C(O)N(R$^7$)-L$^2$-C(O)N(R$^8$)-L$^3$-S—R$^5$;

—Z— is a divalent —C(O)—, —C(O)O—, or —C(O)N(R$^7$)—;

-L$^4$-R$^5$ is —(C1-C10 alkylene)-N(R$^7$)—R$^5$, —(C1-C10 alkylene)-O—R$^5$, —(C1-C10 alkylene)-S—R$^5$, —(C2-C10 alkenylene)-N(R$^7$)—R$^5$, —(C2-C10 alkenylene)-O—R$^5$ or —(C2-C10 alkenylene)-S—R$^5$;

R$^7$, R$^8$ and R$^9$ each is independently —H, C1-C10 alkyl, or C2-C10 alkenyl;

L$^2$ and L$^3$ each is intendedly divalent —(C1-C10 alkyl)-, or —(C2-C10 alkenyl)-; and X is a halogen atom.

Any of the aforementioned adenosine derivatives (e.g., formula (1)-(8), formula (1a), formula (1b), or formula (1-A)-(8-A)) or pharmaceutical compositions comprising the adenosine derivatives can be suitable. The X is a halogen atom and can be selected form fluorine, chlorine, bromine and iodine (alternatively referred to as fluoro (F), chloro (Cl), bromo (Br), and iodo (I)). In some embodiments, X is F. In another embodiment, X is Cl. In yet another embodiment, X is Br.

In some embodiments of the present method, the adenosine derivative has a formula selected from the group consisting of:

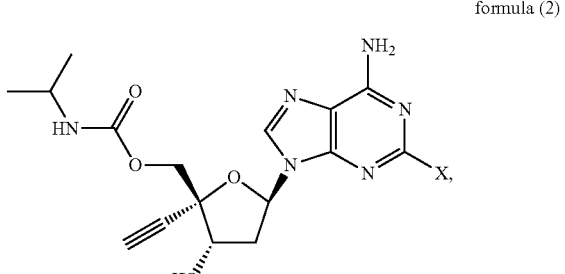

formula (2)

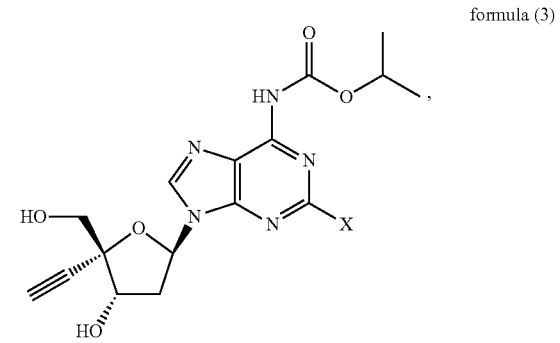

formula (3)

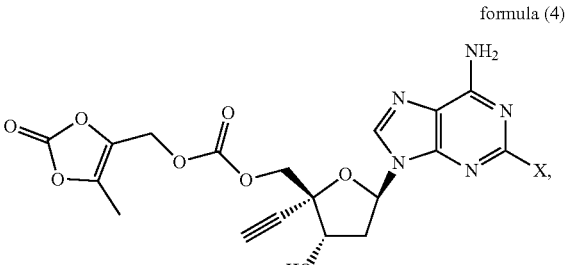

formula (4)

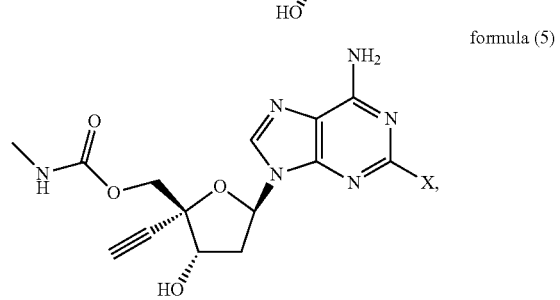

formula (5)

-continued
formula (6)
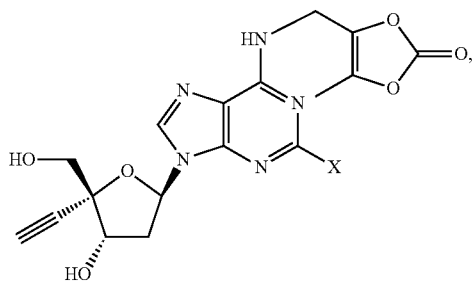
formula (7)
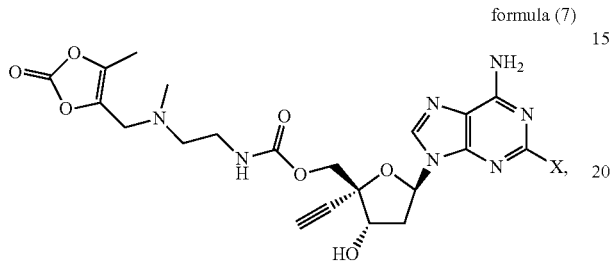
formula (8)
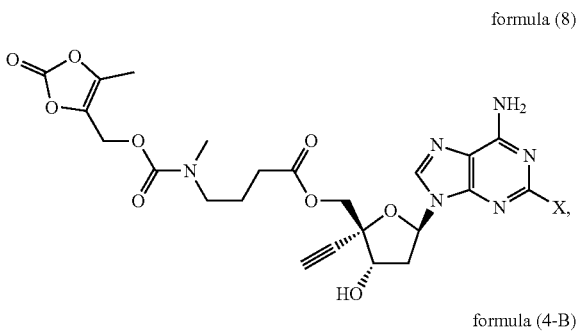
formula (4-B)
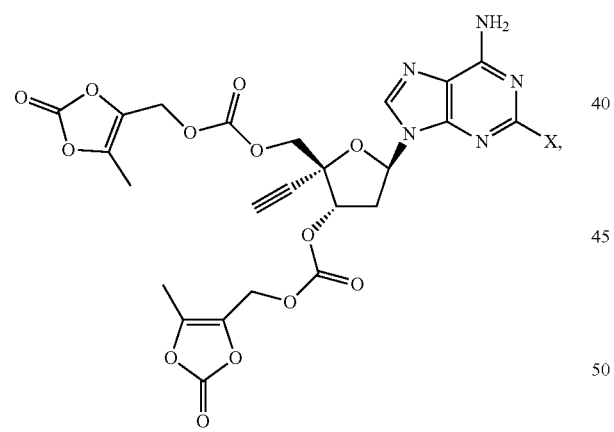
an isomer thereof, or a pharmaceutically acceptable salt thereof.
In some embodiments, X is Cl, F or Br. In some embodiments, X is F.
In some embodiments of the present method, the adenosine derivative has a formula selected from the group consisting of:
formula (2-A)
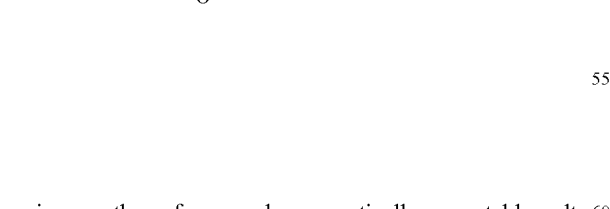
formula (3-A)
formula (4-A)
formula (5-A)
formula (6-A)
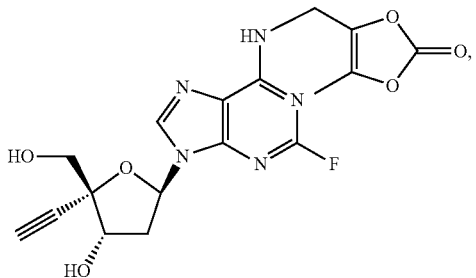

-continued formula (7-A)

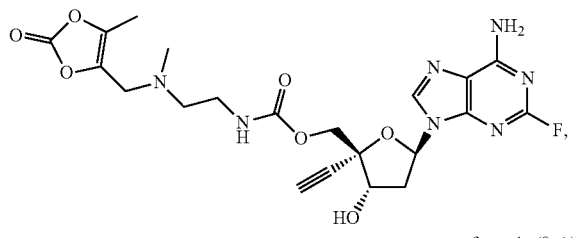

formula (8-A)

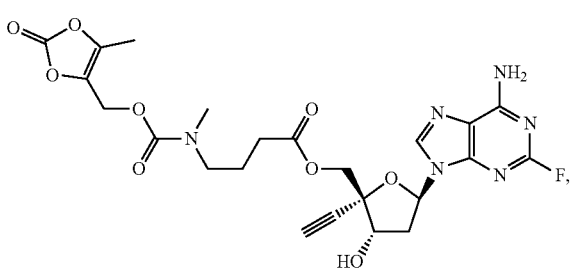

formula (4-C)

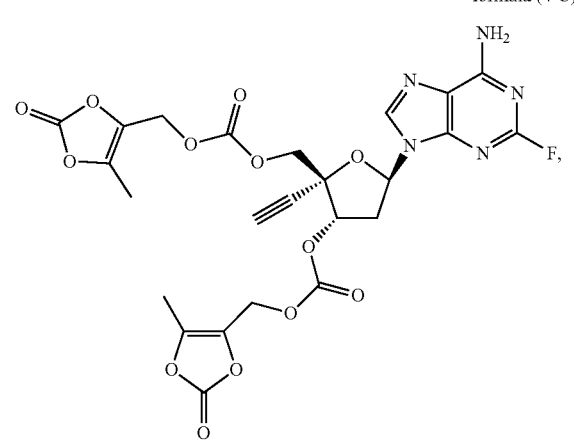

an isomer thereof, or a pharmaceutically acceptable salt thereof.

As disclosed herein, the present method includes administering a pharmaceutical composition comprising an adenosine derivative, wherein the adenosine derivative is ((2R,3S,5R)-5-(6-amino-2-fluoro-9H-purin-9-yl)-2-ethynyl-3-hydroxytetrahydrofuran-2-yl)methyl isopropylcarbamate, isopropyl (9-((2R,4S,5R)-5-ethynyl-4-hydroxy-5-(hydroxymethyl)tetrahydrofuran-2-yl)-2-fluoro-9H-purin-6-yl)carbamate, ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate, ((2R,3 S,5R)-5-(6-amino-2-fluoro-9H-purin-9-yl)-2-ethynyl-3-hydroxytetrahydrofuran-2-yl)methyl methylcarbamate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, or any pharmaceutically acceptable salt thereof.

In the method of the present disclosure, the pharmaceutical composition is administered to a subject via intramuscular (IM) injection, subcutaneous (SC) injection, intravenous (IV) injection, oral administration, topical application, implant application or a combination thereof. An implant application can include an implantable device or a film that contains the pharmaceutical composition disclosed herein. The implant application can comprise vaginal ring, film, membrane, patch, other devices, or a combination thereof.

The method of the present disclosure can further comprise measuring a specimen of the subject to determine a measured level of a target drug in the specimen, wherein the target drug can have a formula (T-1):

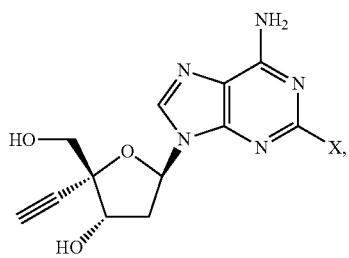

an isomer thereof, or a pharmaceutically acceptable salt thereof. In some embodiments, X is a halogen selected from the group consisting of F, Cl, Br and I. In some embodiments X is I.

Figure 5A:
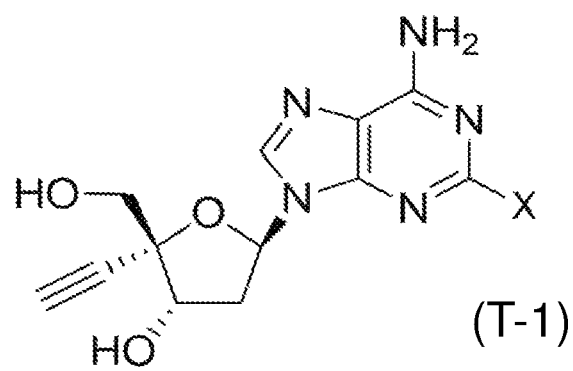
FIG. 5A-FIG. 5B show exemplary chemical structures of 4'-ethynyl-2-halogen-2'-deoxyadenosine (FIG. 5A, formula (T-1)) and 4'-ethynyl-2-fluoro-2'-deoxyadenosine (EFdA) (FIG. 5B, formula (T-1A)).
Figure 5B:
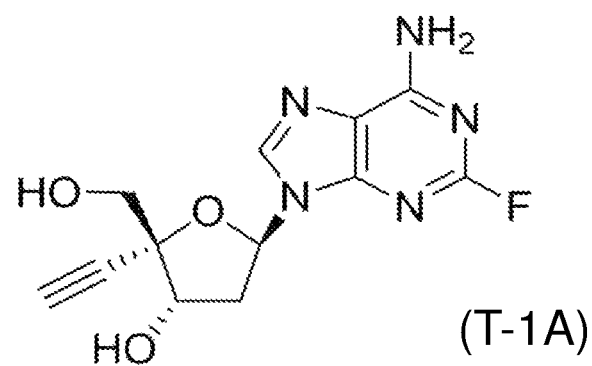

In some embodiments, the target drug can have a formula (T-1A):

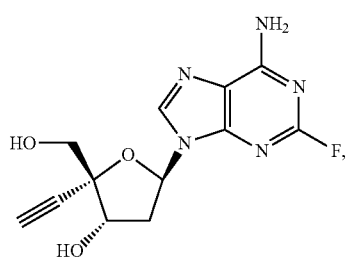

an isomer thereof, or a pharmaceutically acceptable salt thereof (FIG. 5A-FIG. 5B).

In some embodiments, the target drug can be (2R,3S,5R)-5-(6-amino-2-fluoro-9H-purin-9-yl)-2-ethynyl-2-(hydroxymethyl)tetrahydrofuran-3-ol (also referred to as 4'-ethynyl-2-fluoro-2'-deoxyadenosine, EFdA), or a pharmaceutically acceptable salt thereof.

In some embodiments, the target drug can be a degradation or metabolized product of the compound (T-1), (T-1A) or EFdA.

The specimen can be a blood sample, a urine sample, a body fluid sample, a tissue sample or a combination thereof from the subject, such as a patient.

The measured level of the target drug can be determined with analytical method known to those skilled in the art, such as, but not limited to, HPLC, GC, MS, GC-MS, or a combination thereof.

The method of the present disclosure can further comprise adjusting the effective dosage to produce a modified effective dosage if the measured level of the target drug is different from a predetermined target level of the target drug and administering the modified effective dosage to the subject.

In some embodiments of the present method, the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection.

In some embodiments, the method of the present disclosure further comprises administering to a subject an effective dosage of one or more anti-HIV agents selected from the group consisting of abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, and vicriviroc or a combination thereof. Other anti-HIV agents identified or developed, or combination thereof, can also be suitable.

Combinations of the adenosine derivative of the present disclosure (e.g., formula (1)-(8), formula (1a), formula (1b), or formula (1-A)-(8-A)) and the one or more anti-HIV agents described herein can be useful for the treatment or prophylaxis of AIDS or other HIV related symptoms. The anti-HIV agents can be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network.

An adenosine derivative of the present disclosure and the one or more anti-HIV agents described herein can be administered to a subject together or separately via oral administration, parenteral administration or a combination thereof. The adenosine derivative and the one or more anti-HIV agents can be administered to the subject with a daily, weekly, biweekly or monthly administration schedule.

The present disclosure is further directed to a use of the pharmaceutical composition for the treatment of a disease in a subject in need thereof, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. Any of the aforementioned pharmaceutical compositions can be suitable. The pharmaceutical composition can be used together with one or more anti-HIV agents for the treatment of the disease mentioned herein. The adenosine derivative and the one or more anti-HIV agents can be administered to a subject together or separately via oral administration, parenteral administration or a combination thereof. The adenosine derivative and the one or more anti-HIV agents can be administered to the subject with a daily, weekly, biweekly or monthly administration schedule.

The present disclosure is further directed to a use of the adenosine derivative, optionally, one or more pharmaceutically acceptable carriers, disclosed herein for manufacturing a medicament for treating a disease, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. Aforementioned adenosine derivatives can be suitable. Aforementioned pharmaceutically acceptable carriers can be suitable.

The present disclosure is further directed to a method for the prevention of infection in a subject in need thereof, the method comprising administering the subject an effective dosage of a pharmaceutical composition of the present method disclosed herein, wherein the subject is free from detectable symptoms of the infection. In some embodiments, the infection comprises a disease selected from Acquired Immune Deficiency Syndrome (AIDS), an infection of wild-type HIV-1, NRTI-resistant HIV-1, HIV-2, HIV having M184V mutations, HIV having K65R, multidrug resistant HIV, an RNA virus infection, or a combination thereof.

The detectable symptoms include, but are not limited to, symptoms of Acquired Immune Deficiency Syndrome (AIDS), symptoms of infection of HIV viruses comprising wild-type HIV-1, NRTI-resistant HIV-1, HIV-2, HIV having M184V mutations, HIV having K65R, multidrug resistant HIV, or a combination thereof. The detection of the HIV viruses can be done by PCR, reverse PCR, immunodetection of an antigen or an antibody related to AIDS or HIV.

In some embodiments, the pharmaceutical composition of the present method is administered to said subject with a daily, weekly, biweekly or monthly administration schedule.

In some embodiments, the method of the present disclosure further comprises administering the subject an effective dosage of one or more anti-HIV agents selected from abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc or a combination thereof. The one or more anti-HIV agents can be administered to the subject together with the pharmaceutical composition of this disclosure or separately.

Without being bound by any particular theory, an advantage of the adenosine derivatives disclosed herein (e.g., formula (1)-(8), formula (1a), formula (1b), formula (1-A)-(8-A), formula (4-B), or formula (4-C)) is the fast conversion to the target drug. As described below, greater than about 60% of the adenosine derivatives of the present disclosure surprisingly and unexpectedly can be converted to the target drug within about 30 min in contact with human plasma.

The instant disclosure now will be exemplified in the following non-limiting examples.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Properties of the Adenosine Derivatives

Properties of the adenosine derivatives are listed in Table 1.

TABLE 1

Nomenclature and properties.

| Formula ID | IUPAC Nomenclature | Molecular Weight |
|---|---|---|
| T-1A (EFdA) | (2R,3S,5R)-5-(6-amino-2-fluoro-9H-purin-9-yl)-2-ethynyl-2-(hydroxymethyl)tetrahydrofuran-3-ol | 293.25 |
| 2-A | ((2R,3S,5R)-5-(6-amino-2-fluoro-9H-purin-9-yl)-2-ethynyl-3-hydroxytetrahydrofuran-2-yl)methyl isopropylcarbamate | 378.36 |
| 3-A | isopropyl (9-((2R,4S,5R)-5-ethynyl-4-hydroxy-5-(hydroxymethyl)tetrahydrofuran-2-yl)-2-fluoro-9H-purin-6-yl)carbamate | 379.34 |
| 4-A | ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate | 449.35 |
| 5-A | ((2R,3S,5R)-5-(6-amino-2-fluoro-9H-purin-9-yl)-2-ethynyl-3-hydroxytetrahydrofuran-2-yl)methyl methylcarbamate | 350.31 |
| 6-A | 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one | 405.34 |
| 7-A | ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate | 505.46 |
| 8-A | ((2R,3S,5R)-5-(6-amino-2-fluoro-9H-purin-9-yl)-2-ethynyl-3-hydroxytetrahydrofuran-2-yl)methyl 4-(methyl(((5-methyl-2-oxo-1,3-dioxol-4-yl)methoxy)carbonyl)amino)butanoate | 548.48 |
| 4-C | ((2R,3S,5R)-5-(6-amino-2-fluoro-9H-purin-9-yl)-2-ethynyl-3-((((5-methyl-2-oxo-1,3-dioxol-4-yl)methoxy)carbonyl)oxy)tetrahydrofuran-2-yl)methyl ((5-methyl-2-oxo-1,3-dioxol-4-yl)methyl) carbonate | 605.44 |

Synthesis of Adenosine Derivative Prodrugs

Preparation methods, intermediates and synthesis schedules are out lined below.

Intermediate 1 tert-butyl N-[9-[(2R,4S,5R)-5-ethynyl-4-hydroxy-5-(hydroxymethyl)tetrahydrofuran-2-yl]-2-fluoro-purin-6-yl]carbamate

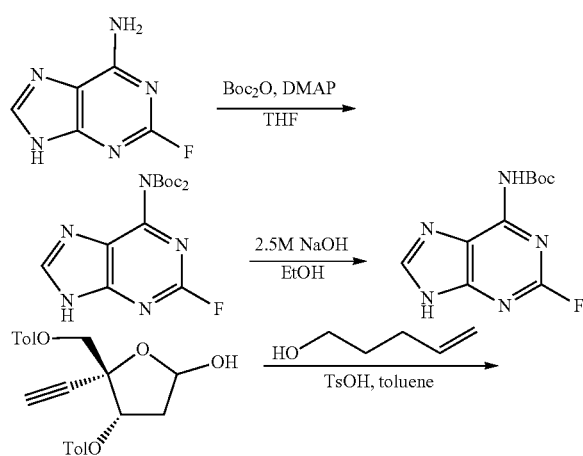

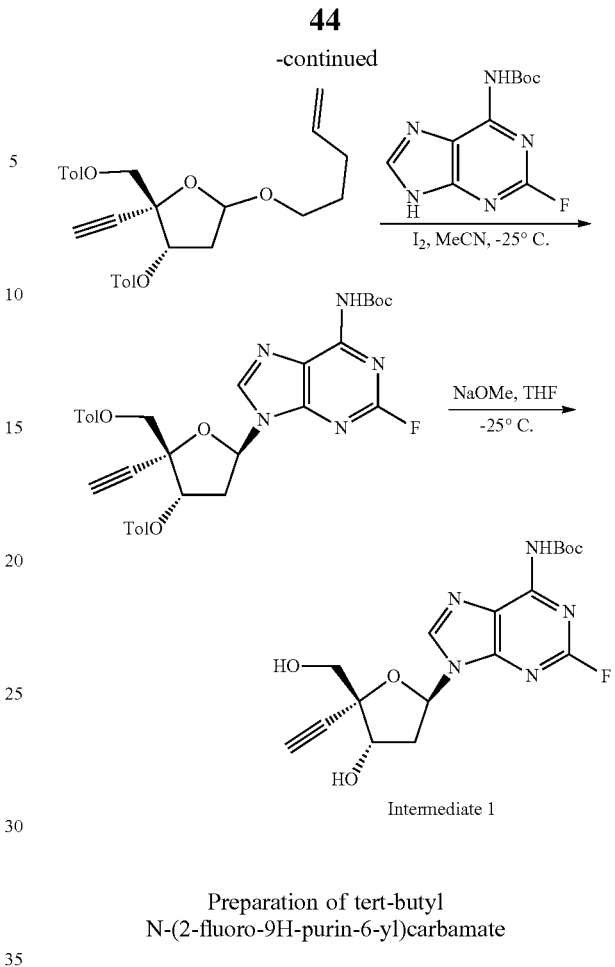

Intermediate 1

Preparation of tert-butyl N-(2-fluoro-9H-purin-6-yl)carbamate

To a stirred suspension of 2-fluoro-9H-purin-6-amine (5 g, 32.65 mmol, 1 eq) and DMAP (399 mg, 3.27 mmol, 0.1 eq) in THF (50 mL) at 0° C. was added (Boc)$_2$O (24.94 g, 114.29 mmol, 26.3 mL, 3.5 eq) in THF (25 mL). The resulting suspension was stirred at 10° C. for 16 h, diluted with MTBE (100 mL) and quenched with water (100 mL). The organic layer was separated, washed with aqueous citric acid (10 wt %, 100 mL), water (2×100 mL) and saturated aqueous sodium chloride (100 mL). The organic layer was concentrated under reduced pressure to give tert-butyl N-tert-butoxycarbonyl-N-(2-fluoro-9H-purin-6-yl)carbamate (11.5 g, crude) as a yellow oil, which was used for next reaction without further purification.

To a mixture of tert-butyl N-tert-butoxycarbonyl-N-(2-fluoro-9H-purin-6-yl)carbamate (11.5 g, 32.55 mmol, 1 eq) in EtOH (100 mL) at 20° C. was added NaOH (2.5 M, 78.1 mL, 6 eq) over 30 min and the resulting mixture was stirred for 48 h at 20° C. LCMS showed one main peak with desired m/z was detected. The mixture was worked up and solvents were distilled under reduced pressure, the aqueous solution was cooled to 0° C. and neutralized with hydrochloric acid (1 M, 150 mL) to give the slurry. The solid was collected by filtration and dissolved in EtOAc (200 mL), washed with water (2×150 mL) and saturated aqueous sodium chloride (150 mL). The resulting solution was concentrated under reduced pressure to give tert-butyl N-(2-fluoro-9H-purin-6-yl)carbamate (4 g, 15.80 mmol, 48.5% yield) as a white solid. The crude product was used for the next reaction without further purification. LCMS (ESI) m/z, $C_{10}H_{12}FN_5O_2$: calculated 253.1, found (M+H)$^+$: 253.9; (M+Na)$^+$: 275.9.

Preparation of [(2R,3S)-2-ethynyl-3-(4-methylbenzoyl)oxy-5-pent-4-enoxy-tetrahydrofuran-2-yl]methyl 4-methylbenzoate

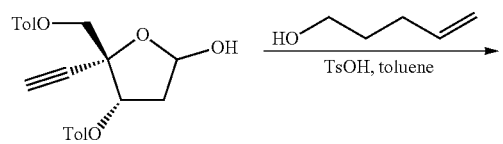

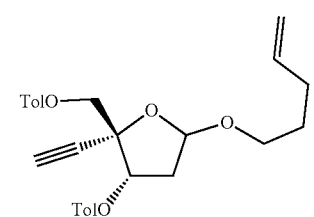

To a stirred solution of 4-methylbenzenesulfonic acid hydrate (964 mg, 5.07 mmol, 1 eq) and pent-4-en-1-ol (480 mg, 5.58 mmol, 1.1 eq) in toluene (28 mL) at 0° C. was added a solution of [(2R,3S)-2-ethynyl-5-hydroxy-3-(4-methylbenzoyl)oxy-tetrahydrofuran-2-yl]methyl 4-methylbenzoate (2 g, 5.07 mmol, 1 eq) in toluene (32 mL). The reaction mixture was stirred at 0° C. for 1 h. The reaction was quenched with water (100 mL). The organic layer was separated, washed with saturated aqueous sodium bicarbonate (100 mL), water (100 mL) and saturated aqueous sodium chloride (100 mL). The organic layer was concentrated under reduced pressure. The crude product was purified by flash silica gel chromatography (ISCO®; 40 g SepaFlash® Silica Flash Column, Eluent of 0~8% ethyl acetate/petroleum ether gradient@40 mL/min) to give [(2R,3S)-2-ethynyl-3-(4-methylbenzoyl)oxy-5-pent-4-enoxy-tetrahydrofuran-2-yl]methyl 4-methylbenzoate (1.38 g, 58.2% yield) as colorless oil. LCMS (ESI) m/z, $C_{28}H_{30}O_6$: calculated 462.2, found (M+Na)$^+$: 485.1.

Preparation of [(2R,3S,5R)-5-[6-(tert-butoxycarbonylamino)-2-fluoro-purin-9-yl]-2-ethynyl-3-(4-methylbenzoyl)oxytetrahydrofuran-2-yl]methyl 4-methylbenzoate

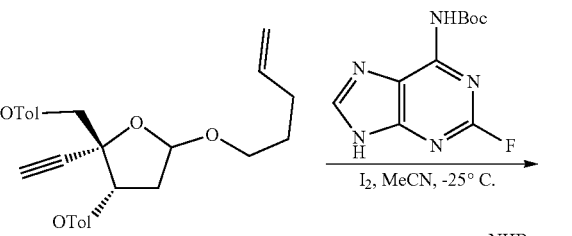

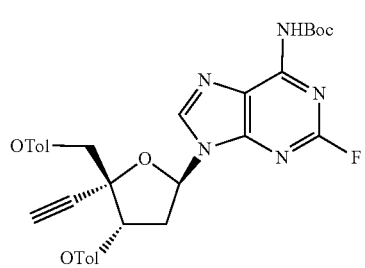

A mixture of [(2R,3S)-2-ethynyl-3-(4-methylbenzoyl)oxy-5-pent-4-enoxy-tetrahydrofuran-2-yl]methyl 4-methylbenzoate (200 mg, 0.43 mmol, 1 eq), tert-butyl N-(2-fluoro-9H-purin-6-yl)carbamate (131 mg, 0.52 mmol, 1.2 eq) and 4 Å MS (1 g, 0.32 mmol) in MeCN (4 mL) was cooled to −25° C. $I_2$ (351 mg, 1.38 mmol, 3.2 eq) was added and the resulting mixture was stirred for 16 h under a nitrogen atmosphere at −25° C. The reaction mixture was then warmed to 0° C. and stirred at 0° C. for 2 h. The reaction was quenched with aqueous sodium sulfite (10 mL), diluted with water (10 mL), and then extracted with MTBE (30 mL). The resulting organic layers were washed with aqueous sodium bicarbonate (10 mL) and then with aqueous sodium chloride (10 mL). The organic layer was then concentrated under reduced pressure and purified by flash silica gel chromatography (ISCO®; 4 g SepaFlash® Silica Flash Column, Eluent of 0~50% ethyl acetate/petroleum ether gradient@20 mL/min) to give [(2R,3S,5R)-5-[6-(tert-butoxycarbonylamino)-2-fluoro-purin-9-yl]-2-ethynyl-3-(4-methylbenzoyl)oxytetrahydrofuran-2-yl]methyl 4-methylbenzoate (155 mg, 50.0% yield) as a white solid. LCMS (ESI) m/z, $C_{35}H_{32}FN_5O_7$: calculated 629.2, found (M+H)$^+$: 630.1.

Preparation of tert-butyl N-[9-[(2R,4S,5R)-5-ethynyl-4-hydroxy-5-(hydroxymethyl)tetrahydrofuran-2-yl]-2-fluoro-purin-6-yl]carbamate

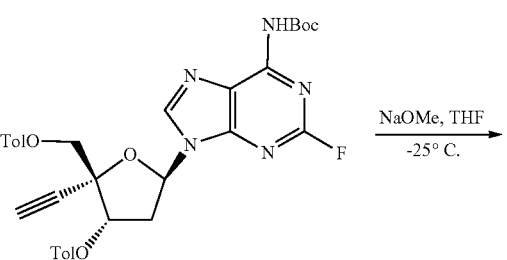

47

-continued

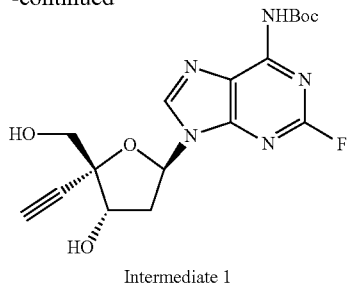

Intermediate 1

To a mixture of [(2R,3S,5R)-5-[6-(tert-butoxycarbonylamino)-2-fluoro-purin-9-yl]-2-ethynyl-3-(4-methylbenzoyl)oxytetrahydrofuran-2-yl]methyl 4-methylbenzoate (155 mg, 0.246 mmol, 1 eq) in THF (1 mL) at −25° C. was added NaOMe (133 mg, 0.739 mmol, 30%, 3 eq) in MeOH (0.5 mL) and the resulting mixture was stirred for 6 h at −25° C. The mixture was then neutralized with AcOH (0.2 mL) and concentrated under reduced pressure. The residue was purified by flash silica gel chromatography (ISCO®; 12 g SepaFlash® Silica Flash Column, Eluent of 0~5% MeOH/DCM gradient@30 mL/min) to give tert-butyl N-[9-[(2R,4S,5R)-5-ethynyl-4-hydroxy-5-(hydroxymethyl)tetrahydrofuran-2-yl]-2-fluoro-purin-6-yl]carbamate (82 mg, 85.4% yield) as a white solid. LCMS (ESI) m/z, $C_{17}H_{20}FN_5O_5$: calculated 393.1, found $(M+Na)^+$: 416.2.

Intermediate 2 (Method 1)

(2R,3S,5R)-5-(6-amino-2-fluoro-purin-9-yl)-2-ethynyl-2-(hydroxymethyl)tetrahydrofuran-3-ol

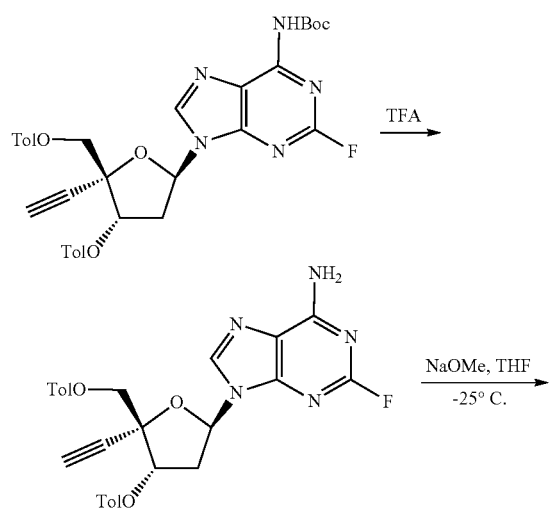

Intermediate 2
Method 1

48

Preparation of [(2R,3S,5R)-5-(6-amino-2-fluoro-purin-9-yl)-2-ethynyl-3-(4-methylbenzoyl)oxy-tetrahydrofuran-2-yl]methyl 4-methylbenzoate

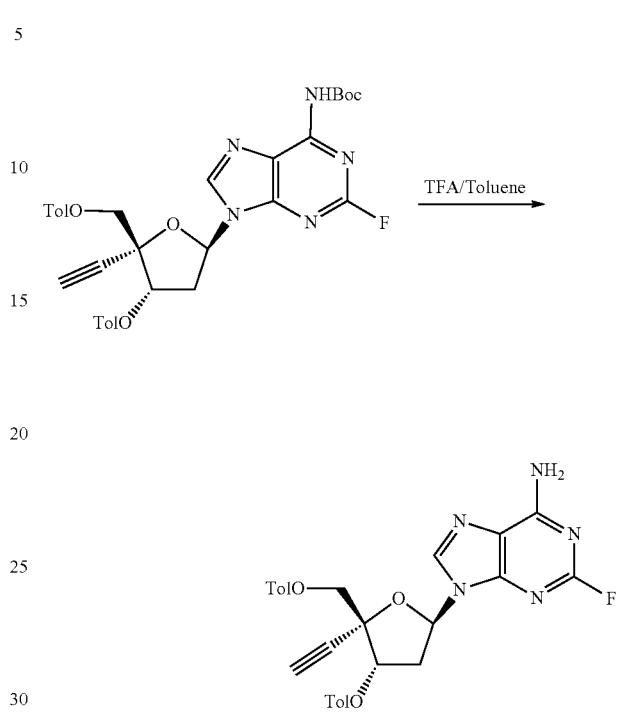

To a solution of (2R,3S,5R)-5-(6-((tert-butoxycarbonyl)amino)-2-fluoro-9H-purin-9-yl)-2-ethynyl-2-(((4-methylbenzoyl)oxy)methyl)tetrahydrofuran-3-yl 4-methylbenzoate (220 mg, 0.35 mmol, 1 eq) in toluene (2.5 mL) was added TFA (0.25 mL) at 10° C. The mixture was stirred at 10° C. for 48 h. The mixture was quenched by the addition of saturated sodium hydrogen carbonate (10 mL) and extracted with EtOAc (2×10 mL). The organic layer was concentrated. The resulting residue was purified by flash silica gel chromatography (ISCO®; 4 g SepaFlash® Silica Flash Column, Eluent of 0~100% ethyl acetate/petroleum ether gradient@20 mL/min) to give (2R,3S,5R)-5-(6-amino-2-fluoro-9H-purin-9-yl)-2-ethynyl-2-(((4-methylbenzoyl)oxy)methyl)tetrahydrofuran-3-yl 4-methylbenzoate (130 mg, 70% yield) as a white solid. LCMS (ESI) m/z for $C_{28}H_{24}FN_5O_5$: calculated 529.5, found $(M+Na)^+$:552.1.

Preparation of (2R,3S,5R)-5-(6-amino-2-fluoro-purin-9-yl)-2-ethynyl-2-(hydroxymethyl)tetrahydrofuran-3-ol

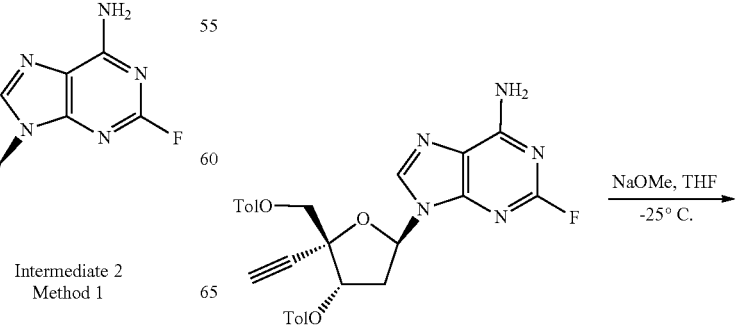

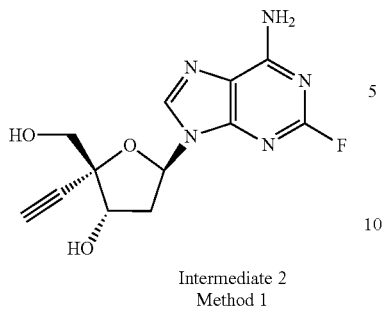

Intermediate 2
Method 1

The mixture of (2R,3S,5R)-5-(6-amino-2-fluoro-9H-purin-9-yl)-2-ethynyl-2-(((4-methylbenzoyl)oxy)methyl)tetrahydrofuran-3-yl 4-methylbenzoate (130 mg, 0.246 mmol, 1 eq) in THF (1 mL) was cooled to −25° C. Then NaOMe (133 mg, 0.737 mmol, 30% purity, 3 eq) in MeOH (0.5 mL) was added and the mixture was stirred for 3 h at −25° C. The mixture was neutralized with AcOH (0.2 mL) and the mixture was concentrated. The resulting residue was purified by flash silica gel chromatography (ISCO®; 4 g SepaFlash® Silica Flash Column, Eluent of 0~8% MeOH/DCM gradient@20 mL/min) to give (2R,3S,5R)-5-(6-amino-2-fluoro-purin-9-yl)-2-ethynyl-2-(hydroxymethyl)tetrahydrofuran-3-ol (46 mg, 64% yield) as a white solid. LCMS (ESI) m/z for $C_{12}H_{12}FN_5O_3$: calculated 293.2, found (M+H)+: 294.1. $^1$H NMR (DMSO-d6, 400 MHz) δ (ppm) 8.30 (s, 1H), 7.89 (br s, 2H), 6.24 (dd, J=7.2, 5.2 Hz, 1H), 5.58 (d, J=5.6 Hz, 1H), 5.30 (t, J=6.4 Hz, 1H), 4.52-4.61 (m, 1H), 3.62-3.68 (m, 1H), 3.55 (dd, J=12.0, 6.8 Hz, 1H), 3.52 (s, 1H), 2.64-2.75 (m, 1H), 2.37-2.47 (m, 1H). $^{19}$F NMR (DMSO-d6, 376 MHz) δ (ppm) −51.98 (br s, 1F).

Intermediate 2 (Method 2)

(2R,3S,5R)-5-(6-amino-2-fluoro-purin-9-yl)-2-ethynyl-2-(hydroxymethyl)tetrahydrofuran-3-ol

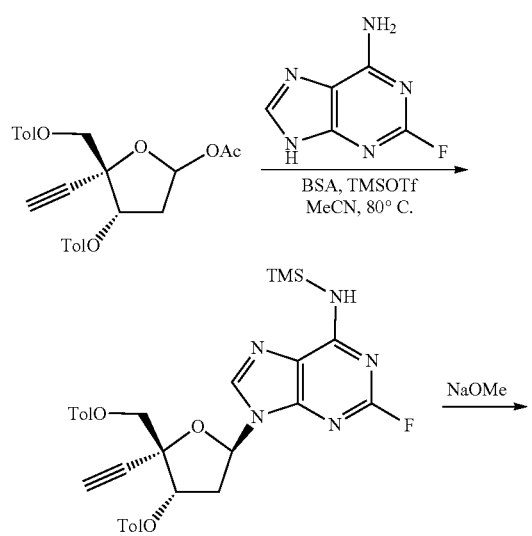

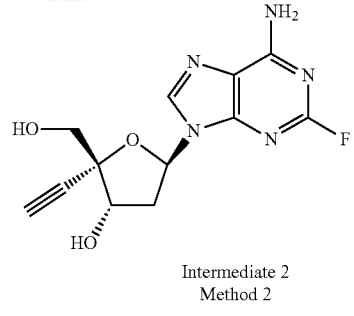

Intermediate 2
Method 2

Preparation of (2R,3S,5R)-2-ethynyl-5-(2-fluoro-6-(((trimethylsilyl)amino)-9H-purin-9-yl)-2-(((4-methylbenzoyl)oxy)methyl)tetrahydrofuran-3-yl 4-methylbenzoate

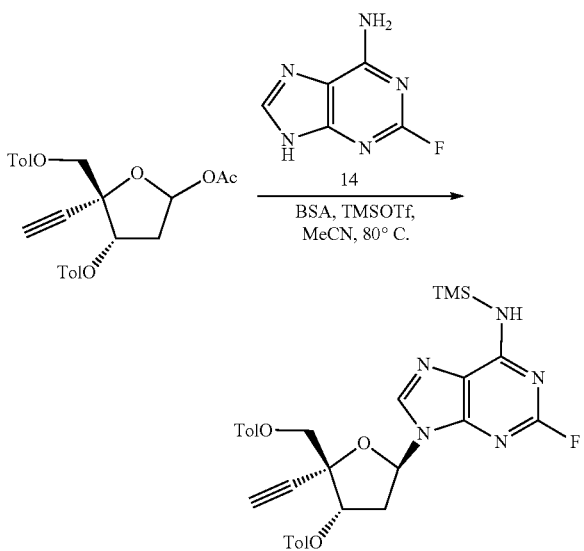

The CaH$_2$ was added to acetonitrile and refluxed for 2 h, then steamed out under the protection of nitrogen to give anhydrous CH$_3$CN.

To a solution of 2-fluoro-9H-purin-6-amine (4.39 g, 28.64 mmol, 1.25 eq) in anhydrous CH$_3$CN (60 mL) was added BSA (13.98 g, 68.74 mmol, 16.99 mL, 3 eq) under N$_2$. The mixture was stirred at 80° C. for 1 h. After the reaction mixture was cooled to 25° C., the TMSOTf (6.11 g, 27.49 mmol, 4.97 mL, 1.2 eq) was added and the reaction mixture was stirred at 25° C. for 1 h, then [(2R,3S)-5-acetoxy-2-ethynyl-3-(4-methylbenzoyl)oxy-tetrahydrofuran-2-yl] methyl 4-methylbenzoate (10 g, 22.91 mmol, 1 eq) in anhydrous CH$_3$CN (60 mL) was added over 1 h at 80° C. and the mixture was stirred at 80° C. for 16 h under N$_2$. Cooled the reaction mixture to room temperature (15° C.) and still standing for 24 h. The slurry was filtered and washed with cold anhydrous MeCN (10 mL), the mixture was dried under vacuum to give [(2R,3S,5R)-2-ethynyl-5-[2-fluoro-6-(trimethylsilylamino)purin-9-yl]-3-(4-methylbenzoyl)oxy-tetrahydrofuran-2-yl]methyl 4-methylbenzoate (6.58 g, 47.7% yield) as a white solid. $^1$H NMR (400 MHz, CDCl$_3$) δ (ppm) 8.02 (d, J=8.0 Hz, 2H), 7.93 (d, J=8.0 Hz, 2H), 7.86 (s, 1H), 7.29 (d, J=8.0 Hz, 2H), 7.23 (d, J=8.0 Hz, 2H), 6.51 (t, J=12

Hz, 1H), 6.05 (m, 1H), 4.82 (d, J=20 Hz, 1H), 4.67 (d, J=20 Hz, 1H), 3.23-3.19 (m, 1H), 2.90-2.85 (m, 1H), 2.68 (s, 1H), 2.43 (d, J=16 Hz, 6H), 0.49-0.29 (m, 9H). $^{19}$F NMR (376 MHz, CDCl$_3$) δ (ppm) −49.34 (s, 1F).

Preparation of (2R,3S,5R)-5-(6-amino-2-fluoro-purin-9-yl)-2-ethynyl-2-(hydroxymethyl) tetrahydrofuran-3-ol

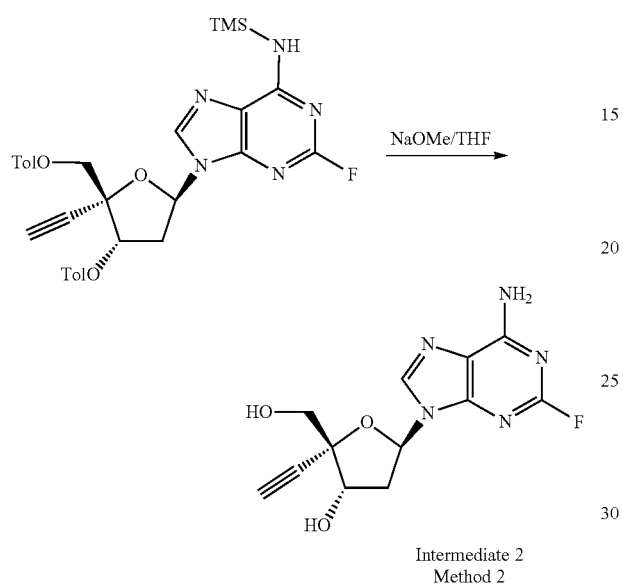

Intermediate 2
Method 2

To a solution of [(2R,3S,5R)-2-ethynyl-5-[2-fluoro-6-(trimethylsilylamino)purin-9-yl]-3-(4-methylbenzoyl)oxy-tetrahydrofuran-2-yl]methyl 4-methylbenzoate (15.5 g, 25.76 mmol, 1 eq) in THF (150 mL) was added NaOMe (6.96 g, 38.64 mmol, 30% purity, 1.5 eq) slowly at −25° C., the reaction mixture was stirred at −25° C. for 16 h. The mixture was neutralized with AcOH (0.5 mL) to pH~7 and the mixture was concentrated. The crude product was triturated with CH$_3$CN:H$_2$O=7:3 (100 mL) at 5° C. for 16 h to give (2R,3S, 5R)-5-(6-amino-2-fluoro-purin-9-yl)-2-ethynyl-2-(hydroxymethyl) tetrahydrofuran-3-ol (6.76 g, 89%) as a white solid. LCMS (ESI) m/z for C$_{12}$H$_{12}$FN$_5$O$_3$: calculated 293.2, found (M+H)$^+$: 294.1. $^1$H NMR (400 MHz, CD$_3$CN) δ (ppm) 7.99 (s, 1H), 6.35 (br s, 2H), 6.29 (t, J=12 Hz, 1H), 4.65 (t, J=5.6 Hz, 1H), 4.41 (br s, 1H), 3.81-3.78 (m, 1H), 3.71-3.68 (m, 1H), 3.55 (br s, 1H), 2.93 (s, 1H), 2.82-2.77 (m, 1H), 2.49-2.45 (m, 1H). $^{19}$F NMR (376 MHz, CD$_3$CN) δ (ppm) −53.4 (s, 1F).

Intermediate 3

(2R,3S,5R)-5-(6-amino-2-fluoro-purin-9-yl)-4,4-dideuterio-2-ethynyl-2-(hydroxymethyl)tetrahydrofuran-3-ol

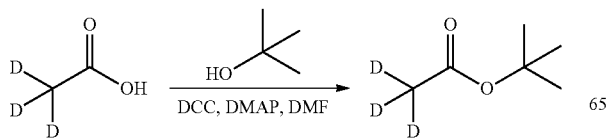

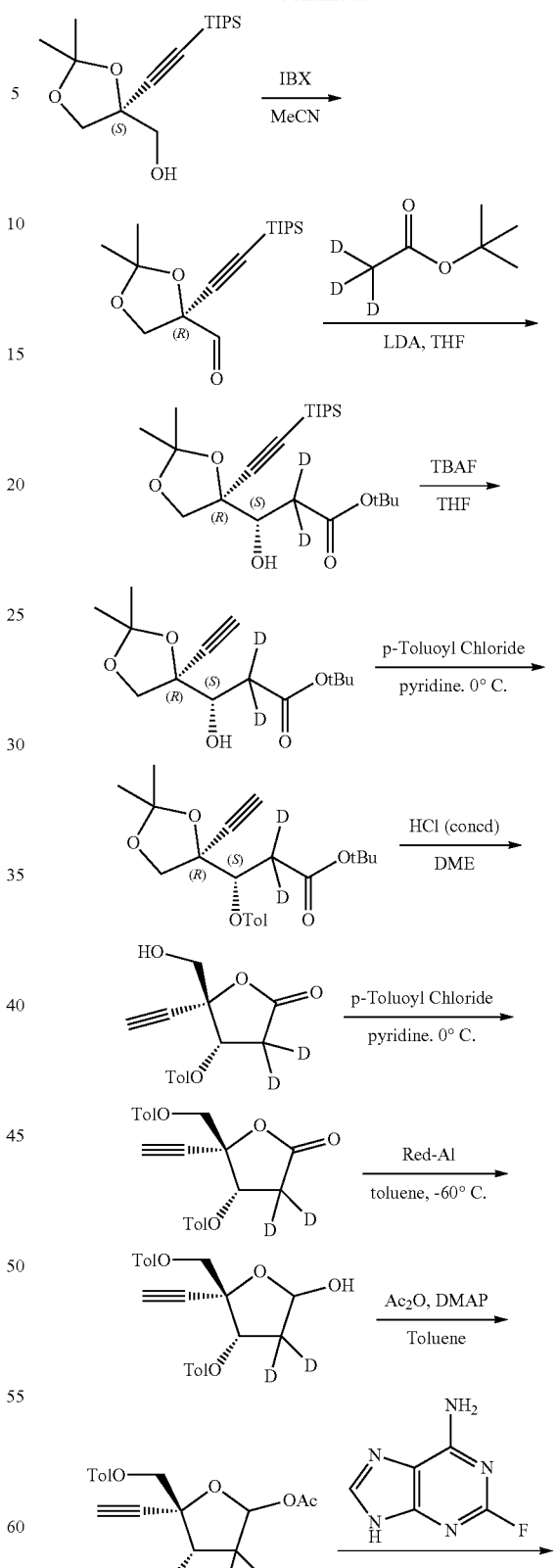

-continued

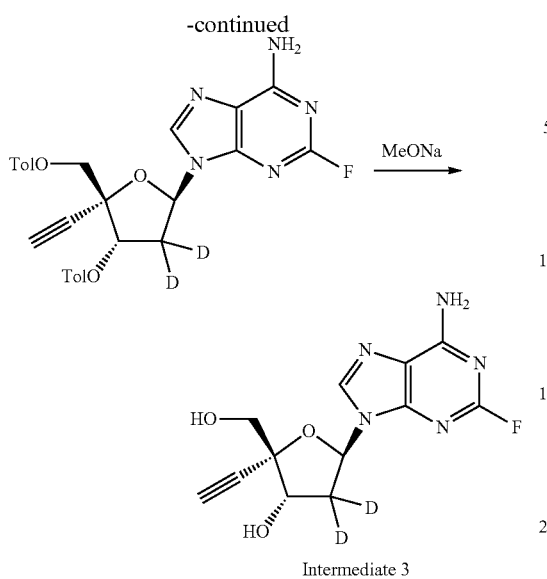

Intermediate 3

Preparation of tert-butyl 2,2,2-trideuterioacetate

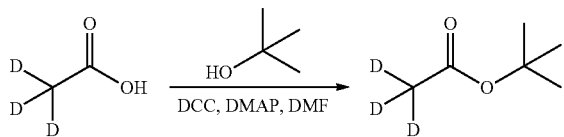

To a mixture of 2-methylpropan-2-ol (40 g, 539.66 mmol, 51.61 mL, 1 eq) and deuterio 2,2,2-trideuterioacetate (51.87 g, 809.49 mmol, 1.5 eq) in DMF (700 mL) was added DCC (167.02 g, 809.49 mmol, 1.5 eq) and DMAP (13.19 g, 107.93 mmol, 0.2 eq), the mixture was stirred at 25° C. for 64 h. The reaction mixture was distilled in vacuum (105° C., 0.1 MPa) to give tert-butyl 2,2,2-trideuterioacetate (25.3 g, 39.3% yield) as a colorless liquid. $^1$H NMR (400 MHz, CDCl$_3$) δ (ppm) 1.45 (s, 9H).

Preparation of (4R)-2,2-dimethyl-4-(2-triisopropylsilylethynyl)-1,3-dioxolane-4-carbaldehyde

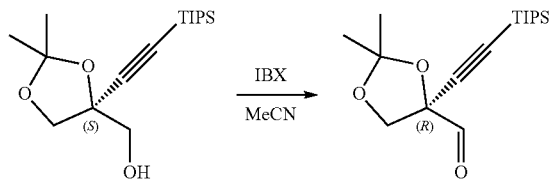

To a solution of [(4S)-2,2-dimethyl-4-(2-triisopropylsilylethynyl)-1,3-dioxolan-4-yl]methanol (40.2 g, 128.63 mmol, 1 eq) in MeCN (220 mL) was added IBX (108.06 g, 385.90 mmol, 3 eq). The mixture was stirred at 85° C. for 2 h. The mixture was filtered and concentrated to give (4R)-2,2-dimethyl-4-(2-triisopropylsilylethynyl)-1,3-dioxolane-4-carbaldehyde (40 g, crude) as a yellow oil.

Preparation of tert-butyl (3S)-2,2-dideuterio-3-[(4R)-2,2-dimethyl-4-(2-triisopropylsilylethynyl)-1,3-dioxolan-4-yl]-3-hydroxy-propanoate

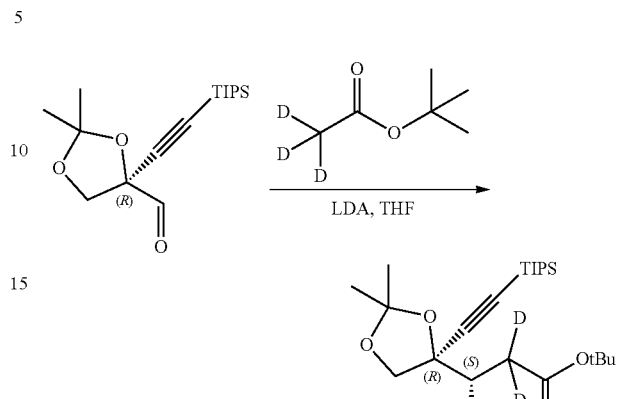

LDA (2 M in THF, 24.15 mL, 1.5 eq) was added to the solution of THF (45 mL) at −78° C., tert-butyl 2,2,2-trideuterioacetate (6.14 g, 51.53 mmol, 1.6 eq) was added at −78° C. and the mixture was stirred at −78° C. for 1 h, (4R)-2,2-dimethyl-4-(2-triisopropylsilylethynyl)-1,3-dioxolane-4-carbaldehyde (10 g, 32.21 mmol, 1 eq) in THF (30 mL) was added at −78° C., then the mixture was stirred at −78° C. for 2 h. D20 (20 mL) was added, then the mixture was extracted with Ethyl acetate (200 mL×2). The combined organic layers were washed with brine (100 mL), dried over Na$_2$SO$_4$, filtered and concentrated. The resulting residue was purified by flash silica gel chromatography (ISCO®; 330 g SepaFlash® Silica Flash Column, eluted with 0~70% DCM/petroleum ether gradient@75 mL/min) to give tert-butyl (3S)-2,2-dideuterio-3-[(4R)-2,2-dimethyl-4-(2-triisopropylsilylethynyl)-1,3-dioxolan-4-yl]-3-hydroxy-propanoate (5.17 g, 37.5% yield) as a colorless oil. $^1$H NMR (400 MHz, CDCl$_3$) δ (ppm) 4.22 (d, J=8.8 Hz, 1H), 4.11 (d, J=8.4 Hz, 1H), 4.01 (d, J=4.8 Hz, 1H), 2.71 (d, J=5.2 Hz, 1H), 1.60 (s, 3H), 1.48 (s, 9H), 1.42 (s, 3H), 1.08 (s, 21H).

Preparation of tert-butyl (3S)-2,2-dideuterio-3-[(4R)-4-ethynyl-2,2-dimethyl-1,3-dioxolan-4-yl]-3-hydroxy-propanoate

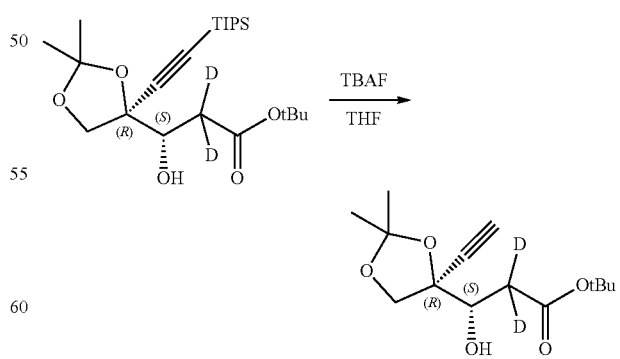

To a solution of tert-butyl (3S)-2,2-dideuterio-3-[(4R)-2,2-dimethyl-4-(2-triisopropylsilylethynyl)-1,3-dioxolan-4-yl]-3-hydroxy-propanoate (13 g, 30.33 mmol, 1 eq) in THF (130 mL) was added TBAF (1 M in THF, 30.33 mL, 1 eq)

at 0° C. The mixture was stirred at 25° C. for 1 h. Ethyl acetate (100 mL) and H$_2$O (100 mL) was added, then the mixture was extracted with ethyl acetate (100 mL×2). The combined organic layers were washed with brine (100 mL), dried over Na$_2$SO$_4$, filtered and concentrated. The resulting residue was purified by flash silica gel chromatography (ISCO®; 120 g SepaFlash® Silica Flash Column, eluted with 0~15% ethyl acetate/petroleum ether gradient@60 mL/min) to give tert-butyl (3S)-2,2-dideuterio-3-[(4R)-4-ethynyl-2,2-dimethyl-1,3-dioxolan-4-yl]-3-hydroxy-propanoate (6.7 g, 81.1% yield) as a light yellow oil. $^1$H NMR (400 MHz, CDCl$_3$) δ(ppm) 4.26 (d, J=8.8 Hz, 1H), 4.16 (d, J=8.4 Hz, 1H), 3.96 (d, J=4.0 Hz, 1H), 3.24-3.20 (m, 1H), 2.55 (s, 1H), 1.62 (s, 3H), 1.50 (s, 9H), 1.42 (s, 3H).

Preparation of [(1S)-3-tert-butoxy-2,2-dideuterio-1-[(4R)-4-ethynyl-2,2-dimethyl-1,3-dioxolan-4-yl]-3-oxo-propyl] 4-methylbenzoate

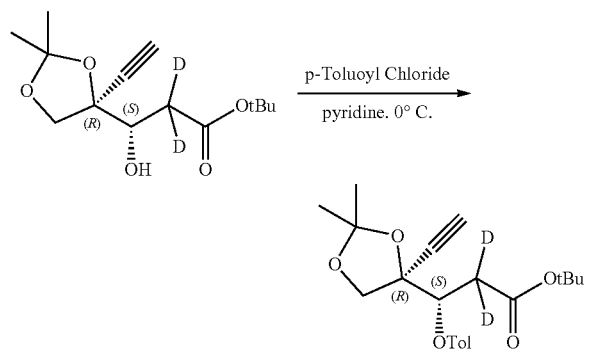

To a solution of 4-methylbenzoyl chloride (5.71 g, 36.90 mmol, 4.88 mL, 1.5 eq) in pyridine (60 mL) was added tert-butyl (3S)-2,2-dideuterio-3-[(4R)-4-ethynyl-2,2-dimethyl-1,3-dioxolan-4-yl]-3-hydroxy-propanoate (6.7 g, 24.60 mmol, 1 eq). The mixture was stirred at 0° C. for 16 h. The ice water (15 mL) was added, then the mixture was stirred at 0° C. for 15 min. The mixture was filtered. The resulting residue was purified by flash silica gel chromatography (ISCO®; 80 g SepaFlash® Silica Flash Column, eluted with 0~100% ethyl acetate/petroleum ether gradient@60 mL/min) to give [(1S)-3-tert-butoxy-2,2-dideuterio-1-[(4R)-4-ethynyl-2,2-dimethyl-1,3-dioxolan-4-yl]-3-oxo-propyl]4-methylbenzoate (9.2 g, 95.8% yield) as a colorless oil.

Preparation of [(2R,3S)-4,4-dideuterio-2-ethynyl-2-(hydroxymethyl)-5-oxo-tetrahydrofuran-3-yl] 4-methylbenzoate

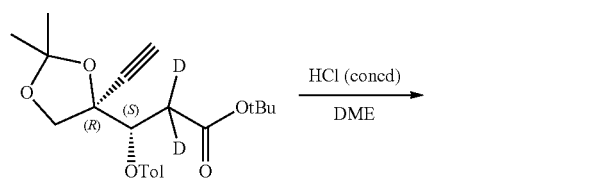

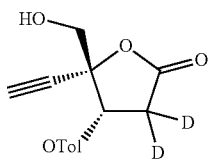

To a solution of [(1S)-3-tert-butoxy-2,2-dideuterio-1-[(4R)-4-ethynyl-2,2-dimethyl-1,3-dioxolan-4-yl]-3-oxo-propyl]4-methylbenzoate (9.2 g, 23.56 mmol, 1 eq) in DME (90 mL) was added HCl (conc.) (7.16 g, 70.68 mmol, 7.02 mL, 36% purity, 3 eq). The mixture was stirred at 50° C. for 16 h. The mixture was concentrated. The resulting residue was purified by flash silica gel chromatography (ISCO®; 25 g SepaFlash® Silica Flash Column, eluted with 0~30% ethyl acetate/petroleum ether gradient@30 mL/min) to give [(2R, 3S)-4,4-dideuterio-2-ethynyl-2-(hydroxymethyl)-5-oxo-tetrahydrofuran-3-yl]4-methylbenzoate (6.4 g, 98.3% yield) as a colorless oil.

Preparation of [(2R,3S)-4,4-dideuterio-2-ethynyl-3-(4-methylbenzoyl)oxy-5-oxo-tetrahydrofuran-2-yl] methyl 4-methylbenzoate

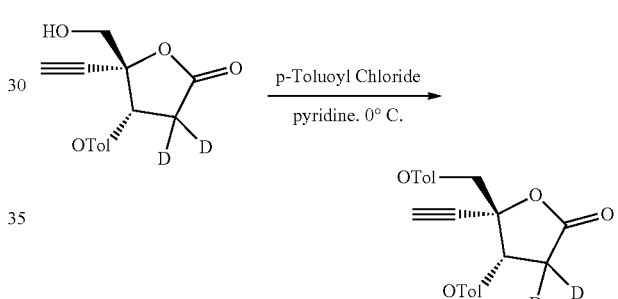

To a mixture of [(2R,3S)-4,4-dideuterio-2-ethynyl-2-(hydroxymethyl)-5-oxo-tetrahydrofuran-3-yl]4-methylbenzoate (2 g, 7.24 mmol, 1 eq) in pyridine (15 mL) was added 4-methylbenzoyl chloride (1.68 g, 10.86 mmol, 1.5 eq). The resulting mixture was stirred at 0° C. for 16 h. Water (50 mL) was added at 0° C., extracted with DCM (2×100 mL). The combined organic layers were dried over Na$_2$SO$_4$, filtered and concentrated. The resulting residue was purified by flash silica gel chromatography (ISCO®; 80 g SepaFlash® Silica Flash Column, eluent with 0~15% ethyl acetate/petroleum ether gradient@60 mL/min) to give [(2R,3S)-4,4-dideuterio-2-ethynyl-3-(4-methylbenzoyl)oxy-5-oxo-tetrahydrofuran-2-yl]methyl 4-methylbenzoate (2.5 g, 87.6% yield) as a white solid.

Preparation of [(2R,3S)-4,4-dideuterio-2-ethynyl-5-hydroxy-3-(4-methylbenzoyl)oxy-tetrahydrofuran-2-yl]methyl 4-methylbenzoate

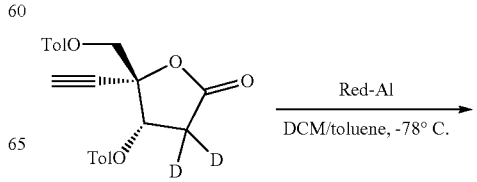

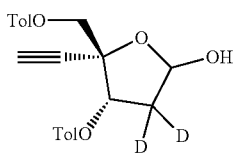

To a solution of [(2R,3S)-4,4-dideuterio-2-ethynyl-3-(4-methylbenzoyl)oxy-5-oxo-tetrahydrofuran-2-yl]methyl 4-methylbenzoate (2.5 g, 6.34 mmol, 1 eq) in DCM (16 mL) and toluene (36 mL) was added sodium bis(2-methoxyethoxy)aluminium hydride (2.75 g, 9.51 mmol, 2.64 mL, 70% purity, 1.5 eq) dropwise at −78° C. The mixture was stirred at −78° C. for 2 h. The reaction was quenched by adding a solution of acetic acid (5 mL) in DCM (20 mL) over 10 min. The reaction mixture was diluted with H₂O (50 mL) and extracted with DCM (50×3 mL), the combined organic layers were washed by brine (50 mL), dried over with Na₂SO₄, filtered and concentrated to give [(2R,3S)-4,4-dideuterio-2-ethynyl-5-hydroxy-3-(4-methylbenzoyl)oxy-tetrahydrofuran-2-yl]methyl 4-methylbenzoate (2.5 g, 99.5% yield) as a light yellow liquid.

Preparation of [(2R,3S)-5-acetoxy-4,4-dideuterio-2-ethynyl-3-(4-methylbenzoyl)oxy-tetrahydrofuran-2-yl]methyl 4-methylbenzoate

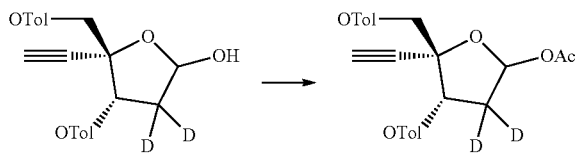

To a mixture of [(2R,3S)-4,4-dideuterio-2-ethynyl-5-hydroxy-3-(4-methylbenzoyl)oxy-tetrahydrofuran-2-yl]methyl 4-methylbenzoate (2.5 g, 6.31 mmol, 1 eq) in toluene (25 mL) was added 4-(dimethylamino)pyridine (131 mg, 1.07 mmol, 0.17 eq) and TEA (747 mg, 7.38 mmol, 1.03 mL, 1.17 eq) at 0° C., then acetic anhydride (644 mg, 6.31 mmol, 0.60 mL, 1 eq) was added. The resulting mixture was stirred at 0° C. for 2 h. The reaction mixture was quenched with H₂O (10 mL). The resulting mixture was warmed to ambient temperature and washed sequentially with aqueous citric acid solution (10 wt %, 30 mL), aqueous sodium bicarbonate solution (5 wt %, 30 mL) and water (30 mL), the organic layer was concentrated. The resulting residue was purified by flash silica gel chromatography (ISCO®; 40 g SepaFlash® Silica Flash Column, eluent with 0~20% ethyl acetate/petroleum ether gradient@30 mL/min) to give [(2R,3 S)-5-acetoxy-4,4-dideuterio-2-ethynyl-3-(4-methylbenzoyl)oxy-tetrahydrofuran-2-yl]methyl 4-methylbenzoate (2.2 g, 79.6% yield) as a colorless oil.

Preparation of [(2R,3S,5R)-5-(6-amino-2-fluoro-purin-9-yl)-4,4-dideuterio-2-ethynyl-3-(4-methylbenzoyl)oxy-tetrahydrofuran-2-yl]methyl 4-methylbenzoate

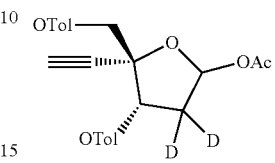

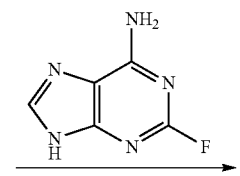

To a solution of 2-fluoro-9H-purin-6-amine (960 mg, 6.27 mmol, 1.25 eq) in MeCN (20 mL) was added Bis(trimethylsilyl)acetamide (3.06 g, 15.05 mmol, 3 eq). The mixture was stirred at 80° C. for 1 h. When the reaction mixture was cooled to 25° C., TMSOTf (1.34 g, 6.02 mmol, 1.09 mL, 1.2 eq) was added and the reaction was stirred at 25° C. for 1 h, then [(2R,3S)-5-acetoxy-4,4-dideuterio-2-ethynyl-3-(4-methylbenzoyl)oxy-tetrahydrofuran-2-yl]methyl 4-methylbenzoate (2.2 g, 5.02 mmol, 1 eq) in MeCN (15 mL) was added over 1 h at 80° C. and the mixture was stirred at 80° C. for 16 h. The DCM (50 mL) and H₂O (50 mL) was added, then the mixture was extracted with DCM (50×2 mL). The combined organic layers were washed with brine (50 mL), dried over Na₂SO₄, filtered and concentrated. The resulting residue was purified by flash silica gel chromatography (ISCO®; 40 g SepaFlash® Silica Flash Column, eluent with 0~40% ethylacetate/DCM @ 30 mL/min) to give [(2R,3S,5R)-5-(6-amino-2-fluoro-purin-9-yl)-4,4-dideuterio-2-ethynyl-3-(4-methylbenzoyl)oxy-tetrahydrofuran-2-yl]methyl 4-methylbenzoate (1.43 g, 53.6% yield) as a light yellow solid.

Preparation of (2R,3S,5R)-5-(6-amino-2-fluoro-purin-9-yl)-4,4-dideuterio-2-ethynyl-2-(hydroxymethyl)tetrahydrofuran-3-ol

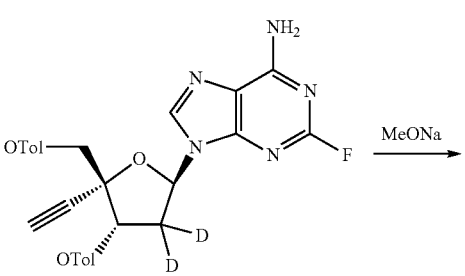

-continued

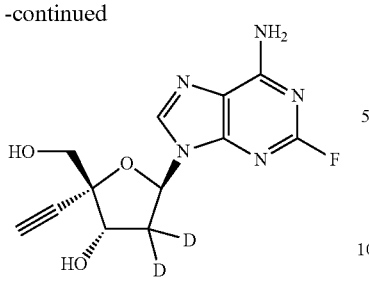

To a mixture of [(2R,3S,5R)-5-(6-amino-2-fluoro-purin-9-yl)-4,4-dideuterio-2-ethynyl-3-(4-methylbenzoyl)oxy-tetrahydrofuran-2-yl]methyl 4-methylbenzoate (1.4 g, 2.63 mmol, 1 eq) in THF (16 mL) was added NaOMe (1.42 g, 7.90 mmol, 30% purity, 3 eq) in MeOH (8 mL). The mixture was stirred at −25° C. for 3 h. The mixture was neutralized with AcOH (0.5 mL) and the mixture was concentrated under reduced pressure to give the residue. The residue was purified by flash silica gel chromatography (ISCO®; 12 g SepaFlash® Silica Flash Column, Eluent with 0~10% methanol/dichloromethane gradient@30 mL/min) to give (2R,3S,5R)-5-(6-amino-2-fluoro-purin-9-yl)-4,4-dideuterio-2-ethynyl-2-(hydroxymethyl)tetrahydrofuran-3-ol (710 mg, 91.3% yield) as a white solid.

Purification of (2R,3S,5R)-5-(6-amino-2-fluoro-purin-9-yl)-4,4-dideuterio-2-ethynyl-2-(hydroxymethyl)tetrahydrofuran-3-ol

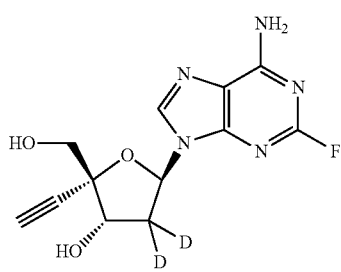 [SMILES: [2H]C1([2H])[C@H](n2cnc3c(N)nc(F)nc32)O[C@](C#C)(CO)[C@H]1O]

(2R,3S,5R)-5-(6-amino-2-fluoro-purin-9-yl)-4,4-dideuterio-2-ethynyl-2-(hydroxymethyl)tetrahydrofuran-3-ol (20 mg, 0.068 mmol, 1 eq) was purified by prep-TLC (SiO2, DCM:MeOH=10:1) to give (2R,3S,5R)-5-(6-amino-2-fluoro-purin-9-yl)-4,4-dideuterio-2-ethynyl-2-(hydroxymethyl)tetrahydrofuran-3-ol (6.2 mg, 31.0% yield) as a white solid. LCMS (ESI) m/z, $C_{12}H_{10}D_2FN_5O_3$: calculated 295.10, found (M+H)$^+$: 296.1. $^1$H NMR (400 MHz, CD$_3$CN) δ ppm 8.01 (s, 1H), 6.40-6.31 (m, 3H), 4.67 (d, J=4.8 Hz, 1H), 4.40-4.37 (m, 1H), 3.84-3.72 (m, 1H), 3.56 (d, J=5.2 Hz, 1H), 2.96 (s, 1H). $^{19}$F NMR (376 MHz, CD$_3$CN) δ ppm −53.40 (s, 1F).

Intermediate 4

(2R,3S,5R)-5-(6-amino-2-fluoro-9H-purin-9-yl)-2-ethynyl-2-(hydroxymethyl-d2)tetrahydrofuran-4,4-d2-3-ol

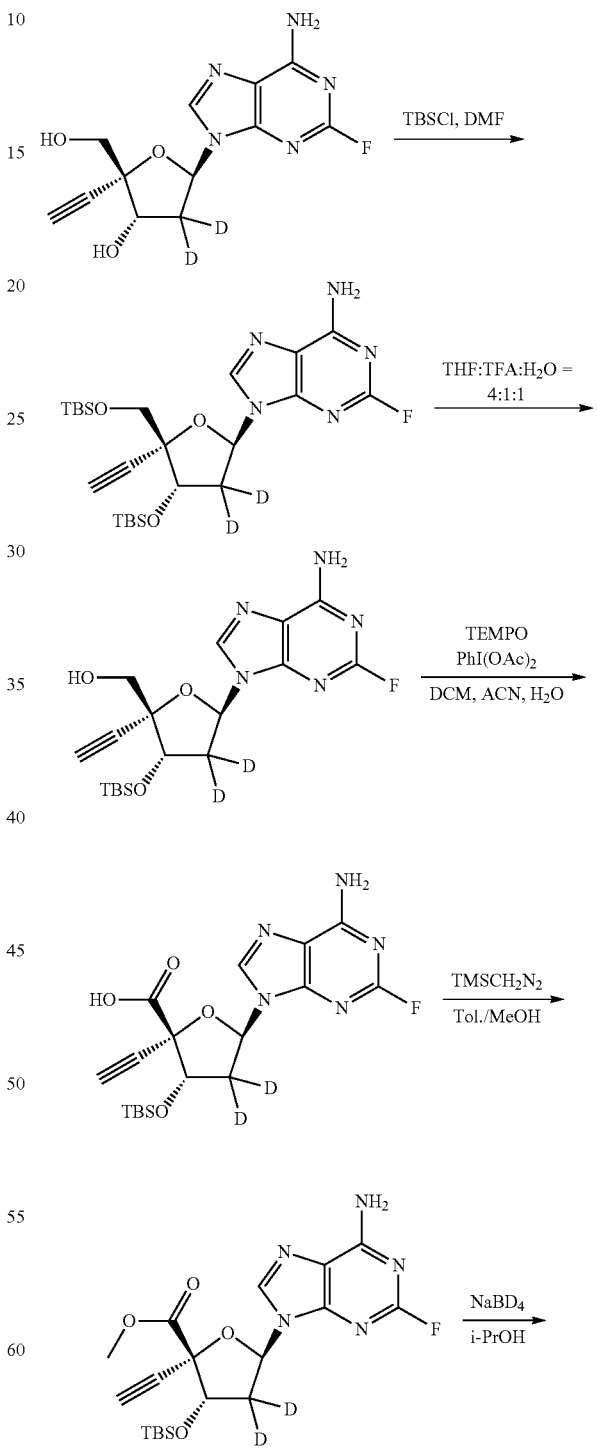

-continued

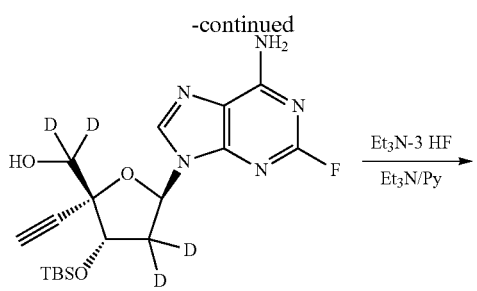

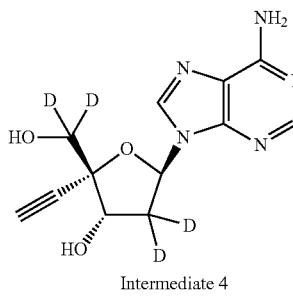

Intermediate 4

Preparation of 9-[(2R,4S,5R)-4-[tert-butyl(dimethyl)silyl]oxy-5-[[tert-butyl(dimethyl)silyl]oxymethyl]-3,3-dideuterio-5-ethynyl-tetrahydrofuran-2-yl]-2-fluoro-purin-6-amine

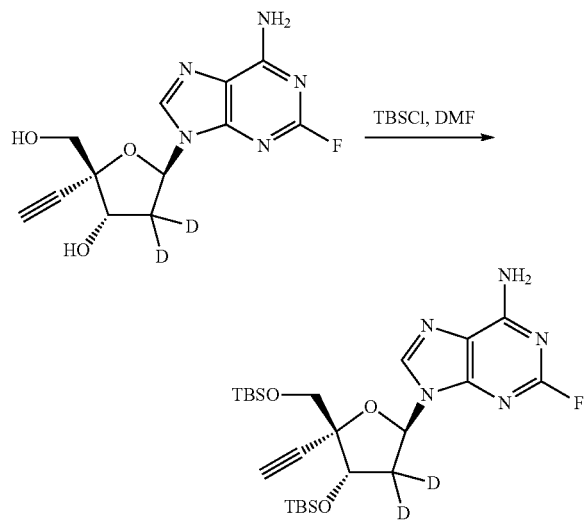

To a mixture of (2R,3S,5R)-5-(6-amino-2-fluoro-purin-9-yl)-4,4-dideuterio-2-ethynyl-2-(hydroxymethyl)tetrahydrofuran-3-ol (690 mg, 2.34 mmol, 1 eq) in DMF (3 mL) was added TBSCl (1.41 g, 9.36 mmol, 1.15 mL, 4 eq) and 1H-imidazole (956 mg, 14.04 mmol, 6 eq). The mixture was stirred at 25° C. for 16 h. The mixture was concentrated and diluted with $H_2O$ (30 mL) and extracted with EtOAc (30×3 mL). The combined organic layers were washed by brine (50 mL), dried over $Na_2SO_4$, filtered and concentrated. The residue was purified by flash silica gel chromatography (ISCO®; 4 g SepaFlash® Silica Flash Column, eluent with 0~10% methanol/dichloromethane gradient@20 mL/min) to give 9-[(2R,4S,5R)-4-[tert-butyl(dimethyl)silyl]oxy-5-[[tert-butyl(dimethyl)silyl]oxymethyl]-3,3-dideuterio-5-ethynyl-tetrahydrofuran-2-yl]-2-fluoro-purin-6-amine (1.1 g, 89.8% yield) as a white solid. LCMS (ESI) m/z for $C_{24}H_{38}D_2FN_5O_3Si_2$: calculated 523.3, found (M+H)+: 524.6.

Preparation of [(2R,3S,5R)-5-(6-amino-2-fluoro-purin-9-yl)-3-[tert-butyl(dimethyl)silyl]oxy-4,4-dideuterio-2-ethynyl-tetrahydrofuran-2-yl]methanol

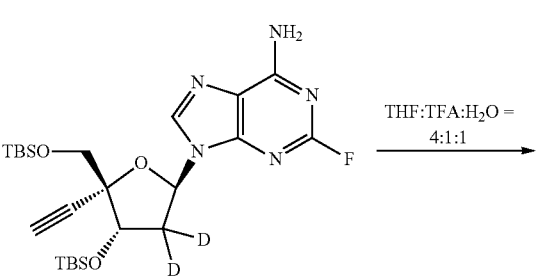

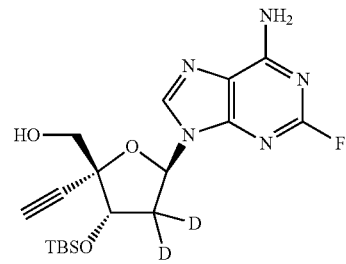

A mixture of 9-[(2R,4S,5R)-4-[tert-butyl(dimethyl)silyl]oxy-5-[[tert-butyl(dimethyl)silyl]oxymethyl]-3,3-dideuterio-5-ethynyl-tetrahydrofuran-2-yl]-2-fluoro-purin-6-amine (1.1 g, 2.10 mmol, 1 eq) in THF (12 mL), $H_2O$ (3 mL), TFA (3 mL). The reaction mixture was stirred at 0° C. for 16 h. The resulting mixture was concentrated. The residue was purified by flash silica gel chromatography (ISCO®; 12 g SepaFlash® Silica Flash Column, eluent with 0~10% ethyl acetate/petroleum ether gradient@30 mL/min) to give [(2R,3S,5R)-5-(6-amino-2-fluoro-purin-9-yl)-3-[tert-butyl(dimethyl)silyl]oxy-4,4-dideuterio-2-ethynyl-tetrahydrofuran-2-yl]methanol (590 mg, 68.6% yield) as a white solid. LCMS (ESI) m/z for $C_{18}H_{24}D_2FN_5O_3Si$: calculated 409.19, found (M+H)+: 410.1.

Preparation of (2S,3S,5R)-5-(6-amino-2-fluoro-purin-9-yl)-3-[tert-butyl(dimethyl)silyl]oxy-4,4-dideuterio-2-ethynyl-tetrahydrofuran-2-carboxylic acid

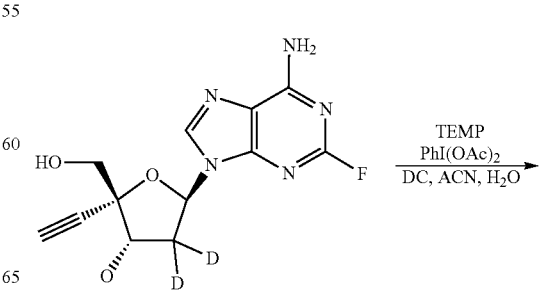

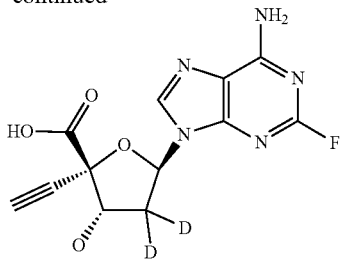

To a mixture of [(2R,3S,5R)-5-(6-amino-2-fluoro-purin-9-yl)-3-[tert-butyl(dimethyl)silyl]oxy-4,4-dideuterio-2-ethynyl-tetrahydrofuran-2-yl]methanol (590 mg, 1.44 mmol, 1 eq) in H₂O (0.05 mL) was added TEMPO (45 mg, 0.29 mmol, 0.2 eq) and PhI(OAc)₂ (557 mg, 1.73 mmol, 1.2 eq). The reaction mixture was stirred at 25° C. for 2 h, then DCM (10 mL) and CH₃CN (0.05 mL) was added. The resulting mixture was stirred at 25° C. for 14 h. The reaction mixture was filtered and the cake was washed by petroleum ether (5 mL), and then concentrated to give (2S,3S,5R)-5-(6-amino-2-fluoro-purin-9-yl)-3-[tert-butyl(dimethyl)silyl]oxy-4,4-dideuterio-2-ethynyl-tetrahydrofuran-2-carboxylic acid (330 mg, 54.1% yield) as a white solid. ¹H NMR (400 MHz, DMSO-d₆) δ (ppm) 8.30 (s, 1H), 7.87 (s, 2H), 6.34 (s, 1H), 4.94 (s, 1H), 3.66 (s, 1H), 0.92 (s, 9H), 0.13-0.12 (d, J=4 Hz, 6H).

Preparation of methyl (2S,3S,5R)-5-(6-amino-2-fluoro-purin-9-yl)-3-[tert-butyl)dimethyl)silyl]oxy-4,4-dideuterio-2-ethynyl-tetrahydrofuran-2-carboxylate

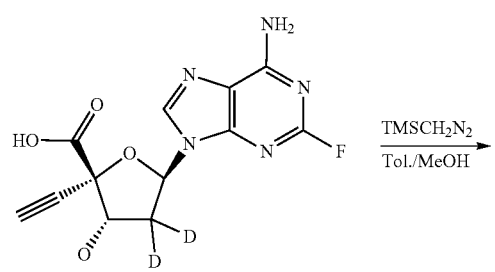

To a mixture of (2S,3S,5R)-5-(6-amino-2-fluoro-purin-9-yl)-3-[tert-butyl(dimethyl)silyl]oxy-4,4-dideuterio-2-ethynyl-tetrahydrofuran-2-carboxylic acid (60 mg, 0.14 mmol, 1 eq) in toluene (4 mL) and MeOH (3.2 mL) was added TMSCHN₂ (2.0 M, 0.22 mL, 3 eq). The reaction mixture was stirred at 25° C. for 2 h. The reaction mixture was concentrated. The resulting residue was purified by flash silica gel chromatography (ISCO®; 4 g SepaFlash® Silica Flash Column, eluent with 0~10% methanol/dichloromethane gradient@20 mL/min) to give methyl (2S,3S,5R)-5-(6-amino-2-fluoro-purin-9-yl)-3-[tert-butyl(dimethyl)silyl]oxy-4,4-dideuterio-2-ethynyl-tetrahydrofuran-2-carboxylate (41 mg, 67% yield) as a white solid. LCMS (ESI) m/z for C₁₉H₂₄D₂FN₅O₄Si: calculated 437.54, found (M+H)⁺: 438.5. ¹H NMR (400 MHz, CDCl₃) δ (ppm) 8.20 (s, 1H), 6.52 (s, 1H), 5.81 (s, 2H), 4.88 (s, 1H), 3.86 (s, 3H), 2.70 (s, 1H), 0.96 (s, 9H), 0.18-0.17 (d, J=4 Hz, 6H). ¹⁹F NMR (376 MHz, CDCl₃) δ (ppm) −50.588 (s, 1F).

Preparation of [(2R,3S,5R)-5-(6-amino-2-fluoro-purin-9-yl)-3-[tert-butyl(dimethyl)silyl]oxy-4,4-dideuterio-2-ethynyl-tetrahydrofuran-2-yl]-dideuterio-methanol

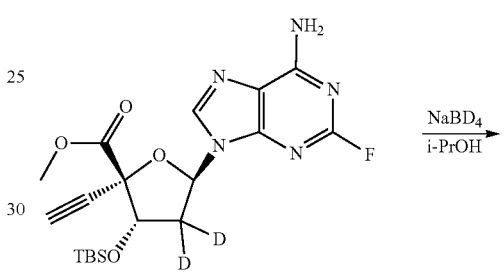

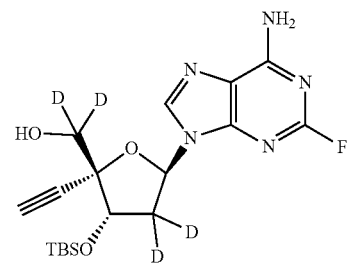

To a mixture of methyl (2S,3S,5R)-5-(6-amino-2-fluoro-purin-9-yl)-3-[tert-butyl(dimethyl)silyl]oxy-4,4-dideuterio-2-ethynyl-tetrahydrofuran-2-carboxylate (150 mg, 0.34 mmol, 1 eq) in i-PrOH (8 mL) was added deuterated sodium borohydride (29 mg, 0.68 mmol, 2 eq) at 0° C. The reaction mixture was stirred at 25° C. for 3 h. The reaction mixture was concentrated. The resulting residue was purified by flash silica gel chromatography (ISCO®; 4 g SepaFlash® Silica Flash Column, eluent with 0~10% methanol/dichloromethane gradient@20 mL/min) to give [(2R,3S,5R)-5-(6-amino-2-fluoro-purin-9-yl)-3-[tert-butyl(dimethyl)silyl]oxy-4,4-dideuterio-2-ethynyl-tetrahydrofuran-2-yl]-dideuterio-methanol (107 mg, 76.4% yield) as a white solid. ¹H NMR (400 MHz, CD₃CN) δ (ppm) 7.98 (s, 1H), 6.38 (s, 2H), 6.27 (s, 1H), 4.78 (s, 1H), 4.28 (s, 1H), 2.86 (s, 1H), 0.94 (s, 9H), 0.15-0.14 (d, J=4 Hz, 6H). ¹⁹F NMR (376 MHz, CD₃CN) δ (ppm) −53.40 (s, 1F).

Preparation of (2R,3S,5R)-5-(6-amino-2-fluoro-purin-9-yl)-4,4-dideuterio-2-[dideuterio(hydroxy)methyl]-2-ethynyl-tetrahydrofuran-3-ol

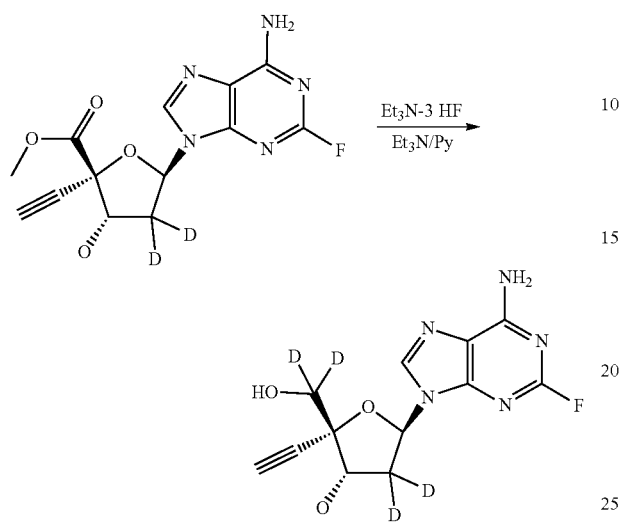

To a mixture of [(2R,3S,5R)-5-(6-amino-2-fluoro-purin-9-yl)-3-[tert-butyl(dimethyl)silyl]oxy-4,4-dideuterio-2-ethynyl-tetrahydrofuran-2-yl]-dideuterio-methanol (180 mg, 0.437 mmol, 1 eq) in pyridine (2.34 g, 29.28 mmol, 2.38 mL, 67 eq) and Et₃N (1.72 g, 17.04 mmol, 2.37 mL, 39 eq) was added N,N-diethylethanamine; trihydrofluoride (4.68 g, 29.06 mmol, 4.74 mL, 66.5 eq) at 0° C. The resulting mixture was stirred at 25° C. for 2 h. The reaction mixture was concentrated. The resulting residue was purified by flash silica gel chromatography (ISCO®; 4 g SepaFlash® Silica Flash Column, eluent with 0~10% methanol/dichloromethane gradient @20 mL/min) to give (2R,3S,5R)-5-(6-amino-2-fluoro-purin-9-yl)-4,4-dideuterio-2-[dideuterio(hydroxy)methyl]-2-ethynyl-tetrahydrofuran-3-ol (80 mg, 61.5% yield) as a white solid. LCMS (ESI) m/z for $C_{12}H_8D_4FN_5O_3$: calculated 297.12, found (M+H)⁺: 298.1. ¹H NMR (400 MHz, DMSO-$d_6$) δ (ppm) 8.30 (s, 1H), 7.85 (s, 2H), 6.23 (s, 1H), 5.57-5.55 (d, J=8 Hz, 1H), 5.25 (s, 1H), 4.56-4.55 (d, J=4 Hz, 1H), 3.51 (s, 1H). ¹⁹F NMR (376 MHz, DMSO-d6) δ (ppm) −51.98 (s, 1F).

Example 1

((2R,3S,5R)-5-(6-amino-2-fluoro-9H-purin-9-yl)-2-ethynyl-3-hydroxytetrahydrofuran-2-yl)methyl isopropylcarbamate

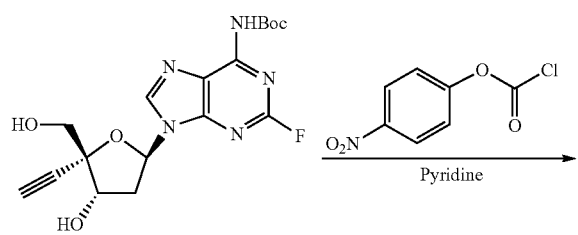

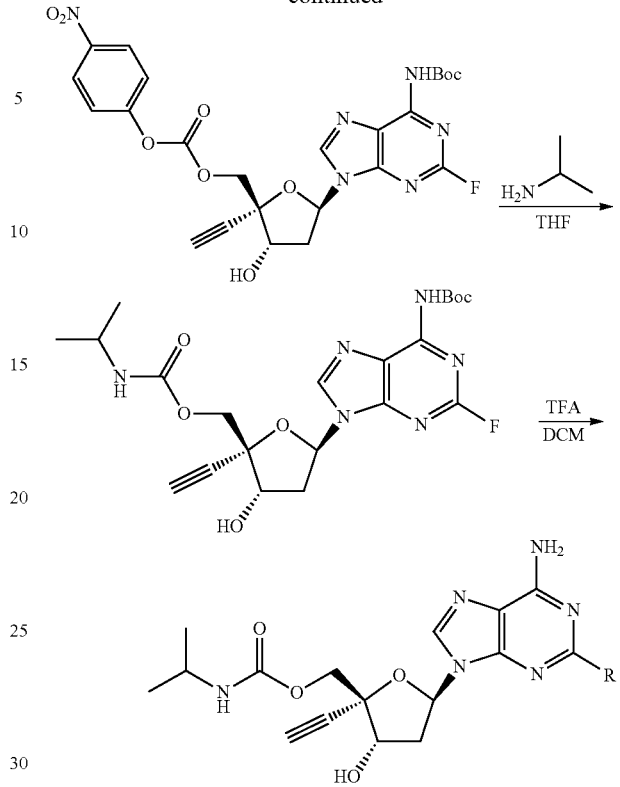

Preparation of [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate

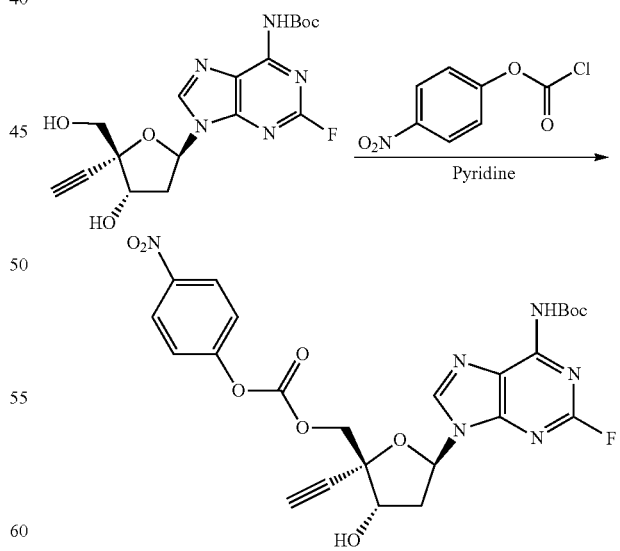

To a solution of tert-butyl N-[9-[(2R,4S,5R)-5-ethynyl-4-hydroxy-5-(hydroxymethyl)tetrahydrofuran-2-yl]-2-fluoro-purin-6-yl]carbamate (80 mg, 0.203 mmol, 1 eq) in pyridine (0.8 mL) at 10° C. was added (4-nitrophenyl) carbonochloridate (41 mg, 0.203 mmol, 1 eq) at 10° C. The mixture was stirred at 10° C. for 16 hr, added water (10 mL) and extracted with EtOAc (10 mL). The organic layers were dried over Na$_2$SO$_4$, filtered and concentrated under reduced pressure to yield the crude product [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate (114 mg, crude) as a yellow oil, which was used for next reaction without further purification. LCMS (ESI) m/z, C$_{24}$H$_{23}$FN$_6$O$_9$: calculated 558.2, measured (M+H)$^+$: 559.1.

Preparation of tert-butyl N-[9-[(2R,4S,5R)-5-ethynyl-4-hydroxy-5-(isopropylcarbamoyloxymethyl)tetrahydrofuran-2-yl]-2-fluoropurin-6-yl]carbamate

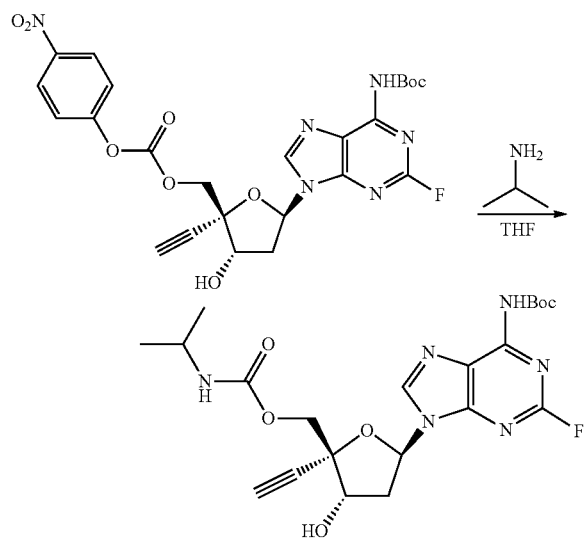

To a mixture of [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate (10 mg, 0.018 mmol, 1 eq) and triethylamine (3.6 mg, 0.035 mmol, 2 eq) in THF (0.5 mL) was added propan-2-amine (1.3 mg, 0.021 mmol, 1.2 eq). The mixture was stirred at 15° C. for 2.5 hr, added water (5 mL) and extracted with EtOAc (2×10 mL). The organic layers were concentrated under reduced pressure. The crude product was purified by prep-HPLC (column: Waters Xbridge Prep OBD C18 150*30 10 u; mobile phase: [water (10 mM NH$_4$HCO$_3$)-ACN]; B %: 15%-45%, 11 min) to give tert-butyl N-[9-[(2R,4S,5R)-5-ethynyl-4-hydroxy-5-(isopropylcarbamoyloxymethyl)tetrahydrofuran-2-yl]-2-fluoropurin-6-yl]carbamate (3.6 mg, 45.0% yield) as a white solid. LCMS (ESI) m/z, C$_{21}$H$_{27}$FN$_6$O$_6$: calculated 478.2, measured (M+H)$^+$: 479.3; (M+Na)$^+$: 501.2.

Preparation of ((2R,3S,5R)-5-(6-amino-2-fluoro-9H-purin-9-yl)-2-ethynyl-3-hydroxytetrahydrofuran-2-yl)methyl isopropylcarbamate

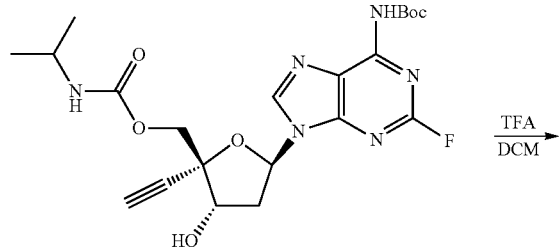

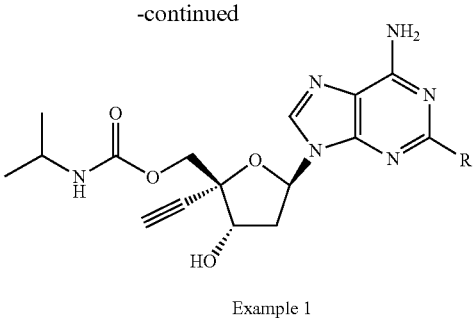

Example 1

To a solution of tert-butyl N-[9-[(2R,4S,5R)-5-ethynyl-4-hydroxy-5-(isopropylcarbamoyloxymethyl)tetrahydrofuran-2-yl]-2-fluoro-purin-6-yl]carbamate (3.6 mg, 0.0075 mmol, 1 eq) in DCM (0.5 mL) was added TFA (77 mg, 0.68 mmol, 0.05 mL, 89.8 eq) at 10° C. The mixture was stirred at 10° C. for 40 hr. The mixture was concentrated under reduced pressure and purified by prep-HPLC (column: Agela DuraShell 150 mm×25 mm×5 um; mobile phase: [water (0.05% HCl)-ACN]; B %: 10%-40%, 8 min) to give ((2R,3S,5R)-5-(6-amino-2-fluoro-9H-purin-9-yl)-2-ethynyl-3-hydroxytetrahydrofuran-2-yl)methyl isopropylcarbamate (1.2 mg, 40.0% yield) as a white solid. LCMS (ESI) m/z, C$_{16}$H$_{19}$FN$_6$O$_4$: calculated 378.2, measured (M+H)$^+$: 379.3; (M+Na)$^+$: 401.2. $^1$H NMR (400 MHz, DMSO-d6) δ (ppm) 8.27 (s, 1H), 7.85 (br s, 2H), 7.13 (br d, J=4.8 Hz, 1H), 6.24 (dd, J=7.6, 5.2 Hz, 1H), 4.55 (br t, J=6.8 Hz, 1H), 4.35 (br d, J=11.6 Hz, 1H), 4.00 (br d, J=11.6 Hz, 1H), 3.61 (s, 1H), 2.70-2.79 (m, 1H), 2.40-2.43 (m, 1H), 0.98-1.07 (m, 7H). $^{19}$F NMR (376 MHz, DMSO-d6) δ (ppm) -51.79 (s).

Example 2

((2R,3S,5R)-5-(6-amino-2-fluoro-9H-purin-9-yl)-2-ethynyl-3-hydroxytetrahydrofuran-2-yl)methyl methylcarbamate Preparation of ((2R,3S,5R)-5-(6-amino-2-fluoro-9H-purin-9-yl)-2-ethynyl-3-hydroxytetrahydrofuran-2-yl)methyl methylcarbamate

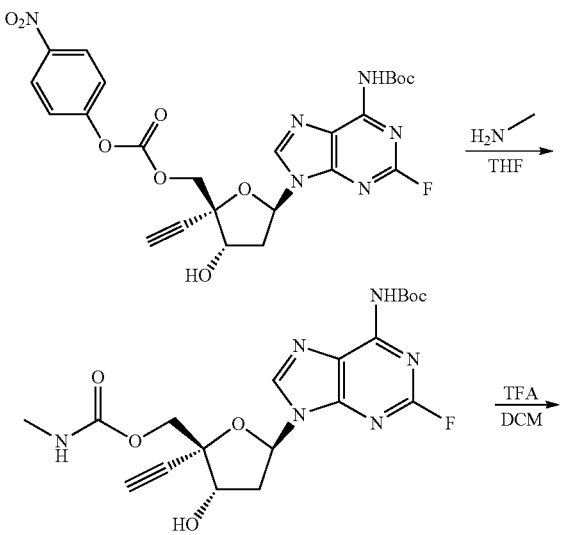

69

-continued

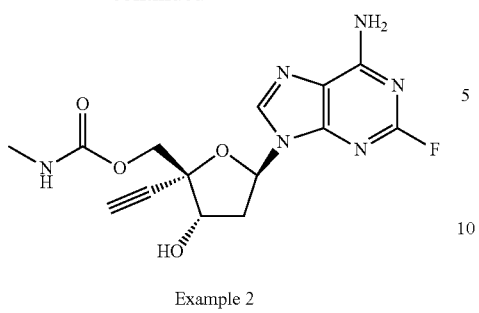

Example 2

((2R,3S,5R)-5-(6-amino-2-fluoro-9H-purin-9-yl)-2-ethynyl-3-hydroxytetrahydrofuran-2-yl)methyl methylcarbamate was prepared using the same procedure as ((2R,3S,5R)-5-(6-amino-2-fluoro-9H-purin-9-yl)-2-ethynyl-3-hydroxytetrahydrofuran-2-yl)methyl isopropylcarbamate except replacing propan-2 amine with methylamine. LCMS (ESI) m/z, $C_{14}H_{15}FN_6O_4$: calculated 350.1, measured (M+H)$^+$: 351.2. $^1$H NMR (400 MHz, DMSO-d6) δ (ppm) 8.26 (s, 1H), 7.87 (br s, 2H), 7.13 (br d, J=4.4 Hz, 1H), 6.24 (dd, J=7.6, 5.0 Hz, 1H), 5.76 (br d, J=4.4 Hz, 1H), 4.55 (br d, J=5.2 Hz, 1H), 4.35 (d, J=11.6 Hz, 1H), 4.03 (d, J=11.6 Hz, 1H), 3.60 (s, 1H), 2.70-2.79 (m, 1H), 2.54 (s, 3H), 2.40-2.45 (m, 1H). $^{19}$F NMR (376 MHz, DMSO-d6) δ (ppm) −51.75 (s).

Example 3

Isopropyl (9-((2R,4S,5R)-5-ethynyl-4-hydroxy-5-(hydroxymethyl)tetrahydrofuran-2-yl)-2-fluoro-9H-purin-6-yl)carbamate

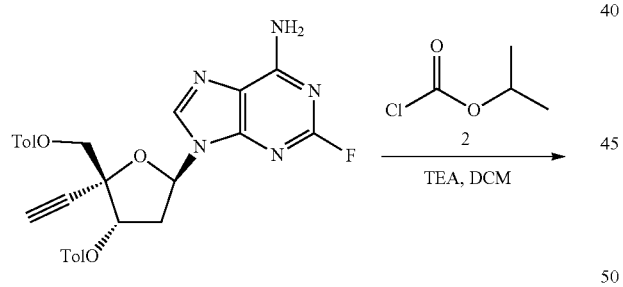

70

-continued

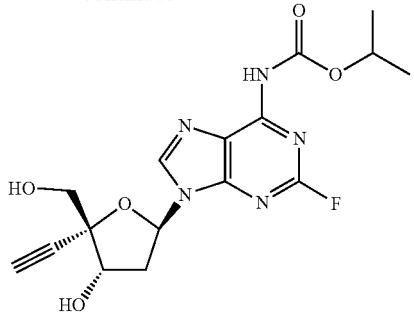

Example 3

Preparation of (2R,3S, 5R)-5-[6-[bis(isopropoxycarbonyl)amino]-2-fluoro-9H-purin-9-yl]-2-ethynyl-2-(((4-methylbenzoyl)oxy)methyl)-tetrahydrofuran-3-yl 4-methylbenzoate

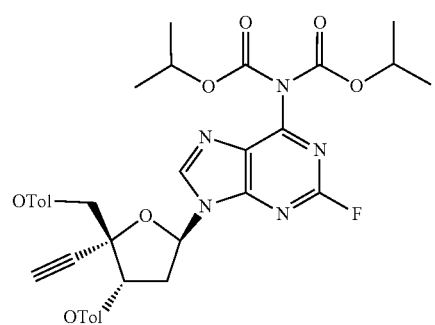

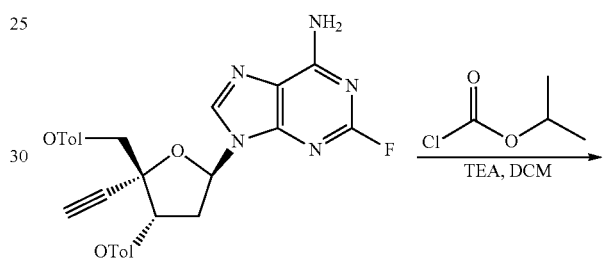

To a mixture of [(2R,3S,5R)-5-(6-amino-2-fluoro-purin-9-yl)-2-ethynyl-3-(4-methylbenzoyl)oxy-tetrahydrofuran-2-yl]methyl 4-methylbenzoate (50 mg, 0.094 mmol, 1 eq) and Et$_3$N (10 mg, 0.094 mmol, 1 eq) in DCM (1 mL) was added isopropyl carbonochloridate (23 mg, 0.19 mmol, 2 eq) at 0° C., the mixture was stirred at 15° C. for 16 hr. The mixture was concentrated under reduced pressure and 2 mL of water was added, extracted with EtOAc (10 mL×2). The combined organic layers were washed with brine (20 mL) and concentrated under reduced pressure to give (2R,3S,5R)-5-(6-(bis(isopropoxycarbonyl)amino)-2-fluoro-9H-purin-9-yl)-2-ethynyl-2-(((4-methylbenzoyl)oxy)methyl) tetrahydrofuran-3-yl 4-methylbenzoate as a crude product, which was used into the next reaction without further purification. LCMS (ESI) m/z, $C_{36}H_{36}FN_5O_9$: calculated 701.3, measured (M+H)$^+$: 702.1.

Preparation of isopropyl (9-((2R,4S,5R)-5-ethynyl-4-hydroxy-5-(hydroxymethyl)tetrahydrofuran-2-yl)-2-fluoro-9H-purin-6-yl)carbamate

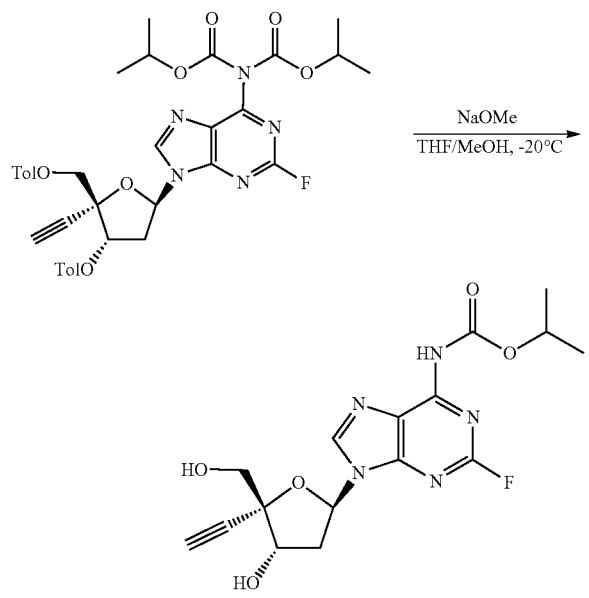

Example 3

To a solution of (2R,3S, 5R)-5-[6-[bis(isopropoxycarbonyl)amino]-2-fluoro-9H-purin-9-yl]-2-ethynyl-2-(((4-methylbenzoyl)oxy)methyl)tetrahydrofuran-3-yl] 4-methylbenzoate (66 mg, 0.094 mmol) in THF (1 mL) was at −20° C. added NaOMe (34 mg, 0.19 mmol, 30%, 2 eq) and the resulting mixture was stirred for 16 hr at −20° C. Additional NaOMe (17 mg, 0.095 mmol, 30%, 1 eq) was added and the mixture was stirred at −20° C. for another 40 hr. The mixture was neutralized with AcOH (0.1 mL), concentrated under reduced pressure, and purified by flash silica gel chromatography (ISCO®; 4 g SepaFlash® Silica Flash Column, Eluent of 0~8% MeOH/DCM gradient @ 20 mL/min) and again by prep-HPLC (column: Waters Xbridge Prep OBD C18 150×30 5 u; mobile phase: [water (10 mM $NH_4HCO_3$)–ACN]; B %: 5%-30%, 7 min) to give isopropyl (9-((2R,4S, 5R)-5-ethynyl-4-hydroxy-5-(hydroxymethyl)tetrahydrofuran-2-yl)-2-fluoro-9H-purin-6-yl)carbamate (3.5 mg, 11% yield) as a white solid. LCMS (ESI) m/z, $C_{16}H_{18}FN_5O_9$: calculated 379.1 (measured (M+Na)$^+$: 402.1). $^1$H NMR (400 MHz, $CDCl_3$) δ (ppm) 8.17 (s, 1H), 7.98 (s, 2H), 6.41 (dd, J=8.8, 5.6 Hz, 1H), 5.13 (dt, J=12.4, 6.4 Hz, 1H), 5.04 (dd, J=11.0, 3.0 Hz, 1H), 4.70-4.75 (m, 1H), 4.09 (dd, J=12.4, 2.4 Hz, 1H), 3.84-3.93 (m, 1H), 3.06-3.15 (m, 1H), 2.83 (s, 1H), 2.48-2.56 (m, 2H), 1.36 (d, J=6.0 Hz, 6H). $^{19}$F NMR (376 MHz, $CDCl_3$) δ (ppm) −46.89 (s).

Example 4 (Method 1)

((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate

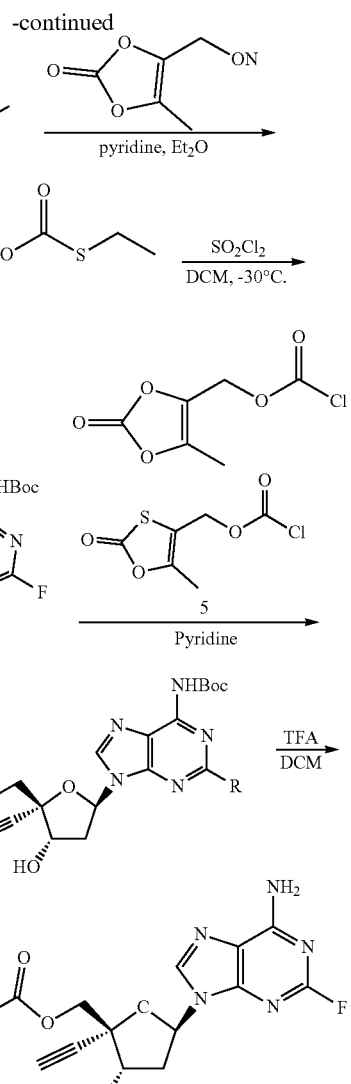

Example 4

Preparation of S-ethyl O-((5-methyl-2-oxo-1,3-dioxol-4-yl)methyl) carbonothioate

To a mixture of ethanethiol (16 g, 257.5 mmol, 19.1 mL, 1 eq), triethyl amine (26.1 g, 257.5 mmol, 35.8 mL, 1 eq) in THF (1 L) at −15° C. was added bis(trichloromethyl) carbonate (76.4 g, 257.5 mmol, 1 eq) in THF (50 mL). The mixture was warm up to 18° C. and stirred at 18° C. for 2 h. The mixture was filtered, and the filtrate was concentrated in vacuo to give S-ethyl chloromethanethioate (13 g, crude) as a yellow oil which was used for the next reaction directly without further purification.

To a mixture of 4-(hydroxymethyl)-5-methyl-1,3-dioxol-2-one (13 g, 99.9 mmol, 1 eq) in Et$_2$O (800 mL) at 0° C. was added pyridine (7.90 g, 99.9 mmol, 8.1 mL, 1 eq) and S-ethyl chloromethanethioate (12.45 g, 99.9 mmol, 1.0 eq) in Et$_2$O (200 mL), the mixture was stirred at 0° C. for 1 h and warm up to 18° C. and stirred at 18° C. for 16 h. The mixture was filtered and concentrated in vacuo, and then taken up in DCM (150 mL) and washed with sat aq. NaHCO$_3$ (150 mL×2), water (150 mL×2). The mixture was concentrated under reduced pressure and purified by flash silica gel chromatography (ISCO®; 120 g SepaFlash® Silica Flash Column, Eluent of 0~15% ethyl acetate/petroleum ether gradient@70 mL/min) to give (5-methyl-2-oxo-1,3-dioxol-4-yl)methyl ethylsulfanylformate (9.2 g, 42.2% yield) as a light yellow oil. $^1$H NMR (400 MHz, CDCl$_3$) δ 4.95 (s, 2H), 2.89 (q, J=7.2 Hz, 2H), 2.19 (s, 3H), 1.32 (t, J=7.2 Hz, 3H).

Preparation of (5-methyl-2-oxo-1,3-dioxol-4-yl)methyl carbonochloridate

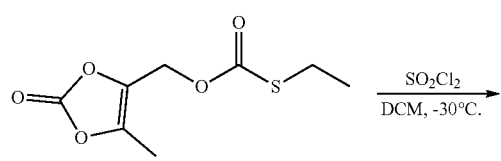

To a mixture of (5-methyl-2-oxo-1,3-dioxol-4-yl)methyl ethylsulfanylformate (500 mg, 2.29 mmol, 1 eq) in DCM (50 mL) was added sulfuryl chloride (618.5 mg, 4.58 mmol, 0.46 mL, 2 eq). The resulting mixture was stirred at 20° C. for 1 h. The reaction mixture was washed with water (50 mL×2), 5% aq Na$_2$CO$_3$ (50 mL×2), brine (50 mL), dried over Na$_2$SO$_4$, filtered and concentrated under reduced pressure to give (5-methyl-2-oxo-1,3-dioxol-4-yl)methyl carbonochloridate (350 mg, crude) as a yellow oil. The product was dissolved in 10 mL DCM and stored in refrigerator.

Preparation of tert-butyl (9-((2R,4S,5R)-5-ethynyl-4-hydroxy-5-(((((5-methyl-2-oxo-1,3-dioxol-4-yl)methoxy)carbonyl)oxy)methyl)tetrahydrofuran-2-yl)-2-fluoro-9H-purin-6-yl)carbamate

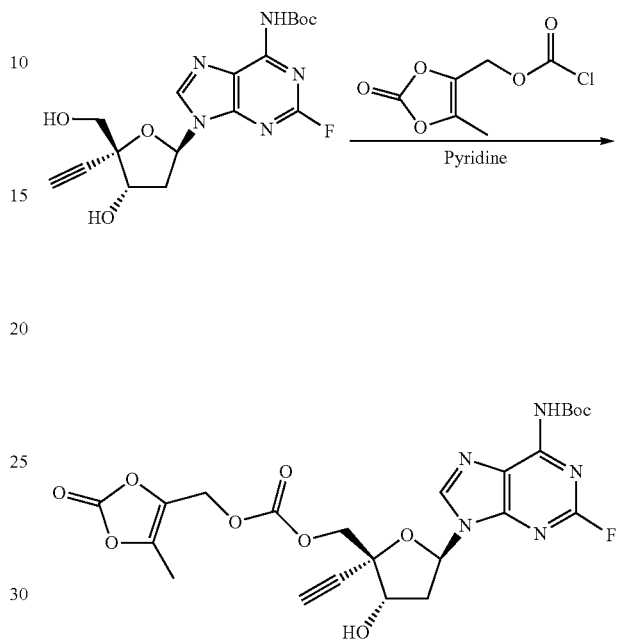

To a mixture of tert-butyl N-[9-[(2R,4S,5R)-5-ethynyl-4-hydroxy-5-(hydroxymethyl)tetrahydrofuran-2-yl]-2-fluoro-purin-6-yl]carbamate (100 mg, 0.25 nmol, 1 eq) in pyridine (2 mL) at 20° C. was added (5-methyl-2-oxo-1,3-dioxol-4-yl)methyl carbonochloridate (140 mg, 0.73 mmol, 4 mL, 2.86 eq, 35 mg/mL in DCM), the mixture was stirred at 20° C. for 16 hr. The mixture was concentrated under reduced pressure, and purified by flash silica gel chromatography (ISCO®; 4 g SepaFlash® Silica Flash Column, Eluent of 0~5% MeOH/DCM gradient @25 mL/min) to give [(2R,3S,5R)-5-[6-(tert-butoxycarbonylamino)-2-fluoro-purin-9-yl]-2-ethynyl-3-hydroxy-tetrahydrofuran-2-yl]methyl(5-methyl-2-oxo-1,3-dioxol-4-yl)methyl carbonate (45 mg, 32.2% yield) as a yellow solid. LCMS (ESI) m/z, C$_{23}$H$_{24}$FN$_5$O$_{10}$: calculated 549.2, measured (M+H)$^+$: 550.1.

Preparation of ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate

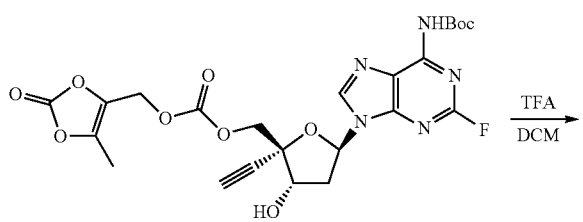

75

-continued

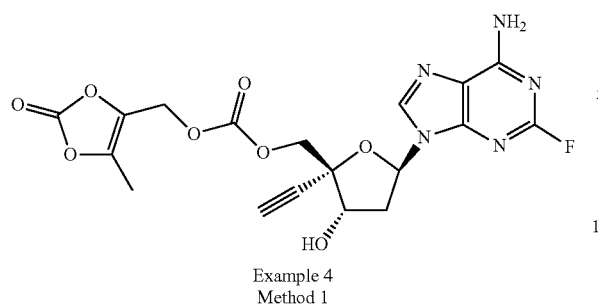

Example 4
Method 1

To a mixture of [(2R,3S,5R)-5-[6-(tert-butoxycarbonylamino)-2-fluoro-purin-9-yl]-2-ethynyl-3-hydroxy-tetrahydrofuran-2-yl]methyl(5-methyl-2-oxo-1,3-dioxol-4-yl) methyl carbonate (45 mg, 0.082 mmol, 1 eq) in toluene (1 mL) at 20° C. was added TFA (154 mg, 1.35 mmol, 0.1 mL, 16.5 eq). The mixture was stirred at 20° C. for 16 hr and then was concentrated under reduced pressure. The resulting residue was purified by prep-HPLC (column: Boston Green ODS 150×30 mm×5 um; mobile phase: [water (0.2% FA)–ACN]; B %: 13%-43%, 8 min) to give ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl) methyl) carbonate (11 mg, 25.4% yield) as a white solid. LCMS (ESI) m/z, $C_{18}H_{16}FN_5O_6$: calculated 449.1, measured (M+H)$^+$: 450.1. $^{19}$F NMR (376 MHz, CD$_3$OD) δ (ppm) −53.00 (s). $^1$H NMR (400 MHz, CD$_3$CN) 7.92 (s, 1H), 6.41-6.21 (m, 3H), 4.87 (d, J=5.2 Hz, 2H), 4.77-4.67 (m, 1H), 4.51 (d, J=11.6 Hz, 1H), 4.30 (d, J=11.6 Hz, 1H), 3.75 (d, J=6.4 Hz, 1H), 3.00 (s, 1H), 2.89-2.81 (m, 1H), 2.61-2.52 (m, 1H), 2.10 (s, 3H).

Example 4 (Method 2)

((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate

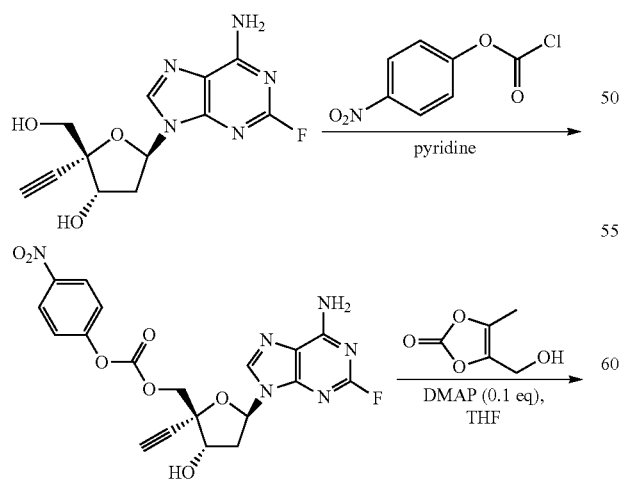

76

-continued

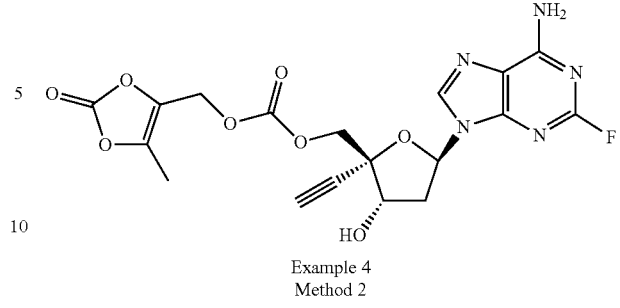

Example 4
Method 2

Preparation of ((2R,3S,5R)-5-(6-amino-2-fluoro-9H-purin-9-yl)-2-ethynyl-3-hydroxytetrahydrofuran-2-yl)methyl (4-nitrophenyl) carbonate

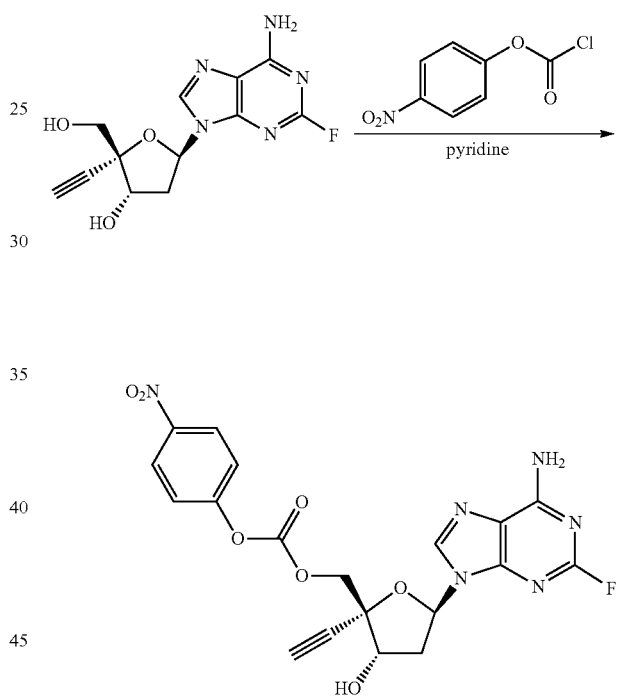

To a mixture of (2R,3S,5R)-5-(6-amino-2-fluoro-purin-9-yl)-2-ethynyl-2-(hydroxymethyl)tetrahydrofuran-3-ol (100 mg, 0.34 mmol, 1 eq) in pyridine (5 mL) was added (4-nitrophenyl) carbonochloridate (82 mg, 0.41 mmol, 1.2 eq), the mixture was stirred at 26° C. for 16 h. (4-nitrophenyl) carbonochloridate (82 mg, 0.41 mmol, 1.2 eq) was added and the mixture was stirred at 26° C. for 24 h. The reaction solution was purified by flash silica gel chromatography (ISCO®; 4 g SepaFlash® Silica Flash Column, Eluent of 0~5% DCM/MeOH gradient@25 mL/min) to give [(2R, 3S,5R)-5-(6-amino-2-fluoro-purin-9-yl)-2-ethynyl-3-hydroxy-tetrahydrofuran-2-yl]methyl (4-nitrophenyl) carbonate (80 mg, 51.2% yield) as a white solid. LCMS (ESI) m/z, $C_{19}H_{15}FN_6O_7$: calculated 458.4, found (M+H)$^+$: 459.1.

Preparation of ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate

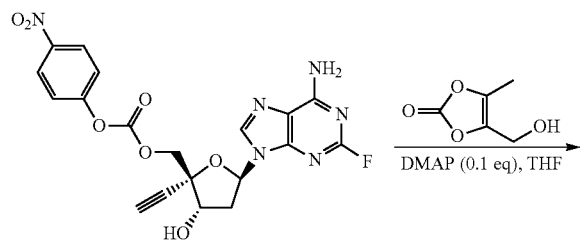

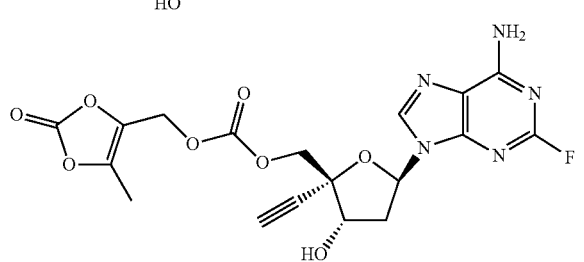

To a mixture of [(2R,3S,5R)-5-(6-amino-2-fluoro-purin-9-yl)-2-ethynyl-3-hydroxy-tetrahydrofuran-2-yl]methyl (4-nitrophenyl) carbonate (150 mg, 0.298 mmol, 1 eq) and 4-(hydroxymethyl)-5-methyl-1,3-dioxol-2-one (96 mg, 0.745 mmol, 2.5 eq) in THF (3 mL) was added DMAP (3.6 mg, 0.023 mmol, 0.1 eq), the mixture was stirred at 25° C. for 2 h. The reaction solution was purified by flash silica gel chromatography (ISCO®; 24 g SepaFlash® Silica Flash Column, Eluent of 0~2.5% DCM/MeOH gradient@25 mL/min) to give [(2R,3S,5R)-5-(6-amino-2-fluoro-purin-9-yl)-2-ethynyl-3-hydroxy-tetrahydrofuran-2-yl]methyl(5-methyl-2-oxo-1,3-dioxol-4-yl)methyl carbonate (85 mg, 63.5% yield) as a white solid. LCMS (ESI) m/z, $C_{18}H_{16}FN_5O_8$ calculated 449.4, found 450.1 (M+H)$^+$. $^1$H NMR (400 MHz, CD$_3$CN) (ppm) 7.91 (s, 1H), 6.42-6.16 (m, 3H), 4.93-4.79 (m, 2H), 4.76-4.67 (m, 1H), 4.53-4.46 (m, 1H), 4.34-4.25 (m, 1H), 3.77-3.69 (m, 1H), 3.00 (s, 1H), 2.90-2.78 (m, 1H), 2.62-2.50 (m, 1H), 2.10 (s, 3H). $^{19}$F NMR (376 MHz, CD$_3$CN) δ (ppm) −52.87 (s, 1F).

Example 4 (Method 3)

((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate

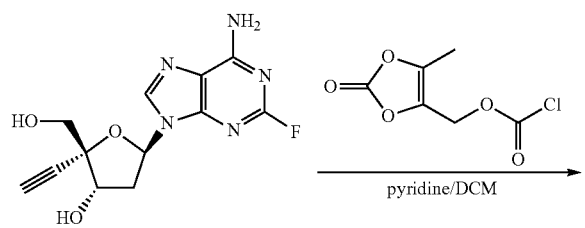

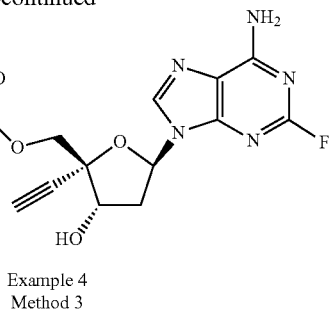

Example 4
Method 3

Preparation of ((2R,3S,5R)-5-(6-amino-2-fluoro-9H-purin-9-yl)-2-ethynyl-3-hydroxytetrahydrofuran-2-yl)methyl (4-nitrophenyl) carbonate

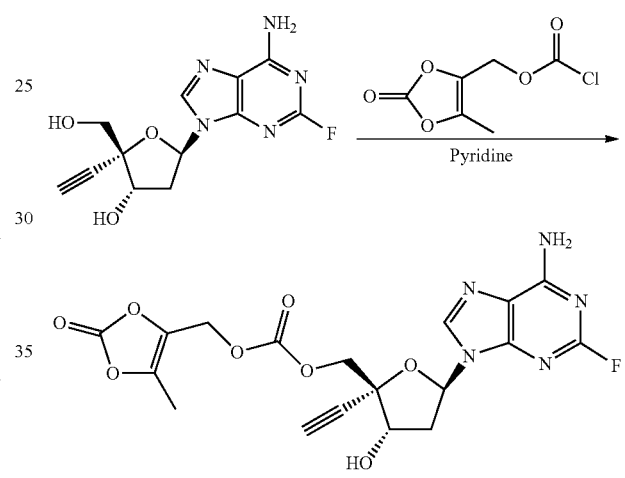

To a mixture of (2R,3S,5R)-5-(6-amino-2-fluoro-purin-9-yl)-2-ethynyl-2-(hydroxymethyl)tetrahydrofuran-3-ol (5 g, 17.05 mmol, 1 eq) in pyridine (50 mL) was dropwise added (5-methyl-2-oxo-1,3-dioxol-4-yl)methyl carbonochloridate (16.42 g, 85.25 mmol, 5 eq) in DCM (16 mL) at 0° C. over a period of 2 h, after that the mixture was stirred at 16° C. for 10 min. The mixture was diluted with DCM (200 mL) and washed with water (150 mL), brine (150 mL×2), dried over Na$_2$SO$_4$, filtered and concentrated. The resulting residue was purified by flash silica gel chromatography (ISCO®; 80 g SepaFlash® Silica Flash Column, Eluent of 0~5% MeOH/DCM gradient @ 65 mL/min) to give [(2R,3S,5R)-5-(6-amino-2-fluoro-purin-9-yl)-2-ethynyl-3-hydroxy-tetrahydrofuran-2-yl]methyl (5-methyl-2-oxo-1,3-dioxol-4-yl)methyl carbonate (5.10 g, 11.35 mmol, 66.6% yield) as a light yellow solid. LCMS (ESI) m/z, $C_{18}H_{16}FN_5O_8$: calculated 449.4, found (M+H)$^+$: 450.1. $^1$H NMR (400 MHz, CD$_3$CN) (ppm) 7.92 (s, 1H), 6.34 (br s, 2H), 6.29-6.23 (m, 1H), 4.93-4.81 (m, 2H), 4.77-4.69 (m, 1H), 4.51 (d, J=11.6 Hz, 1H), 4.30 (d, J=11.6 Hz, 1H), 3.74 (d, J=6.4 Hz, 1H), 3.00 (s, 1H), 2.91-2.79 (m, 1H), 2.62-2.51 (m, 1H), 2.10 (s, 3H). $^{19}$F NMR (376 MHz, CD$_3$CN) δ (ppm) −52.84 (s, 1F).

Recrystallization of ((2R,3S,5R)-5-(6-amino-2-fluoro-9H-purin-9-yl)-2-ethynyl-3-hydroxytetrahydrofuran-2-yl)methyl (4-nitrophenyl) carbonate

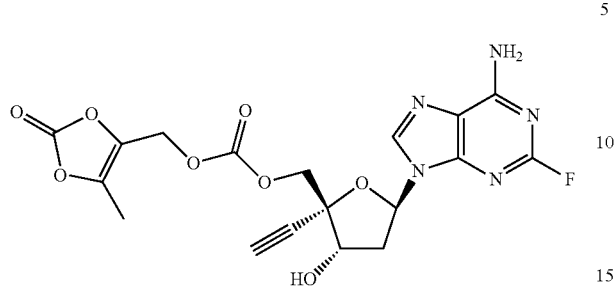

A mixture of [(2R,3S,5R)-5-(6-amino-2-fluoro-purin-9-yl)-2-ethynyl-3-hydroxy-tetrahydrofuran-2-yl]methyl (5-methyl-2-oxo-1,3-dioxol-4-yl)methyl carbonate (9.5 g, 21.14 mmol, 1 eq) in MeCN (50 mL) and EtOAc (50 mL) was heated at 80° C. for 30 min and dissolution of the solids was observed. After cooling to room temperature (20° C.), the mixture was stirred at 20° C. for 16 h. The mixture was filtered and the filter cake was dried in vacuum to give [(2R,3S,5R)-5-(6-amino-2-fluoro-purin-9-yl)-2-ethynyl-3-hydroxy-tetrahydrofuran-2-yl]methyl (5-methyl-2-oxo-1,3-dioxol-4-yl)methyl carbonate (8.0 g, 17.80 mmol, 84.2% yield) as a white solid. LCMS (ESI) m/z, $C_{18}H_{16}FN_5O_8$: calculated 449.4, found (M+H)$^+$: 450.1. $^1$H NMR (400 MHz, CD$_3$CN) δ (ppm) 7.92 (s, 1H), 6.31 (br s, 2H), 6.27-6.24 (m, 1H), 4.92-4.81 (m, 2H), 4.77-4.69 (m, 1H), 4.51 (d, J=11.6 Hz, 1H), 4.30 (d, J=11.6 Hz, 1H), 3.73 (d, J=6.4 Hz, 1H), 3.00 (s, 1H), 2.89-2.81 (m, 1H), 2.62-2.51 (m, 1H), 2.10 (s, 3H). $^{19}$F NMR (376 MHz, CD$_3$CN) δ (ppm) −52.84 (s, 1F).

Example 5 (Method 1)

4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one

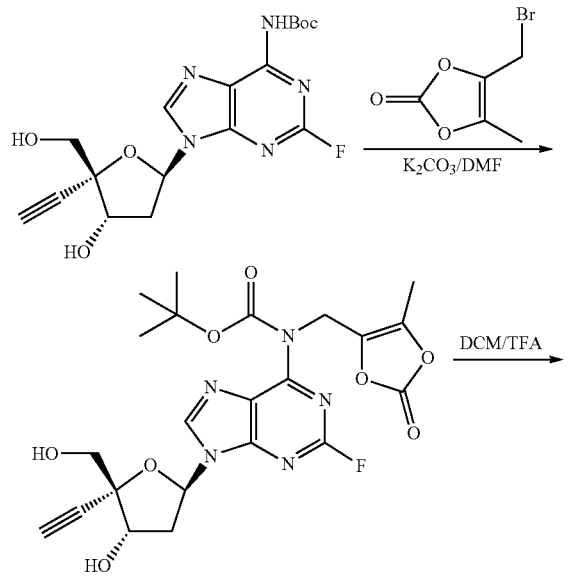

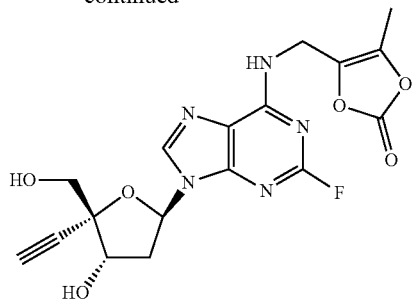

Example 5
Method 1

Preparation of tert-butyl(9-((2R,4S,5R)-5-ethynyl-4-hydroxy-5-(hydroxymethyl)tetrahydrofuran-2-yl)-2-fluoro-9H-purin-6-yl)((5-methyl-2-oxo-1,3-dioxol-4-yl)methyl)carbamate

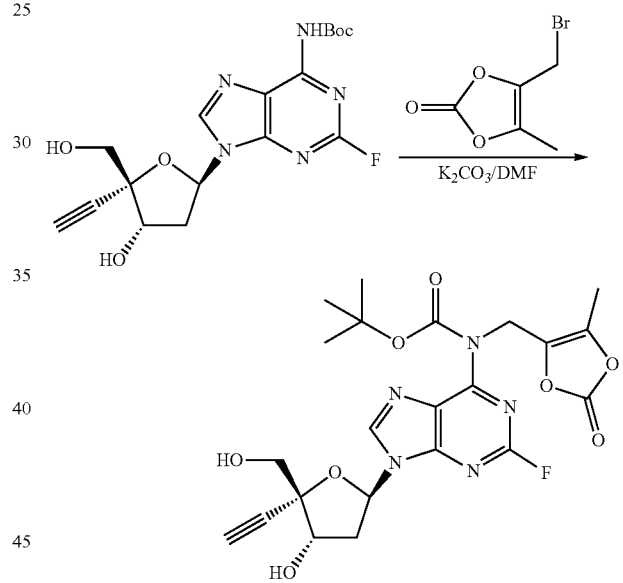

To a mixture of tert-butyl N-[9-[(2R,4S,5R)-5-ethynyl-4-hydroxy-5-(hydroxymethyl)tetrahydrofuran-2-yl]-2-fluoro-purin-6-yl]carbamate (100 mg, 0.25 nmol, 1 eq) in DMF (5 mL) was added K$_2$CO$_3$ (70 mg, 0.51 mmol, 2 eq) and 4-(bromomethyl)-5-methyl-1,3-dioxol-2-one (147 mg, 0.76 mmol, 3 eq). The reaction mixture was then heated at 60° C. for 12 hr, concentrated and then diluted with H$_2$O (30 mL). The resulting mixture was extracted with EtOAc (30×3 mL). The combined organic layers were washed with brine (50 mL), dried over Na$_2$SO$_4$, filtered and concentrated. The resulting residue was purified by flash silica gel chromatography (ISCO®; 4 g SepaFlash® Silica Flash Column, Eluent of 0~10% methanol/dichloromethane gradient @30 mL/min) to give tert-butyl N-[9-[(2R,4S,5R)-5-ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl] carbamate (45 mg, 35.0% yield) as a light yellow oil. $^1$H NMR (400 MHz, CDCl$_3$) δ (ppm) 8.02 (s, 1H), 6.40-6.43 (m, 1H), 5.02 (s, 2H), 4.70-4.73 (m, 2H), 4.09 (d, J=12 Hz, 1H), 3.90-3.92 (m, 1H), 3.11-3.14 (m, 1H), 2.85 (s, 1H), 2.50-2.55 (m, 1H), 2.45 (bs, 1H), 2.22 (s, 3H), 1.53 (s, 9H).

Preparation of 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one

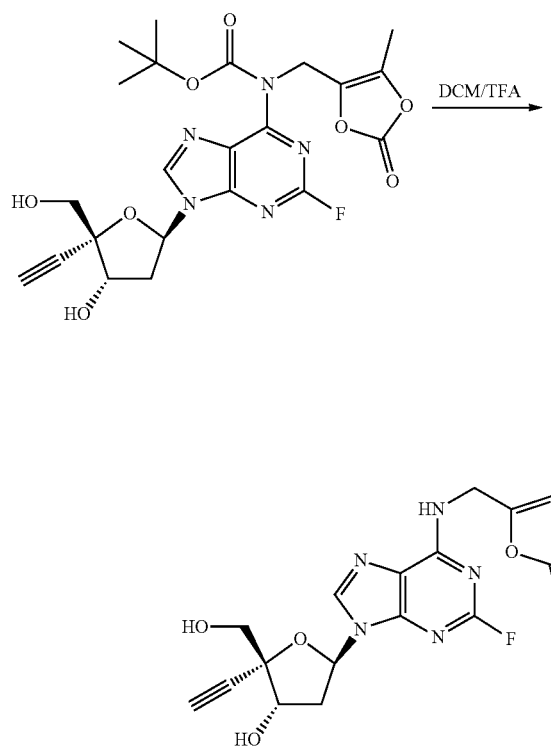

Example 5
Method 1

To a solution of tert-butyl N-[9-[(2R,4S,5R)-5-ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl]carbamate (40 mg, 0.079 mmol, 1 eq) in dichloromethane (DCM) (3 mL) at 25° C. was added TFA (0.5 mL). The mixture was stirred at 25° C. for 12 hr. The reaction mixture was concentrated and purified by prep-HPLC (column: Boston Green ODS 150*30 mm*5um; mobile phase: [water (0.2% FA)–ACN]; B %: 15%-45%, 8 min) to give 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one (1.7 mg, 5% yield) as a white solid. LCMS (ESI) m/z, $C_{17}H_{16}FN_5O_6$: calculated 405.1, measured (M+H)$^+$: 406.1. (M+Na)$^+$: 428.1. $^1$H NMR (400 MHz, CD$_3$OD) δ (ppm) 8.26 (s, 1H), 6.38-6.35 (m, 1H), 4.76-4.72 (m, 1H), 4.51 (s, 1H), 3.87-3.84 (d, J=12 Hz, 1H), 3.78-3.75 (d, J=12 Hz, 1H), 3.09 (s, 2H), 2.80-2.75 (m, 1H), 2.64-2.57 (m, 1H), 2.24 (s, 3H). $^{19}$F NMR (376 MHz, CD$_3$OD) δ (ppm) −53.00.

Example 5 (Method 2)

4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one

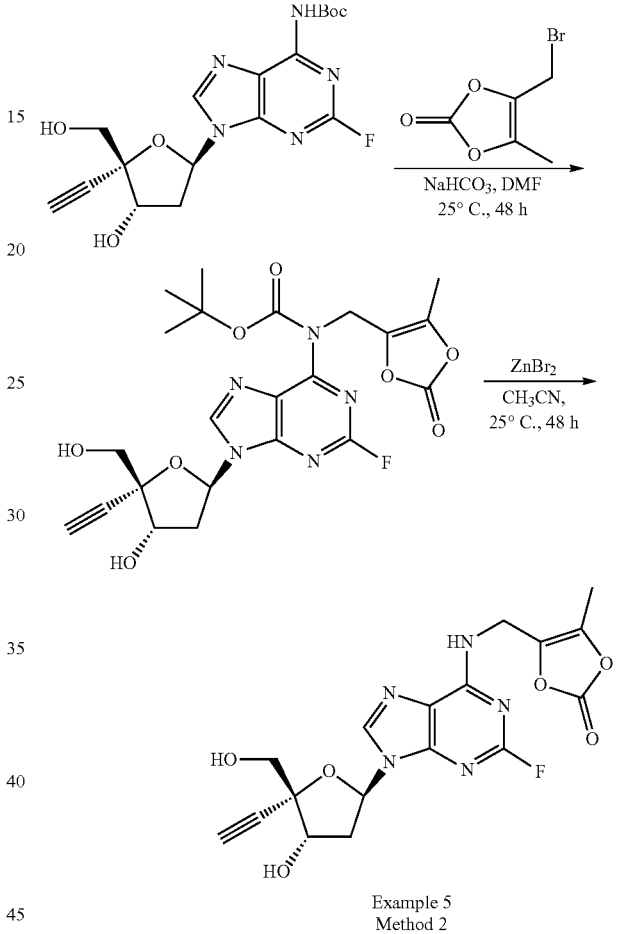

Example 5
Method 2

Preparation of tert-butyl-N-[9-[(2R,4S,5R)-5-ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl]carbamate

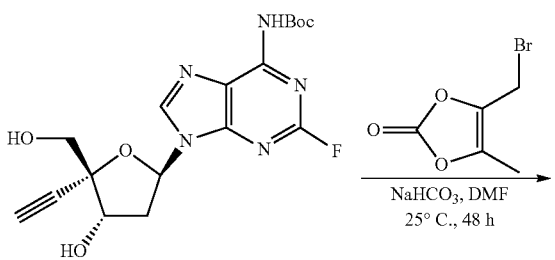

83

-continued

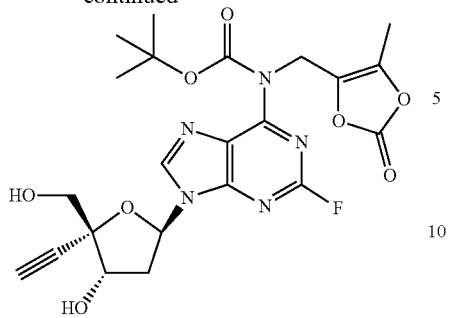

To a solution of tert-butyl N-[9-[(2R,4S,5R)-5-ethynyl-4-hydroxy-5-(hydroxymethyl) tetrahydrofuran-2-yl]-2-fluoro-purin-6-yl]carbamate (300 mg, 0.76 mmol, 1 eq) in DMF (5 mL) was added NaHCO$_3$ (128 mg, 1.52 mmol, 2 eq), then 4-(bromomethyl)-5-methyl-1,3-dioxol-2-one (294 mg, 1.52 mmol, 2 eq) was added. The mixture was stirred at 25° C. for 48 h. The mixture was concentrated. The resulting residue was purified by flash silica gel chromatography (ISCO®; 4 g SepaFlash® Silica Flash Column, eluent with 0~100% ethyl acetate/petroleum ether gradient@20 mL/min) to give tert-butyl N-[9-[(2R,4S,5R)-5ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl] carbamate (200 mg, 52% yield) as a white solid. $^1$H NMR (400 MHz, CDCl$_3$) δ (ppm) 7.98 (s, 1H), 6.45-6.33 (m, 1H), 4.99 (s, 1H), 5.03-4.94 (m, 1H), 4.78 (br d, J=11.2 Hz, 1H), 4.71 (br s, 1H), 4.16-4.02 (m, 2H), 3.11 (br s, 1H), 2.80 (s, 1H), 2.49 (br d, J=7.2 Hz, 1H), 2.42 (br s, 1H), 2.19 (s, 3H), 1.55 (s, 9H).

Preparation of 4-[[[9-[(2R,4S,5R)-5-ethynyl-4-hydroxy-5-(hydroxymethyl)tetrahydrofuran-2-yl]-2-fluoro-purin-6-yl]amino]methyl]-5-methyl-1,3-dioxol-2-one

84

-continued

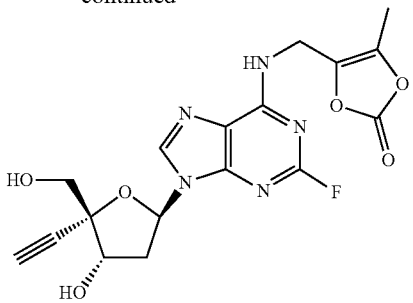

Example 5
Method 2

To a solution of tert-butyl N-[9-[(2R,4S,5R)-5-ethynyl-4-hydroxy-5-(hydroxymethyl) tetrahydrofuran-2-yl]-2-fluoro-purin-6-yl]-N-[(5-methyl-2-oxo-1,3-dioxol-4-yl)methyl] carbamate (50 mg, 0.10 mmol, 1 eq) in CH$_3$CN (5 mL) was added ZnBr$_2$ (45 mg, 0.20 mmol, 2 eq). The mixture was stirred at 25° C. for 48 h. The reaction was filtered, and the filtrate was concentrated. The resulting residue was purified by prep-HPLC (FA condition; column: 3 Phenomenex Luna C18 75×30 mm×3 um; mobile phase: [water (0.2% FA)–ACN]; B %: 22%-52%, 6 min) to give 4-[[[9-[(2R,4S,5R)-5-ethynyl-4-hydroxy-5-(hydroxymethyl)tetrahydrofuran-2-yl]-2-fluoro-purin-6-yl]amino]methyl]-5-methyl-1,3-dioxol-2-one (19.8 mg, 48.8% yield) as a white solid. LCMS (ESI) m/z, C$_{17}$H$_{16}$FN$_5$O$_6$: calculated 405.34, found (M+H)$^+$: 406.1. $^1$H NMR (400 MHz, CD$_3$OD) δ (ppm) 8.26 (s, 1H), 6.38-6.35 (m, 1H), 4.76-4.72 (m, 1H), 4.51 (br s, 2H), 3.87-3.84 (d, J=12 Hz, 1H), 3.78-3.75 (d, J=12 Hz, 1H), 3.09 (s, 1H), 2.80-2.75 (m, 1H), 2.64-2.57 (m, 1H), 2.24 (s, 3H). $^{19}$F NMR (376 MHz, CD$_3$OD) δ (ppm) −52.33.

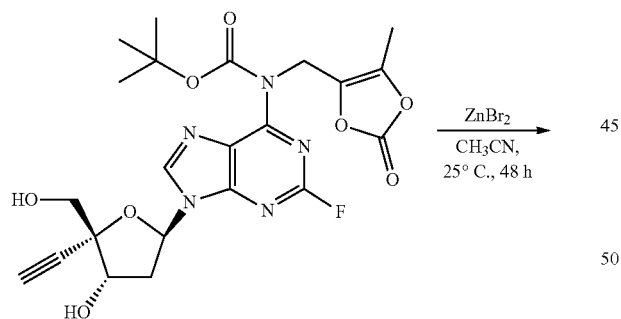

Example 6

((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate

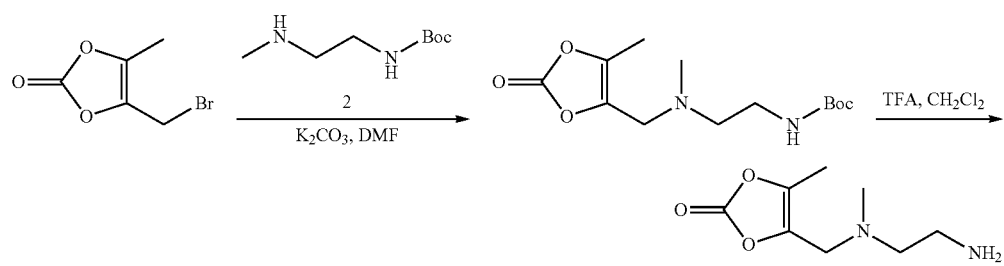

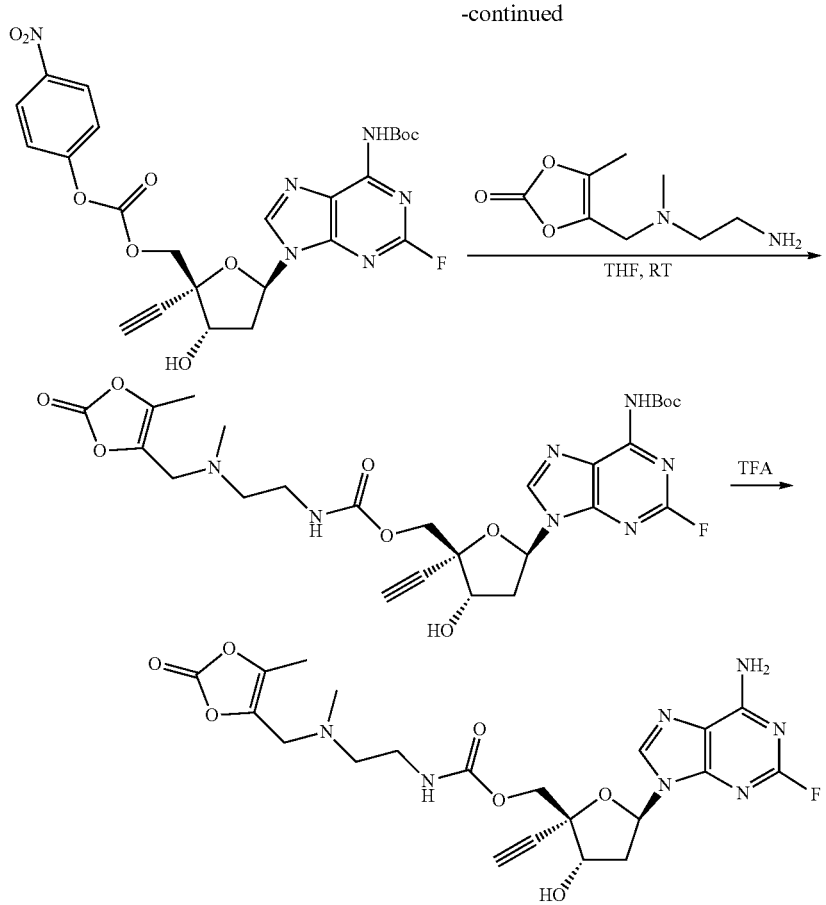

Example 6

Preparation of tert-butyl (2-(methyl((5-methyl-2-oxo-1,3-dioxol-4-yl)methyl)amino)ethyl)carbamate

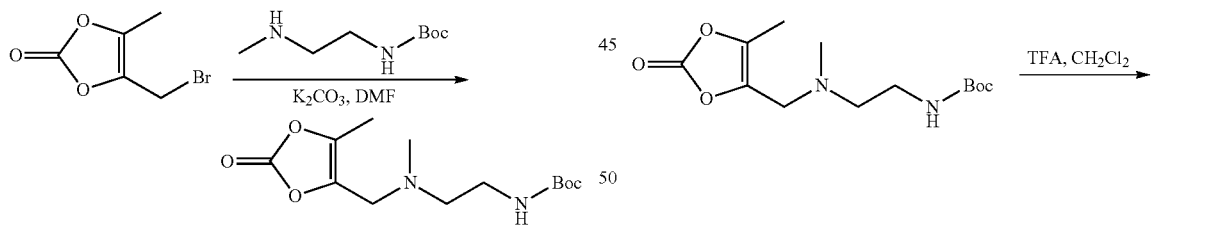

To a mixture of tert-butyl N-[2-(methylamino)ethyl]carbamate (451 mg, 2.59 mmol, 1 eq) and K₂CO₃ (393.9 mg, 2.85 mmol, 1.1 eq) in DMF (15 mL) was added 4-(bromomethyl)-5-methyl-1,3-dioxol-2-one (500 mg, 2.59 mmol, 1 eq), the mixture was stirred at 20° C. for 16 hr. The mixture was concentrated under reduced pressure, purified by flash silica gel chromatography (ISCO®; 12 g SepaFlash® Silica Flash Column, Eluent of 0-20% ethyl acetate/petroleum ether gradient @30 mL/min) to give tert-butylN-[2-[methyl-[(5-methyl-2-oxo-1,3-dioxol-4-yl)methyl]amino]ethyl]carbamate (500 mg, 1.75 mmol, 67.4% yield) as a yellow oil. $^1$H NMR (400 MHz, DMSO-d6) δ (ppm) 6.65 (m, 1H), 3.37 (s, 2H), 2.99 (m, 2H), 2.39 (m, 2H), 2.18 (s, 3H), 2.09 (s, 3H), 1.37 (s, 9H).

Preparation of 4-(((2-aminoethyl)(methyl)amino)methyl)-5-methyl-1,3-dioxol-2-one To a mixture of tert-butyl N-[2-[methyl-[(5-methyl-2-oxo-1,3-dioxol-4-yl)methyl]amino]ethyl]carbamate (200 mg, 0.699 nmol, 1 eq) in dichloromethane (2 mL) at 20° C. was added TFA (1.54 g, 13.51 mmol, 1 mL, 19.34 eq), the mixture was stirred at 20° C. for 16 hr. The mixture was concentrated under reduced pressure to give 4-[[2-aminoethyl(methyl)amino]methyl]-5methyl-1,3-dioxol-2-one (120 mg, crude, 3TFA) as a yellow oil. LCMS (ESI) m/z, $C_8H_{14}N_2O_3$: calculated 186.1, measured (M+H)⁺: 187.2.

Preparation tert-butyl (9-((2R,4S,5R)-5-ethynyl-4-hydroxy-5-((((2-(methyl((5-methyl-2-oxo-1,3-dioxol-4-yl)methyl)amino)ethyl)carbamoyl)oxy)methyl)tetrahydrofuran-2-yl)-2-fluoro-9H-purin-6-yl)carbamate

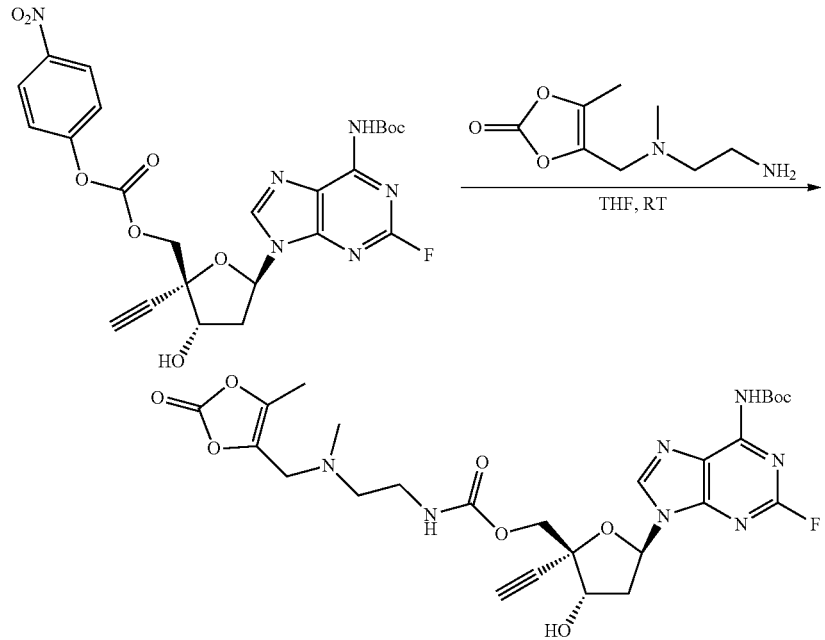

To a mixture of [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate (34 mg, 0.060 mmol, 1 eq) and triethyl amine (30 mg, 0.30 mmol, 5 eq) in dichloromethane (2 mL) at 20° C. was added 4-[[2-aminoethyl(methyl)amino]methyl]-5-methyl-1,3-dioxol-2-one (38 mg, 0.072 mmol, 1.2 eq, 3TFA), the mixture was stirred at 20° C. for 16 hr. The mixture was then concentrated under reduced pressure and purified by flash silica gel chromatography (ISCO®; 4 g SepaFlash® Silica Flash Column, Eluent of 0-5% dichloromethane/MeOH gradient @25 mL/min) to give tert-butyl N-[9-[(2R,4S,5R)-5-ethynyl-4-hydroxy-5-[2-[methyl-[(5-methyl-2-oxo-1,3-dioxol-4-yl)methyl]amino]ethylcarbamoyloxymethyl]tetrahydrofuran-2-yl]-2-fluoro-purin-6-yl]carbamate (34 mg, 92.1% yield) as a yellow solid. LCMS (ESI) m/z, $C_{26}H_{32}FN_7O_9$: calculated 605.2, measured (M+Na)$^+$: 628.2.

Preparation of ((2R,3S,5R)-5-(6-amino-2-fluoro-9H-purin-9-yl)-2-ethynyl-3-hydroxytetrahydrofuran-2-yl)methyl(2-(methyl((5-methyl-2-oxo-1,3-dioxol-4-yl)methyl)amino)ethyl)carbamate

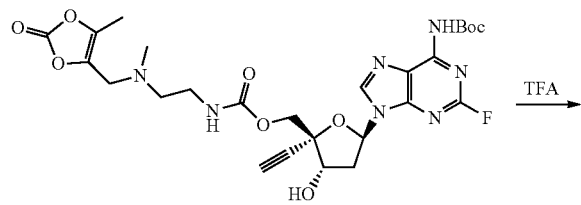

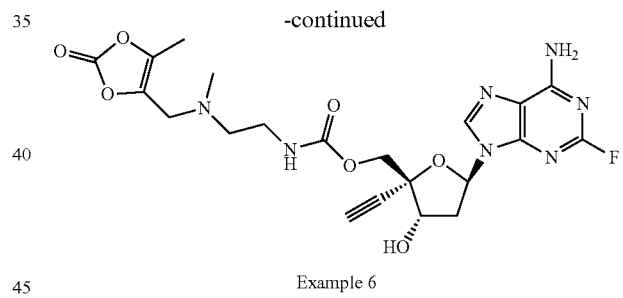

Example 6

To a mixture of tert-butylN-[9-[(2R,4S,5R)-5-ethynyl-4-hydroxy-5-[2-[methyl-[(5-methyl-2-oxo-1,3-dioxol-4-yl)methyl]amino]ethyl carbamoyloxymethyl]tetrahydrofuran-2-yl]-2-fluoro-purin-6-yl]carbamate (34 mg, 0.055 mmol, 1 eq) in toluene (1 mL) was added TFA (129 mg, 1.13 mmol, 0.084 mL, 20.45 eq), the mixture was stirred at 20° C. for 16 hr. The mixture was concentrated under reduced pressure and purified by prep-HPLC (column: Phenomenex Gemini-NX 150×30 mm×5 um; mobile phase: [water (0.05% HCl)-ACN]; B %: 0%-30%, 7 min), and then re-purified by prep-HPLC (column: Welch Xtimate C18 150×25 mm×5 um; mobile phase: [water (0.2% FA)-ACN]; B %: 1%-20%, 8 min) to give 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one (2.0 mg, 20.0% yield) as a white solid. LCMS (ESI) m/z, $C_{21}H_{24}FN_7O_7$: calculated 505.2, measured (M+H)$^+$: 506.3, (M+Na)$^+$: 528.2. $^1$H NMR (400 MHz, CD$_3$OD) δ (ppm) 8.15 (s, 1H), 6.32 (dd, J=8.0, 4.0 Hz, 1H), 4.80 (m, 1H), 4.47 (d, J=11.6 Hz, 1H), 4.24 (d, J=11.6 Hz, 1H), 3.45 (s, 2H), 3.19 (t, J=6.8, 2H), 3.17 (s, 1H), 2.84 (m, 1H), 2.66 (m, 1H), 2.51 (t, J=6.8, 2H), 2.30 (s, 3H), 2.14 (s, 3H). $^{19}$F NMR (376 MHz, CD$_3$OD) δ (ppm) −52.93 (s).
Example 7
((2R,3S,5R)-5-(6-amino-2-fluoro-9H-purin-9-yl)-2-ethynyl-3-hydroxytetrahydrofuran-2-yl)methyl 4-(methyl(((5-methyl-2-oxo-1,3-dioxol-4-yl)methoxy)carbonyl)amino)butanoate
Preparation of 4-(methylamino)butanoic acid
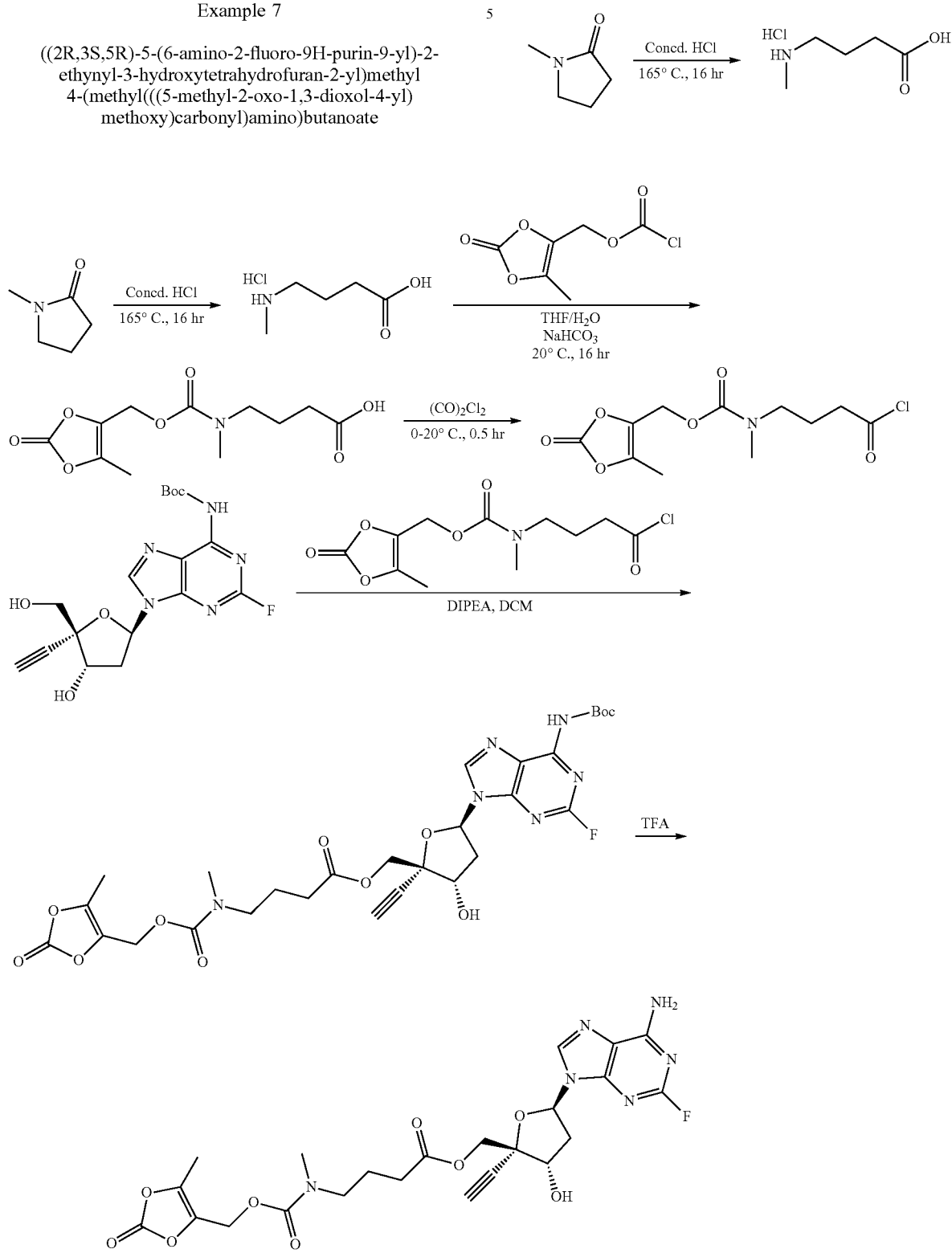
Example 7

A mixture of 1-methylpyrrolidin-2-one (5.0 g, 50.44 mmol, 4.90 mL, 1 eq), HCl (51.0 g, 531.53 mmol, 50 mL, 38% purity, 10.54 eq) was stirred at 165° C. for 16 hr. The reaction mixture concentrated. The resulting residue was triturated from acetone to give 4-(methylamino)butanoic acid (4 g, 51.6% yield, HCl salt) as a white solid.

Preparation of 4-[methyl-[(5-methyl-2-oxo-1,3-dioxol-4-yl)methoxycarbonyl]amino]butanoic acid

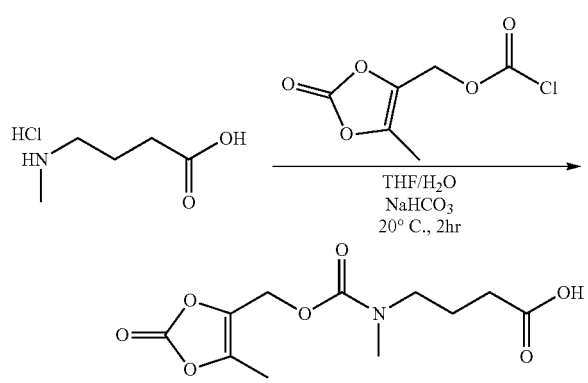

To a solution of 4-(methylamino)butanoic acid HCl salt (1.36 g, 8.83 mmol, 1 eq) in H$_2$O (25 mL) was added NaHCO$_3$ (2.23 g, 26.49 mmol, 1.03 mL, 3 eq) followed by (5-methyl-2-oxo-1,3-dioxol-4-yl)methyl carbonochloridate (1.7 g, 8.83 mmol, 1 eq) in THF (25 mL). The mixture was stirred at 20° C. for 16 hr. The reaction mixture was concentrated and purified by flash silica gel chromatography (ISCO®; 12 g SepaFlash® Silica Flash Column, Eluent of 0-5% methanol/dichlomethane@20 mL/min) to give 4-[methyl-[(5-methyl-2-oxo-1,3-dioxol-4-yl)methoxycarbonyl]amino]butanoic acid (1.5 g, 62.2% yield) as a colorless oil. $^1$H NMR (400 MHz, DMSO-d$_6$) δ (ppm) 12.07 (br s, 1H), 4.89 (s, 2H), 3.22 (br t, J=7.2 Hz, 2H), 2.81 (s, 3H), 2.28-2.03 (m, 5H), 1.69 (m, 2H).

Preparation of (5-methyl-2-oxo-1,3-dioxol-4-yl)methylN-(4-chloro-4-oxo-butyl)-N-methyl-carbamate

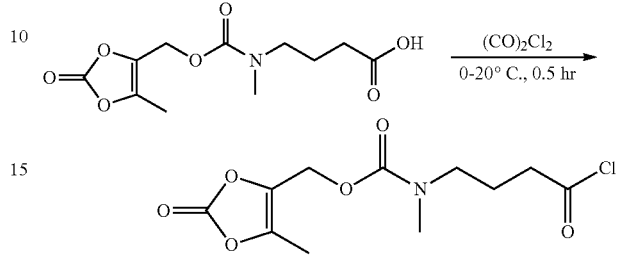

To a solution of 4-[methyl-[(5-methyl-2-oxo-1,3-dioxol-4-yl)methoxycarbonyl]amino]butanoic acid (70 mg, 0.256 mmol, 1 eq) in DCM (5 mL) at 0° C. was added DMF (0.2 mg, 0.0026 mmol, 0.01 eq) and oxalyl chloride (65 mg, 0.512 mmol, 0.045 mL, 2 eq). The mixture was stirred at 20° C. for 0.5 hr. The reaction was concentrated to dryness to give (5-methyl-2-oxo-1,3-dioxol-4-yl)methyl N-(4-chloro-4-oxo-butyl)-N-methyl-carbamate (50 mg, crude) as a yellow oil, which was used for next reaction without further purification.

Preparation of [(2R,3S,5R)-5-[6-(tert-butoxycarbonylamino)-2-fluoro-purin-9-yl]-2-ethynyl-3-hydroxy-tetrahydrofuran-2-yl]methyl 4-[methyl-[(5-methyl-2-oxo-1,3-dioxol-4-yl)methoxycarbonyl]amino]butanoate

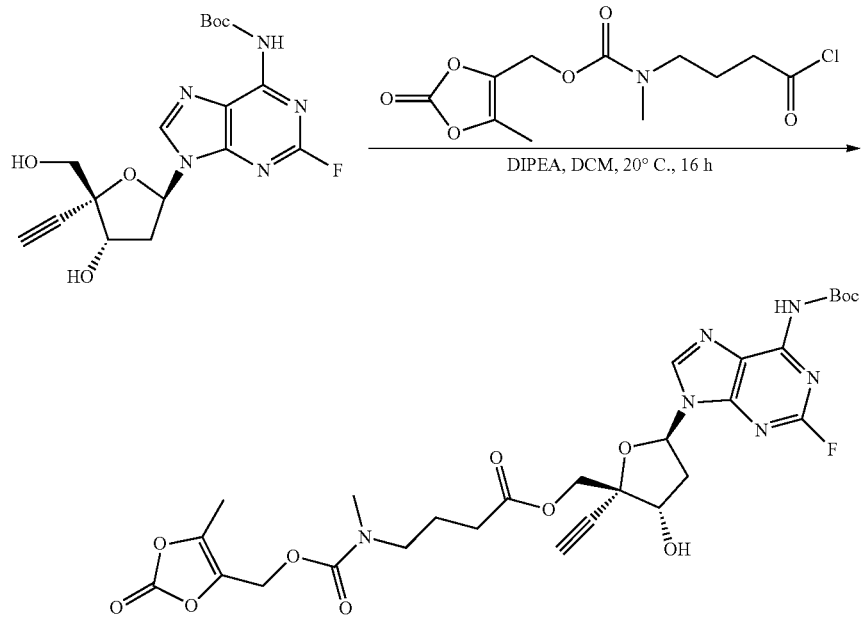

To a solution of tert-butyl N-[9-[(2R,4S,5R)-5-ethynyl-4-hydroxy-5-(hydroxymethyl)tetrahydrofuran-2-yl]-2-fluoro-

93 purin-6-yl]carbamate (20 mg, 0.0508 mmol, 1 eq) in pyridine (2 mL) was added (5-methyl-2-oxo-1,3-dioxol-4-yl)methyl-(4-chloro-4-oxo-butyl)-N-methyl-carbamate (66 mg, 0.226 mmol, 4.45 eq). The mixture was stirred at 20° C. for 16 hr. The reaction was concentrated to give [(2R,3S,5R)-5-[6-(tert-butoxy carbonylamino)-2-fluoro-purin-9-yl]-2-ethynyl-3-hydroxy-tetrahydrofuran-2-yl]methyl 4-[methyl-[(5-methyl-2-oxo-1,3-dioxol-4-yl)methoxycarbonyl]amino]butanoate (35 mg, crude) as a yellow oil, which was used for next reaction without further purification.

Preparation of ((2R,3S,5R)-5-(6-amino-2-fluoro-9H-purin-9-yl)-2-ethynyl-3-hydroxytetrahydrofuran-2-yl)methyl 4-(methyl(((5-methyl-2-oxo-1,3-dioxol-4-yl)methoxy)carbonyl)amino)butanoate

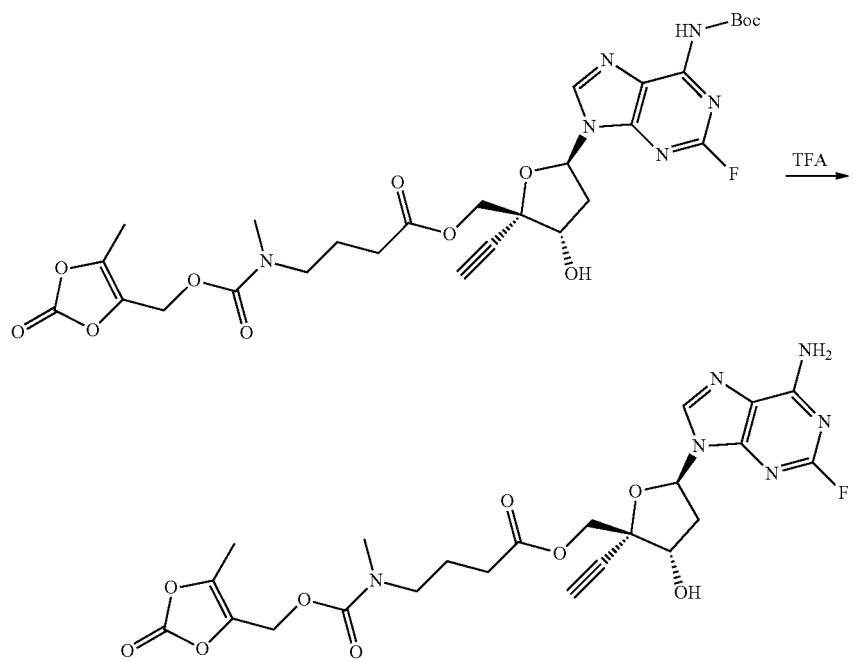

Example 7

To a solution of [(2R,3S,5R)-5-[6-(tert-butoxycarbonylamino)-2-fluoro-purin-9-yl]-2-ethynyl-3-hydroxy-tetrahydrofuran-2-yl]methyl 4-[methyl-[(5-methyl-2-oxo-1,3-dioxol-4-yl) methoxy carbonyl]amino]butanoate (25 mg, 0.0386 mmol, 1 eq) in toluene (2 mL) was added TFA (770 mg, 0.675 mmol, 0.50 mL, 10%, 17.52 eq). The mixture was stirred at 20° C. for 16 hr and then concentrated to dryness. The residue was purified by prep-HPLC (TFA condition; column: Boston Green ODS 150*30 mm*5um; mobile phase: [water (0.075% TFA)–ACN]; B %: 20%-50%, 12 min) to give ((2R,3S,5R)-5-(6-amino-2-fluoro-9H-purin-9-yl)-2-ethynyl-3-hydroxytetrahydrofuran-2-yl)methyl 4-(methyl(((5-methyl-2-oxo-1,3-dioxol-4-yl)methoxy)carbonyl)amino)butanoate (1.8 mg, 8.51% yield) was obtained as a light yellow solid. LCMS (ESI) m/z, $C_{23}H_{26}FN_6O_9$, calculated 548.2, found (M+H)$^+$: 549.2. $^1$H NMR (400 MHz, CD$_3$OD) δ (ppm) 8.14 (s, 1H), 6.29 (m, 1H), 4.88 (s, 2H), 4.44 (t, J=11.2 Hz, 1H), 4.25 (t, J=11.2 Hz, 1H), 3.26-3.13 (m, 3H), 2.96-2.86 (m, 2H), 2.82 (s, 2H), 2.64 (m, 1H), 2.25 (m, 2H), 2.16-2.07 (m, 3H), 1.74 (m, 2H), 1.31 (s, 1H). $^{19}$F NMR (376 MHz, CD$_3$OD) δ (ppm) −52.82 (s).

94

Example 8

N-(9-((2R,4S,5R)-5-ethynyl-4-hydroxy-5-(hydroxymethyl)tetrahydrofuran-2-yl)-2-fluoro-9H-purin-6-yl)butyramide

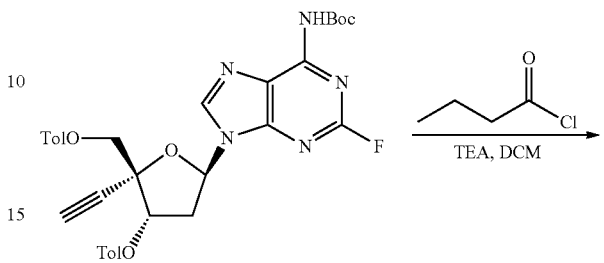

-continued

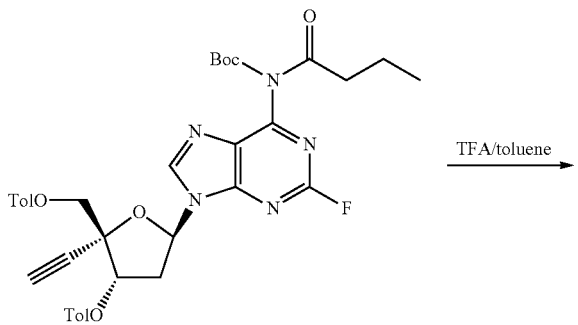

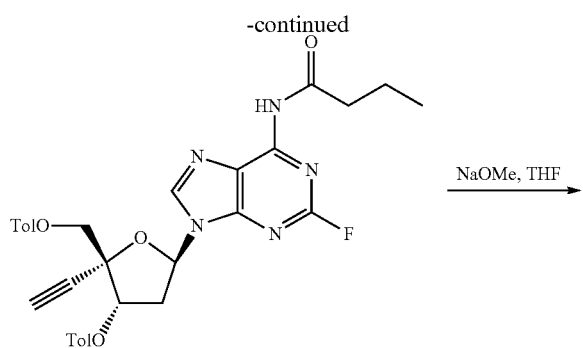

Preparation of [(2R,3S,5R)-5-[6-[butanoyl(tert-butoxycarbonyl)amino]-2-fluoro-purin-9-yl]-2-ethynyl-3-(4-methylbenzoyl)oxy-tetrahydrofuran-2-yl]methyl 4-methylbenzoate

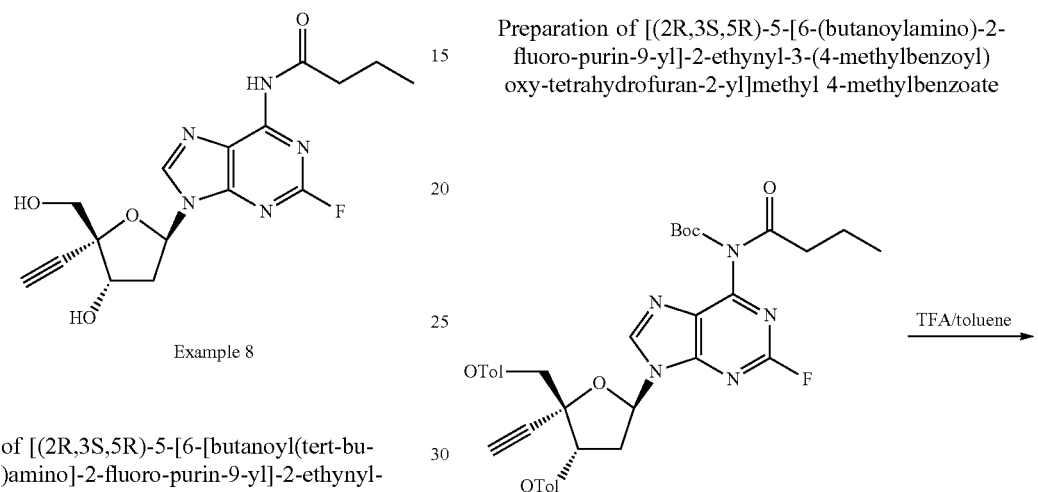

To a solution of [(2R,3S,5R)-5-[6-(tert-butoxycarbonylamino)-2-fluoro-purin-9-yl]-2-ethynyl-3-(4-methylbenzoyl)oxy-tetrahydrofuran-2-yl]methyl 4-methylbenzoate (74 mg, 0.118 mmol, 1 eq) in DCM (5 mL) was added DMAP (1.5 mg, 0.012 mmol, 0.1 eq), TEA (36 mg, 0.354 mmol, 3.0 eq) and butanoyl chloride (25 mg, 0.235 mmol, 2 eq). The mixture was stirred at 25° C. for 16 h. The mixture was concentrated and diluted with H$_2$O (30 mL), then extracted with EtOAc (15×3 mL). The combined organic layers were washed with brine (30 mL), dried over Na$_2$SO$_4$, filtered and concentrated. The resulting residue was purified by flash silica gel chromatography (ISCO®; 4 g SepaFlash® Silica Flash Column, eluent of 0-20% ethyl acetate/petroleum ether gradient @18 mL/min) to give [(2R,3S,5R)-5-[6-[butanoyl(tert-butoxy carbonyl)amino]-2-fluoro-purin-9-yl]-2-ethynyl-3-(4-methylbenzoyl)oxy-tetrahydrofuran-2-yl]methyl 4-methylbenzoate (30 mg, 30% yield) as light yellow oil. LCMS (ESI) m/z, C$_{37}$H$_{38}$FN$_5$O$_8$: calculated 700.3, found (M+H)$^+$: 701.3.

Preparation of [(2R,3S,5R)-5-[6-(butanoylamino)-2-fluoro-purin-9-yl]-2-ethynyl-3-(4-methylbenzoyl)oxy-tetrahydrofuran-2-yl]methyl 4-methylbenzoate

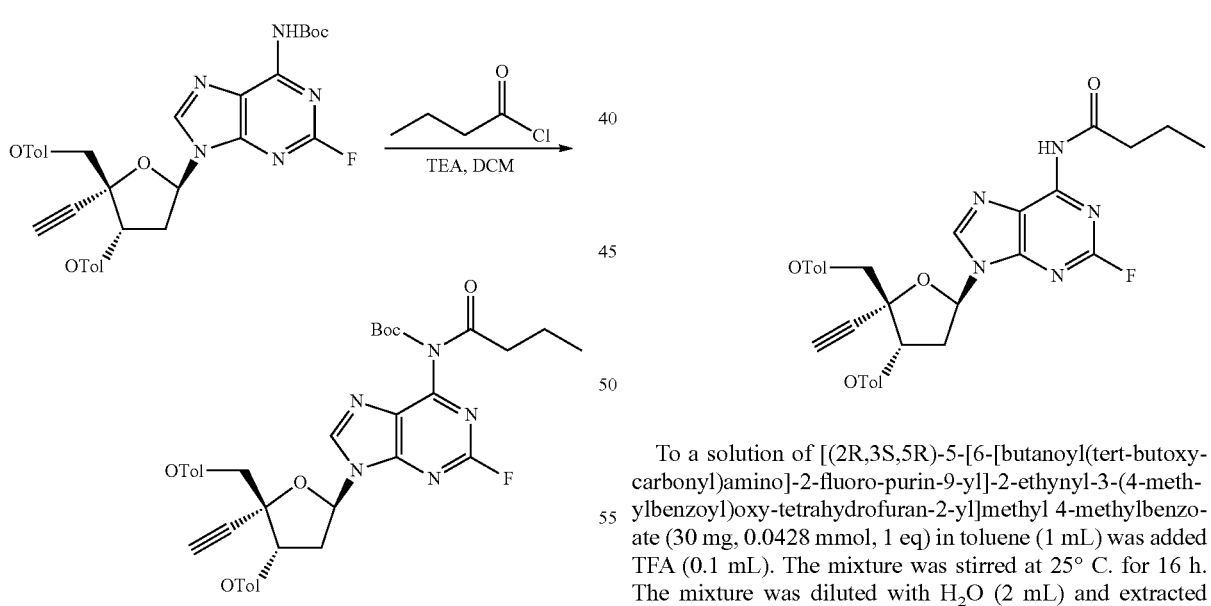

To a solution of [(2R,3S,5R)-5-[6-[butanoyl(tert-butoxycarbonyl)amino]-2-fluoro-purin-9-yl]-2-ethynyl-3-(4-methylbenzoyl)oxy-tetrahydrofuran-2-yl]methyl 4-methylbenzoate (30 mg, 0.0428 mmol, 1 eq) in toluene (1 mL) was added TFA (0.1 mL). The mixture was stirred at 25° C. for 16 h. The mixture was diluted with H$_2$O (2 mL) and extracted with EtOAc (3×3 mL), the combined organic layer was washed with brine (15×3 mL), dried over Na$_2$SO$_4$, filtered and concentrated. The resulting residue was purified by prep-TLC (SiO2, petroleum ether/ethyl acetate=1:1) to give [(2R,3S,5R)-5-[6-(butanoylamino)-2-fluoro-purin-9-yl]-2-ethynyl-3-(4-methylbenzoyl)oxy-tetrahydrofuran-2-yl] methyl 4-methylbenzoate (18 mg, 64% yield) as an light yellow oil. LCMS (ESI) m/z, C$_{32}$H$_{30}$FN$_5$O$_6$: calculated 600.2, found (M+H)$^+$: 601.3.

Preparation of N-[9-[(2R,4S,5R)-5-ethynyl-4-hydroxy-5-(hydroxymethyl)tetrahydrofuran-2-yl]-2-fluoro-purin-6-yl]butanamide

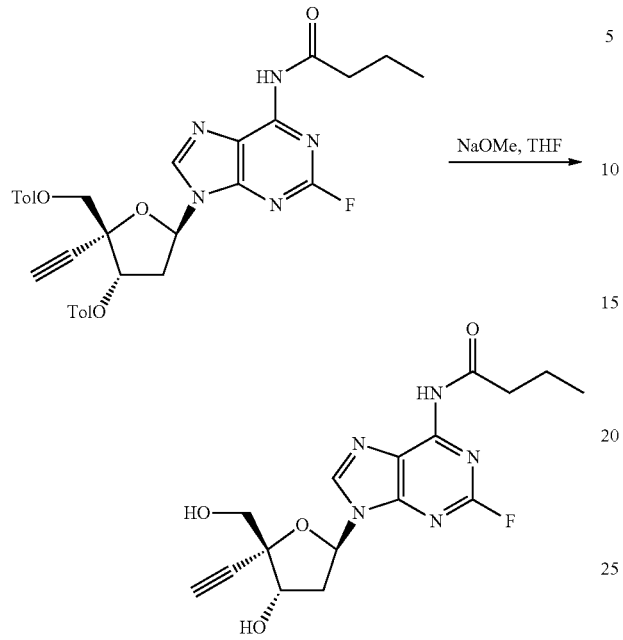

To a solution of [(2R,3S,5R)-5-[6-(butanoylamino)-2-fluoro-purin-9-yl]-2-ethynyl-3-(4-methylbenzoyl)oxy-tetrahydrofuran-2-yl]methyl 4-methylbenzoate (18 mg, 0.030 mmol, 1 eq) in THF (2 mL) was added $CH_3ONa$ (54 mg, 0.30 mmol, 30% purity in MeOH, 10 eq). The mixture was stirred at −25° C. for 4 h. The mixture was acidified with HOAc to pH=7, then the mixture was concentrated. The resulting residue was purified by prep-HPLC (FA condition; column: 3_Phenomenex Luna C18 75×30 mm×3 um; mobile phase: [water (0.2% FA)–ACN]; B %: 15%~45%, 6 min) to give N-[9-[(2R,4S,5R)-5-ethynyl-4-hydroxy-5-(hydroxymethyl)tetrahydrofuran-2-yl]-2-fluoro-purin-6-yl]butanamide (4.4 mg, 40% yield) as a white solid. LCMS (ESI) m/z, $C_{16}H_{18}FN_5O_4$: calculated 364.1, found (M+H)$^+$: 365.2. $^1$H NMR (400 MHz, $CD_3CN$) δ (ppm) 9.15 (bs, 1H), 8.26 (s, 1H), 6.37-6.34 (m, 1H), 4.70 (t, J=6.4 Hz, 1H), 3.82-3.78 (m, 1H), 3.74-3.69 (m, 1H), 2.96-2.93 (m, 1H), 2.84-2.75 (m, 2H), 2.66 (t, J=7.6 Hz, 2H), 2.59-2.52 (m, 2H), 1.74-1.67 (m, 2H), 0.99 (t, J=7.6 Hz, 3H). $^{19}$F NMR (376 MHz, $CD_3CN$) δ (ppm) −51.9 (s, 1F).

Example 9

[(2R,3S,5R)-5-(6-amino-2-fluoro-purin-9-yl)-4,4-dideuterio-2-ethynyl-3-hydroxy-tetrahydrofuran-2-yl]methyl (5-methyl-2-oxo-1,3-dioxol-4-yl)methyl carbonate

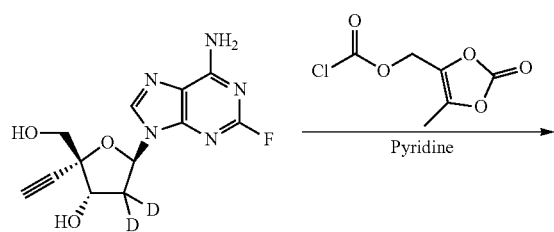

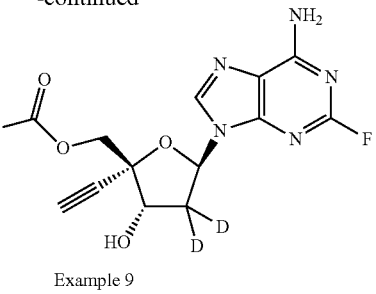

Preparation of [(2R,3S,5R)-5-(6-amino-2-fluoro-purin-9-yl)-4,4-dideuterio-2-ethynyl-3-hydroxy-tetrahydrofuran-2-yl]methyl (5-methyl-2-oxo-1,3-dioxol-4-yl)methyl carbonate

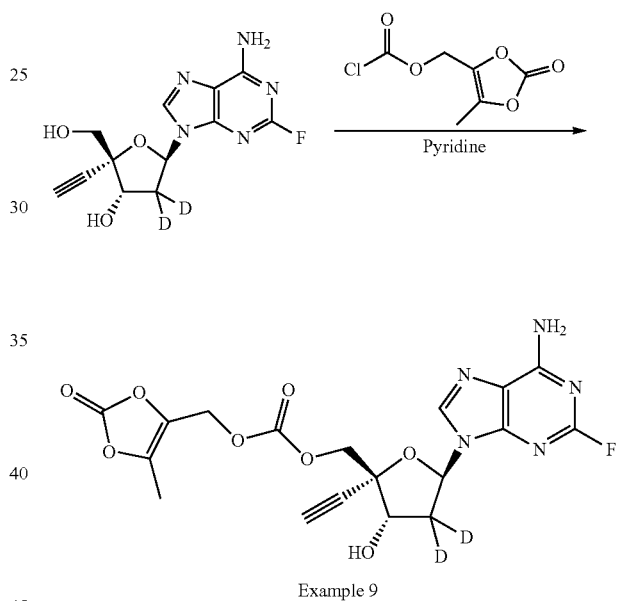

To a mixture of (2R,3S,5R)-5-(6-amino-2-fluoro-purin-9-yl)-4,4-dideuterio-2-ethynyl-2-(hydroxymethyl)tetrahydrofuran-3-ol (60 mg, 0.203 mmol, 1 eq) in pyridine (0.5 mL) was dropwise added (5-methyl-2-oxo-1,3-dioxol-4-yl) methyl carbonochloridate (195 mg, 1.02 mmol, 5 eq) in DCM (0.5 mL). The resulting mixture was stirred at 25° C. for 3 h. The reaction mixture was concentrated. The resulting residue was purified by flash silica gel chromatography (ISCO®; 4 g SepaFlash® Silica Flash Column, eluent with 0-5% methanol/dichloromethane gradient@18 mL/min) to give [(2R,3S,5R)-5-(6-amino-2-fluoro-purin-9-yl)-4,4-dideuterio-2-ethynyl-3-hydroxy-tetrahydrofuran-2-yl]methyl (5-methyl-2-oxo-1,3-dioxol-4-yl)methyl carbonate (21 mg, 22.9% yield) as a white solid. LCMS (ESI) m/z, $C_{18}H_{14}D_2FN_5O_8$: calculated 451.11 found (M+H)$^+$: 452.1. $^1$H NMR (400 MHz, $CD_3CN$) δ (ppm) 7.92 (s, 1H), 6.31 (s, 2H), 6.25 (s, 1H), 4.9-4.82 (m, 2H), 4.73-4.71 (m, 1H), 4.52-4.50 (d, J=8 Hz, 1H), 4.32-4.29 (d, J=12 Hz, 1H), 3.74-3.72 (d, J=8 Hz, 1H), 3.00 (s, 1H), 2.10 (s, 3H). $^{19}$F NMR (376 MHz, $CD_3CN$) δ (ppm) −52.84 (s, 1F).

Example 10

[[(2R,3S,5R)-5-(6-amino-2-fluoro-purin-9-yl)-4,4-dideuterio-2-ethynyl-3-hydroxy-tetrahydrofuran-2-yl]-dideuterio-methyl] (5-methyl-2-oxo-1,3-dioxol-4-yl)methyl carbonate

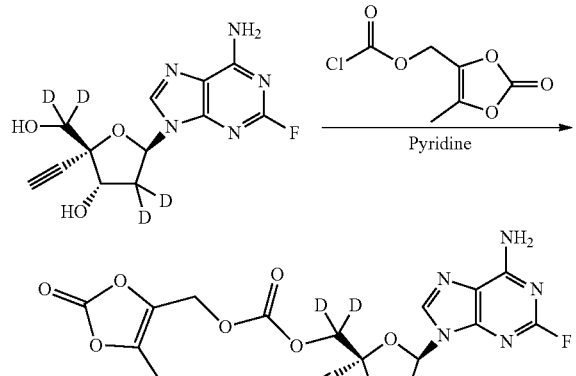

Example 10

Preparation of [[(2R,3S,5R)-5-(6-amino-2-fluoro-purin-9-yl)-4,4-dideuterio-2-ethynyl-3-hydroxy-tetrahydrofuran-2-yl]-dideuterio-methyl] (5-methyl-2-oxo-1,3-dioxol-4-yl)methyl carbonate

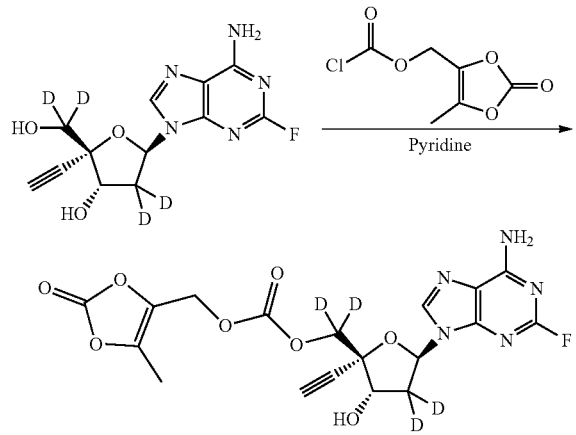

Example 10

To a mixture of (2R,3S,5R)-5-(6-amino-2-fluoro-purin-9-yl)-4,4-dideuterio-2-[dideuterio(hydroxy)methyl]-2-ethynyl-tetrahydrofuran-3-ol (50 mg, 0.168 mmol, 1 eq) in pyridine (0.5 mL) was dropwise added (5-methyl-2-oxo-1,3-dioxol-4-yl)methyl carbonochloridate (162 mg, 0.84 mmol, 5 eq) in DCM (0.5 mL). The resulting mixture was stirred at 25° C. for 3 h. The reaction mixture was concentrated. The resulting residue was purified by flash silica gel chromatography (ISCO®; 4 g SepaFlash® Silica Flash Column, Eluent with 0-5% methanol/dichloromethane gradient@18 mL/min) to give [[(2R,3S,5R)-5-(6-amino-2-fluoro-purin-9-yl)-4,4-dideuterio-2-ethynyl-3-hydroxy-tetrahydrofuran-2-yl]-dideuterio-methyl](5-methyl-2-oxo-1,3-dioxol-4-yl)methyl carbonate (40.6 mg, 53% yield) as a white solid. LCMS (ESI) m/z, $C_{18}H_{12}D_4FN_5O_8$: calculated 453.3, found (M+H)$^+$: 454.2. $^1$H NMR (400 MHz, DMSO-$d_6$) δ (ppm) 7.92 (s, 1H), 6.31 (s, 2H), 6.25 (s, 1H), 4.91-4.82 (m, 2H), 4.72-4.71 (d, J=4 Hz, 1H), 3.74-3.72 (d, J=8 Hz, 1H), 3.00 (s, 1H), 2.10 (s, 3H). $^{19}$F NMR (376 MHz, DMSO-$d_6$) δ (ppm) −52.85 (s, 1F).

Example 11

((2R,3S,5R)-5-(6-amino-2-fluoro-9H-purin-9-yl)-2-ethynyl-3-hydroxytetrahydrofuran-2-yl)methyl butyl carbonate

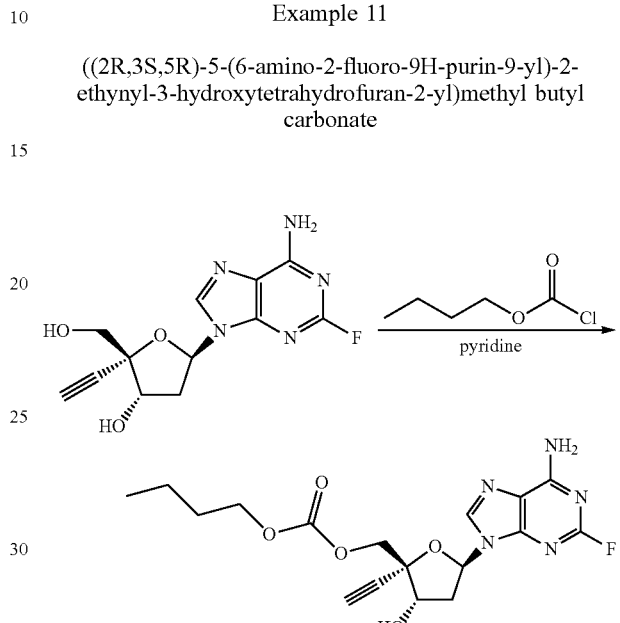

Example 11

Preparation of ((2R,3S,5R)-5-(6-amino-2-fluoro-9H-purin-9-yl)-2-ethynyl-3-hydroxytetrahydrofuran-2-yl)methyl butyl carbonate

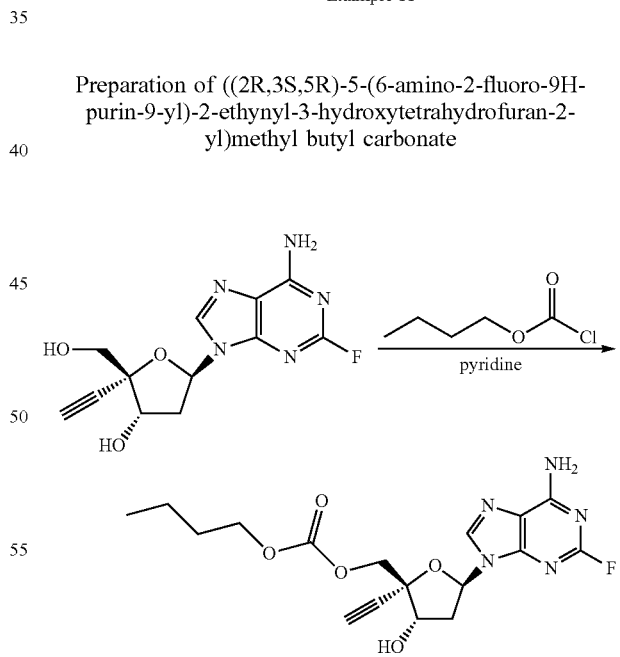

To a solution of (2R,3S,5R)-5-(6-amino-2-fluoro-9H-purin-9-yl)-2-ethynyl-2-(hydroxymethyl)tetrahydrofuran-3-ol (50 mg, 0.17 mmol, 1 eq) in pyridine (0.5 mL) was added butyl carbonochloridate (26 mg, 0.187 mmol, 0.024 mL, 1.1 eq) slowly at 0° C. and stirred the mixture for 2 h. The reaction mixture was concentrated, the resulting residue was purified by flash silica gel chromatography (ISCO®; 4 g SepaFlash® Silica Flash Column, eluted with 0-5% MeOH/DCM@30 mL/min) to give compound ((2R,3S,5R)-5-(6-amino-2-fluoro-9H-purin-9-yl)-2-ethynyl-3-hydroxytetrahydrofuran-2-yl)methyl butyl carbonate (7.6 mg, 11.3% yield) as a white solid. LCMS (ESI) m/z, $C_{17}H_{20}FN_5O_5$: calculated 393.14, found (M+H)$^+$: 394.1. $^1$H NMR (400 MHz, CD$_3$CN) δ (ppm): 7.96 (s, 1H), 6.27 (m, 3H), 4.73 (q, J=6.8 Hz, 1H), 4.46 (d, J=11.6 Hz, 1H), 4.31-4.23 (m, 1H), 4.10-3.99 (m, 2H), 3.75-3.66 (m, 1H), 2.99 (s, 1H), 2.85 (m, 1H), 2.57 (m, 1H), 1.61-1.52 (m, 2H), 1.28 (m, 2H), 0.94-0.87 (m, 3H); $^{19}$F NMR (376 MHz, CD$_3$CN) δ (ppm): −52.86 (s, 1F).

Example 12

(2R,3S,5R)-5-(6-amino-2-fluoro-9H-purin-9-yl)-2-ethynyl-2-(hydroxymethyl)tetrahydrofuran-3-yl((5-methyl-2-oxo-1,3-dioxol-4-yl)methyl) carbonate

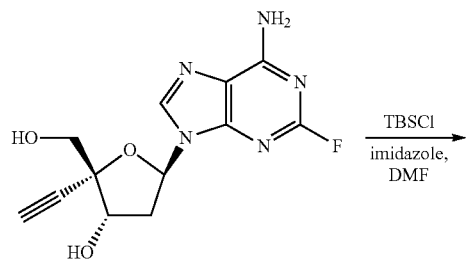

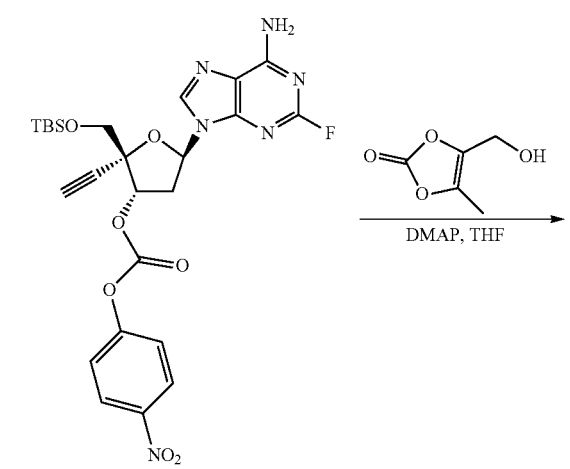

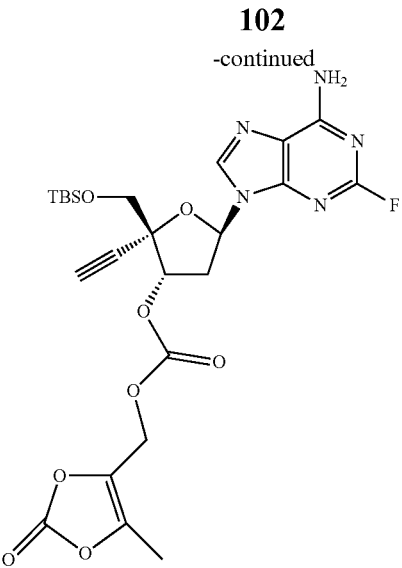

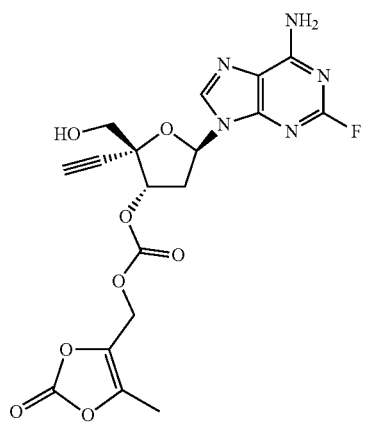

Example 12

Preparation of (2R,3S,5R)-5-(6-amino-2-fluoro-9H-purin-9-yl)-2-(((tert-butyldimethylsilyl)oxy)methyl)-2-ethynyltetrahydrofuran-3-ol

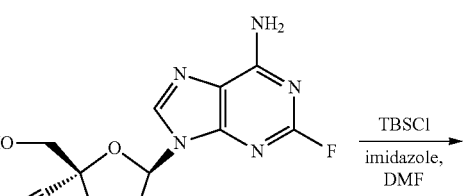

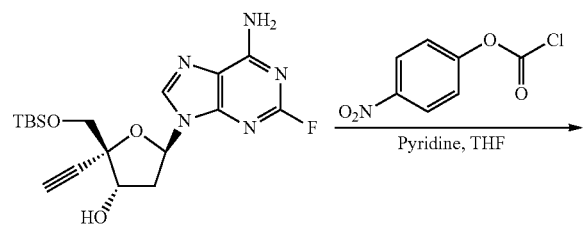

To a solution of (2R,3S,5R)-5-(6-amino-2-fluoro-9H-purin-9-yl)-2-ethynyl-2-(hydroxymethyl)tetrahydrofuran-3-ol (0.5 g, 1.71 mmol, 1 eq) in DMF (5 mL) was added imidazole (349 mg, 5.13 mmol, 3 eq) and TBSCl (386 mg, 2.56 mmol, 1.5 eq). The mixture was stirred at 25° C. for 16 h. The reaction mixture was concentrated. The resulting residue was purified by flash silica gel chromatography (ISCO®; 4 g SepaFlash® Silica Flash Column, eluted with 0~5% MeOH/DCM@18 mL/min) to give (2R,3S,5R)-5-(6-amino-2-fluoro-9H-purin-9-yl)-2-(((tert-butyldimethylsilyl)oxy)methyl)-2-ethynyltetrahydrofuran-3-ol (331 mg, 47.5% yield) as a light yellow solid. $^1$H NMR (400 MHz, CD$_3$CN) δ (ppm) 8.03 (s, 1H), 6.39-6.17 (m, 3H), 4.71 (q, J=6.8 Hz, 1H), 3.93-3.87 (m, 1H), 3.84-3.76 (m, 1H), 3.49 (d, J=6.4 Hz, 1H), 2.91 (s, 1H), 2.85-2.73 (m, 1H), 2.55 (m, 1H), 2.50 (s, 2H), 0.88-0.82 (m, 9H), 0.02 (d, J=16 Hz, 6H); $^{19}$F NMR (376 MHz, CD$_3$CN) δ (ppm) −53.04 (s, 1F).

Preparation of [(2R,3S, 5R)-5-(6-amino-2-fluoro-purin-9-yl)-2-[[tert-butyl (dimethyl) silyl]oxymethyl]-2-ethynyl- tetrahydrofuran-3-yl] (4-nitrophenyl) carbonate

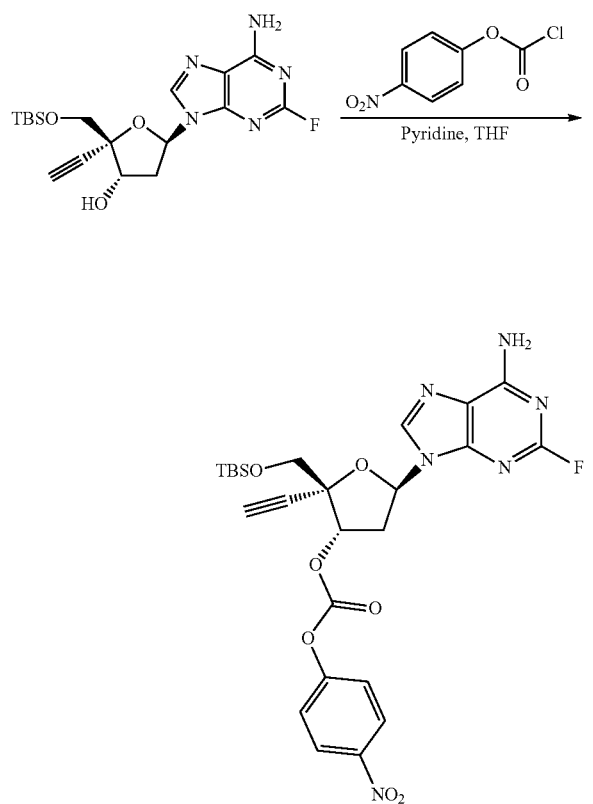

To a solution of (2R,3S,5R)-5-(6-amino-2-fluoro-9H-purin-9-yl)-2-(((tert-butyldimethylsilyl)oxy)methyl)-2-ethynyltetrahydrofuran-3-ol (100 mg, 0.245 mmol, 1 eq) in THF (2 mL) was added pyridine (0.40 mL, 20 eq) and (4-nitrophenyl) carbonochloridate (494 mg, 2.45 mmol, 10 eq). The mixture was stirred at 25° C. for 50 h. The reaction mixture was concentrated. The resulting residue was purified by flash silica gel chromatography (ISCO®; 4 g SepaFlash® Silica Flash Column, eluted with 0-5% MeOH/DCM@18 mL/min) to give compound [(2R,3S, 5R)-5-(6-amino-2-fluoro-purin-9-yl)-2-[[tert-butyl (dimethyl) silyl]oxymethyl]-2-ethynyl-tetrahydrofuran-3-yl](4-nitrophenyl) carbonate (178 mg, crude) as a light yellow solid.

Preparation of [(2R,3S, 5R)-5-(6-amino-2-fluoro-purin-9-yl)-2-[[tert-butyl (dimethyl) silyl]oxymethyl]-2-ethynyl-tetrahydrofuran-3-yl](5-methyl-2-oxo-1,3-dioxol-4-yl)methyl carbonate

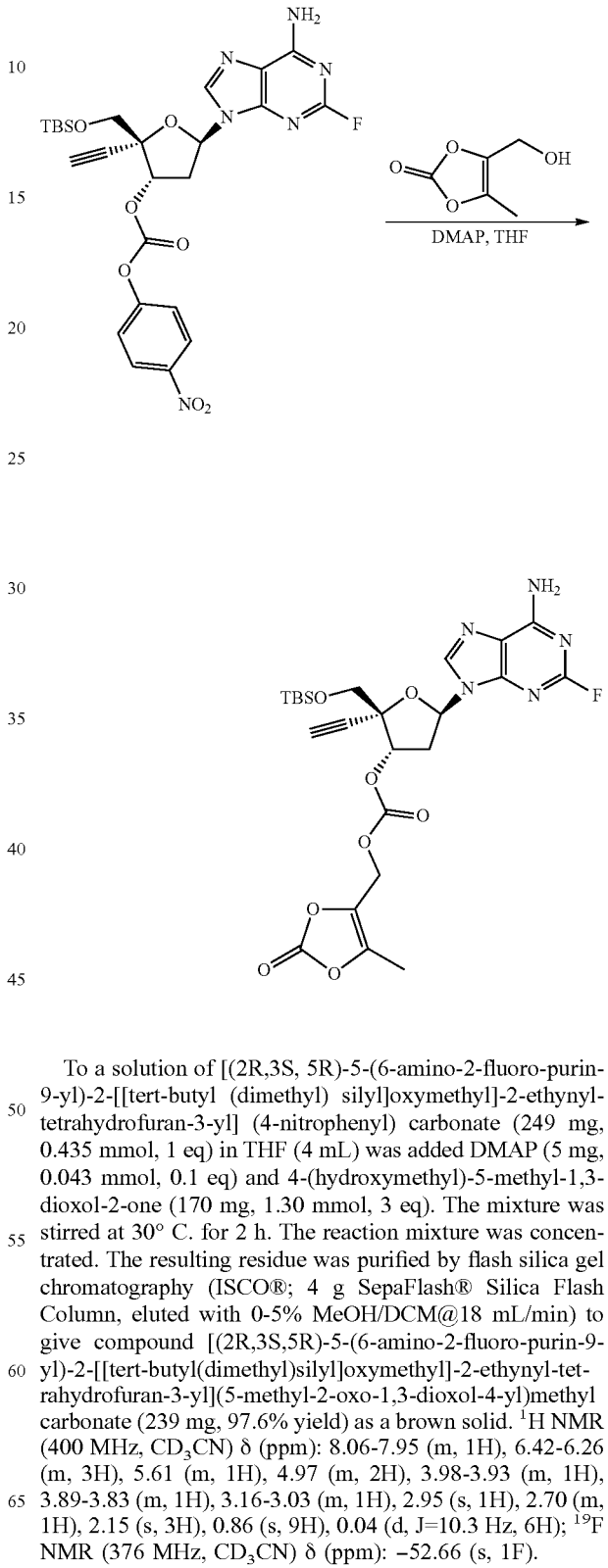

To a solution of [(2R,3S, 5R)-5-(6-amino-2-fluoro-purin-9-yl)-2-[[tert-butyl (dimethyl) silyl]oxymethyl]-2-ethynyl-tetrahydrofuran-3-yl] (4-nitrophenyl) carbonate (249 mg, 0.435 mmol, 1 eq) in THF (4 mL) was added DMAP (5 mg, 0.043 mmol, 0.1 eq) and 4-(hydroxymethyl)-5-methyl-1,3-dioxol-2-one (170 mg, 1.30 mmol, 3 eq). The mixture was stirred at 30° C. for 2 h. The reaction mixture was concentrated. The resulting residue was purified by flash silica gel chromatography (ISCO®; 4 g SepaFlash® Silica Flash Column, eluted with 0-5% MeOH/DCM@18 mL/min) to give compound [(2R,3S,5R)-5-(6-amino-2-fluoro-purin-9-yl)-2-[[tert-butyl(dimethyl)silyl]oxymethyl]-2-ethynyl-tetrahydrofuran-3-yl](5-methyl-2-oxo-1,3-dioxol-4-yl)methyl carbonate (239 mg, 97.6% yield) as a brown solid. $^1$H NMR (400 MHz, CD$_3$CN) δ (ppm): 8.06-7.95 (m, 1H), 6.42-6.26 (m, 3H), 5.61 (m, 1H), 4.97 (m, 2H), 3.98-3.93 (m, 1H), 3.89-3.83 (m, 1H), 3.16-3.03 (m, 1H), 2.95 (s, 1H), 2.70 (m, 1H), 2.15 (s, 3H), 0.86 (s, 9H), 0.04 (d, J=10.3 Hz, 6H); $^{19}$F NMR (376 MHz, CD$_3$CN) δ (ppm): −52.66 (s, 1F).

Preparation of (2R,3S,5R)-5-(6-amino-2-fluoro-9H-purin-9-yl)-2-ethynyl-2-(hydroxymethyl)tetrahydrofuran-3-yl((5-methyl-2-oxo-1,3-dioxol-4-yl)methyl) carbonate

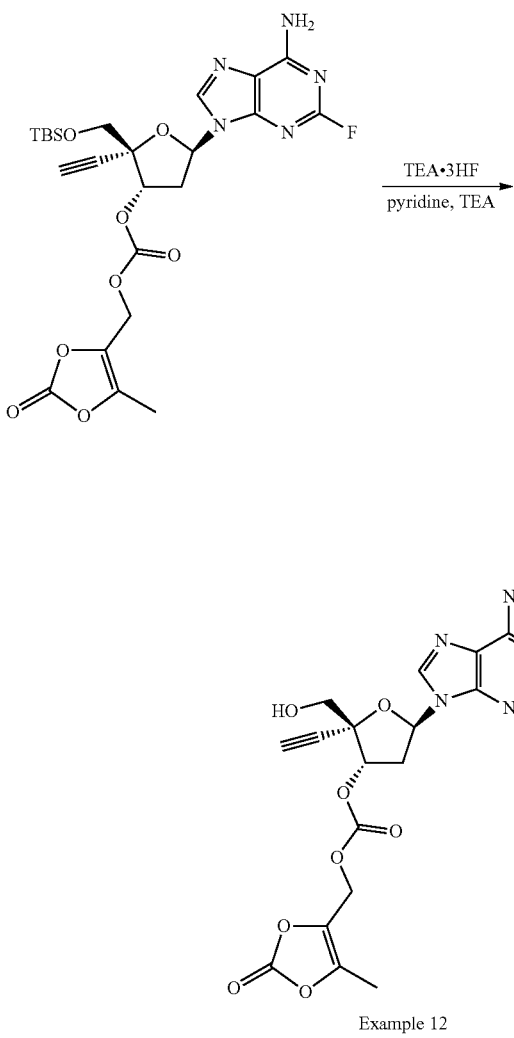

Example 12

To a solution of [(2R,3S,5R)-5-(6-amino-2-fluoro-purin-9-yl)-2-[[tert-butyl(dimethyl)silyl]oxymethyl]-2-ethynyl-tetrahydrofuran-3-yl](5-methyl-2-oxo-1,3-dioxol-4-yl) methyl carbonate (359 mg, 0.637 mmol, 1 eq) in pyridine (3.5 mL) and TEA (3.5 mL) was added N,N-diethyl-ethanamine; trihydrofluoride (3.55 g, 22.02 mmol, 34.58 eq) at 0° C., then the mixture was stirred at 25° C. for 1 h. The reaction mixture was concentrated. The resulting residue was purified by flash silica gel chromatography (ISCO®; 4 g SepaFlash® Silica Flash Column, eluted with 0~5% MeOH/DCM@18 mL/min) to give (2R,3S,5R)-5-(6-amino-2-fluoro-9H-purin-9-yl)-2-ethynyl-2-(hydroxymethyl)tetrahydrofuran-3-yl((5-methyl-2-oxo-1,3-dioxol-4-yl)methyl) carbonate (230 mg, 80% yield) as a white solid. LCMS (ESI) m/z, $C_{18}H_{16}FN_5O_8$: 449.1, found (M+H)⁺: 450.1. ¹H NMR (400 MHz, $CD_3CN$) δ(ppm): 7.95 (s, 1H), 6.47 (s, 2H), 6.34 (m, 1H), 5.53 (m, 1H), 5.02-4.93 (m, 3H), 3.92-3.70 (m, 2H), 3.07 (m, 1H), 2.95 (s, 1H), 2.61 (m, 1H), 2.15 (s, 3H); ¹⁹F NMR (376 MHz, $CD_3CN$) δ (ppm): −53.27 (s, 1F).

Example 13

((2R,3S,5R)-5-(6-amino-2-fluoro-9H-purin-9-yl)-2-ethynyl-3-4((((5-methyl-2-oxo-1,3-dioxol-4-yl)methoxy)carbonyl)oxy)tetrahydrofuran-2-yl)methyl ((5-methyl-2-oxo-1,3-dioxol-4-yl)methyl) carbonate

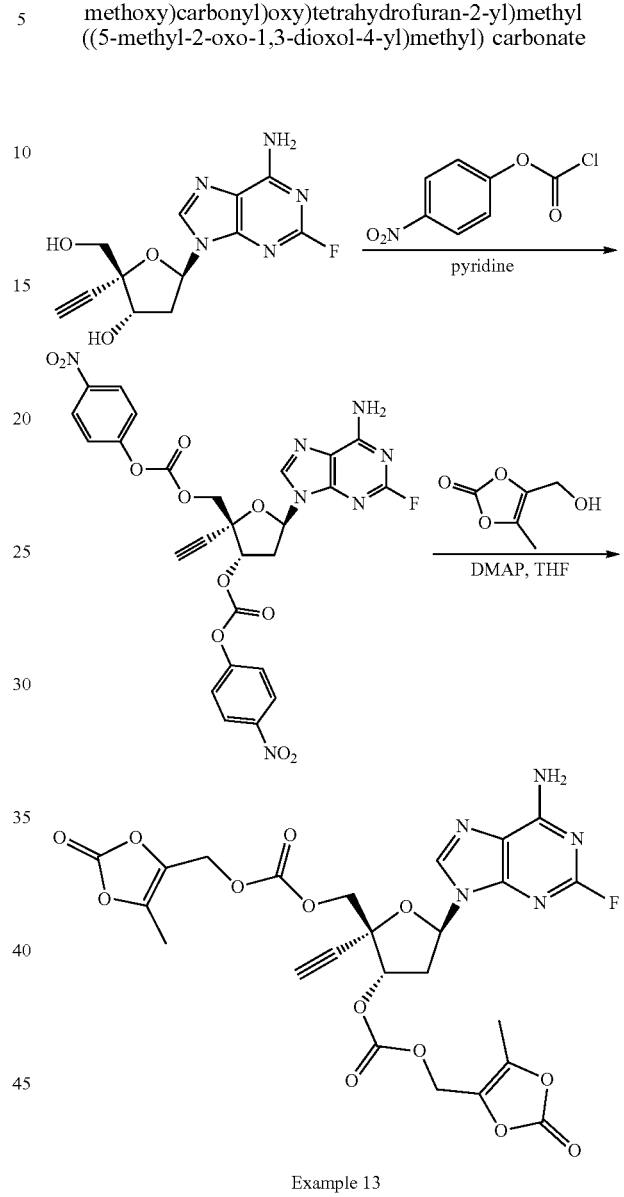

Example 13

Preparation of [(2R,3S,5R)-5-(6-Amino-2-fluoro-purin-9-yl)-2-ethynyl-2-[(4-nitrophenoxy)carbonyloxymethyl]tetrahydrofuran-3-yl](4-nitrophenyl) carbonate

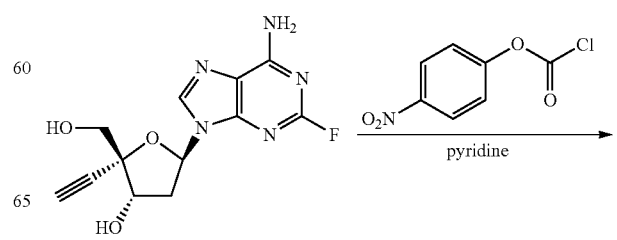

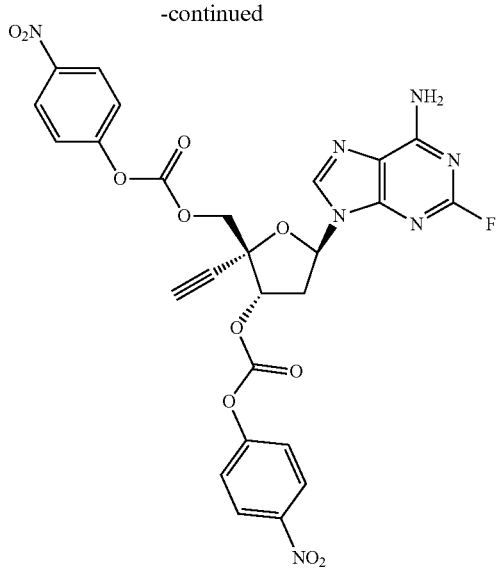

To a solution of (2R,3S,5R)-5-(6-amino-2-fluoro-purin-9-yl)-2-ethynyl-2-(hydroxymethyl)tetrahydrofuran-3-ol (100 mg, 0.341 mmol, 1 eq) in DCM (5 mL) was added pyridine (674 mg, 8.53 mmol, 25 eq) and (4-nitrophenyl) carbonochloridate (1.03 g, 5.12 mmol, 15 eq) at 26° C. The mixture was stirred at 26° C. for 4 hr. The mixture was quenched with $H_2O$ (30 mL). The mixture was added DCM (30 mL) and washed with $H_2O$ (30 mL), brine (30 mL). The organic layer was dried over $Na_2SO_4$ and concentrated. The residue was purified by flash silica gel chromatography (ISCO®; 4 g SepaFlash® Silica Flash Column, Eluent of 0-6% Methanol/Dichloromethane gradient@18 mL/min) to give [(2R,3S,5R)-5-(6-amino-2-fluoro-purin-9-yl)-2-ethynyl-2-[(4-nitrophenoxy)carbonyloxymethyl]tetrahydrofuran-3-yl](4-nitrophenyl) carbonate (137 mg, 51% yield, 80% purity) as a white solid. LCMS (ESI) m/z, $C_{26}H_{18}FN_7O_{11}$: calculated 623.10, found 624.1 $(M+H)^+$.

Preparation of [(2R,3S,5R)-5-(6-amino-2-fluoro-purin-9-yl)-2-ethynyl-2-[(5-methyl-2-oxo-1,3-dioxol-4-yl)methoxycarbonyloxymethyl]tetrahydrofuran-3-yl] (5-methyl-2-oxo-1,3-dioxol-4-yl)methyl carbonate

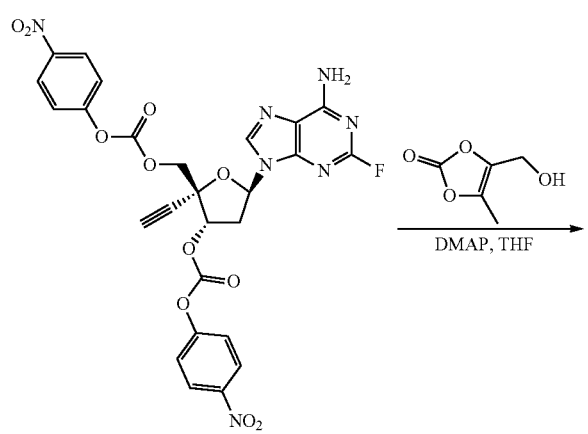

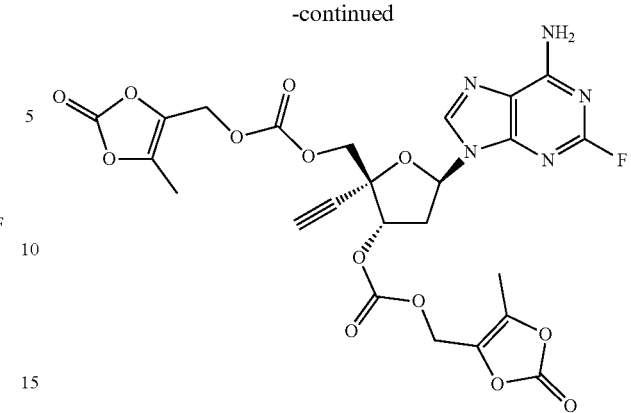

To a solution of [(2R,3S,5R)-5-(6-amino-2-fluoro-purin-9-yl)-2-ethynyl-2-[(4-nitrophenoxy)carbonyloxymethyl]tetrahydrofuran-3-yl](4-nitrophenyl) carbonate (99 mg, 0.159 mmol, 1 eq) in THF (5 mL) was added DMAP (1.9 mg, 0.016 mmol, 0.1 eq) and 4-(hydroxymethyl)-5-methyl-1,3-dioxol-2-one (248 mg, 1.91 mmol, 12 eq). The mixture was stirred at 25° C. for 16 h. The mixture was quenched with $H_2O$ (30 mL). The mixture was added DCM (30 mL). The mixture was washed with $H_2O$ (30 mL) and brine (30 mL). The organic layer was dried over $Na_2SO_4$ and concentrated. The resulting residue was purified by flash silica gel chromatography (ISCO®; 4 g SepaFlash® Silica Flash Column, Eluent of 0~10% Methanol/Dichloromethane gradient@18 mL/min) to give [(2R,3S,5R)-5-(6-amino-2-fluoro-purin-9-yl)-2-ethynyl-2-[(5-methyl-2-oxo-1,3-dioxol-4-yl)methoxycarbonyloxymethyl]tetrahydrofuran-3-yl](5-methyl-2-oxo-1,3-dioxol-4-yl)methyl carbonate (89 mg, 56% yield, 60% purity). The material was further purified with flash silica gel chromatography and recrystallized ($CH_3CN$/Hep) to provide [(2R,3S,5R)-5-(6-amino-2-fluoro-purin-9-yl)-2-ethynyl-2-[(5-methyl-2-oxo-1,3-dioxol-4-yl)methoxycarbonyl oxymethyl]tetrahydrofuran-3-yl](5-methyl-2-oxo-1,3-dioxol-4-yl)methyl carbonate as a white solid. LCMS (ESI) m/z, $C_{24}H_{20}FN_5O_{13}$: calculated 605.10, found $(M+H)^+$: 606.1. $^1H$ NMR (400 MHz, DMSO-$d_6$) δ (ppm) 8.30 (s, 1H), 7.89 (br s, 2H), 6.38-6.34 (m, 1H), 5.62-5.59 (m, 1H), 5.14-5.06 (m, 2H), 4.99 (s, 2H), 4.53 (d, J=11.6 Hz, 1H), 4.37 (d, J=11.6 Hz, 1H), 3.83 (s, 1H), 3.21-3.17 (m, 1H), 2.73-2.70 (m, 1H), 2.19 (s, 3H), 2.14 (s, 3H). $^{19}F$ NMR (376 MHz, DMSO-$d_6$) δ (ppm) −51.47 (s, 1F).

Example 14

Conversion and Stability of the Adenosine Derivative Prodrugs

Stability of prodrugs and conversion of the prodrugs to the parent EFdA (formula T-1A) were measured in both plasma and liver S9 assays and the data are shown in Table 2.

Plasma Stability

The pooled frozen plasma was thawed in a water bath at 37° C. prior to experiment. Plasma was centrifuged at 4000 rpm for 5 min and the clots were removed if any. The pH will be adjusted to 7.4±0.1 if required.

Preparation of test compounds and positive control (propantheline bromide): 1 mM intermediate solution was prepared by diluting 10 μL of the stock solution with 90 μL MeOH; 1 mM intermediate of positive control Propantheline was prepared by diluting 10 µL of the stock solution with 90 µL ultrapure water. 100 µM dosing solution was prepared by diluting 20 µL of the intermediate solution (1 mM) with 180 µL MeOH. 98 µL of blank plasma was spiked with 2 µL of dosing solution (100 µM) to achieve 2 µM of the final concentration in duplicate and samples were incubated at 37° C. in a water bath. At each time point (0, 10, 30, 60 and 120 min), 400 µL of stop solution (0.1% FA in MeOH containing 200 ng/mL tolbutamide and 200 ng/mL Labetalol) was added to precipitate protein and mixed thoroughly. Centrifuged sample plates at 4,000 rpm for 10 min. An aliquot of supernatant (100 µL) was transferred from each well to another plates.

Data analysis: The % remaining of test compound after incubation in plasma was calculated using following equation:

% Remaining=100×(PAR at appointed incubation time/PAR at T0 time)

where PAR is the peak area ratio of analyte versus internal standard (IS) (LC/MS/MS mobile phase condition: 0.1% Formic Acid in Water/0.1% Formic Acid in Acetonitrile. The appointed incubation time points are T0 (0 min), Tn (n=0, 10, 30, 60, 120 min).

Liver S9 Stability

Intermediate solution: Dilute 5 µL of compounds or controls (7-ethoxycoumarin) from stock solution (10 mM) with 495 µL MeOH (Conc.: 100 µM, 1% DMSO, 99% MeOH). Stop solution: Cold ACN (including 100 ng/mL Tolbutamide and Labetalol as internal standard). Add 2 µL test compound or control working solution/well to all plates (T0, T5, T10, T20, T30, T60, NCF60) except matrix blank. Add 600 µL/well stop solution (cold in 4° C., including 100 ng/mL Tolbutamide/100 ng/mL Labetalol) to terminate the T0 plate, then put it on ice. Dispense 840 µL/well S9 solution to 96-well plate as reservoir according to plate map. Then add 100 µL/well to every plate by Apricot. Incubate S9 solution and compound at 37° C. for about 10 min except NCF60 and T0. After adding S9 solution and 98 µL PB buffer to NCF60, incubate at 37° C. without pre-warming, start timer 1. After 60 min, add 600 µL/well stop solution to terminate the reaction. After pre-warming, dispense 760 µL/well cofactor solution to 96-well plate as reservoir according to plate map. Then add 98 µL/well to every plate by Apricot to start reaction. Incubate at 37° C., start timer 2, Add 600 µL/well stop solution (cold in 4° C., including 100 ng/mL Tolbutamide and Labetalol) to terminate the reaction. Samples are centrifuged at 4000 rpm for 20 min. While centrifuging, load 8×new 96-well plate with 300 µL HPLC water, then transfer 100 µL supernatant, mix with water for LC/MS/MS, transferred to Bioanalytical Services for LC-MS/MS analysis. Use equation of first order kinetics to calculate $t_{1/2}$ and CL: Equation of first order kinetics:

$$C_t = C_0 \cdot e^{-k_e \cdot t}$$

$$C_t = \frac{1}{2}C_0, \quad T_{1/2} = \frac{\ln 2}{-k_e} = \frac{0.693}{-k_e}$$

$$CL_{int(S9)} = Vd \cdot k_e$$

$$Vd = 1 \text{ mL/mg}$$

The stability results of exemplary compounds in human plasm and human liver S9 were listed in Table 2 below.

TABLE 2

Conversion and Half Life Data.

| Formula | Stability in Human Plasma | | Stability in Human Liver S9 | |
|---|---|---|---|---|
| | Half-life | Formation of EFdA | Half-life | Formation of EFdA |
| 2-A | A | No | B | No |
| 3-A | A | No | B | No |
| 4-A | C | Yes | C | Yes |
| 5-A | A | No | B | No |
| 6-A | C | No | C | Yes |
| 7-A | B | No | C | No |
| 4-C | C | Yes | C | Yes |

Half-life ranges:
A: >200 minutes;
B: 50-200 minutes;
C: <50 minutes.

Data showed that adenosine derivative 4-A and 4-C can be converted to the target drug efficiently in human plasma and liver S9 assays, and 6-A can be converted to the target drug efficiently in liver S9 assay.

Example 15

Plasma Exposures Following Oral Administration of Prodrugs to Beagle Dogs

The pharmacokinetics of FRIA and prodrug formula 4-A were studied in dogs after oral administration of a 5 mg-equivalent/kg ERR dose.

Formulations: The prodrugs were formulated as solutions at 1.65 mg/mL in 20% PEG400 aqueous solution within 0.5 hour prior to dose.

Dose Administration and Sample Collection: The in-life phase of this study was conducted at the Charles River Laboratory (CRL) at Worcester, MA in accordance with the CRL Institutional Animal Care and Use Committee (IACUC) standard animal procedures along with the IACUC guidelines that are in compliance with the Animal Welfare Act, the Guide for the Care and Use of Laboratory Animals. and was approved by the IACUA Committee. Fasted male beagle dogs (10+/–2 kg) were used for the studies. Each drug was administered as a single dose by oral gavage (5 ml/kg). The prodrug formula 4-A dose (8.25 mg/kg) was dose-equivalent to 5 mg/kg of EFdA. Plasma samples were collected at 0 (pre-dose), 30 min, 1, 2, 4, 6, 8, 12 and 24 h post-dose. Blood (approximately 0.1 to 0.2 mL) was processed immediately for plasma by centrifugation at 3,500 rpm at 5° C. for 10 min immediately after collection. Plasma samples were frozen and maintained at –70° C. until analyzed. To stabilize the prodrug at the sample collection and subsequent analysis, the following stabilizing reagents were added to the blood collection K2EDTA tubes on wet ice prior to sample collection: for each 100 mL of blood, 15 mL of premade inhibitor cocktail consists of 1 mM DFP, 100 mM dichlorvos, 100 mM 2-Hydroxyquinoline, 100 mM PCMB, 1 mM Paraoxon, 100 mM PMSF, 100 mM NaF, 30.0 mM EDTA, and 15 mM Citric Acid, 10 mL of 0.2M eserine, and 10 mL of 0.2M BNPP solutions.

Determination of EFdA and Prodrugs in plasma: Briefly, plasma (20 µL) was mixed with 100 µl acetonitrile to precipitate protein. Consistent with sample collection procedure, the same cocktail protocol was also added to stabilize the prodrug in the standard and QC samples.

Bioanalysis: A Sciex API-6500 triplequadrupole mass spectrometer coupled with a Shimadzu HPLC system (Framingham, MA 01701) was used for quantitative analysis of plasma samples. The column was a Waters HSS T3 column (2.1×50 mm, 1.8 mm). The mobile phases used were: A, 5% acetonitrile in 2 mM ammonium formate buffer; B, 95% acetonitrile in 2 mM ammonium formate buffer, pH 6.0. The flow rate was 0.6 mL/min with a total run time of 3.0 min. The HPLC gradient was initiated at 98% A/2% B for 0.20 min, followed by linear gradient increase to 25% over the next 1.40 min; the gradient was subsequently increased to 100% of mobile B over the next 1.0 min and then held for additional 0.2 min before ramping down to 2% mobile phase B within the following 0.2 min. Detection of the prodrug and EFdA were achieved using positive ion electrospray mass spectroscopic mode using unit resolution mode. Multiple reaction monitoring (MRM) modes were used to quantify both prodrug and EFdA, e.g. the MRM transition for EFdA was 294.0-153.90 Da, and the transition for prodrug 4-A was 450.0-153.9 Da. Peak areas were integrated by the Sciex program Analyst®, version 1.6.3, operating on a Windows 7 computer where concentrations were determined by a weighted (1/×2) linear regression of peak area ratios (peak area of EFdA/peak area of corresponding IS) versus the nominal concentrations of the plasma calibration standards. Calculations were performed on unrounded numbers. Overall, Analyst® determined the precision and accuracy for the calibration standards and QC samples.

Pharmacokinetic Calculations: The noncompartmental (NCA) analysis of EFdA and prodrug individual plasma concentration-time data were conducted using WinNonlin module in the Phoenix PK/PD Platform (version 8.3.0.5005, Certara Inc., Princeton, NJ 08540). Calculations were performed prior to rounding and nominal sampling times were used in the pharmacokinetic analysis. Exposures were expressed as areas under concentration curves in plasma from zero to 24 hours ($AUC_{0-24\,h}$). The AUC values were calculated using the linear trapezoidal rule.

Plasma Concentrations: The results of the PK studies are shown in Tables 3 and 4, These data establish in vivo that prodrug formula 4-A can be readily delivered orally, and can efficiently release EFdA in vivo with minimal prodrug detected in the systemic circulation. For example, prodrug formula 4-A can release significantly more EFdA in vivo than a dose-equivalent EFdA, i.e., 91%, 102%, 55%, 79%, and 200% more at 0.25, 0.5, 1, 2, and 4-hour time points (see Table 3). Further, prodrug formula 4-A can produce a higher AUC and $C_{max}$ than a dose-equivalent EFdA (see Table 4).

TABLE 3

Plasma concentration of EFdA and prodrug formula 4-A after a single oral dose to male beagle dogs

| Prodrug formula 4-A PO (8.25 mg/kg) | Animal ID | | | | | |
|---|---|---|---|---|---|---|
| Time Points (hrs) | 2001 | 2002 | 2003 | Mean | SD | % CV |
| EFdA Concentrations (ng/mL) in Dog Plasma | | | | | | |
| 0.250 | 463 | 533 | 1040 | 679 | 315 | 46.4% |
| 0.500 | 593 | 621 | 749 | 654 | 83.2 | 12.7% |
| 1.00 | 585 | 555 | 538 | 559 | 23.8 | 4.3% |
| 2.00 | 369 | 410 | 239 | 339 | 89.3 | 26.3% |
| 4.00 | 33.4 | 45.4 | 31.9 | 36.9 | 7.40 | 20.1% |
| 6.00 | 4.93 | 5.39 | 2.45 | 4.26 | 1.58 | 37.1% |
| 8.00 | 1.30 | 1.84 | 1.76 | 1.63 | 0.291 | 17.9% |
| 12.0 | BQL | BQL | BQL | NA | NA | NA |
| 24.0 | BQL | BQL | BQL | NA | NA | NA |
| Prodrug formula 4-A Concentrations (ng/mL) in Dog Plasma | | | | | | |
| 0.250 | 1.13 | 1.63 | 1.09 | 1.28 | 0.301 | 23.5% |
| 0.500 | BQL | 1.68 | BQL | 1.68 | NA | NA |
| 1.00 | BQL | BQL | 1.43 | 1.43 | NA | NA |
| 2.00 | BQL | BQL | BQL | NA | NA | NA |
| 4.00 | BQL | BQL | BQL | NA | NA | NA |
| 6.00 | BQL | BQL | BQL | NA | NA | NA |
| 8.00 | BQL | BQL | BQL | NA | NA | NA |
| 12.0 | BQL | BQL | BQL | NA | NA | NA |
| 24.0 | BQL | BQL | BQL | NA | NA | NA |
| EFdA Concentrations (ng/mL) in Dog Plasma | | | | | | |
| EFdA PO (5 mg/kg) | Animal ID | | | | | |
| Time Points (hrs) | 4001 | 4002 | 4003 | Mean | SD | % CV |
| 0.250 | 456 | 333 | 276 | 355 | 92.0 | 25.9% |
| 0.500 | 391 | 299 | 280 | 323 | 59.4 | 18.4% |
| 1.00 | 369 | 353 | 361 | 361 | 8.00 | 2.2% |
| 2.00 | 211 | 212 | 143 | 189 | 39.6 | 21.0% |
| 4.00 | 12.6 | 17.9 | 6.30 | 12.3 | 5.81 | 47.2% |
| 6.00 | BQL | BQL | BQL | NA | NA | NA |
| 8.00 | BQL | BQL | BQL | NA | NA | NA |
| 12.0 | BQL | BQL | BQL | NA | NA | NA |
| 24.0 | BQL | BQL | BQL | NA | NA | NA |

BQL = below quantitation level;
NA = not applicable

TABLE 4

EFdA Exposure in Plasma from Oral Administration of EFdA and Prodrug formula 4-A in Dogs

| Compound | Dose (mg/kg) | AUC (ng * hr/mL) | $C_{max}$ (ng/mL) |
|---|---|---|---|
| EFdA | 5 | 792 | 392 |
| Prodrug formula 4-A | 8.25 (~5 mg eq EFdA) | 1432 | 753 |

Numbered Embodiments of the Disclosure

Other subject matter contemplated by the present disclosure is set out in the following numbered embodiments:

1. An adenosine derivative having a formula (1) or a pharmaceutically acceptable salt, stereoisomer, tautomer, or solvate thereof:

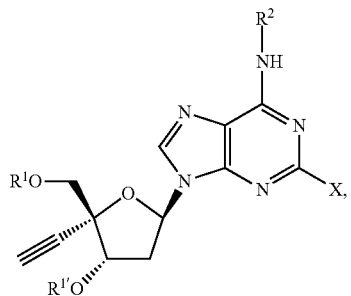

wherein,

R$^1$, R$^{1'}$, and R$^2$ each is independently —H, —C(O)N(R$^3$)(R$^{3'}$), —C(O)OR$^4$, —R$^5$, -L$^1$-R$^5$, or —Z-L$^4$-R$^5$, wherein at least one of R$^1$ and R$^2$ is not —H;

R$^3$, R$^{3'}$ and R$^4$ each is independently —H, C1-C10 alkyl, C2-C10 alkenyl, C3-C10 cycloalkyl, 3- to 10-membered heterocycloalkyl, aryl, or heteroaryl;

R$^5$ is:

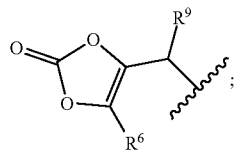

R$^6$ is —H, C1-C10 alkyl, C2-C10 alkenyl, C3-C10 cycloalkyl, 3- to 10-membered heterocycloalkyl, aryl, or heteroaryl;

L$^1$-R$^5$ is —(C1-C10 alkyl)-N(R$^7$)—R$^5$, —(C1-C10 alkyl)-O—R$^5$, —(C1-C10 alkyl)-S—R$^5$, —(C2-C10 alkenyl)-N(R$^7$)—R$^5$, —(C2-C10 alkenyl)-O—R$^5$, —(C2-C10 alkenyl)-S—R$^5$, —C(O)O—R$^5$, —C(O)O-L$^2$-N(R$^7$)—R$^5$, —C(O)O-L$^2$-O—R$^5$, —C(O)O-L$^2$-S—R$^5$, —C(O)O-L$^2$-C(O)O—R$^5$, —C(O)O-L$^2$-C(O)N(R$^7$)—R$^5$, —C(O)O-L$^2$-C(O)N(R$^7$)-L$^3$-N(R$^7$)—R$^5$, —C(O)O-L$^2$-C(O)N(R$^7$)-L$^3$-O—R$^5$, —C(O)O-L$^2$-C(O)N(R$^7$)-L$^3$-S—R$^5$, —C(O)N(R$^7$)—R$^5$, —C(O)N(R$^7$)-L$^2$-N(R$^7$)—R$^5$, —C(O)N(R$^7$)-L$^2$-O—R$^5$, —C(O)N(R$^7$)-L$^2$-S—R$^5$, —C(O)N(R$^7$)-L$^2$-C(O)—R$^5$, —C(O)N(R$^7$)-L$^2$-C(O)O—R$^5$, —C(O)N(R$^7$)-L$^2$-C(O)N(R$^8$)—R$^5$—, —C(O)N(R$^7$)-L$^2$-C(O)N(R$^8$)-L$^3$-N(R$^7$)—R$^5$, —C(O)O-L$^2$-N(R$^7$)C(O)O—R$^5$, —C(O)N(R$^8$)-L$^2$-N(R$^7$)C(O)O—R$^5$, —C(O)O-L$^2$-N(R$^7$)C(O)N(R$^8$)—R$^5$, —C(O)N(R$^7$)-L$^2$-N(R$^7$)C(O)N(R$^8$)—R$^5$, —C(O)N(R$^7$)-L$^2$-C(O)N(R$^8$)-L$^3$-O—R$^5$ or —C(O)N(R$^7$)-L$^2$-C(O)N(R$^8$)-L$^3$-S—R$^5$;

—Z— is a divalent —C(O)—, —C(O)O—, or —C(O)N(R$^7$)—;

L$^4$-R$^5$ is —(C1-C10 alkyl)-N(R$^7$)—R$^5$, —(C1-C10 alkyl)-O—R$^5$, —(C1-C10 alkyl)-S—R$^5$, —(C2-C10 alkenyl)-N(R$^7$)—R$^5$, —(C2-C10 alkenyl)-O—R$^5$ or —(C2-C10 alkenyl)-S—R$^5$;

R$^7$, R$^8$ and R$^9$ each is independently —H, C1-C10 alkyl, or C2-C10 alkenyl;

L$^2$ and L$^3$ each is intendedly divalent —(C1-C10 alkyl)-, or —(C2-C10 alkenyl)-; and X is a halogen atom.

2. The adenosine derivative of embodiment 1, wherein said adenosine derivative has a

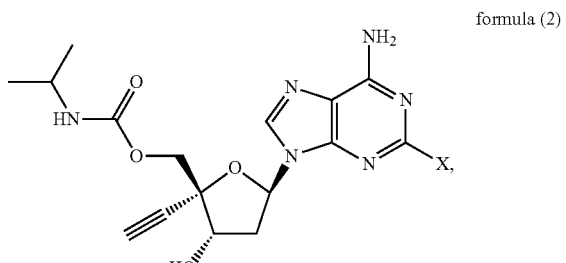

formula (2)

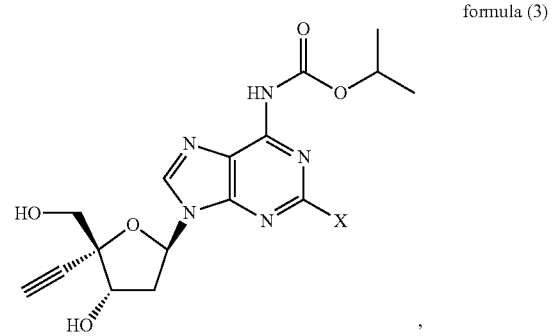

formula (3)

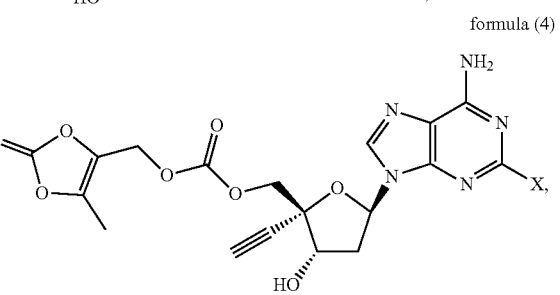

formula (4)

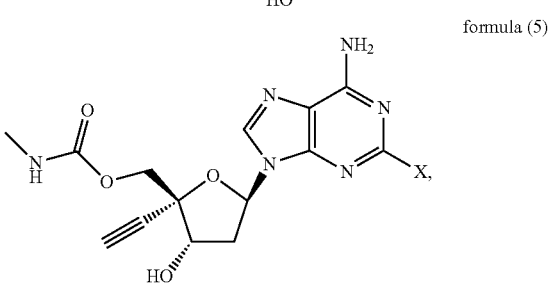

formula (5)

formula (6)
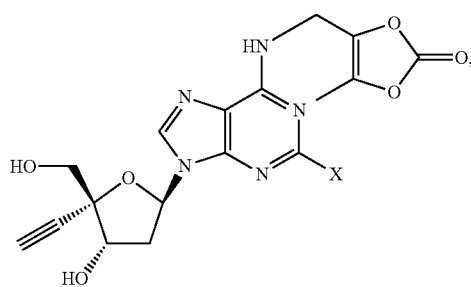
formula (7)
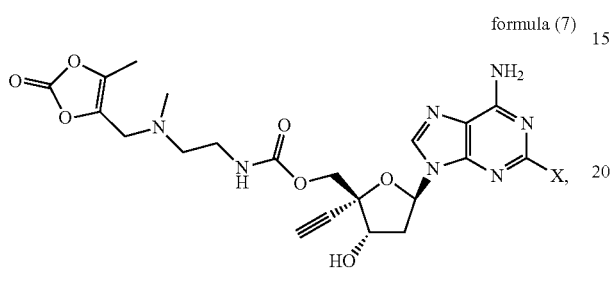
formula (8)
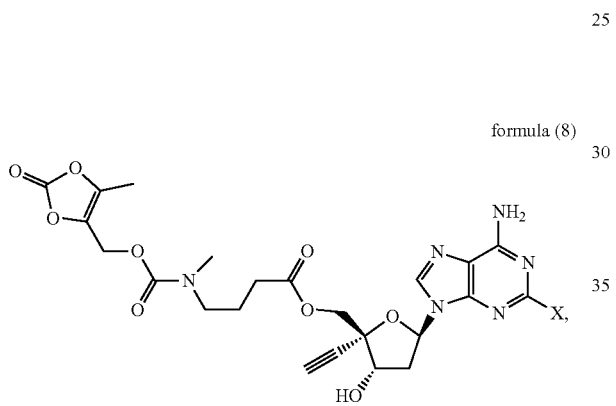
formula (4-B)
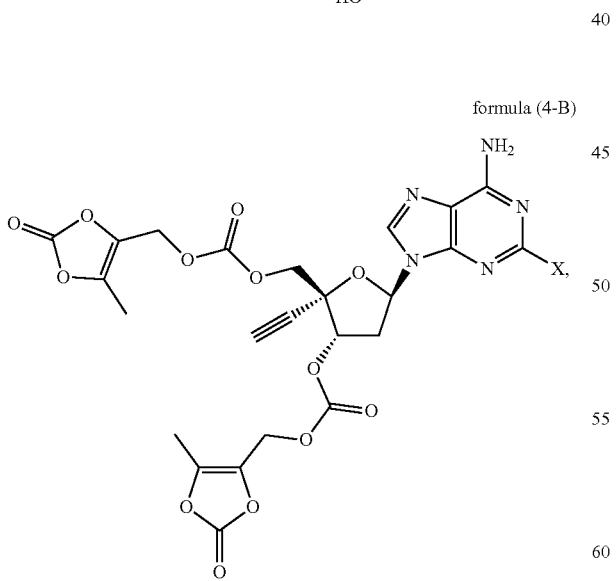
or a pharmaceutically acceptable salt, stereoisomer, tautomer, or solvate thereof
3. The adenosine derivative of embodiment 1, wherein said adenosine derivative has a
formula (2-A)
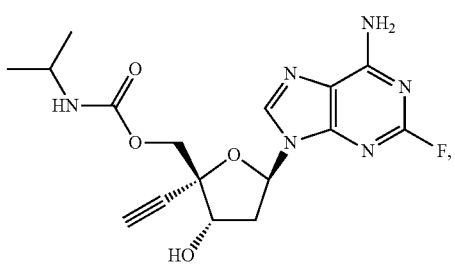
formula (3-A)
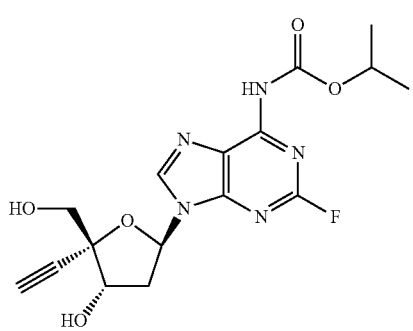
formula (4-A)
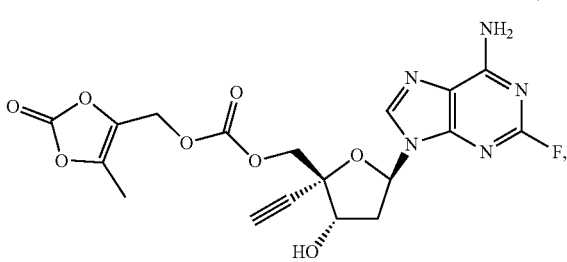
formula (5-A)
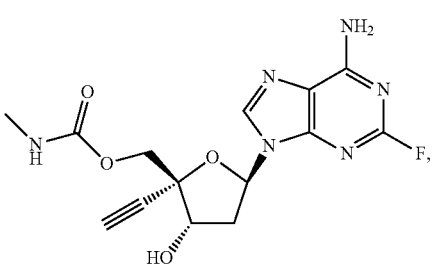
formula (6-A)
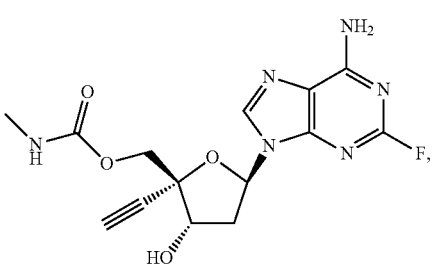

-continued

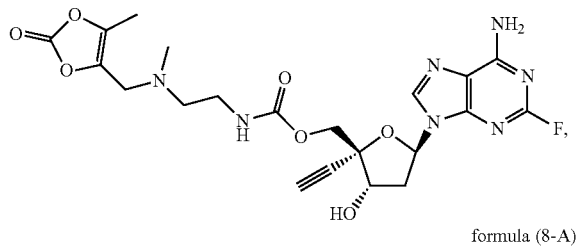
formula (7-A)

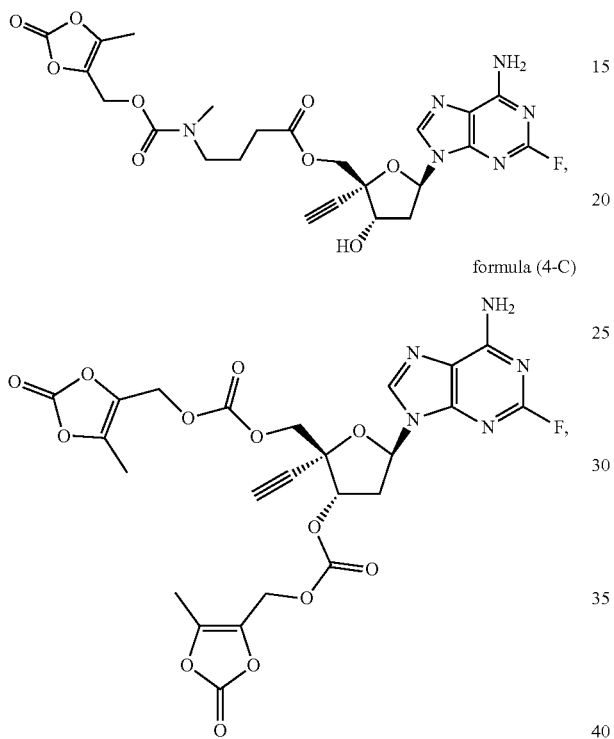
formula (8-A)
formula (4-C)

or a pharmaceutically acceptable salt, stereoisomer, tautomer, or solvate thereof 4. The adenosine derivative of embodiment 1, wherein said adenosine derivative is ((2R,3S,5R)-5-(6-amino-2-fluoro-9H-purin-9-yl)-2-ethynyl-3-hydroxytetrahydrofuran-2-yl)methyl isopropylcarbamate.

5. The adenosine derivative of embodiment 1, wherein said adenosine derivative is isopropyl (9-((2R,4S,5R)-5-ethynyl-4-hydroxy-5-(hydroxymethyl)tetrahydrofuran-2-yl)-2-fluoro-9H-purin-6-yl)carbamate.

6. The adenosine derivative of embodiment 1, wherein said adenosine derivative is ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate.

7. The adenosine derivative of embodiment 1, wherein said adenosine derivative is ((2R,3S,5R)-5-(6-amino-2-fluoro-9H-purin-9-yl)-2-ethynyl-3-hydroxytetrahydrofuran-2-yl)methyl methylcarbamate.

8. The adenosine derivative of embodiment 1, wherein said adenosine derivative is 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one.

9. The adenosine derivative of embodiment 1, wherein said adenosine derivative is ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate.

10. The adenosine derivative of embodiment 1, wherein said adenosine derivative is [(2R,3S,5R)-5-(6-amino-2-fluoro-purin-9-yl)-2-ethynyl-3-hydroxy-tetrahydrofuran-2-yl] methyl 4-[methyl-[(5-methyl-2-oxo-1,3-dioxol-4-yl)methoxycarbonyl]amino]butanoate.

11. The adenosine derivative of embodiment 1, wherein said $R^5$, $-L^1-R^5$ or $-Z-L^4-R^5$ is selected from formulas 9-24:

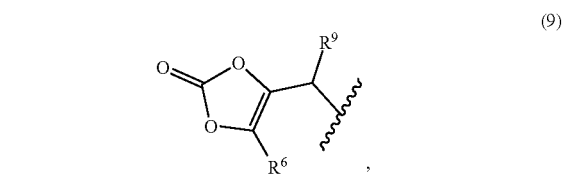
(9)

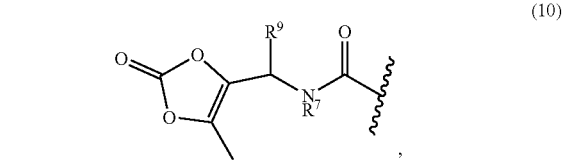
(10)

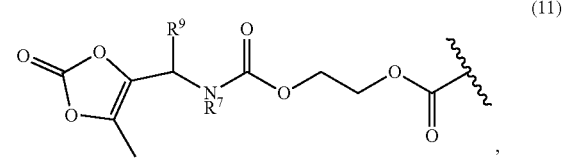
(11)

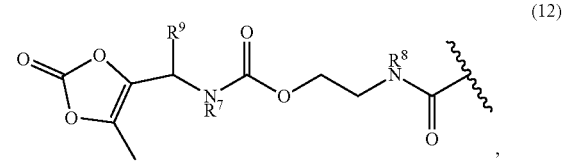
(12)

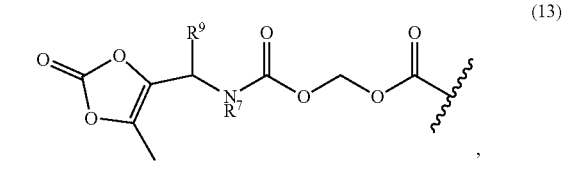
(13)

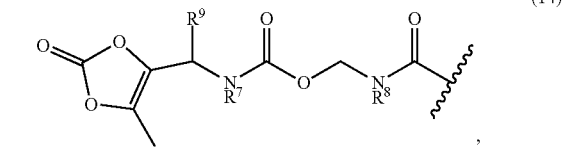
(14)

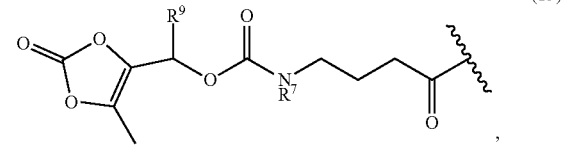
(15)

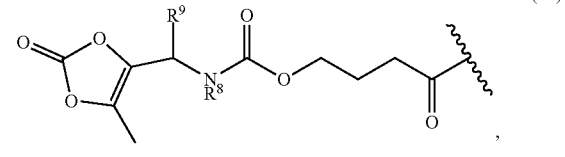
(16)

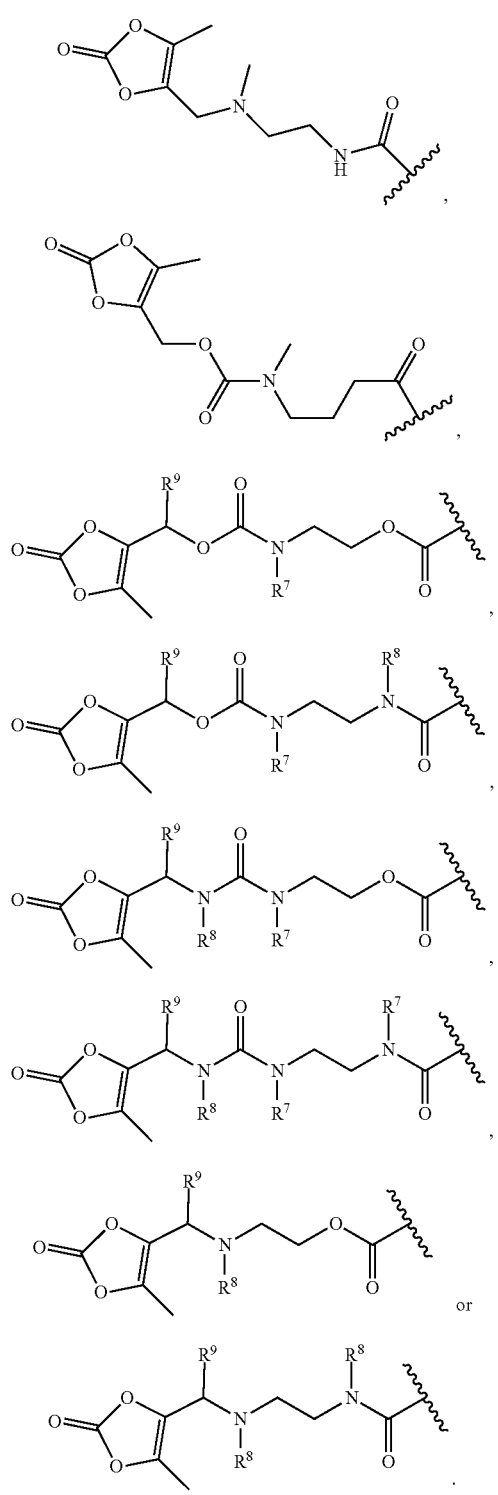

12. The adenosine derivative of any one of embodiments 1-11, wherein said adenosine derivative comprises a reverse transcriptase inhibitor activity in vivo, a reverse transcriptase chain terminator activity in vivo, DNA translocation inhibitor activity in vivo, or a combination thereof 13. A pharmaceutical composition comprising an adenosine derivative having a formula (1):

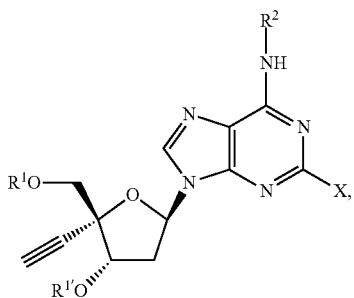

wherein,
  $R^1$, $R^{1'}$, and $R^2$ each is independently —H, —C(O)N$(R^3)(R^{3'})$, —C(O)OR$^4$, —R$^5$, -L$^1$-R$^5$, or —Z-L$^4$-R$^5$, wherein at least one of $R^1$ and $R^2$ is not —H;
  $R^3$, $R^{3'}$ and $R^4$ each is independently —H, C1-C10 alkyl, C2-C10 alkenyl, C3-C10 cycloalkyl, 3- to 10-membered heterocycloalkyl, aryl, or heteroaryl;
  $R^5$ is:

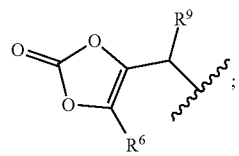

$R^6$ is —H, C1-C10 alkyl, C2-C10 alkenyl, C3-C10 cycloalkyl, 3- to 10-membered heterocycloalkyl, aryl, or heteroaryl;
  $L^1$-$R^5$ is —(C1-C10 alkyl)-N(R$^7$)—R$^5$, —(C1-C10 alkyl)-O—R$^5$, —(C1-C10 alkyl)-S—R$^5$, —(C2-C10 alkenyl)-N(R$^7$)—R$^5$, —(C2-C10 alkenyl)-O—R$^5$, —(C2-C10 alkenyl)-S—R$^5$, —C(O)O—R$^5$, —C(O)O-L$^2$-N(R$^7$)—R$^5$, —C(O)O-L$^2$-O—R$^5$, —C(O)O-L$^2$-S—R$^5$, —C(O)O-L$^2$-C(O)O—R$^5$, —C(O)O-L$^2$-C(O)N(R$^7$)—R$^5$, —C(O)O-L$^2$-C(O)N(R$^7$)-L$^3$-N(R$^7$)—R$^5$, —C(O)O-L$^2$-C(O)N(R$^7$)-L$^3$-O—R$^5$, —C(O)O-L$^2$-C(O)N(R$^7$)-L$^3$-S—R$^5$, —C(O)N(R$^7$)—R$^5$, —C(O)N(R$^7$)-L$^2$-N(R$^7$)—R$^5$, —C(O)N(R$^7$)-L$^2$-O—R$^5$, —C(O)N(R$^7$)-L$^2$-S—R$^5$, —C(O)N(R$^7$)-L$^2$-C(O)O—R$^5$, —C(O)N(R$^7$)-L$^2$-C(O)N(R$^8$)—R$^5$—, —C(O)N(R$^7$)-L$^2$-C(O)N(R$^8$)-L$^3$-N(R$^7$)—R$^5$, —C(O)O-L$^2$-N(R$^7$)C(O)O—R$^5$, —C(O)N(R$^8$)-L$^2$-N(R$^7$)C(O)O—R$^5$, —C(O)O-L$^2$-N(R$^7$)C(O)N(R$^8$)—R$^5$, —C(O)N(R$^7$)-L$^2$-N(R$^7$)C(O)N(R$^8$)—R$^5$, —C(O)N(R$^7$)-L$^2$-C(O)N(R$^8$)-L$^3$-O—R$^5$ or —C(O)N(R$^7$)-L$^2$-C(O)N(R$^8$)-L$^3$-S—R$^5$;
  —Z— is a divalent —C(O)—, —C(O)O—, or —C(O)N(R$^7$)—;
  $L^4$-$R^5$ is —(C1-C10 alkyl)-N(R$^7$)—R$^5$, —(C1-C10 alkyl)-O—R$^5$, —(C1-C10 alkyl)-S—R$^5$, —(C2-C10 alkenyl)-N(R$^7$)—R$^5$, —(C2-C10 alkenyl)-O—R$^5$ or —(C2-C10 alkenyl)-S—R$^5$;
  $R^7$, $R^8$ and $R^9$ each is independently —H, C1-C10 alkyl, or C2-C10 alkenyl;
  $L^2$ and $L^3$ each is intendedly divalent —(C1-C10 alkyl)-, or —(C2-C10 alkenyl)-; and
  X is a halogen atom.

14. The pharmaceutical composition of embodiment 13, wherein said adenosine derivative has a formula (2):

formula (2)
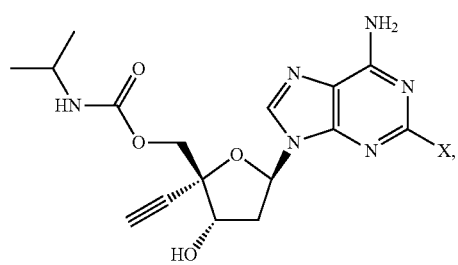
formula (3)
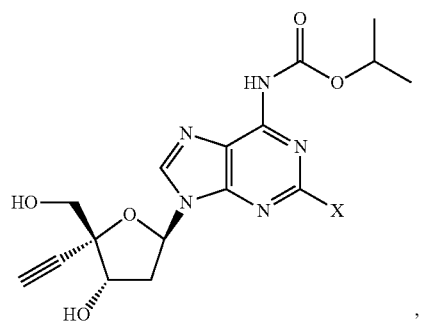
,
formula (4)
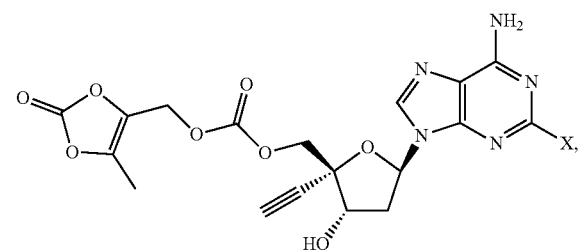
formula (5)
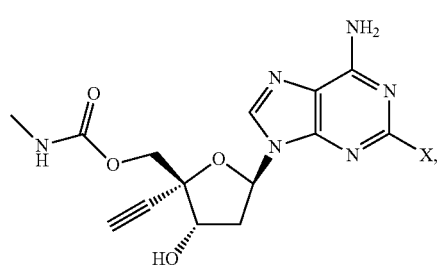
formula (6)
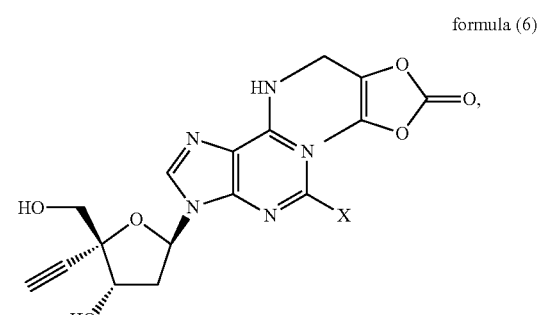
formula (7)
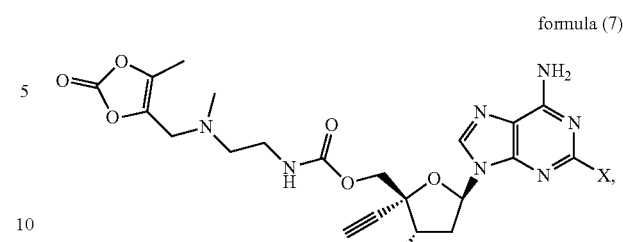
formula (8)
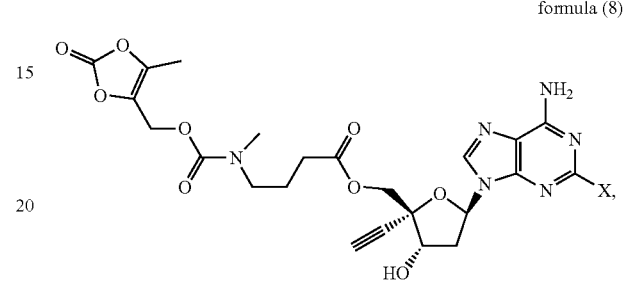
formula (4-B)
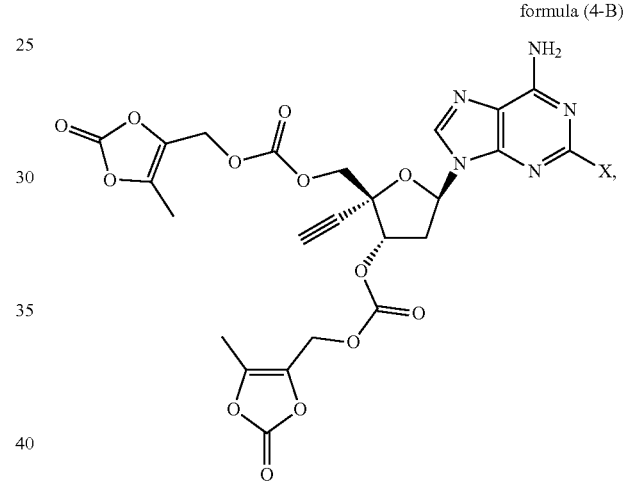
or a pharmaceutically acceptable salt, stereoisomer, tautomer, or solvate thereof
15. The pharmaceutical composition of embodiment 13, wherein said adenosine derivative has a
formula (2-A)
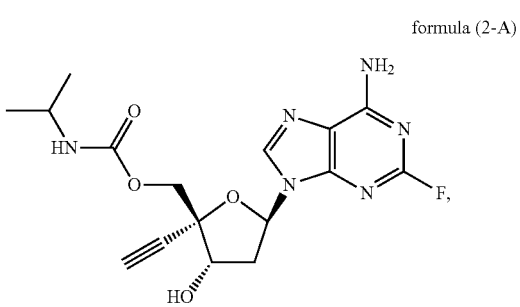

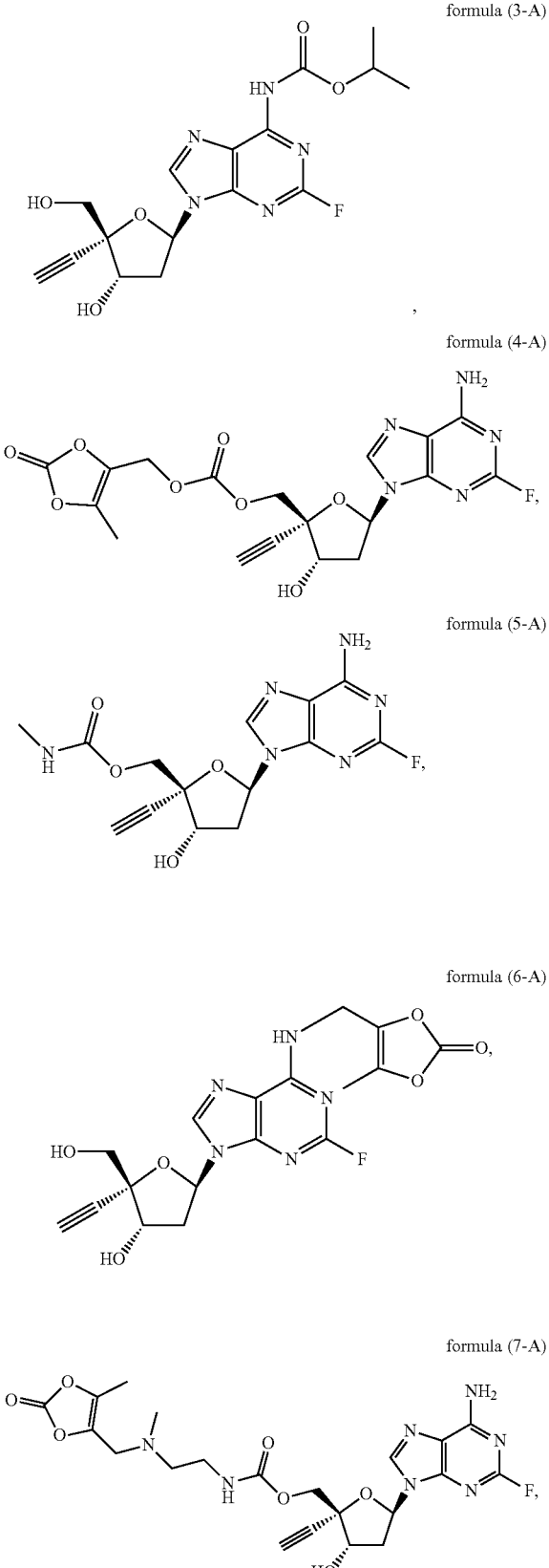

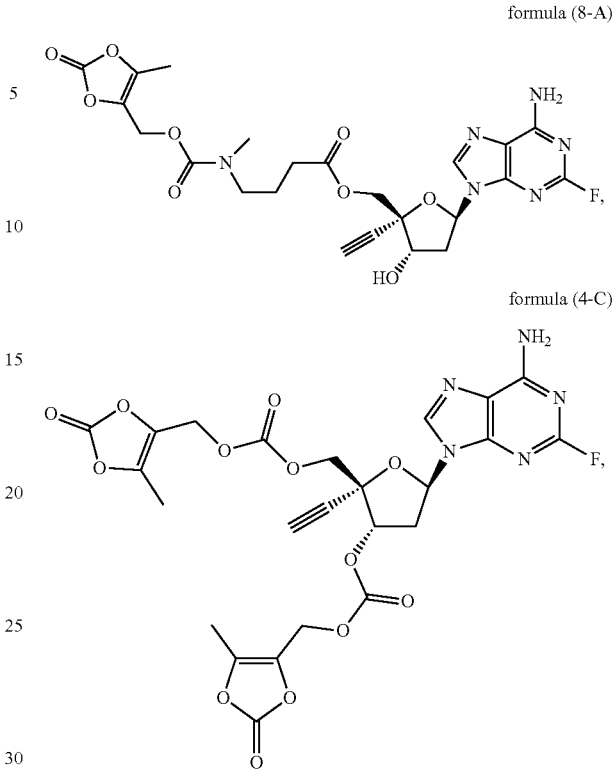

or a pharmaceutically acceptable salt, stereoisomer, tautomer, or solvate thereof 16. The pharmaceutical composition of embodiment 13, wherein said adenosine derivative comprises ((2R,3S,5R)-5-(6-amino-2-fluoro-9H-purin-9-yl)-2-ethynyl-3-hydroxytetrahydrofuran-2-yl)methyl isopropylcarbamate, or a pharmaceutically acceptable salt thereof 17. The pharmaceutical composition of embodiment 13, wherein said adenosine derivative comprises isopropyl (9-42R,4S,5R)-5-ethynyl-4-hydroxy-5-(hydroxymethyl)tetrahydrofuran-2-yl)-2-fluoro-9H-purin-6-yl)carbamate, or a pharmaceutically acceptable salt thereof 18. The pharmaceutical composition of embodiment 13, wherein said adenosine derivative comprises ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate, or a pharmaceutically acceptable salt thereof 19. The pharmaceutical composition of embodiment 13, wherein said adenosine derivative comprises ((2R,3S,5R)-5-(6-amino-2-fluoro-9H-purin-9-yl)-2-ethynyl-3-hydroxytetrahydrofuran-2-yl)methyl methylcarbamate, or a pharmaceutically acceptable salt thereof 20. The pharmaceutical composition of embodiment 13, wherein said adenosine derivative comprises 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, or a pharmaceutically acceptable salt thereof 21. The pharmaceutical composition of embodiment 13, wherein said adenosine derivative is ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate, or a pharmaceutically acceptable salt thereof 22. The pharmaceutical composition of embodiment 13, wherein said adenosine derivative is [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino]butanoate, or a pharmaceutically acceptable salt thereof 23. The pharmaceutical composition of embodiment 13, wherein said $R^5$, -$L^1$-$R^5$ or —Z-$L^4$-$R^5$ is selected from formulas 9-24:

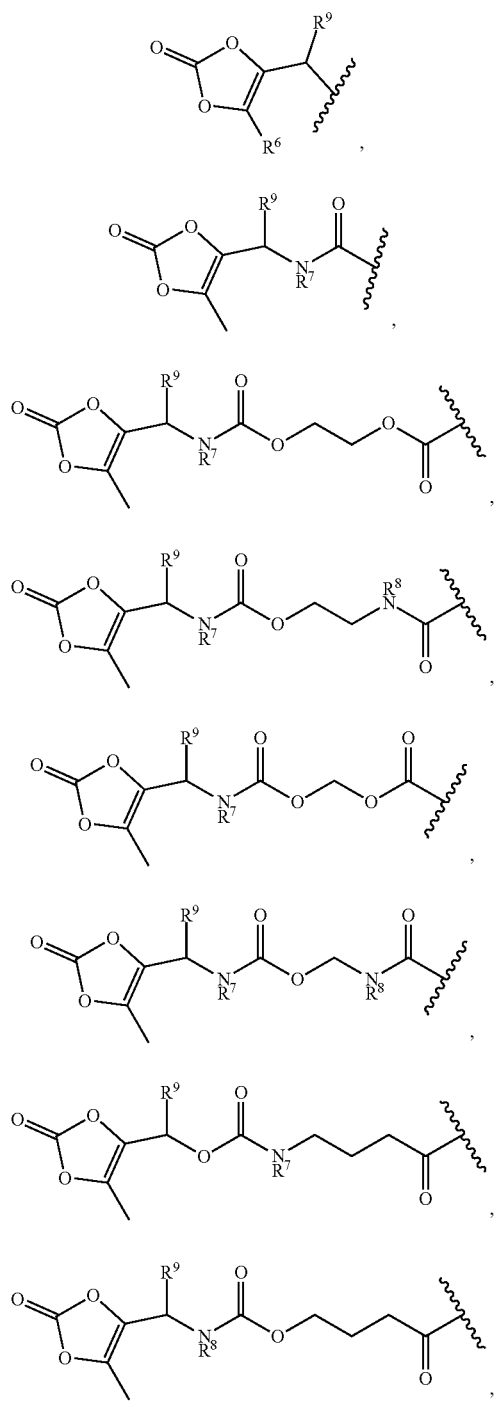

24. The pharmaceutical composition of any one of embodiments 13-23 further comprising a pharmaceutically acceptable carrier.

25. The pharmaceutical composition of any one of embodiments 13-24 further comprising an effective dosage of one or more HIV antiviral agent selected from abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc or a combination thereof 26. A method for the treatment of a disease, said method comprising administering a subject in need thereof an effective dosage of a pharmaceutical composition comprising an adenosine derivative having a formula (1) or a pharmaceutically acceptable salt, stereoisomer, tautomer, or solvate thereof:

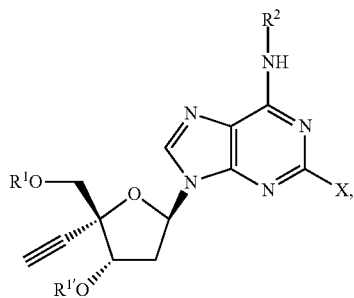

wherein, $R^1$, $R^{1'}$, and $R^2$ each is independently —H, —C(O)N($R^3$)($R^{3'}$), —C(O)O$R^4$, —$R^5$, -$L^1$-$R^5$, or —Z-$L^4$-$R^5$, wherein at least one of $R^1$ and $R^2$ is not —H;

$R^3$, $R^{3'}$ and $R^4$ each is independently —H, C1-C10 alkyl, C2-C10 alkenyl, C3-C10 cycloalkyl, 3- to 10-membered heterocycloalkyl, aryl, or heteroaryl;

$R^5$ is:

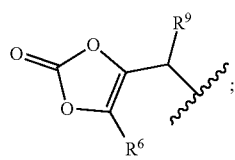

$R^6$ is —H, C1-C10 alkyl, C2-C10 alkenyl, C3-C10 cycloalkyl, 3- to 10-membered heterocycloalkyl, aryl, or heteroaryl;

$L^1$-$R^5$ is —(C1-C10 alkyl)-N($R^7$)—$R^5$, —(C1-C10 alkyl)-O—$R^5$, —(C1-C10 alkyl)-S—$R^5$, —(C2-C10 alkenyl)-N($R^7$)—$R^5$, —(C2-C10 alkenyl)-O—$R^5$, —(C2-C10 alkenyl)-S—$R^5$, —C(O)O—$R^5$, —C(O)O-$L^2$-N($R^7$)—$R^5$, —COO-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$—, —C(O)N($R^7$)-$L^2$-C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N ($R^8$)—$R^5$, —C(O)N($R^7$)-$L^2$-C(O)N($R^8$)-$L^3$-O—$R^5$ or —C(O)N($R^7$)-$L^2$-C(O)N($R^8$)-$L^3$-S—$R^5$;

—Z— is a divalent —C(O)—, —C(O)O—, or —C(O)N($R^7$)—;

$L^4$-$R^5$ is —(C1-C10 alkyl)-N($R^7$)—$R^5$, —(C1-C10 alkyl)-O—$R^5$, —(C1-C10 alkyl)-S—$R^5$, —(C2-C10 alkenyl)-N($R^7$)—$R^5$, —(C2-C10 alkenyl)-O—$R^5$ or —(C2-C10 alkenyl)-S—$R^5$;

$R^7$, $R^8$ and $R^9$ each is independently —H, C1-C10 alkyl, or C2-C10 alkenyl;

$L^2$ and $L^3$ each is intendedly divalent —(C1-C10 alkyl)-, or —(C2-C10 alkenyl)-; and X is a halogen atom.

27. The method of embodiment 26, wherein said adenosine derivative has a formula (2):

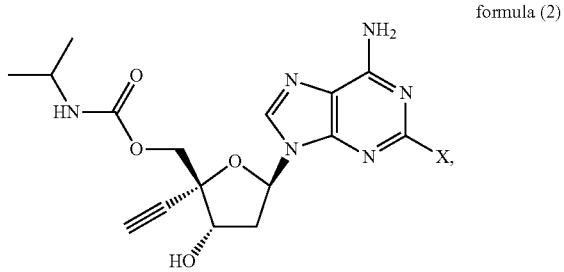

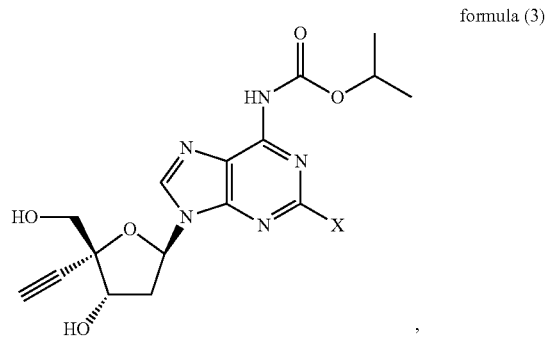

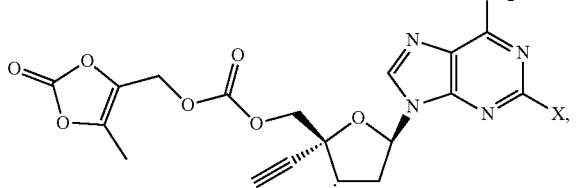

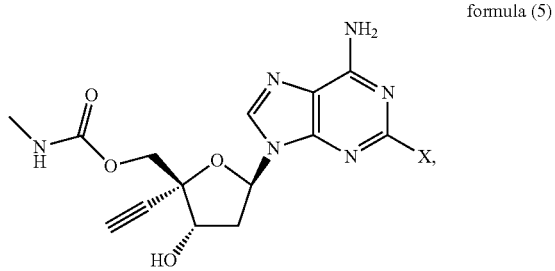

formula (6)
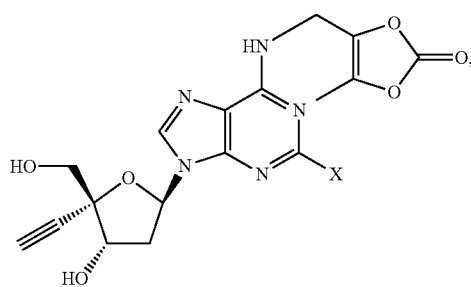
formula (7)
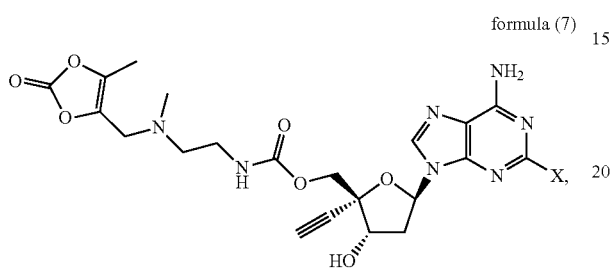
formula (8)
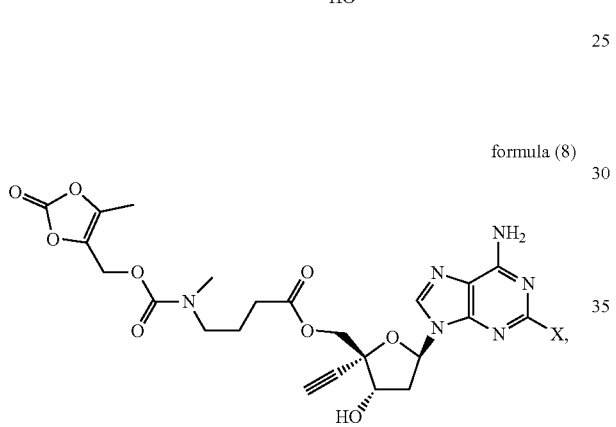
formula (4-B)
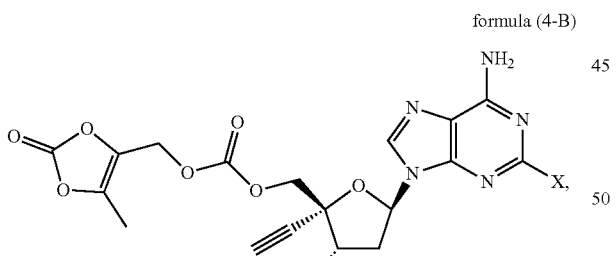
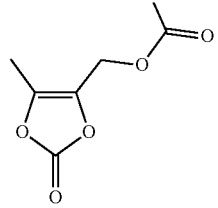
or a pharmaceutically acceptable salt, stereoisomer, tautomer, or solvate thereof
28. The method of embodiment 26, wherein said adenosine derivative has a formula (2-A):
formula (2-A)
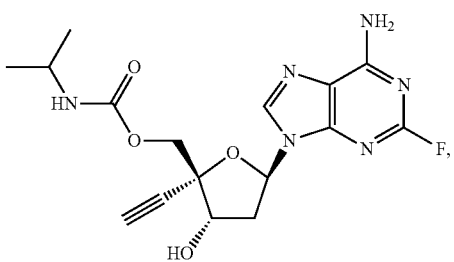
formula (3-A)
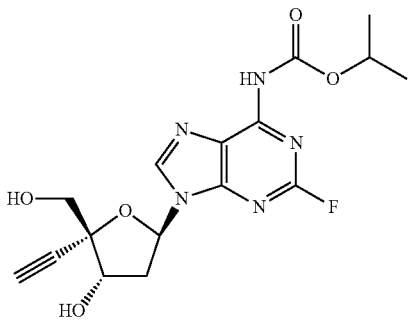
formula (4-A)
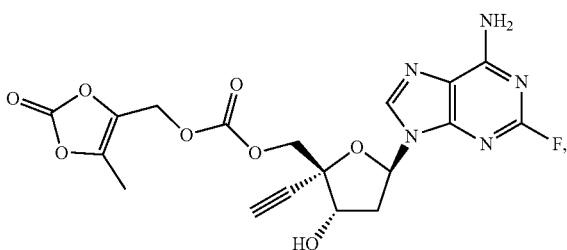
formula (5-A)
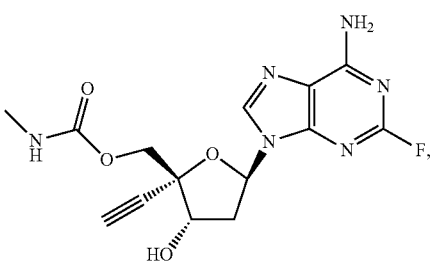
formula (6-A)
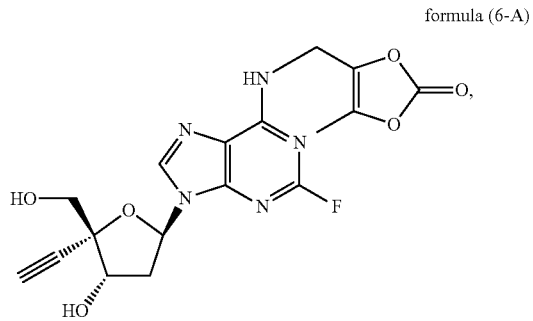

-continued formula (7-A)

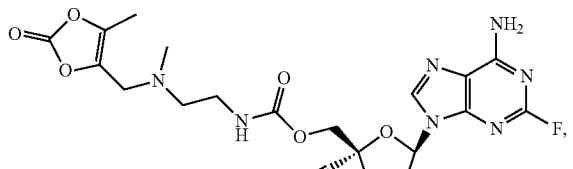

formula (8-A)

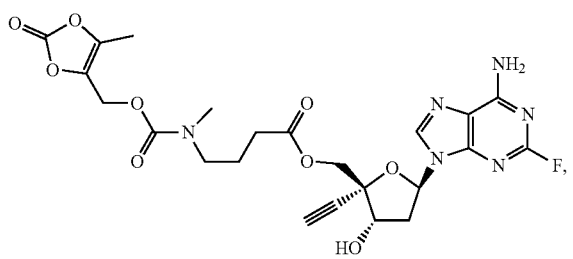

formula (4-C)

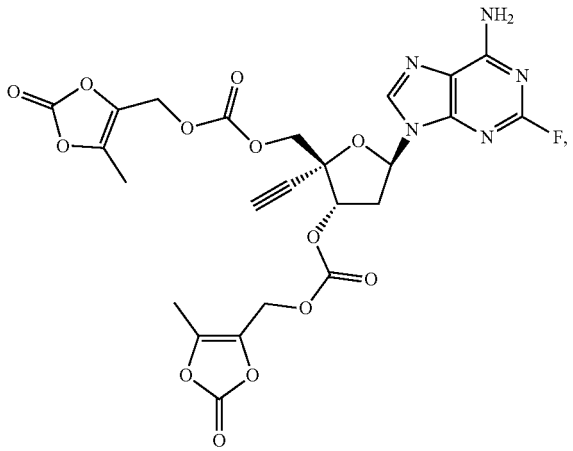

or a pharmaceutically acceptable salt, stereoisomer, tautomer, or solvate thereof 29. The method of embodiment 26, wherein said adenosine derivative comprises ((2R,3S,5R)-5-(6-amino-2-fluoro-9H-purin-9-yl)-2-ethynyl-3-hydroxytetrahydrofuran-2-yl)methyl isopropylcarbamate, or a pharmaceutically acceptable salt thereof 30. The method of embodiment 26, wherein said adenosine derivative comprises isopropyl (9-((2R,4S,5R)-5-ethynyl-4-hydroxy-5-(hydroxymethyl)tetrahydrofuran-2-yl)-2-fluoro-9H-purin-6-yl)carbamate, or a pharmaceutically acceptable salt thereof 31. The method of embodiment 26, wherein said adenosine derivative comprises ((2R,3S,5R)-5-(6-amino-2-fluoro-9H-purin-9-yl)-2-ethynyl-3-hydroxytetrahydrofuran-2-yl)methyl((5-methyl-2-oxo-1,3-dioxol-4-yl)methyl) carbonate, or a pharmaceutically acceptable salt thereof 32. The method of embodiment 26, wherein said adenosine derivative comprises ((2R,3S,5R)-5-(6-amino-2-fluoro-9H-purin-9-yl)-2-ethynyl-3-hydroxytetrahydrofuran-2-yl)methyl methylcarbamate, or a pharmaceutically acceptable salt thereof 33. The method of embodiment 26, wherein said adenosine derivative comprises 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, or a pharmaceutically acceptable salt thereof 34. The method of embodiment 26, wherein said adenosine derivative is ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate, or a pharmaceutically acceptable salt thereof 35. The method of embodiment 26, wherein said adenosine derivative is [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino]butanoate, or a pharmaceutically acceptable salt thereof 36. The method of embodiment 26, wherein said adenosine derivative comprises said $R^5$, $-L^1-R^5$ or $-Z-L^4-R^5$ selected from formulas 9-24:

(9)

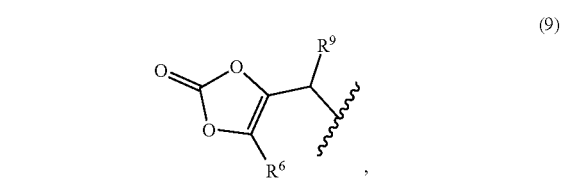

(10)

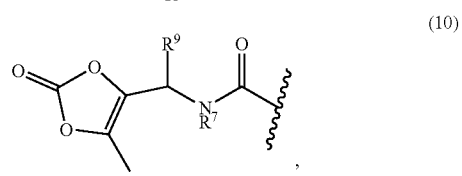

(11)

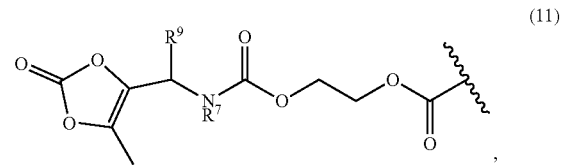

(12)

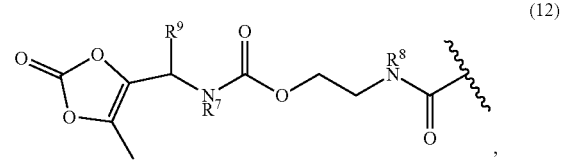

(13)

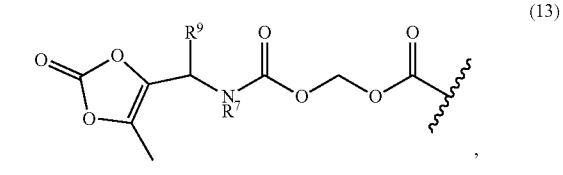

(14)

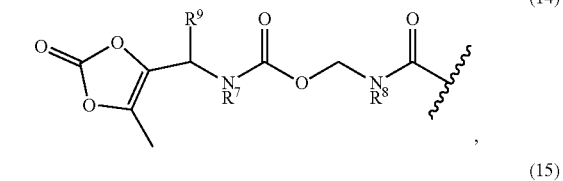

(15)

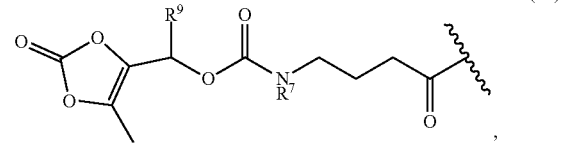

(16) 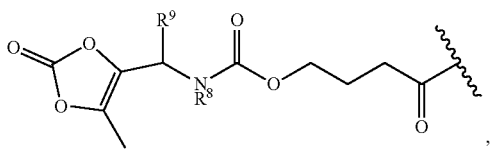

(17) 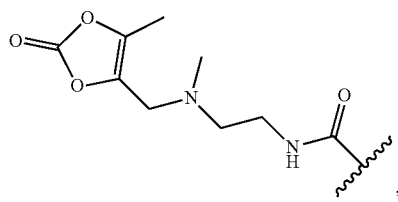

(18) 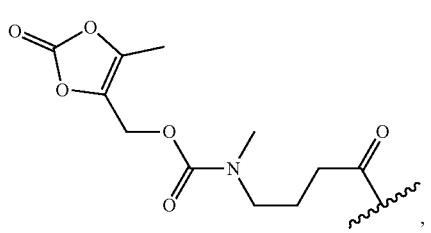

(19) 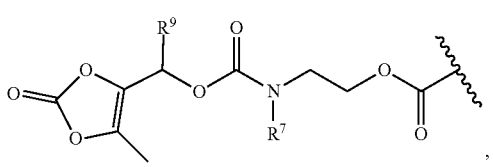

(20) 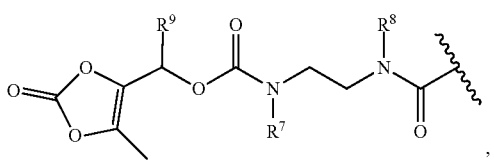

(21) 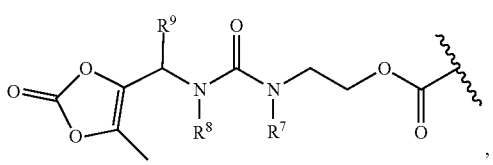

(22) 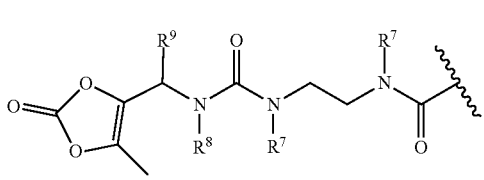

(23) 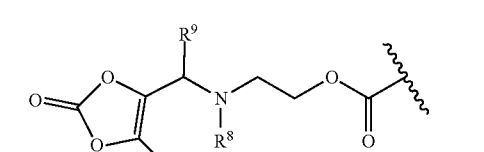
or

(24) 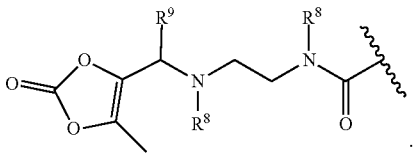

37. The method of any one of embodiments 26-36, said pharmaceutical composition is administered to said subject via intramuscular (IM) injection, subcutaneous (SC) injection, intravenous (IV) injection, oral administration, topical application, implant application or a combination thereof 38. The method of any one of embodiments 26-37 further comprising measuring a specimen of said subject to determine a measured level of a target drug in said specimen, wherein said target drug has a formula (T-1):

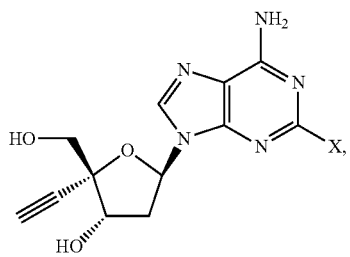

an isomer thereof, or a pharmaceutically acceptable salt thereof

39. The method of embodiment 38, wherein said target drug has a formula (T-1A):

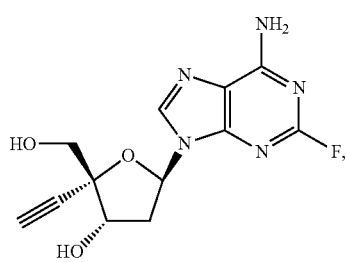

an isomer thereof, or a pharmaceutically acceptable salt thereof

40. The method of embodiment 38, wherein said target drug is (2R,3S,5R)-5-(6-amino-2-fluoro-9H-purin-9-yl)-2-ethynyl-2-(hydroxymethyl)tetrahydrofuran-3-ol, or a pharmaceutically acceptable salt thereof 41. The method of any one of embodiments 38-40 further comprising adjusting said effective dosage to produce a modified effective dosage if said measured level of said target drug is different from a predetermined target level of said target drug and administering said modified effective dosage to said subject.

42. The method of any one of embodiments 26-41, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

43. The method of any one of embodiments 26-42 further comprising administering said subject an effective dosage of one or more anti-HIV agents selected from abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc or a combination thereof 44. The method of embodiment 43, wherein said adenosine derivative and said one or more anti-HIV agents are administered to said subject together or separately via oral administration, parenteral administration or a combination thereof 45. The method of embodiment 44, wherein said adenosine derivative and said one or more anti-HIV agents are administered to said subject with a daily, weekly, biweekly or monthly administration schedule.

46. A use of the pharmaceutical composition of any one of embodiments 13-25 for the treatment of a disease in a subject in need thereof, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

47. A use of the method of any one of embodiments 26-45 for the treatment of a disease in a subject in need thereof, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

48. Use of the adenosine derivative of any one of embodiments 1-12 for manufacturing a medicament for treating a disease, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

49. A method for the prevention of infection in a subject in need thereof, said method comprising administering said subject an effective dosage of a pharmaceutical composition of any one of embodiments 13-25, wherein said subject is free from detectable symptoms of said infection.

50. The method of embodiment 49, wherein said infection comprises a disease selected from Acquired Immune Deficiency Syndrome (AIDS), an infection of wild-type HIV-1, NRTI-resistant HIV-1, HIV-2, HIV having M184V mutations, HIV having K65R, or multidrug resistant HIV, or a combination thereof 51. The method of embodiment 50, wherein said detectable symptoms comprise symptoms of Acquired Immune Deficiency Syndrome (AIDS), symptoms of infection of HIV viruses comprising wild-type HIV-1, NRTI-resistant HIV-1, HIV-2, HIV having M184V mutations, HIV having K65R, multidrug resistant HIV, or a combination thereof 52. The method of embodiment 51, wherein said pharmaceutical composition administered to said subject with a daily, weekly, biweekly or monthly administration schedule.

53. The method of embodiment 52 further comprising administering said subject an effective dosage of one or more anti-HIV agents selected from abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc or a combination thereof 54. The method of embodiment 53, wherein said one or more anti-HIV agents are administered to said subject together with said pharmaceutical composition or separately.

55. A method for treating HIV infection, comprising: administering a subject in need thereof an effective dosage of the pharmaceutical composition of any one of embodiment 1-25.

56. A method for preventing HIV infection, comprising: administering a subject in need thereof an effective dosage of the pharmaceutical composition of any one of embodiment 1-25.

57. The method of embodiment 55 or 56, wherein the HIV infection is caused by wild-type HIV-1, NRTI-resistant HIV-1, HIV-2, HIV having M184V mutations, HIV having K65R, or multidrug resistant HIV.

58. The method of any one of embodiment 55-57, wherein the administration is by oral administration.

59. The method of any one of embodiments 55-57, wherein the administration is by parenteral administration.

60. The method of embodiment 59, wherein the parenteral administration is by intramuscular or subcutaneous injection.

61. The method of any one of embodiments 55-60, wherein the administration of the pharmaceutical composition results in a higher plasma concentration of EFdA when compared to administration of a dose-equivalent EFdA under the same condition.

62. The method of embodiment 61, wherein the administration of the pharmaceutical composition results in at least 10%, 20%, 30%, 40%, 50%, 60%, 70%, 80%, 90%, 100%, or 200% higher plasma concentration of EFdA when compared to administration of a dose-equivalent EFdA under the same condition.

63. The method of embodiment 61, wherein the administration of the pharmaceutical composition results in 50%-80%, 50%-100%, or 50%-200% higher plasma concentration of EFdA when compared to administration of a dose-equivalent EFdA under the same condition.

64. The method of any one of embodiments 55-63, wherein the administration of the pharmaceutical composition results in a prolonged release of EFdA when compared to administration of a dose-equivalent EFdA under the same condition.

65. The method of any one of embodiments 55-64, wherein the administration of the pharmaceutical composition results in a higher AUC of EFdA when compared to administration of a dose-equivalent EFdA under the same condition.

66. The method of embodiment 65, wherein the administration of the pharmaceutical composition results in at least 10%, 20%, 30%, 40%, 50%, 60%, 70%, 80%, 90%, or 100% higher AUC of EFdA when compared to administration of a dose-equivalent EFdA under the same condition.

67. The method of embodiment 65, wherein the administration of the pharmaceutical composition results in 50%-200%, 50%-150%, or 80%-120% higher AUC of EFdA when compared to administration of a dose-equivalent EFdA under the same condition.

68. The method of any one of embodiments 55-67, wherein the administration of the pharmaceutical composition results in a higher C. of EFdA when compared to administration of a dose-equivalent EFdA under the same condition.
69. The method of embodiment 68, wherein the administration of the pharmaceutical composition results in at least 10%, 20%, 30%, 40%, 50%, 60%, 70%, 80%, or 90% higher C. of EFdA when compared to administration of a dose-equivalent EFdA under the same condition.
70. The method of embodiment 68, wherein the administration of the pharmaceutical composition results in 50%-200%, 50%-150%, or 80%-100% higher C. of EFdA when compared to administration of a dose-equivalent EFdA under the same condition.

The invention claimed is:

1. A compound of formula (4-A), or a pharmaceutically acceptable salt or stereoisomer thereof:

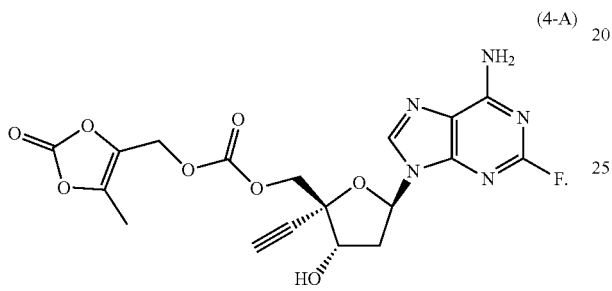

(4-A)

2. The compound of claim 1, wherein the compound has the structure:

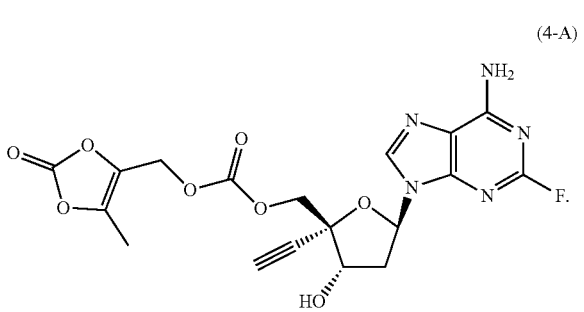 [SMILES: C#C[C@]1(COC(=O)OCc2oc(=O)oc2C)O[C@@H](n2cnc3c(N)nc(F)nc32)C[C@@H]1O]

(4-A)

3. The compound of claim 1, wherein the compound is a pharmaceutically acceptable salt of the compound of formula (4-A)

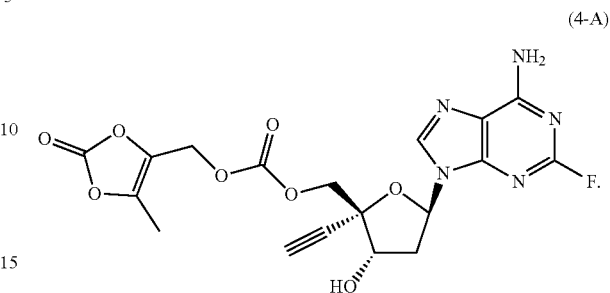

(4-A)

4. An orally administered pharmaceutical composition comprising the compound of claim 1, or a pharmaceutically acceptable salt or stereoisomer thereof, and a pharmaceutically acceptable carrier.

5. An orally administered pharmaceutical composition comprising the compound of claim 2 and a pharmaceutically acceptable carrier.

6. An orally administered pharmaceutical composition comprising the compound of claim 3 and a pharmaceutically acceptable carrier.

7. The orally administered pharmaceutical composition of claim 5, wherein the pharmaceutical composition is a liquid dosage form.

8. The orally administered pharmaceutical composition of claim 5, wherein the pharmaceutical composition is a solid dosage form.

9. The orally administered pharmaceutical composition of claim 6, wherein the pharmaceutical composition is a liquid dosage form.

10. The orally administered pharmaceutical composition of claim 6, wherein the pharmaceutical composition is a solid dosage form.

\* \* \* \* \*